US010771607B2

(12) United States Patent
Mandapaka et al.

(10) Patent No.: US 10,771,607 B2
(45) Date of Patent: Sep. 8, 2020

(54) SYSTEM AND METHOD FOR WIRELESS COMMUNICATION OF GLUCOSE DATA

(71) Applicant: DexCom, Inc., San Diego, CA (US)

(72) Inventors: Aditya Mandapaka, San Diego, CA (US); Jorge Valdes, San Diego, CA (US); Jeffrey R. Wedekind, San Diego, CA (US); Eric Cohen, San Diego, CA (US); Douglas William Burnette, San Diego, CA (US); Francis William Pascual, San Diego, CA (US); Hari Hampapuram, Portland, OR (US); Mark Dervaes, Carlsbad, CA (US); Michael Robert Mensinger, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 0 days.

(21) Appl. No.: 15/651,851

(22) Filed: Jul. 17, 2017

(65) Prior Publication Data
US 2018/0027412 A1    Jan. 25, 2018

Related U.S. Application Data

(63) Continuation of application No. 15/651,310, filed on Jul. 17, 2017, now Pat. No. 10,375,222.
(Continued)

(51) Int. Cl.
*H04M 1/725* (2006.01)
*H04W 74/04* (2009.01)
(Continued)

(52) U.S. Cl.
CPC ......... *H04M 1/7253* (2013.01); *A61B 5/0004* (2013.01); *A61B 5/14503* (2013.01);
(Continued)

(58) Field of Classification Search
CPC .............................. H04W 4/80; A61B 5/0002
(Continued)

(56) References Cited

U.S. PATENT DOCUMENTS 7,174,130 B2    2/2007  Kurisko et al.
8,707,392 B2    4/2014  Birtwhistle et al.
(Continued)

FOREIGN PATENT DOCUMENTS

WO    WO 2014/070471    5/2014

*Primary Examiner* — Wen W Huang
(74) *Attorney, Agent, or Firm* — Knobbe, Martens, Olson & Bear, LLP

(57) ABSTRACT

Systems, devices, and methods are disclosed for wireless communication of analyte data. One such method includes, during a first interval, establishing a first connection between an analyte sensor system and a display device. During the first connection, the method includes exchanging information related to authentication between the analyte sensor system and the display device. The method includes making a determination regarding whether authentication was performed during the first interval. During a second interval, the method may include establishing a second connection between the analyte sensor system and the display device for transmission of an encrypted analyte value, and bypassing the exchanging of information related to authentication performed during the first connection. The method also includes, during the second interval, the analyte sensor system transmitting the encrypted analyte value to the display device, if the determination indicates that the authentication was performed during the first interval.

20 Claims, 40 Drawing Sheets

Related U.S. Application Data

(60) Provisional application No. 62/364,771, filed on Jul. 20, 2016.

(51) Int. Cl.

| | | |
|---|---|---|
| *H04B 17/23* | (2015.01) | |
| *H04W 4/38* | (2018.01) | |
| *G16H 40/63* | (2018.01) | |
| *H04W 4/80* | (2018.01) | |
| *A61B 5/00* | (2006.01) | |
| *A61B 5/145* | (2006.01) | |
| *H04W 12/04* | (2009.01) | |
| *H04W 12/06* | (2009.01) | |
| *H04W 76/25* | (2018.01) | |
| *H04W 76/10* | (2018.01) | |
| *G06F 19/00* | (2018.01) | |
| *H04L 29/06* | (2006.01) | |
| *H04L 29/08* | (2006.01) | |
| *H04W 72/04* | (2009.01) | |
| *H04W 72/08* | (2009.01) | |
| *H04B 17/318* | (2015.01) | |
| *G16H 40/67* | (2018.01) | |
| *G16H 20/17* | (2018.01) | |
| *G16H 10/60* | (2018.01) | |
| *H04W 84/18* | (2009.01) | |
| *H04Q 9/00* | (2006.01) | |

(52) U.S. Cl.
CPC .......... *A61B 5/14532* (2013.01); *A61B 5/742* (2013.01); *G06F 19/3418* (2013.01); *G16H 40/63* (2018.01); *G16H 40/67* (2018.01); *H04B 17/23* (2015.01); *H04B 17/318* (2015.01); *H04L 63/0428* (2013.01); *H04L 63/06* (2013.01); *H04L 63/0869* (2013.01); *H04L 63/168* (2013.01); *H04L 67/12* (2013.01); *H04W 4/38* (2018.02); *H04W 4/80* (2018.02); *H04W 12/04* (2013.01); *H04W 12/06* (2013.01); *H04W 72/0446* (2013.01); *H04W 72/085* (2013.01); *H04W 74/04* (2013.01); *H04W 76/10* (2018.02); *H04W 76/25* (2018.02); *G16H 10/60* (2018.01); *G16H 20/17* (2018.01); *H04Q 9/00* (2013.01); *H04Q 2209/40* (2013.01); *H04Q 2209/823* (2013.01); *H04W 84/18* (2013.01)

(58) Field of Classification Search
USPC ...................... 455/41.1, 41.2, 41.3
See application file for complete search history.

(56) References Cited

U.S. PATENT DOCUMENTS

| | | | |
|---|---|---|---|
| 8,907,782 B2 | 12/2014 | Baker et al. | |
| 9,008,658 B2 | 4/2015 | Baker et al. | |
| 9,232,352 B2 | 1/2016 | Wang et al. | |
| 9,299,238 B1* | 3/2016 | Ahmad | A61B 5/4833 |
| 9,326,093 B2 | 4/2016 | Xie et al. | |
| 9,398,437 B2 | 7/2016 | Kasslin et al. | |
| 9,421,324 B2 | 8/2016 | Sloan | |
| 9,463,325 B1* | 10/2016 | Young | A61N 1/37217 |
| 9,473,941 B1* | 10/2016 | Palin | H04W 12/06 |
| 9,475,356 B2 | 10/2016 | Wilson | |
| 9,482,635 B2 | 11/2016 | Morales et al. | |
| 9,544,075 B2 | 1/2017 | Altman et al. | |
| 9,544,313 B2 | 1/2017 | Love et al. | |
| 9,578,450 B2 | 2/2017 | Seidenberg et al. | |
| 9,730,620 B2 | 8/2017 | Cohen et al. | |
| 9,763,644 B2 | 9/2017 | Pelissier et al. | |
| 9,866,389 B2 | 1/2018 | Reed et al. | |
| 9,999,025 B2 | 6/2018 | Wiser | |
| 10,021,510 B2 | 7/2018 | Hong et al. | |
| 10,021,512 B2 | 7/2018 | Reunamaki | |
| 10,028,324 B2 | 7/2018 | Kwon et al. | |
| 10,086,208 B2 | 10/2018 | Hoffman et al. | |
| 10,111,071 B2 | 10/2018 | Polo et al. | |
| 2003/0050009 A1 | 3/2003 | Kurisko et al. | |
| 2010/0265073 A1* | 10/2010 | Harper | H04W 4/80 |
| | | | 340/573.1 |
| 2010/0274218 A1 | 10/2010 | Yodfat et al. | |
| 2012/0271557 A1* | 10/2012 | Sekimoto | A61B 5/743 |
| | | | 702/19 |
| 2013/0059541 A1 | 3/2013 | Sloan et al. | |
| 2013/0078912 A1* | 3/2013 | San Vicente | A61B 5/0015 |
| | | | 455/39 |
| 2013/0113632 A1* | 5/2013 | Bernstein | G16H 50/20 |
| | | | 340/870.02 |
| 2013/0331036 A1* | 12/2013 | Baker | G06F 19/3418 |
| | | | 455/41.3 |
| 2014/0107449 A1* | 4/2014 | Ecoff | A61B 5/0015 |
| | | | 600/365 |
| 2014/0179276 A1 | 6/2014 | Kang et al. | |
| 2014/0187889 A1 | 7/2014 | Cohen et al. | |
| 2014/0362728 A1 | 12/2014 | Krochmal et al. | |
| 2015/0038818 A1* | 2/2015 | Cole | A61B 5/746 |
| | | | 600/365 |
| 2015/0112264 A1 | 4/2015 | Kamen et al. | |
| 2015/0164391 A1 | 6/2015 | Hernandez-Rosas et al. | |
| 2015/0182115 A1* | 7/2015 | DeHennis | G16H 40/63 |
| | | | 600/316 |
| 2015/0205947 A1* | 7/2015 | Berman | G06F 21/44 |
| | | | 726/16 |
| 2015/0207626 A1 | 7/2015 | Neftel et al. | |
| 2015/0207796 A1 | 7/2015 | Love et al. | |
| 2015/0304803 A1* | 10/2015 | Chen | H04W 4/008 |
| | | | 455/41.2 |
| 2015/0382150 A1* | 12/2015 | Ansermet | G06Q 10/0639 |
| | | | 455/41.1 |
| 2016/0048827 A1 | 2/2016 | Corbalis et al. | |
| 2016/0099936 A1* | 4/2016 | Enke | H04L 63/0428 |
| | | | 726/7 |
| 2016/0134709 A1 | 5/2016 | Savolainen | |
| 2016/0174346 A1 | 6/2016 | Korlyama et al. | |
| 2016/0232318 A1 | 8/2016 | Mensinger et al. | |
| 2017/0026778 A1* | 1/2017 | Yamada | H04W 4/008 |
| 2017/0201931 A1* | 7/2017 | Swanzey | H04W 48/10 |
| 2017/0265164 A1* | 9/2017 | Wiser | H04W 72/005 |
| 2017/0265789 A1 | 9/2017 | Naseri et al. | |
| 2017/0374629 A1* | 12/2017 | Ramappa | H04W 4/80 |
| 2018/0027104 A1 | 1/2018 | Mandapaka et al. | |
| 2018/0027106 A1 | 1/2018 | Mandapaka et al. | |
| 2018/0089656 A1 | 3/2018 | Jones et al. | |
| 2018/0217917 A1* | 8/2018 | Hayter | A61B 5/7282 |

* cited by examiner

| Address 805 | Description 810 | Value 815 |
|---|---|---|
| Range 805a | Preamble 810a | Bytes 815a |
| Range 805b | Access Address 810b | Bytes 815b |
| Range 805c | Header 810c | Bytes 815c |
| Range 805d | MAC Address 810d | Bytes 815d |
| Range 805e | Device Name 810e | Bytes 815e |
| Range 805f | Flags 810f | Bytes 815f |
| Range 805g | Identifier 810g | Bytes 815g |
| Range 805h | Manufacturing Data 810h | Bytes 815h |
| Range 805i | Error Checking 810i | Bytes 815i |

FIG. 8

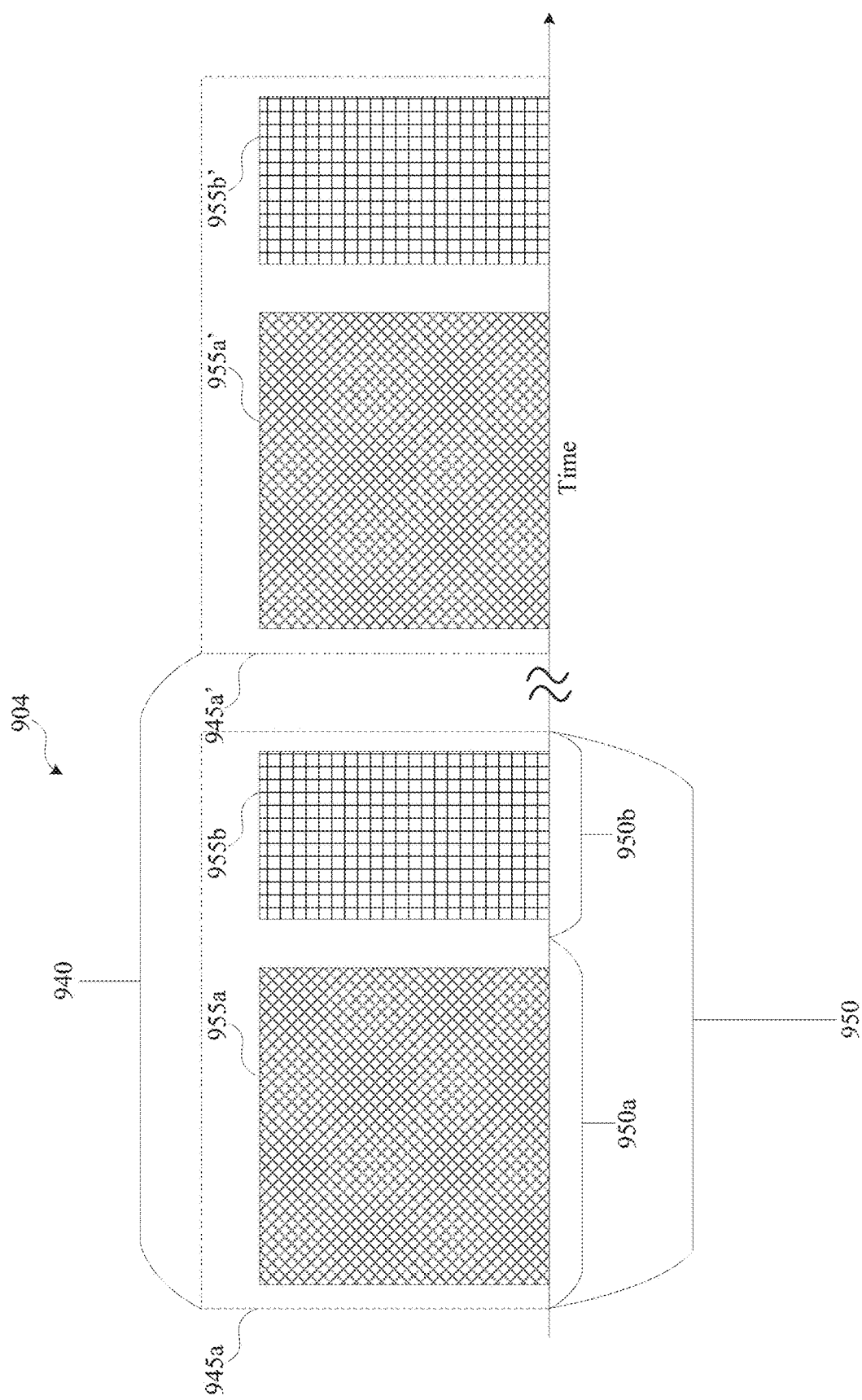

```
┌─────────────────────────────────────────────────────────────────────┐
│   TRANSMIT 1ST ADVERTISEMENT INCLUDING 1ST ADDRESS DURING 1ST PERIOD│
│                              1505A                                  │
└─────────────────────────────────────────────────────────────────────┘
                                  ▼
┌─────────────────────────────────────────────────────────────────────┐
│  DETERMINE WHETHER 1ST CONNECTION ESTABLISHED WITH 1ST DEVICE OR    │
│          2ND CONNECTION ESTABLISHED WITH 2ND DEVICE                 │
│                              1505B                                  │
└─────────────────────────────────────────────────────────────────────┘
                                  ▼
┌─────────────────────────────────────────────────────────────────────┐
│       IF 1ST CONNECTION ESTABLISHED, TRANSMIT 2ND ADVERTISEMENT     │
│      INCLUDING 2ND ADDRESS SPECIFIC TO 2ND DEVICE DURING 2ND PERIOD │
│                              1505C                                  │
└─────────────────────────────────────────────────────────────────────┘
                                  ▼
┌─────────────────────────────────────────────────────────────────────┐
│       IF 2ND CONNECTION ESTABLISHED, TRANSMIT 3RD ADVERTISEMENT     │
│      INCLUDING 3RD ADDRESS SPECIFIC TO 1ST DEVICE DURING 2ND PERIOD │
│                              1505D                                  │
└─────────────────────────────────────────────────────────────────────┘
                                  ▼
┌─────────────────────────────────────────────────────────────────────┐
│          ASSESS WHETHER LIST INCLUDES 1ST DEVICE AND 2ND DEVICE     │
│                              1505E                                  │
└─────────────────────────────────────────────────────────────────────┘
                                  ▼
┌─────────────────────────────────────────────────────────────────────┐
│    IF SO, ALLOCATE 1ST SEGMENT OF 3RD PERIOD TO 2ND DEVICE AND 2ND  │
│              SEGMENT OF 3RD PERIOD TO 1ST DEVICE                    │
│                              1505F                                  │
└─────────────────────────────────────────────────────────────────────┘
                                  ▼
┌─────────────────────────────────────────────────────────────────────┐
│   TRANSMIT 3RD ADVERTISEMENT IF CONNECTION WITH 1ST DEVICE LOST AND │
│       2ND ADVERTISEMENT IF CONNECTION WITH 2ND DEVICE LOST          │
│                              1505G                                  │
└─────────────────────────────────────────────────────────────────────┘
                                  ▼
┌─────────────────────────────────────────────────────────────────────┐
│   DEFINE SETS OF DEVICE GROUPS ACCORDING TO A CLASSIFICATION SCHEME │
│                              1505H                                  │
└─────────────────────────────────────────────────────────────────────┘
                                  ▼
┌─────────────────────────────────────────────────────────────────────┐
│     SELECT BETWEEN ADVERTISEMENTS SPECIFIC TO DEVICE GROUPS BASED ON│
│       RELATIVE CONNECTION QUALITIES, LOCATIONS, TIME, AND BATTERY   │
│                              1505J                                  │
└─────────────────────────────────────────────────────────────────────┘
```

FIG. 15A              1500

SYSTEM AND METHOD FOR WIRELESS COMMUNICATION OF GLUCOSE DATA

INCORPORATION BY REFERENCE TO RELATED APPLICATION

Any and all priority claims identified in the Application Data Sheet, or any correction thereto, are hereby incorporated by reference under 37 CFR 1.57. This application is a continuation of U.S. application Ser. No. 15/651,310, filed Jul. 17, 2017, which claims the benefit of U.S. Provisional Appl. No. 62/364,771, filed on Jul. 20, 2016. Each of the aforementioned applications is incorporated by reference herein in its entirety, and each is hereby expressly made a part of this specification.

TECHNICAL FIELD

The present disclosure relates generally to continuous monitoring of analyte values received from an analyte sensor system. More particularly, the present disclosure is directed to systems, methods, apparatuses, and devices, for the wireless communication of glucose data.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically requires uncomfortable finger pricking methods. Due to the lack of comfort and convenience, a diabetic will normally only measure his or her glucose level two to four times per day. Unfortunately, these time intervals are spread so far apart that the diabetic will likely be alerted to a hyperglycemic or hypoglycemic condition too late, sometimes incurring dangerous side effects as a result. In fact, it is not only unlikely that a diabetic will take a timely SMBG value, but will not know if his blood glucose value is going up (higher) or down (lower), due to limitations of conventional methods.

Consequently, a variety of non-invasive, transdermal (e.g., transcutaneous) and/or implantable electrochemical sensors are being developed for continuously detecting and/or quantifying blood glucose values. These devices generally transmit raw or minimally processed data for subsequent analysis at a remote device, which can include a display. The transmission to wireless display devices can be wireless.

With respect to the wireless transmission of glucose and other analyte data gathered using an implanted sensor, battery life of the transmitter acting in conjunction with the sensor is typically a concern. In order to conserve battery life or to increase the efficiency associated with the transmission of glucose and other analyte data, transmissions may, for example, need to be intermittent. The intermittent transmission of monitored data can introduce reliability issues, however. In some cases, reliability is thus sacrificed for battery life in conventional sensor systems.

SUMMARY

In a first aspect, a method for wireless communication of analyte data includes, during a first interval, establishing a first connection between an analyte sensor system and a display device. The method further includes, during the first connection, exchanging information related to authentication between the analyte sensor system and the display device. In addition, the method includes making a determination regarding whether authentication was performed during the first interval. The method also includes, during a second interval, the analyte sensor system transmitting an encrypted analyte value to the display device, if the determination indicates that the authentication was performed during the first interval.

In certain implementations of the first aspect, which may be generally applicable but are also particularly applicable in connection with any other implementation of the first aspect, the information related to authentication includes an application key. In embodiments, the method further includes using the application key to encrypt an analyte value and generate the encrypted analyte value. In embodiments, characteristics of the application key are based on one or more of: a type of data to be encrypted with the application key; a network environment; and user settings. In embodiments, the method further includes modifying the application key responsive to one or more of: the passage of a predetermined amount of time; the analyte sensor system or the display device being restarted; a trigger related to another device attempting to connect to the analyte sensor system; and user input. In embodiments, the application key was received by the display device from a server.

In certain implementations of the first aspect, which may be generally applicable but are also particularly applicable in connection with any other implementation of the first aspect, the method further includes, during the second interval: establishing a second connection between the analyte sensor system and the display device for the transmitting of the encrypted analyte value by the analyte sensor system; and bypassing the exchanging of information related to authentication performed during the first connection.

In certain implementations of the first aspect, which may be generally applicable but are also particularly applicable in connection with any other implementation of the first aspect, at least a portion of the encrypted analyte value is transmitted to the display device in one or more advertisement messages transmitted by the analyte sensor system. In embodiments, the method further includes determining a number of advertisement messages to use for transmission of the encrypted analyte value. In embodiments, if the number of advertisement messages to use for transmission of the encrypted analyte value is determined to be greater than 1, a first of the one or more advertisement messages comprises a first portion of the encrypted analyte value and an indication that a second of the one or more advertisement messages will comprise a second portion of the encrypted analyte value. If the number of advertisement messages to use for transmission of the encrypted analyte value is determined to be 1, a first of the one or more advertisement messages may include the encrypted analyte value.

In certain implementations of the first aspect, which may be generally applicable but are also particularly applicable in connection with any other implementation of the first aspect, exchanging the information related to authentication includes performing a two-way authentication. In embodiments, performing the two-way authentication includes several operations. Such operations include the analyte sensor system transmitting a first value to the display device. Such operations include the analyte sensor system receiving from the display device a second value and a third value. The second value is based on the first value and an application key. Such operations include the analyte sensor system validating the second value. Other such operations include the analyte sensor system generating a fourth value using the third value. More such options include the analyte sensor system transmitting the fourth value to the display device for validation.

In certain implementations of the first aspect, which may be generally applicable but are also particularly applicable in connection with any other implementation of the first aspect, exchanging the information related to authentication includes several operations. Such operations include the analyte sensor system receiving a first value from the display device. Additional options include the analyte sensor system generating a second value based on the first value and an application key. Further options include the analyte sensor system transmitting to the display device the second value for validation by the display device.

In certain implementations of the first aspect, which may be generally applicable but are also particularly applicable in connection with any other implementation of the first aspect, the information related to authentication includes an application key used to generate the encrypted analyte value. In some such cases, using the application key to encrypt the analyte value and generate the encrypted analyte value allows bypassing, during the second interval, the exchanging of information related to authentication.

In certain implementations of the first aspect, which may be generally applicable but are also particularly applicable in connection with any other implementation of the first aspect, establishing the first connection and exchanging the information related to authentication are done using a first wireless protocol. In some such cases, transmitting the encrypted analyte value to the display device is done using a second wireless protocol different than the first wireless protocol. In embodiments, using the first wireless protocol allows bypassing, during the second interval, the exchanging of information related to authentication.

In a second aspect, a method for wireless communication of analyte data includes during a first interval, using a first wireless protocol to perform an exchange of information related to authentication information with a display device. The method also includes during a second interval, bypassing the exchange of information related to authentication by using a second wireless protocol to transmit an encrypted analyte value to the display device. The encrypted analyte value has been generated using the information related to authentication. The first wireless protocol is different than the second wireless protocol. The first wireless protocol may be WiFi or Near Field Communication (NFC). The second wireless protocol may be Bluetooth Low Energy (BLE).

In certain implementations of the second aspect, which may be generally applicable but are also particularly applicable in connection with any other implementation of the second aspect, the information related to authentication includes an application key. In some such implementations, the method includes the display device receiving the application key from a server.

In a third aspect, an analyte sensor system configured for wireless communication of analyte data includes an analyte sensor. The analyte sensor system also includes a transceiver configured to transmit and receive wireless signals. Further, the analyte sensor system includes a processor operatively coupled to the analyte sensor and the transceiver and configured to cause the analyte sensor system to perform certain operations. Such operations include, during a first interval, establishing a first connection between the analyte sensor system and a display device. Such operations include, during the first connection, exchanging information related to authentication between the analyte sensor system and the display device. Such operations include making a determination regarding whether authentication was performed during the first interval. Further, such operations include, during a second interval, transmitting an encrypted analyte value to the display device, if the determination indicates that the authentication was performed during the first interval.

In certain implementations of the third aspect, which may be generally applicable but are also particularly applicable in connection with any other implementation of the third aspect, the information related to authentication includes an application key, and the processor is further configured to cause the analyte sensor system to encrypt an analyte value to generate the encrypted analyte value.

In certain implementations of the third aspect, which may be generally applicable but are also particularly applicable in connection with any other implementation of the third aspect, the processor is further configured to cause the analyte sensor system to perform certain operations. Such operations include, during the second interval, establishing a second connection between the analyte sensor system and the display device. Such operations include, during the second connection, bypassing the exchange of the information related to authentication.

In certain implementations of the third aspect, which may be generally applicable but are also particularly applicable in connection with any other implementation of the third aspect, the information related to authentication includes an application key, and the processor is further configured to cause the analyte sensor system to use the application key to encrypt an analyte value to generate the encrypted analyte value. The use of the application key may allow the analyte sensor system to bypass the exchange.

In certain implementations of the third aspect, which may be generally applicable but are also particularly applicable in connection with any other implementation of the third aspect, the processor is further configured to cause the analyte sensor system to perform certain operations. Such operations include establishing the first connection and exchange the information related to authentication using a first wireless protocol. Such operations include transmitting the encrypted analyte data using a second wireless protocol. The first wireless protocol may allow bypassing, during the second interval, the exchange of information related to authentication.

In a fourth aspect, a mobile device configured for wireless communication of analyte data with an analyte sensor system includes a user interface. The mobile device also includes a transceiver configured to transmit and receive wireless signals. Further, the mobile device includes circuitry operatively coupled to the user interface and the transceiver. The mobile devices includes a non-transitory computer-readable medium operatively coupled to the circuitry and storing instructions that, when executed, cause the circuitry to perform certain operations. Such operations include, during a first interval, establishing a first connection between the analyte sensor system and the mobile device. Such operations include, during the first connection, exchanging information related to authentication between the analyte sensor system and the mobile device. Moreover, such operations include obtaining a determination regarding whether authentication was performed during the first interval. Such operations also include, during a second interval, receiving an encrypted analyte value from the analyte sensor system, if the determination indicates that the authentication was performed during the first interval.

In a fifth aspect, a system includes a display device. The system also includes an analyte sensor system. The analyte sensor system includes a transceiver configured to transmit and receive wireless signals. The analyte sensor system also includes a processor operatively coupled to the analyte sensor and the transceiver and configured to cause the analyte sensor system to perform certain operations. Such operations include, during a first interval, establishing a first connection between the analyte sensor system and the display device. Such operations include, during the first connection, exchanging information related to authentication between the analyte sensor system and the display device. Further, such operations include making a determination regarding whether authentication was performed during the first interval. Such operations also include, during a second interval, transmitting an encrypted analyte value to the display device, if the determination indicates that the authentication was performed during the first interval.

In certain implementations of the fifth aspect, which may be generally applicable but are also particularly applicable in connection with any other implementation of the fifth aspect, the system further includes a server configured to send at least some of the information related to authentication to one or more of the analyte sensor system and the display device.

In a sixth aspect, a method for wireless communication of analyte data includes establishing a first connection between an analyte sensor system and a first display device, in order to exchange pairing information between the analyte sensor system and the first display device. The method also includes maintaining the first connection by periodically exchanging messages between the analyte sensor system and the first display device. Also, the method includes, while the analyte sensor system and the display device remain connected, the analyte sensor system transmitting the analyte data to the first display device, upon the analyte data becoming available for transmission.

In certain implementations of the sixth aspect, which may be generally applicable but are also particularly applicable in connection with any other implementation of the sixth aspect, establishing the first connection includes performing a two-way authentication between the analyte sensor system and the first display device. Performing the two-way authentication may include one or more additional operations. Such operations include the analyte sensor system transmitting a first value to the first display device. Such operations include the analyte sensor system receiving from the first display device a second value and a third value. The second value is based on the first value and an application key. Such operations include the analyte sensor system validating the second value. Such operations include the analyte sensor system generating a fourth value using the third value. Also, such operations include the analyte sensor system transmitting the fourth value to the first display device for validation.

In certain implementations of the sixth aspect, which may be generally applicable but are also particularly applicable in connection with any other implementation of the sixth aspect, the combination of periodically exchanging messages and transmitting the analyte data to the first display device, upon the analyte data becoming available for transmission, is done responsive to an indication of a user preference for the first display device.

In certain implementations of the sixth aspect, which may be generally applicable but are also particularly applicable in connection with any other implementation of the sixth aspect, the combination of periodically exchanging messages and transmitting the analyte data to the display device, upon the analyte data becoming available for transmission, is done adaptively.

In certain implementations of the sixth aspect, which may be generally applicable but are also particularly applicable in connection with any other implementation of the sixth aspect, the messages exchanged periodically between the analyte sensor system and the first display device include a first message and a second message, the first and second messages being configured for sequential exchange. The first message includes a messaging interval corresponding to a scheduled amount of time between the sequential exchange of the first message and second messages.

In certain implementations of the sixth aspect, which may be generally applicable but are also particularly applicable in connection with any other implementation of the sixth aspect, each of the messages exchanged periodically between the analyte sensor system and the first display device includes a message interval corresponding to an amount of time until a successive message is to be exchanged.

In certain implementations of the sixth aspect, which may be generally applicable but are also particularly applicable in connection with any other implementation of the sixth aspect, the method further includes sending a request to modify the message interval. The method may also include terminating the analyte sensor system periodically exchanging messages with the first display device, such that the analyte sensor system and the display device do not remain connected, responsive to the request being denied.

In certain implementations of the sixth aspect, which may be generally applicable but are also particularly applicable in connection with any other implementation of the sixth aspect, each of the messages exchanged periodically between the analyte sensor system and the first display device includes a timeout value. The method may further include terminating the analyte sensor system periodically exchanging messages with the first display device, such that the analyte sensor system and the first display device do not remain connected, if the timeout value included in a first message of the messages is exceeded before a second message of the messages successive to the first message is exchanged.

In certain implementations of the sixth aspect, which may be generally applicable but are also particularly applicable in connection with any other implementation of the sixth aspect, the method further includes the first display device establishing a second connection with a second display device such that the first display device and the second display device remain connected. The method may also include, while the first and second display devices remain connected, the first display device transmitting information related to the analyte data to the second display device, after receiving the analyte data from the analyte sensor system.

In a seventh aspect, a method for wireless communication of analyte data includes establishing a first connection between an analyte sensor system and a first display device, in order to exchange pairing information between the analyte sensor system and the first display device. The method also includes operation in a first mode. Operating in the first mode includes the analyte sensor system periodically exchanging messages with the first display device such that the analyte sensor system and the first display device remain connected. While the analyte sensor system and the first display device remain connected, operating in the first mode includes the analyte sensor system transmitting the analyte data to the first display device, upon the analyte data becoming available for transmission. Additionally, the method includes operating in a second mode. Operating in the second mode includes periodically establishing a second connection between the analyte sensor system and the first display device. After the second connection has been established, operating in the second mode includes transmitting the analyte data to the first display device.

In certain implementations of the seventh aspect, which may be generally applicable but are also particularly applicable in connection with any other implementation of the seventh aspect, operating in the first mode occurs responsive to an indication related to one or more of: user input regarding a use preference for the first display device; time of day; location; packet loss; and a priority scheme that includes the first display device.

In certain implementations of the seventh aspect, which may be generally applicable but are also particularly applicable in connection with any other implementation of the seventh aspect, operating in the second mode occurs if the analyte sensor system is transmitting analyte data and is not operating in the first mode.

In certain implementations of the seventh aspect, which may be generally applicable but are also particularly applicable in connection with any other implementation of the seventh aspect, while operating in the first mode, the method includes the analyte sensor system transmitting the analyte data to the first display device comprises the analyte sensor system transmitting the analyte data to a second display device that is not connected to analyte sensor system.

In certain implementations of the seventh aspect, which may be generally applicable but are also particularly applicable in connection with any other implementation of the seventh aspect, the method further includes switching between operating in the first mode and operating in the second mode.

In an eighth aspect, an analyte sensor system configured for wireless communication of analyte data includes an analyte sensor. The analyte sensor system also includes a transceiver configured to transmit and receive wireless signals. Moreover, the analyte sensor system includes a processor operatively coupled to the analyte sensor and the transceiver and configured to cause the analyte sensor system to perform a number of operations. Such operations include establishing a first connection between the analyte sensor system and a first display device, in order to exchange pairing information between the analyte sensor system and the first display device. Such operations include maintaining the first connection by periodically exchanging messages between the analyte sensor system and the first display device. Moreover, during the first connection, such operations include transmitting the analyte data to the first display device, upon the analyte data becoming available for transmission.

In certain implementations of the eighth aspect, which may be generally applicable but are also particularly applicable in connection with any other implementation of the eighth aspect, the processor is further configured to cause the analyte sensor system perform a two-way authentication in connection with the first connection being established.

In certain implementations of the eighth aspect, which may be generally applicable but are also particularly applicable in connection with any other implementation of the eighth aspect, the processor is further configured to cause the analyte sensor system to maintain the first connection transmit the analyte data to the first display device, upon the analyte data becoming available for transmission, responsive to an indication of a user preference for the first display device.

In certain implementations of the eighth aspect, which may be generally applicable but are also particularly applicable in connection with any other implementation of the eighth aspect, the processor is further configured to adaptively cause the analyte sensor system to maintain the first connection transmit the analyte data to the first display device, upon the analyte data becoming available for transmission.

In certain implementations of the eighth aspect, which may be generally applicable but are also particularly applicable in connection with any other implementation of the eighth aspect, the messages exchanged periodically between the analyte sensor system and the first display device includes a first message and a second message. Moreover, the processor is further configured to cause the analyte sensor system to sequentially exchange the first and second messages with the first display device. The first message includes a messaging interval corresponding to a scheduled amount of time between the exchange of the first and second messages. The processor may be further configured to cause the analyte sensor system modify the messaging interval.

In a ninth aspect, a system includes a first display device and an analyte sensor system. The analyte sensor system includes a transceiver configured to transmit and receive wireless signals. The analyte sensor system also includes a processor operatively coupled to the analyte sensor and the transceiver and configured to cause the analyte sensor system to perform certain operations. One such operation is to establish a first connection between the analyte sensor system and the first display device, in order to exchange pairing information between the analyte sensor system and the first display device. One such operation is to maintain the first connection by periodically exchanging messages between the analyte sensor system and the first display device. During the first connection, another such operation is to transmit the analyte data to the first display device, upon the analyte data becoming available for transmission. The analyte sensor system also includes a second display device. The first display device is configured to establish a second connection with the second display device such that the first and second display devices remain connected. The first display device is further configured to, while the first and second display devices remain connected, transmit information related to the analyte data to the second display device, after receiving the analyte data from the analyte sensor system.

In a tenth aspect, an analyte sensor system configured for wireless communication of analyte data includes an analyte sensor. The analyte sensor system also includes a transceiver configured to transmit and receive wireless signals. Also, the analyte sensor system includes a processor operatively coupled to the analyte sensor and the transceiver and configured to cause the analyte sensor system to perform certain operations. One such operation is to establish a first connection between the analyte sensor system and a first display device, in order to exchange pairing information between the analyte sensor system and the first display device. Another such operation is to operate in a first mode, in which messages are periodically exchanged with the first display device such that the analyte sensor system and the first display device remain connected, and in which the analyte sensor system transmits analyte data to the first display device, upon the analyte data becoming available for transmission. Another such operation is to operate in a second mode, in which a second connection with the first display device is periodically established for the transmission of analyte data.

In certain implementations of the tenth aspect, which may be generally applicable but are also particularly applicable in connection with any other implementation of the tenth aspect, the processor is further configured to cause the analyte sensor system to operate in the second mode if the analyte sensor system is transmitting data and is not operating in the first mode.

In certain implementations of the tenth aspect, which may be generally applicable but are also particularly applicable in connection with any other implementation of the tenth aspect, the processor is further configured to cause the analyte sensor system to operate in the first mode responsive to an indication related to one or more of: user input regarding a user preference for the first display device; time of day; location; packet loss; and a priority scheme that includes the first display device.

In an eleventh aspect, a method for connecting an analyte sensor system to an analyte display device and a second display device includes using an advertisement duration structure in attempt to pair the analyte sensor system with the analyte display device and the second display device. According to the advertisement duration structure, an advertisement duration includes a first time segment and a second time segment. The first time segment is allocated to the second display device. The second time segment is allocated to the analyte display device. The first time segment precedes the second time segment within the advertisement duration. The method also includes reconfiguring the advertisement duration structure such that the second time segment precedes the first time segment. The first time segment may be about 20 seconds long and the second time segment may be about 2 seconds long.

In certain implementations of the eleventh aspect, which may be generally applicable but are also particularly applicable in connection with any other implementation of the eleventh aspect, reconfiguring the advertisement duration structure includes extending the first time segment to a span of time less than or equal to a remainder of the advertisement duration.

In a twelfth aspect, an analyte sensor system configured for wireless communication of analyte data includes an analyte sensor and a transceiver configured to transmit and receive wireless signals. The analyte sensor system also includes a processor operatively coupled to the analyte sensor and the transceiver and configured to cause the analyte sensor system to perform certain operations. One such operation is to transmit advertisement messages according to an advertisement duration structure in attempt to pair the analyte sensor system with an analyte display device and a second display device. According to the advertisement duration structure, an advertisement duration includes a first time segment and a second time segment. The first time segment is allocated to the second display device. The second time segment is allocated to the analyte display device. The first time segment precedes the second time segment within the advertisement duration. Another such operation is to reconfigure the advertisement duration structure such that the second time segment precedes the first time segment.

In a thirteenth aspect, a method for connecting an analyte sensor system to an analyte display device and a second display device includes assessing a value that indicates whether or not the analyte sensor system has paired with the second display device. If the value indicates that the analyte sensor system has paired with the second display device, the method includes setting a first time segment of a first advertisement duration to a first length, and transmitting a first set of advertisement messages to the second display device during the first time segment. If the value indicates that the analyte sensor system has not paired with the second display device, the method includes setting the first time segment to a second length, and transmitting a second set of advertisement messages to the second display device during the first time segment, if the second length is not zero seconds. The second length may be about 7 seconds. The first length may be about 20 seconds. The value may be an entry on a list, and the entry may correspond to the second display device.

In certain implementations of the thirteenth aspect, which may be generally applicable but are also particularly applicable in connection with any other implementation of the thirteenth aspect, the method further includes setting the second length to zero seconds if the value indicates that the analyte sensor system has not paired with the second display device.

In certain implementations of the thirteenth aspect, which may be generally applicable but are also particularly applicable in connection with any other implementation of the thirteenth aspect, the method further includes setting the first time segment to the first length, responsive to a signaling received via Near Field Communication.

In a fourteenth aspect, an analyte sensor system configured for wireless communication of analyte data includes an analyte sensor. The analyte sensor system also includes a transceiver configured to transmit and receive wireless signals. The analyte sensor system also includes a processor operatively coupled to the analyte sensor and the transceiver and configured to cause the analyte sensor system to perform certain operations. Such operations include assessing a value that indicates whether or not the analyte sensor system has paired with a second display device. Such operations include, if the value indicates that the analyte sensor system has paired with the second display device, setting a first time segment of a first advertisement duration to a first length, and transmitting a first set of advertisement messages to the second display device during the first time segment. Such operations also include, if the value indicates that the analyte sensor system has not paired with the second display device, setting the first time segment to a second length, and transmitting a second set of advertisement messages to the second display device during the first time segment, if the second length is not zero seconds. The second length is less than the first length.

In a fifteenth aspect, a method for connecting an analyte sensor system to an analyte display device and a second display device includes, during a first time segment within an advertisement duration, transmitting a first set of advertisement messages to the second display device according to a first advertisement interval. During a second time segment within the advertisement duration, the method includes transmitting a second set of advertisement messages to an analyte display device according to a second advertisement interval. One or more of the first advertisement interval, the second advertisement interval, a length of the first time segment, a length of the second time segment, the advertisement duration, and a sequence of the first and second time segments, is configurable. The first advertisement interval may be configurable to be between about 20 milliseconds and about 90 milliseconds. The advertisement duration may be configurable between about 2 seconds and about 90 seconds.

In certain implementations of the fifteenth aspect, which may be generally applicable but are also particularly applicable in connection with any other implementation of the fifteenth aspect, the method further includes altering the sequence of the first and second time segments such that the second time segment precedes the first time segment.

In certain implementations of the fifteenth aspect, which may be generally applicable but are also particularly applicable in connection with any other implementation of the fifteenth aspect, the method further includes altering the sequence of the first and second time segments based on a value that indicates whether or not the analyte sensor system has paired with the second display device.

In certain implementations of the fifteenth aspect, which may be generally applicable but are also particularly applicable in connection with any other implementation of the fifteenth aspect, the method further includes obtaining an indication of a quality of a connection between the analyte sensor system and the analyte display device. The method further includes modifying one or more of the length of the second time segment and the second advertisement interval, based on the indication of the quality.

In certain implementations of the fifteenth aspect, which may be generally applicable but are also particularly applicable in connection with any other implementation of the fifteenth aspect, modifying one or more of the length of the second time segment and the second advertisement interval is done by the analyte sensor system responsive to a signal received from the analyte display device.

In certain implementations of the fifteenth aspect, which may be generally applicable but are also particularly applicable in connection with any other implementation of the fifteenth aspect, the method further includes comparing the indication of the quality to a threshold. If the indication of the quality exceeds the threshold, modifying one or more of the length of the second time segment and the second advertisement interval includes one or more of: decreasing the length of the second time segment; and increasing the second advertisement interval. If the indication of the quality falls below the threshold, modifying one or more of the length of the second time segment and the second advertisement interval includes one or more of: increasing the length of the second time segment; and decreasing the second advertisement interval. The quality has been determined using one or more of a received signal strength indication (RSSI) and a return trip delay time (RTDT).

In certain implementations of the fifteenth aspect, which may be generally applicable but are also particularly applicable in connection with any other implementation of the fifteenth aspect, the method further includes performing a measurement of one or more of an RSSI and an RTDT. Performing the measurement may be done by one or more of the analyte sensor system and the analyte display device. The method also includes determining the quality based on the measurement.

In certain implementations of the fifteenth aspect, which may be generally applicable but are also particularly applicable in connection with any other implementation of the fifteenth aspect, the method further includes obtaining an indication of a quality of a connection between the analyte sensor system and the second display device. The method also includes modifying one or more of the length of the first time segment and the first advertisement interval, based on the indication of the quality.

In certain implementations of the fifteenth aspect, which may be generally applicable but are also particularly applicable in connection with any other implementation of the fifteenth aspect, modifying one or more of the length of the first time segment and the first advertisement interval is done by the analyte sensor system responsive to a signal received from the analyte display device.

In certain implementations of the fifteenth aspect, which may be generally applicable but are also particularly applicable in connection with any other implementation of the fifteenth aspect, the method further includes comparing the indication of the quality to a threshold. If the indication of the quality exceeds the threshold, modifying one or more of the length of the first time segment and the first advertisement interval includes one or more of: decreasing the length of the first time segment; and increasing the first advertisement interval. If the indication of the quality falls below the threshold, modifying one or more of the length of the first time segment and the first advertisement interval includes one or more of: increasing the length of the first time segment; and decreasing the first advertisement interval. The quality has been determined using one or more of an RSSI and an RTDT.

In certain implementations of the fifteenth aspect, which may be generally applicable but are also particularly applicable in connection with any other implementation of the fifteenth aspect, the method further includes performing a measurement of one or more of an RSSI and an RTDT. The method also includes determining the quality based on the measurement. Performing the measurement may be done by one or more of the analyte sensor system and the second display device.

In certain implementations of the fifteenth aspect, which may be generally applicable but are also particularly applicable in connection with any other implementation of the fifteenth aspect, the method further includes modifying one or more of the length of the first time segment, the first advertisement interval, the length of the second time segment, the second advertisement interval, and the sequence of the first and second time segments, based on an indication related to one or more of a location of the analyte sensor system and a location of the second display device.

In certain implementations of the fifteenth aspect, which may be generally applicable but are also particularly applicable in connection with any other implementation of the fifteenth aspect, the method further includes modifying one or more of the length of the second time segment, the second advertisement interval, and the sequence of the first and second time segments, based on an indication related to one or more of a location of the analyte sensor system and a location of the analyte display device.

In certain implementations of the fifteenth aspect, which may be generally applicable but are also particularly applicable in connection with any other implementation of the fifteenth aspect, the method further includes modifying one or more of the length of the first time segment, the first advertisement interval, the length of the second time segment, the second advertisement interval, and the sequence of the first and second time segments, based on an indication related to a time of day.

In certain implementations of the fifteenth aspect, which may be generally applicable but are also particularly applicable in connection with any other implementation of the fifteenth aspect, the method further includes generating an indication of a battery life for the analyte sensor system. The method also includes modifying one or more of the length of the first time segment, the first advertisement interval, the length of the second time segment, the second advertisement interval, and the sequence of the first and second time segments, based on the indication of the battery life.

In a sixteenth aspect, an analyte sensor system configured for wireless communication of analyte data includes an analyte sensor. The analyte sensor system also includes a transceiver configured to transmit and receive wireless signals. Additionally, the analyte sensor system includes a processor operatively coupled to the analyte sensor and the transceiver and configured to cause the analyte sensor system to certain operations. One such operation is to, during a first time segment within an advertisement duration, transmit a first set of advertisement messages to a second display device according to a first advertisement interval. Another such operation is to, during a second time segment within the advertisement duration, transmit a second set of advertisement messages to an analyte display device according to a second advertisement interval. One or more of the first advertisement interval, the second advertisement interval, a length of the first time segment, length of the second time segment, the advertisement duration, and a sequence of the first and second time segments, is configurable.

In certain implementations of the sixteenth aspect, which may be generally applicable but are also particularly applicable in connection with any other implementation of the sixteenth aspect, the processor is further configured to cause the analyte sensor system to alter the sequence of the first and second time segments. The analyte sensor system may alter the sequence of the first and second time segments based on a value that indicates whether or not the second display device is present on a list.

In certain implementations of the sixteenth aspect, which may be generally applicable but are also particularly applicable in connection with any other implementation of the sixteenth aspect, the processor is further configured to cause the analyte sensor system to obtain a value for an input parameter related to the analyte display device. Additionally, the processor is configured to cause the analyte sensor system to modify one or more of the length of the second time segment and the second advertisement interval, based on the value for the input parameter.

In certain implementations of the sixteenth aspect, which may be generally applicable but are also particularly applicable in connection with any other implementation of the sixteenth aspect, the processor is further configured to cause the analyte sensor system to obtain a value for an input parameter related to the second display device. Additionally, the processor is configured to cause the analyte sensor system to modify one or more of the length of the first time segment and the first advertisement interval, based on the value for the input parameter.

In a seventeenth aspect, a method for connecting an analyte sensor system to an analyte display device and a second display device includes, during a first time segment within an advertisement duration, transmitting a first set of advertisement messages to the second display device. The method also includes, during a second time segment within the advertisement duration, transmitting a second set of advertisement messages to an analyte display device, if a length of the second time segment has not been set to zero seconds. The method also includes, during a third time segment within the advertisement duration, transmitting a third set of advertisement messages to the second display device, if a condition is satisfied.

In certain implementations of the seventeenth aspect, which may be generally applicable but are also particularly applicable in connection with any other implementation of the seventeenth aspect, transmitting the first set of advertisement messages is done according to a first advertisement interval. The first advertisement interval may be about 20 milliseconds. A length of the first time segment may be about 10 seconds.

In certain implementations of the seventeenth aspect, which may be generally applicable but are also particularly applicable in connection with any other implementation of the seventeenth aspect, transmitting the third set of advertisement messages is done according to a third advertisement interval. The third advertisement interval may be about 152.5 milliseconds. A length of the third time segment may be about 60 seconds.

In certain implementations of the seventeenth aspect, which may be generally applicable but are also particularly applicable in connection with any other implementation of the seventeenth aspect, the condition is satisfied if the second display device did not connect to the analyte sensor system during the first time segment.

In certain implementations of the seventeenth aspect, which may be generally applicable but are also particularly applicable in connection with any other implementation of the seventeenth aspect, the method further includes setting the length of the second time segment to zero to disable connection to the analyte display device.

In certain implementations of the seventeenth aspect, which may be generally applicable but are also particularly applicable in connection with any other implementation of the seventeenth aspect, the method further includes obtaining an indication of a quality of a connection between the analyte sensor system and the second display device. The method also includes determining whether the condition satisfied, based on the indication of the quality. Determining whether the condition satisfied may be done by the analyte sensor system responsive to a signal received from the second display device. Determining whether the condition satisfied may include comparing the indication of the quality to a threshold. The quality may have been determined using one or more of a received signal strength indication (RSSI) and a return trip delay time (RTDT).

In certain implementations of the seventeenth aspect, which may be generally applicable but are also particularly applicable in connection with any other implementation of the seventeenth aspect, the method further includes performing a measurement of one or more of an RSSI and an RTDT. Also, the method includes determining the quality based on the measurement. Performing the measurement may be done by one or more of the analyte sensor system and the second display device.

In certain implementations of the seventeenth aspect, which may be generally applicable but are also particularly applicable in connection with any other implementation of the seventeenth aspect, the method further includes determining whether the condition satisfied, based on an indication related to one or more of a location of the analyte sensor system and a location of the second display device.

In certain implementations of the seventeenth aspect, which may be generally applicable but are also particularly applicable in connection with any other implementation of the seventeenth aspect, the method further includes determining whether the condition satisfied, based on an indication related to a time of day.

In certain implementations of the seventeenth aspect, which may be generally applicable but are also particularly applicable in connection with any other implementation of the seventeenth aspect, the method further includes generating an indication of a battery life for the analyte sensor system. The method further includes determining whether the condition satisfied, based on the indication of the battery life.

In certain implementations of the seventeenth aspect, which may be generally applicable but are also particularly applicable in connection with any other implementation of the seventeenth aspect, the first time segment precedes the second time segment, and the second time segment precedes the third time segment.

In certain implementations of the seventeenth aspect, which may be generally applicable but are also particularly applicable in connection with any other implementation of the seventeenth aspect, the second time segment precedes the first time segment, and the first time segment precedes the third time segment.

In certain implementations of the seventeenth aspect, which may be generally applicable but are also particularly applicable in connection with any other implementation of the seventeenth aspect, the method further includes configuring the second time segment to precede the first time segment and the first time segment to precede the third time segment, based on an input parameter. The input parameter may be based on one or more of a location of the analyte display device and a location of the second display device. The input parameter may be based on an indication of a quality of a connection with the analyte sensor system. The indication may have been determined based on one or more of a received signal strength and a return trip delay time. The input parameter may be based on a time of day. The input parameter may be based on an indication of a battery life for the analyte sensor system.

In an eighteenth aspect, a system for the wireless communication of analyte data includes an analyte sensor system configured to transmit analyte sensor data and advertisement messages to one or more of a plurality of display devices during an advertisement duration. The system also includes a second display device of the plurality of display devices. The second display device is configured to receive and respond to a first set of advertisement messages transmitted from the analyte sensor system during a first time segment within the advertisement duration. The system also includes an analyte display device of the plurality of display devices. The analyte display device is configured to receive and respond to a second set of advertisement messages transmitted from the analyte sensor system during a second time segment within the advertisement duration, if a length of the second time segment has not been set to zero seconds. The second display device is further configured to receive a third set of advertisement messages during a third time segment of the advertisement duration, if a condition is satisfied.

In certain implementations of the eighteenth aspect, which may be generally applicable but are also particularly applicable in connection with any other implementation of the eighteenth aspect, the condition is satisfied if the second display device did not connect to the analyte sensor system during the first time segment.

In certain implementations of the eighteenth aspect, which may be generally applicable but are also particularly applicable in connection with any other implementation of the eighteenth aspect, the analyte sensor system is further configured to set the length of the second time segment in order to zero to disable connection to the analyte display device.

In certain implementations of the eighteenth aspect, which may be generally applicable but are also particularly applicable in connection with any other implementation of the eighteenth aspect, one or more of the analyte sensor system, the second display device, and the analyte display device is further configured to obtain an indication regarding one or more connections made to the analyte sensor system and determine whether the condition satisfied, based on the indication.

In certain implementations of the eighteenth aspect, which may be generally applicable but are also particularly applicable in connection with any other implementation of the eighteenth aspect, one or more of the analyte sensor system, the second display device, and the analyte display device is further configured to determine whether the condition satisfied by comparing the indication to a threshold.

In certain implementations of the eighteenth aspect, which may be generally applicable but are also particularly applicable in connection with any other implementation of the eighteenth aspect, the first time segment precedes the second time segment, and the second time segment precedes the third time segment.

In certain implementations of the eighteenth aspect, which may be generally applicable but are also particularly applicable in connection with any other implementation of the eighteenth aspect, the second time segment precedes the first time segment, and the first time segment precedes the third time segment.

In certain implementations of the eighteenth aspect, which may be generally applicable but are also particularly applicable in connection with any other implementation of the eighteenth aspect, the analyte sensor system is further configured to arrange the second time segment to precede the first time segment and the first time segment to precede the third time segment, based on an input parameter. The input parameter may be based on one or more of a location of the analyte display device and a location of the second display device. The input parameter may be based on an indication of one or more of a quality of a connection with the analyte sensor system, a time of day, and a battery life for the analyte sensor system.

In a nineteenth aspect, an analyte sensor system configured for wireless communication of analyte data, the analyte sensor system includes an analyte sensor. The analyte sensor system also includes a transceiver configured to transmit and receive wireless signals. Additionally, the analyte sensor system includes a processor operatively coupled to the analyte sensor and the transceiver and configured to cause the analyte sensor system to perform certain operations. One such operation is to, during a first time segment within an advertisement duration, transmit a first set of advertisement messages to the second display. One such operation is to, during a second time segment within the advertisement duration, transmit a second set of advertisement messages to an analyte display device, if a length of the second time segment has not been set to zero seconds. Another such operation is to, during a third time segment within the advertisement duration, transmit a third set of advertisement messages to the second display device, if a condition is satisfied.

In certain implementations of the nineteenth aspect, which may be generally applicable but are also particularly applicable in connection with any other implementation of the nineteenth aspect, the condition is satisfied if the second display device did not connect to the analyte sensor system during the first time segment.

In certain implementations of the nineteenth aspect, which may be generally applicable but are also particularly applicable in connection with any other implementation of the nineteenth aspect, the processor is further configured to cause the analyte sensor system to set the length of the second time segment in order to zero to disable connection to the analyte display device.

In certain implementations of the nineteenth aspect, which may be generally applicable but are also particularly applicable in connection with any other implementation of the nineteenth aspect, the processor is further configured to cause the analyte sensor system to obtain an indication regarding one or more connections made to the analyte sensor system and determine whether the condition satisfied, based on the indication.

In certain implementations of the nineteenth aspect, which may be generally applicable but are also particularly applicable in connection with any other implementation of the nineteenth aspect, the processor is further configured to cause the analyte sensor system to determine whether the condition satisfied by comparing the indication to a threshold.

In certain implementations of the nineteenth aspect, which may be generally applicable but are also particularly applicable in connection with any other implementation of the nineteenth aspect, the first time segment precedes the second time segment, and the second time segment precedes the third time segment.

In certain implementations of the nineteenth aspect, which may be generally applicable but are also particularly applicable in connection with any other implementation of the nineteenth aspect, the second time segment precedes the first time segment, and the first time segment precedes the third time segment.

In certain implementations of the nineteenth aspect, which may be generally applicable but are also particularly applicable in connection with any other implementation of the nineteenth aspect, the processor is further configured to indicate that the second time segment should precede the first time segment and the first time segment should precede the third time segment, based on an input parameter. The input parameter may be based on one or more of a location of the analyte sensor system and a location of the second display device. The input parameter may be based on an indication of one or more of a quality of a connection with the analyte sensor system, a time of day, and a battery life for the analyte sensor system.

In a twentieth aspect, a display device configured for wireless communication of analyte data includes a transceiver configured to transmit and receive wireless signals. The display device also includes a processor operatively coupled to the transceiver and configured to cause the mobile device to perform certain operations. One such operation is to, during a first time segment within an advertisement duration, receive and respond to a first set of advertisement messages sent by an analyte sensor system. Another such operation is to, during a second time segment within the advertisement duration, receive but not respond to a second set of advertisement messages sent by the analyte sensor system. Another such operation is to, during a third time segment within the advertisement duration, receive and, if a condition is satisfied, respond to a third set of advertisement messages sent by the analyte sensor system. The condition may be satisfied if the display device did not connect to the analyte sensor system during the first time segment.

In certain implementations of the twentieth aspect, which may be generally applicable but are also particularly applicable in connection with any other implementation of the twentieth aspect, the processor is further configured to cause the display device to obtain an indication regarding one or more connections made to the analyte sensor system and determine whether the condition satisfied, based on the indication.

In certain implementations of the twentieth aspect, which may be generally applicable but are also particularly applicable in connection with any other implementation of the twentieth aspect, the processor is further configured to cause the display device to determine whether the condition satisfied by comparing the indication to a threshold.

In certain implementations of the twentieth aspect, which may be generally applicable but are also particularly applicable in connection with any other implementation of the twentieth aspect, the first time segment precedes the second time segment, and the second time segment precedes the third time segment.

In certain implementations of the twentieth aspect, which may be generally applicable but are also particularly applicable in connection with any other implementation of the twentieth aspect, the second time segment precedes the first time segment, and the first time segment precedes the third time segment.

In certain implementations of the twentieth aspect, which may be generally applicable but are also particularly applicable in connection with any other implementation of the twentieth aspect, the processor is further configured to cause display device indicate that the second time segment should precede the first time segment and the first time segment should precede the third time segment, based on an input parameter. The input parameter may be based on a location of the display device. The input parameter may be based on an indication of one or more of a quality of a connection with the analyte sensor system, a time of day, and a battery life for the analyte sensor system.

In a twenty-first aspect, a method for wireless communication of analyte data includes, during a first advertisement period, an analyte sensor system transmitting a first advertisement message that includes a first address. The method also includes, during a second advertisement period, if a first connection has been established between the analyte sensor system and an analyte display device, the analyte sensor system transmitting a second advertisement message that includes a second address specific to one or more secondary display devices. Additionally, the method includes, during the second advertisement period, if a second connection has been established between the analyte sensor system and a first display device of the one or more secondary display devices, transmitting a third advertisement message comprising a third address specific to the analyte display device. The first and second advertisement periods may be general advertising periods. The first address may be common between the analyte display device and the one or more secondary display devices.

In certain implementations of the twenty-first aspect, which may be generally applicable but are also particularly applicable in connection with any other implementation of the twenty-first aspect, the method further includes assessing whether a list comprises the analyte display device and the first display device. If the list comprises the analyte display device and the first display device, the method includes allocating a first time segment of a third advertising period for transmission of the second advertisement message to the one or more secondary display devices; and allocating a second time segment of the third advertising period for transmission of the third advertisement message to the analyte display device. The inclusion of the analyte display device on the list may indicate that the analyte sensor system has connected to the analyte display device. The inclusion of the first display device on the list may indicate that the analyte sensor system has connected to the first display device.

In certain implementations of the twenty-first aspect, which may be generally applicable but are also particularly applicable in connection with any other implementation of the twenty-first aspect, the one or more secondary display devices include personal electronic devices.

In certain implementations of the twenty-first aspect, which may be generally applicable but are also particularly applicable in connection with any other implementation of the twenty-first aspect, the personal electronic devices include one or more of a smartphone, a smartwatch, a tablet, a computer, and a television.

In certain implementations of the twenty-first aspect, which may be generally applicable but are also particularly applicable in connection with any other implementation of the twenty-first aspect, the method further includes defining a set of the one or more secondary display devices according to a classification scheme.

In certain implementations of the twenty-first aspect, which may be generally applicable but are also particularly applicable in connection with any other implementation of the twenty-first aspect, the method further includes, responsive to an unexpected loss of a connection to the analyte display device, the analyte sensor system transmitting the third advertisement message. The method further includes, responsive to an unexpected loss of a connection to the first display device, the analyte sensor system transmitting the second advertisement message.

In certain implementations of the twenty-first aspect, which may be generally applicable but are also particularly applicable in connection with any other implementation of the twenty-first aspect, the second address is specific to a first set of the secondary display devices. A fourth address may be specific to a second set of the secondary display devices. The method further includes selecting between the second and fourth addresses for transmission, based on one or more of the following indications. An indication of relative qualities of connection to the analyte sensor system, as between the first and second sets of the secondary display devices. An indication related to one or more of a location of the first set of the secondary display devices and a location of the second set of the secondary display devices. An indication related to a time of day. And an indication related to a battery life for the analyte sensor system.

In a twenty-second aspect, an analyte sensor system configured for wireless communication of analyte data includes an analyte sensor. The analyte sensor system also includes a transceiver configured to transmit and receive wireless signals. The analyte sensor system also includes a processor operatively coupled to the analyte sensor and the transceiver and configured to cause the analyte sensor system to perform certain operations. One such operation is to, during a first advertisement period, transmit a first advertisement message that includes a first address. One such operation is to, during a second advertisement period, if a first connection has been established between the analyte sensor system and an analyte display device, transmit a second advertisement message that includes a second address specific to one or more secondary display devices. Another such operation is to, during the second advertisement period, if a second connection has been established between the analyte sensor system and a first display device of the one or more secondary display devices, transmit a third advertisement message that includes a third address specific to the analyte display device. The first and second advertisement periods may be general advertising periods. The first address may be common between the analyte display device and the one or more secondary display devices.

In certain implementations of the twenty-second aspect, which may be generally applicable but are also particularly applicable in connection with any other implementation of the twenty-second aspect, the processor is further configured to cause the analyte sensor system to assess whether a list includes the analyte display device and the first display device. If the list includes the analyte display device and the first display device, the analyte sensor system allocates a first time segment of a third advertising period for transmission of the second advertisement message to the one or more secondary display devices; and allocates a second time segment of the third advertising period for transmission of the third advertisement message to the analyte display device. The inclusion of the analyte display device on the list indicates that the analyte sensor system has previously connected to the analyte display device. The inclusion of the first display device on the list indicates that the analyte sensor system has previously connected to the first display device.

In certain implementations of the twenty-second aspect, which may be generally applicable but are also particularly applicable in connection with any other implementation of the twenty-second aspect, the one or more secondary display devices include personal electronic devices.

In certain implementations of the twenty-second aspect, which may be generally applicable but are also particularly applicable in connection with any other implementation of the twenty-second aspect, the personal electronic devices comprise one or more of a smartphone, a smartwatch, a tablet, a computer, and a television.

In certain implementations of the twenty-second aspect, which may be generally applicable but are also particularly applicable in connection with any other implementation of the twenty-second aspect, the processor is further configured to cause the analyte sensor system to define a set of the one or more secondary display devices according to a classification scheme.

In certain implementations of the twenty-second aspect, which may be generally applicable but are also particularly applicable in connection with any other implementation of the twenty-second aspect, the processor is further configured to cause the analyte sensor system to, responsive to an unexpected loss of a connection to the analyte display device, transmit the third advertisement message. The processor is further configured to cause the analyte sensor system to, responsive to an unexpected loss of a connection to the first display device, transmit the second advertisement message.

In certain implementations of the twenty-second aspect, which may be generally applicable but are also particularly applicable in connection with any other implementation of the twenty-second aspect, the second address is specific to a first set of the secondary display devices. A fourth address may be specific to a second set of the secondary display devices. The processor is further configured to cause the analyte sensor system to select between the second and fourth addresses for transmission, based on one or more of the following indications. An indication of relative qualities of connection to the analyte sensor system, as between the first and second sets of display devices. An indication related to one or more of a location of the first set of display devices and a location of the second set of display devices. An indication related to a time of day. And an indication related to a battery life for the analyte sensor system.

In a twenty-third aspect, a system for wireless communication of analyte data includes an analyte display device. The system also includes one or more secondary display devices. In addition, the system includes an analyte sensor system. The analyte sensory system includes circuitry configured to process, transmit, and receive wireless signals, and further configured to cause the analyte sensor system to perform certain operations. One such operation is to, during a first advertisement period, transmit a first advertisement message that includes a first address. Another such operation is to, during a second advertisement period, if a first connection has been established between the analyte sensor system and the analyte display device, transmit a second advertisement message that includes a second address specific to one or more of the secondary display devices. One such operation is to, during the second advertisement period, if a second connection has been established between the analyte sensor system and a first display device of the one or more secondary display devices, transmit a third advertisement message that includes a third address specific to the analyte display device. Another such operation is to assess whether a list includes the analyte display device and the first display device. If the list comprises the analyte display device and the first display device, the analyte sensor system allocates a first time segment of a third advertising period for transmission of the second advertisement message to the one or more secondary display devices; and allocates a second time segment of the third advertising period for transmission of the third advertisement message to the analyte display device.

In a twenty-fourth aspect, a method for wireless communication of analyte data includes during a first advertisement period, an analyte sensor system transmitting one of: a first advertisement message that includes a first address, the first address being specific to one or more display devices; and a second advertisement message comprising a second address, the second address being specific to an analyte display device. The method also includes during a second advertisement period subsequent to the first advertisement period, if a first connection has been established between the analyte sensor system and a first display device of the one or more display devices, transmitting the second advertisement message. Additionally, the message includes, during a third advertisement period subsequent to the first advertisement period, if a second connection has been established between the analyte sensor system and the analyte display device, transmitting the first advertisement message.

In certain implementations of the twenty-fourth aspect, which may be generally applicable but are also particularly applicable in connection with any other implementation of the twenty-fourth aspect, the method further includes, before the first advertisement period, receiving information regarding the analyte display device and the one or more display devices. Receiving the information may be done by NFC. Receiving the information may be done by programming the analyte sensor system.

In a twenty-fifth aspect, a method for wireless communication of analyte data includes an analyte sensor system receiving an indication regarding a level of preference for one or more of a plurality of display devices capable of being connected to the analyte sensor system. Responsive to the indication, the method includes implementing a procedure to support the preference. 184. The method of Claim 170, wherein the indication has been received from a user via a mobile application running on one of the plurality of display devices. The indication may include an instruction to switch from a first to a second of the plurality of display devices. The instruction may be generated via a graphical user interface (GUI).

In certain implementations of the twenty-fifth aspect, which may be generally applicable but are also particularly applicable in connection with any other implementation of the twenty-fifth aspect, the method further includes the analyte sensor system transmitting a message comprising an indication that the procedure is being implemented.

In certain implementations of the twenty-fifth aspect, which may be generally applicable but are also particularly applicable in connection with any other implementation of the twenty-fifth aspect, implementing the procedure includes modifying maintenance of a list of an overall level of preference for the one or more display devices.

In certain implementations of the twenty-fifth aspect, which may be generally applicable but are also particularly applicable in connection with any other implementation of the twenty-fifth aspect, modifying the maintenance of the list includes keeping the one or more display devices on the list, according to the indication; and allowing any of the one or more display devices that become unavailable for connection to be removed from the list.

In certain implementations of the twenty-fifth aspect, which may be generally applicable but are also particularly applicable in connection with any other implementation of the twenty-fifth aspect, modifying the maintenance of the list includes adding one or more of the plurality of display devices to the list, according to the indication.

In certain implementations of the twenty-fifth aspect, which may be generally applicable but are also particularly applicable in connection with any other implementation of the twenty-fifth aspect, modifying the maintenance of the list includes removing one or more of the plurality of display devices from the list, according to the indication.

In certain implementations of the twenty-fifth aspect, which may be generally applicable but are also particularly applicable in connection with any other implementation of the twenty-fifth aspect, the method further includes transmitting a message that includes an indication that the one or more of the plurality of display devices have been removed from the list.

In certain implementations of the twenty-fifth aspect, which may be generally applicable but are also particularly applicable in connection with any other implementation of the twenty-fifth aspect, the list represents one or more of the plurality of display devices that have previously connected to the analyte sensor system. The list may be a whitelist.

In certain implementations of the twenty-fifth aspect, which may be generally applicable but are also particularly applicable in connection with any other implementation of the twenty-fifth aspect, implementing the procedure includes the analyte sensor system transmitting an advertisement message that includes an address specific to at least one of the one or more display devices, according to the indication.

In certain implementations of the twenty-fifth aspect, which may be generally applicable but are also particularly applicable in connection with any other implementation of the twenty-fifth aspect, implementing the procedure includes the analyte sensor system transmitting, for each of the one or more display devices, an advertisement message specific to the display device, according to the indication.

In certain implementations of the twenty-fifth aspect, which may be generally applicable but are also particularly applicable in connection with any other implementation of the twenty-fifth aspect, the preference includes a prioritization for one or more of the display devices.

In certain implementations of the twenty-fifth aspect, which may be generally applicable but are also particularly applicable in connection with any other implementation of the twenty-fifth aspect, implementing the procedure includes the analyte sensor system transmitting, for each of the one or more display devices, an advertisement message specific to the display device, using a configuration based on the prioritization.

In certain implementations of the twenty-fifth aspect, which may be generally applicable but are also particularly applicable in connection with any other implementation of the twenty-fifth aspect, implementing the procedure includes the analyte sensor system transmitting, for each of the one or more display devices, an advertisement message specific to the display device, in an order based on the prioritization.

In a twenty-sixth aspect, an analyte sensor system configured for wireless communication of analyte data includes an analyte sensor. The analyte sensor system also includes a transceiver configured to transmit and receive wireless signals. In addition, the analyte sensor system includes a processor operatively coupled to the analyte sensor and the transceiver and configured to cause the analyte sensor system to perform certain operations. One such operation is to receive an indication regarding a level of preference for one or more of a plurality of display devices capable of being connected to the analyte sensor system. Another such operation is to, responsive to the indication, implement a procedure to support the preference.

In certain implementations of the twenty-sixth aspect, which may be generally applicable but are also particularly applicable in connection with any other implementation of the twenty-sixth aspect, the processor is further configured to cause the analyte sensor system to transmit a message that includes an indication that the procedure is being implemented.

In certain implementations of the twenty-sixth aspect, which may be generally applicable but are also particularly applicable in connection with any other implementation of the twenty-sixth aspect, the processor is further configured to cause the analyte sensor system to modify maintenance of a list of an overall level of preference for the one or more display devices, in order to implement the procedure.

In certain implementations of the twenty-sixth aspect, which may be generally applicable but are also particularly applicable in connection with any other implementation of the twenty-sixth aspect, in order to modify the maintenance of the list, the processor is further configured to keep the one or more display devices on the list, according to the indication; and allow any of the one or more display devices that become unavailable for connection to be removed from the list.

In certain implementations of the twenty-sixth aspect, which may be generally applicable but are also particularly applicable in connection with any other implementation of the twenty-sixth aspect, in order to modify the maintenance of the list, the processor is further configured to add one or more of the plurality of display devices to the list, according to the indication.

In certain implementations of the twenty-sixth aspect, which may be generally applicable but are also particularly applicable in connection with any other implementation of the twenty-sixth aspect, in order to modify the maintenance of the list, the processor is further configured to remove one or more of the plurality of display devices from the list, according to the indication.

In certain implementations of the twenty-sixth aspect, which may be generally applicable but are also particularly applicable in connection with any other implementation of the twenty-sixth aspect, the processor is further configured to transmit a message comprising an indication that the one or more of the plurality of display devices have been removed from the list.

In certain implementations of the twenty-sixth aspect, which may be generally applicable but are also particularly applicable in connection with any other implementation of the twenty-sixth aspect, the list represents one or more of the plurality of display devices that have previously connected to the analyte sensor system. The list may be a whitelist.

In certain implementations of the twenty-sixth aspect, which may be generally applicable but are also particularly applicable in connection with any other implementation of the twenty-sixth aspect, the processor is further configured to transmit an advertisement message that includes an address specific to at least one of the one or more display devices, according to the indication, in order to implement the procedure.

In certain implementations of the twenty-sixth aspect, which may be generally applicable but are also particularly applicable in connection with any other implementation of the twenty-sixth aspect, the processor is further configured to transmit, for each of the one or more display devices, an advertisement message specific to the display device, according to the indication, in order to implement the procedure.

In certain implementations of the twenty-sixth aspect, which may be generally applicable but are also particularly applicable in connection with any other implementation of the twenty-sixth aspect, the preference includes a prioritization for one or more of the display devices.

In certain implementations of the twenty-sixth aspect, which may be generally applicable but are also particularly applicable in connection with any other implementation of the twenty-sixth aspect, the processor is further configured to transmit, for each of the one or more display devices, an advertisement message specific to the display device, according to a configuration based on the prioritization, in order to implement the procedure.

In certain implementations of the twenty-sixth aspect, which may be generally applicable but are also particularly applicable in connection with any other implementation of the twenty-sixth aspect, the processor is further configured to transmit, for each of the one or more display devices, an advertisement message specific to the display device, in an order based on the prioritization, in order to implement the procedure.

In certain implementations of the twenty-sixth aspect, which may be generally applicable but are also particularly applicable in connection with any other implementation of the twenty-sixth aspect, the indication has been received from a user via a mobile application running on one of the plurality of display devices. The indication may include an instruction to switch from a first to a second of the plurality of display devices. The instruction may have been generated via a graphical user interface (GUI).

In a twenty-seventh aspect, a method for wireless communication of analyte data includes a mobile device receiving an indication regarding a level of preference for one or more of a plurality of display devices capable of being connected to an analyte sensor system. The method also includes, responsive to the indication, initiating a procedure to support the preference.

In certain implementations of the twenty-seventh aspect, which may be generally applicable but are also particularly applicable in connection with any other implementation of the twenty-seventh aspect, initiating the procedure includes the mobile device transmitting a message to the analyte sensor system. The message includes an indication that the procedure should be implemented.

In certain implementations of the twenty-seventh aspect, which may be generally applicable but are also particularly applicable in connection with any other implementation of the twenty-seventh aspect, the method further includes the mobile device receiving from the analyte sensor system a message that includes an indication that the procedure is being implemented.

In certain implementations of the twenty-seventh aspect, which may be generally applicable but are also particularly applicable in connection with any other implementation of the twenty-seventh aspect, the procedure includes modifying maintenance of a list of an overall level of preference for the one or more display devices, responsive to user input received via a graphical user interface (GUI) displayed by the mobile device.

In certain implementations of the twenty-seventh aspect, which may be generally applicable but are also particularly applicable in connection with any other implementation of the twenty-seventh aspect, modifying the maintenance of the list includes adding one or more of the plurality of display devices to the list, according to the user input.

In certain implementations of the twenty-seventh aspect, which may be generally applicable but are also particularly applicable in connection with any other implementation of the twenty-seventh aspect, modifying the maintenance of the list includes removing one or more of the plurality of display devices from the list, according to the user input.

In certain implementations of the twenty-seventh aspect, which may be generally applicable but are also particularly applicable in connection with any other implementation of the twenty-seventh aspect, the method further includes the mobile device receiving a message that includes an indication that the one or more of the plurality of display devices have been added to or removed from removed from the list based on the user input.

In certain implementations of the twenty-seventh aspect, which may be generally applicable but are also particularly applicable in connection with any other implementation of the twenty-seventh aspect, the procedure includes the mobile device receiving, for each of the one or more display devices, an advertisement message specific to the display device, based on user input received via a GUI displayed by the mobile device.

In certain implementations of the twenty-seventh aspect, which may be generally applicable but are also particularly applicable in connection with any other implementation of the twenty-seventh aspect, the indication has been received from a user via a GUI presented on a display of the mobile device by a mobile application running the mobile device. The indication may include an instruction to switch from a first to a second of the plurality of display devices. The mobile device may be one of the first or the second of the plurality of display devices.

In a twenty-eighth aspect, a mobile device configured for wireless communication of analyte data includes a display configured to present a GUI to a user of the mobile device. The mobile device also includes a transceiver configured to transmit and receive wireless signals. Further, the mobile device includes a processor operatively coupled to the display and the transceiver and configured to cause the mobile device to perform certain operations. One such operation is to receive an indication regarding a level of preference for one or more of a plurality of display devices capable of being connected to the analyte sensor system. Another such operation is to, responsive to the indication, implement a procedure to support the preference.

In certain implementations of the twenty-eighth aspect, which may be generally applicable but are also particularly applicable in connection with any other implementation of the twenty-eighth aspect, the processor is further configured to cause the mobile device to transmit a message to the analyte sensor system. The message includes an indication that the procedure should be implemented.

In certain implementations of the twenty-eighth aspect, which may be generally applicable but are also particularly applicable in connection with any other implementation of the twenty-eighth aspect, the processor is further configured to cause the mobile device to receive from the analyte sensor system a message that includes an indication that the procedure is being implemented.

In certain implementations of the twenty-eighth aspect, which may be generally applicable but are also particularly applicable in connection with any other implementation of the twenty-eighth aspect, the processor is further configured to cause the mobile device to initiate modification of maintenance of a list of an overall level of preference for the one or more display devices, responsive to user input received via a GUI displayed by the mobile device.

In certain implementations of the twenty-eighth aspect, which may be generally applicable but are also particularly applicable in connection with any other implementation of the twenty-eighth aspect, in connection with modification of maintenance of the list, the processor is further configured to cause the mobile device generate an instruction for one or more of the plurality of display devices to be added the list, according to the user input.

In certain implementations of the twenty-eighth aspect, which may be generally applicable but are also particularly applicable in connection with any other implementation of the twenty-eighth aspect, in connection with modification of maintenance of the list, the processor is further configured to cause the mobile device to generate an instruction for one or more of the plurality of display devices to be removed from the list, according to the user input.

In certain implementations of the twenty-eighth aspect, which may be generally applicable but are also particularly applicable in connection with any other implementation of the twenty-eighth aspect, the processor is further configured to cause the mobile device to receive a message that includes an indication that the one or more of the plurality of display devices have been added to or removed from removed from the list based on the user input.

In certain implementations of the twenty-eighth aspect, which may be generally applicable but are also particularly applicable in connection with any other implementation of the twenty-eighth aspect, in connection with modification of maintenance of the list, the processor is further configured to cause the mobile device to receive an advertisement message specific to the mobile device, based on user input received via the GUI.

In certain implementations of the twenty-eighth aspect, which may be generally applicable but are also particularly applicable in connection with any other implementation of the twenty-eighth aspect, the indication has been received from a user via a GUI presented on a display of the mobile device by a mobile application running the mobile device.

In certain implementations of the twenty-eighth aspect, which may be generally applicable but are also particularly applicable in connection with any other implementation of the twenty-eighth aspect, the indication includes an instruction to switch from a first to a second of the plurality of display devices. The mobile device may be one of the first or the second of the plurality of display devices.

In a twenty-ninth aspect, a method for wireless communication of analyte data includes a mobile device receiving an indication regarding a level of preference for one or more of a plurality of display devices capable of being connected to the analyte sensor system. The method also includes the mobile device transmitting the indication to an analyte sensor system. The method further includes the analyte sensor system receiving the indication. Responsive to the indication, the method includes the analyte sensor system implementing a procedure to support the preference.

In certain implementations of the twenty-ninth aspect, which may be generally applicable but are also particularly applicable in connection with any other implementation of the twenty-ninth aspect, the method further includes the analyte sensor system transmitting a message to the mobile device. The message includes an indication that the procedure is being implemented.

In certain implementations of the twenty-ninth aspect, which may be generally applicable but are also particularly applicable in connection with any other implementation of the twenty-ninth aspect, the method further includes the analyte sensor system transmitting a message to the mobile device. The message includes information regarding a list maintained in connection with implementing the procedure. The list may be a whitelist for the analyte sensor system.

In certain implementations of the twenty-ninth aspect, which may be generally applicable but are also particularly applicable in connection with any other implementation of the twenty-ninth aspect, implementing the procedure includes the analyte sensor system transmitting an advertisement message that includes an address specific to the mobile device, according to the indication.

In certain implementations of the twenty-ninth aspect, which may be generally applicable but are also particularly applicable in connection with any other implementation of the twenty-ninth aspect, the plurality of display devices includes the mobile device, and implementing the procedure includes the analyte sensor system transmitting, for each of the one or more display devices, an advertisement message specific to the display device, according to the indication.

In certain implementations of the twenty-ninth aspect, which may be generally applicable but are also particularly applicable in connection with any other implementation of the twenty-ninth aspect, the preference includes a prioritization for one or more of the display devices. The prioritization may be determined based on user input received via a GUI displayed by the mobile device.

In certain implementations of the twenty-ninth aspect, which may be generally applicable but are also particularly applicable in connection with any other implementation of the twenty-ninth aspect, implementing the procedure includes the analyte sensor system transmitting, for each of the one or more display devices, an advertisement message specific to the display device, using a configuration based on the prioritization.

In certain implementations of the twenty-ninth aspect, which may be generally applicable but are also particularly applicable in connection with any other implementation of the twenty-ninth aspect, implementing the procedure includes the analyte sensor system transmitting, for each of the one or more display devices, an advertisement message specific to the display device, in an order based on the prioritization.

In certain implementations of the twenty-ninth aspect, which may be generally applicable but are also particularly applicable in connection with any other implementation of the twenty-ninth aspect, the indication has been received from a user via a mobile application running on the mobile device. The indication may include an instruction to switch from a first to a second of the plurality of display devices. The instruction may have been generated using a GUI presented by the mobile application.

In a thirtieth aspect, a method for wireless communication of analyte data includes establishing a first connection between an analyte sensor system and a first display device via a first wireless protocol. The method also includes transferring information related to the first connection from the analyte sensor system to the first display device. Additionally, the method includes a second display device establishing a second connection to the first display device via a second wireless protocol. Moreover, the method includes transferring the information related to the first connection from the first display device to the second display device using the second wireless protocol.

In certain implementations of the thirtieth aspect, which may be generally applicable but are also particularly applicable in connection with any other implementation of the thirtieth aspect, the method further includes establishing a third connection between the second display device and the analyte sensor system using the first wireless protocol and the information transferred from the first display device, in order for analyte data to be communicated between the analyte sensor system and the second display device.

In certain implementations of the thirtieth aspect, which may be generally applicable but are also particularly applicable in connection with any other implementation of the thirtieth aspect, the first wireless protocol is BLE. The second wireless protocol may be NFC or WiFi.

In certain implementations of the thirtieth aspect, which may be generally applicable but are also particularly applicable in connection with any other implementation of the thirtieth aspect, the information related to the first connection includes one or more of: transmitter identification information; alert setting information; historical continuous glucose monitoring data; scheduling information for an upcoming transmission; current EGV; information regarding active alerts; calibration data; information regarding an application key; and information regarding encryption.

In a thirty-first aspect, a method for wireless communication of analyte data includes establishing a first connection between an analyte sensor system and a first display device via a first wireless protocol. The method also includes the analyte sensor system transferring to the first display device information related to the first connection. Additionally, the method includes the analyte sensor system establishing a second connection between the analyte sensor system and a second display device via the first wireless protocol using at least some of the information related to the first connection. The second display device may have received the at least some of the information related to the connection from the first display device via a second wireless protocol.

In certain implementations of the thirty-first aspect, which may be generally applicable but are also particularly applicable in connection with any other implementation of the thirty-first aspect, the first wireless protocol is BLE; and the second wireless protocol is NFC or WiFi.

In certain implementations of the thirty-first aspect, which may be generally applicable but are also particularly applicable in connection with any other implementation of the thirty-first aspect, the information related to the first connection includes one or more of: transmitter identification information; alert setting information; historical continuous glucose monitoring data; scheduling information for an upcoming transmission; current EGV; information regarding active alerts; calibration data; and information regarding an application key; and information regarding encryption.

In a thirty-second aspect, an analyte sensor system configured for wireless communication of analyte data includes an analyte sensor. The analyte sensor system also includes a transceiver configured to transmit and receive wireless signals. Further, the analyte sensor system includes a processor operatively coupled to the analyte sensor and the transceiver and configured to cause the analyte sensor system to perform certain operations. One such operation is to establish a first connection with a first display device via a first wireless protocol. Another such operation is to transfer to the first display device information related to the first connection. Another such operation is to establish a second connection to a second display device via the first wireless protocol using at least some of the information related to the first connection. The second display device may have received the at least some of the information related to the first connection from the first display device via a second wireless protocol.

In certain implementations of the thirty-second aspect, which may be generally applicable but are also particularly applicable in connection with any other implementation of the thirty-second aspect, the first wireless protocol is BLE, and/or the second wireless protocol is NFC or WiFi.

In certain implementations of the thirty-second aspect, which may be generally applicable but are also particularly applicable in connection with any other implementation of the thirty-second aspect, the information related to the first connection comprises one or more of: transmitter identification information; alert setting information; historical continuous glucose monitoring data; scheduling information for an upcoming transmission; current EGV; information regarding active alerts; calibration data; information regarding an application key; and information regarding encryption.

In a thirty-third aspect, a mobile device configured for wireless communication of analyte data includes a transceiver configured to transmit and receive wireless signals. The mobile device also includes a processor operatively coupled to the transceiver and configured to cause the mobile device to perform certain operations. One such operation is to receive from a display device, via a first wireless protocol, information related to a first connection between the display device and an analyte sensor system. Another such operation is to establish a second connection with the analyte sensor system via a second wireless protocol using the information related to the first connection.

In certain implementations of the thirty-third aspect, which may be generally applicable but are also particularly applicable in connection with any other implementation of the thirty-third aspect, the first wireless protocol is NFC or WiFi, and/or the second wireless protocol is BLE.

In certain implementations of the thirty-third aspect, which may be generally applicable but are also particularly applicable in connection with any other implementation of the thirty-third aspect, the information related to the first connection includes one or more of: transmitter identification information; alert setting information; historical continuous glucose monitoring data; scheduling information for an upcoming transmission; current EGV; information regarding active alerts; calibration data; information regarding an application key; and information regarding encryption.

In a thirty-fourth aspect, a method for wireless communication of analyte data includes establishing a first connection between an analyte sensor system and a first display device via a first wireless protocol. The method also includes the analyte sensor system transferring to the first display device information related to the first connection. Additionally, the method includes the first display device establishing a second connection with a second display device via a second wireless protocol. Moreover, the method includes the first display device transferring to the second display device, via the second wireless protocol, the information related to the first connection. The method also includes the analyte sensor system establishing a third connection between the analyte sensor system and the second display device via the first wireless protocol using at least some of the information related to the first connection.

BRIEF DESCRIPTION OF THE DRAWINGS

Further aspects of the present disclosure will be more readily appreciated upon review of the detailed description of the various disclosed embodiments, described below, when taken in conjunction with the accompanying figures.

FIG. 8 illustrates an example structure for an advertisement message in accordance with embodiments of the present disclosure.

FIG. 9C is a timing diagram illustrating example aspects of the transmission of advertisement messages in accordance with embodiments of the present disclosure.

FIG. 15A is an operational flow diagram illustrating various operations that may be performed in accordance with embodiments of the disclosure.

Figure 1A:
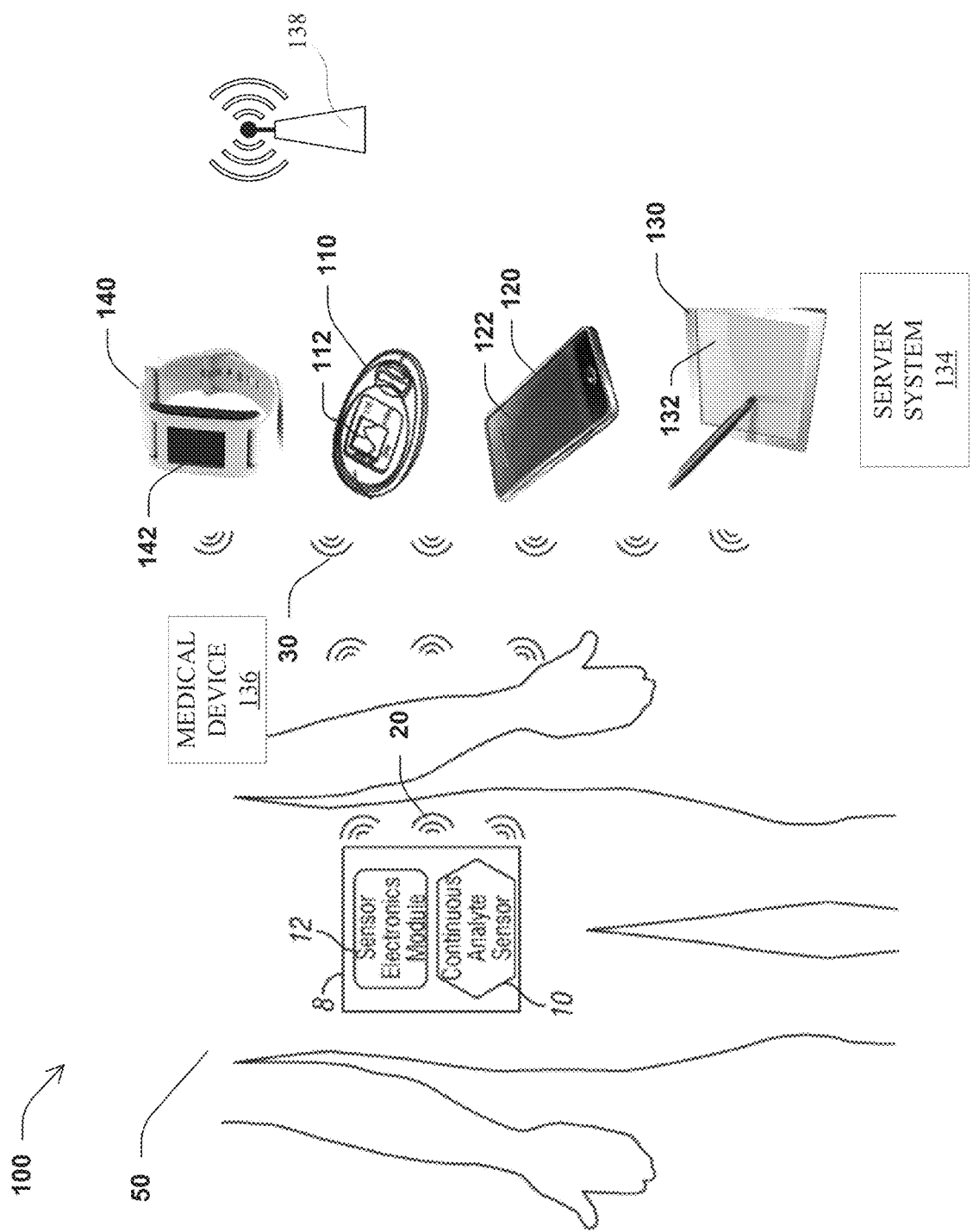
FIG. 1A illustrates aspects of an example system that may be used in connection with implementing embodiments of the disclosure.

The figures are described in greater detail in the description and examples below, are provided for purposes of illustration only, and merely depict typical or example embodiments of the disclosure. The figures are not intended to be exhaustive or to limit the disclosure to the precise form disclosed. It should also be understood that the disclosure may be practiced with modification or alteration, and that the disclosure may be limited only by the claims and the equivalents thereof.

DETAILED DESCRIPTION

Embodiments of the present disclosure are directed to systems, methods, and devices for wireless communication of analyte data. In various deployments described herein, the analyte data is glucose data generated by an analyte sensor system configured to connect to display devices and the like. Implementing aspects of the present disclosure, as described in detail herein, may reduce the power consumption of the analyte sensor system by increasing the efficiency thereof with respect to wireless communications the analyte sensor system and other devices. Moreover, implementing aspects of the present disclosure may also allow for reduced power consumption while maintaining and/or improving performance with respect to the reliability, speed, and accuracy of wireless communications, as well as the connection protocols associated therewith. In particular, such aspects of the disclosure relate to, for example, authentication and encryption, connection protocols and timing for devices, advertisement message structure and content, and device pairing.

The details of some example embodiments of the systems, methods, and devices of the present disclosure are set forth in this description and in some cases, in other portions of the disclosure. Other features, objects, and advantages of the disclosure will be apparent to one of skill in the art upon examination of the present disclosure, description, figures, examples, and claims. It is intended that all such additional systems, methods, devices, features, and advantages be included within this description (whether explicitly or by reference), be within the scope of the present disclosure, and be protected by one or more of the accompanying claims.

A. Overview

In some embodiments, a system is provided for continuous measurement of an analyte in a host. The system may include: a continuous analyte sensor configured to continuously measure a concentration of the analyte in the host, and a sensor electronics module physically connected to the continuous analyte sensor during sensor use. In certain embodiments, the sensor electronics module includes electronics configured to process a data stream associated with an analyte concentration measured by the continuous analyte sensor, in order to generate sensor information that includes raw sensor data, transformed sensor data, and/or any other sensor data, for example. The sensor electronics module may further be configured to generate sensor information that is customized for respective display devices, such that different display devices may receive different sensor information.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is analyte. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, rickettsia (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferring; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

B. Alerts

In certain embodiments, one or more alerts are associated with a sensor electronics module. For example, each alert may include one or more alert conditions that indicate when the respective alert has been triggered. For example, a hypoglycemic alert may include alert conditions indicating a minimum glucose level. The alert conditions may also be based on transformed sensor data, such as trending data, and/or sensor data from multiple different sensors (e.g. an alert may be based on sensor data from both a glucose sensor and a temperature sensor). For example, a hypoglycemic alert may include alert conditions indicating a minimum required trend in the host's glucose level that must be present before triggering the alert. The term "trend," as used herein refers generally to data indicating some attribute of data that is acquired over time, e.g., such as calibrated or filtered data from a continuous glucose sensor. A trend may indicate amplitude, rate of change, acceleration, direction, etc., of data, such as sensor data, including transformed or raw sensor data.

In certain embodiments, each of the alerts is associated with one or more actions that are to be performed in response to triggering of the alert. Alert actions may include, for example, activating an alarm, such as displaying information on a display of the sensor electronics module or activating an audible or vibratory alarm coupled to the sensor electronics module, and/or transmitting data to one or more display devices external to the sensor electronics module. For any delivery action that is associated with a triggered alert, one or more delivery options define the content and/or format of the data to be transmitted, the device to which the data is to be transmitted, when the data is to be transmitted, and/or a communication protocol for delivery of the data.

In certain embodiments, multiple delivery actions (each having respective delivery options) may be associated with a single alert such that displayable sensor information having different content and formatting, for example, is transmitted to respective display devices in response to triggering of a single alert. For example, a mobile telephone may receive a data package including minimal displayable sensor information (that may be formatted specifically for display on the mobile telephone), while a desktop computer may receive a data package including most (or all) of the displayable sensor information that is generated by the sensor electronics module in response to triggering of a common alert. Advantageously, the sensor electronics module is not tied to a single display device, rather it is configured to communicate with a plurality of different display devices directly, systematically, simultaneously (e.g., via broadcasting), regularly, periodically, randomly, on-demand, in response to a query, based on alerts or alarms, and/or the like.

In some embodiments, clinical risk alerts are provided that include alert conditions that combine intelligent and dynamic estimative algorithms that estimate present or predicted danger with greater accuracy, more timeliness in pending danger, avoidance of false alarms, and less annoyance for the patient. In general, clinical risk alerts include dynamic and intelligent estimative algorithms based on analyte value, rate of change, acceleration, clinical risk, statistical probabilities, known physiological constraints, and/or individual physiological patterns, thereby providing more appropriate, clinically safe, and patient-friendly alarms. U.S. Patent Publication No. 2007/0208246, which is incorporated herein by reference in its entirety, describes some systems and methods associated with the clinical risk alerts (or alarms) described herein. In some embodiments, clinical risk alerts can be triggered for a predetermined time period to allow for the user to attend to his/her condition. Additionally, the clinical risk alerts can be de-activated when leaving a clinical risk zone so as not to annoy the patient by repeated clinical alarms (e.g., visual, audible or vibratory), when the patient's condition is improving. In some embodiments, dynamic and intelligent estimation determines a possibility of the patient avoiding clinical risk, based on the analyte concentration, the rate of change, and other aspects of the dynamic and intelligent estimative algorithms. If there is minimal or no possibility of avoiding the clinical risk, a clinical risk alert will be triggered. However, if there is a possibility of avoiding the clinical risk, the system is configured to wait a predetermined amount of time and re-analyze the possibility of avoiding the clinical risk. In some embodiments, when there is a possibility of avoiding the clinical risk, the system is further configured to provide targets, therapy recommendations, or other information that can aid the patient in proactively avoiding the clinical risk.

In some embodiments, the sensor electronics module is configured to search for one or more display devices within communication range of the sensor electronics module and to wirelessly communicate sensor information (e.g., a data package including displayable sensor information, one or more alarm conditions, and/or other alarm information) thereto. Accordingly, the display device is configured to display at least some of the sensor information and/or alarm the host (and/or care taker), wherein the alarm mechanism is located on the display device.

In some embodiments, the sensor electronics module is configured to provide one or a plurality of different alarms via the sensor electronics module and/or via transmission of a data package indicating an alarm should be initiated by one or a plurality of display devices (e.g., sequentially and/or simultaneously). In certain embodiments, the sensor electronics module merely provides a data field indicating that an alarm conditions exists and the display device, upon reading the data field indicating the existence of the alarm condition, may decide to trigger an alarm. In some embodiments, the sensor electronics module determines which of the one or more alarms to trigger based on one or more alerts that are triggered. For example, when an alert trigger indicates severe hypoglycemia, the sensor electronics module can perform multiple actions, such as activating an alarm on the sensor electronics module, transmitting a data package to a monitoring device indicating activation of an alarm on the display, and transmitting a data package as a text message to a care provider. As an example, a text message can appear on a custom monitoring device, cell phone, pager device, and/or the like, including displayable sensor information that indicates the host's condition (e.g., "severe hypoglycemia").

In some embodiments, the sensor electronics module is configured to wait a time period for the host to respond to a triggered alert (e.g., by pressing or selecting a snooze and/or off function and/or button on the sensor electronics module and/or a display device), after which additional alerts are triggered (e.g., in an escalating manner) until one or more alerts are responded to. In some embodiments, the sensor electronics module is configured to send control signals (e.g., a stop signal) to a medical device associated with an alarm condition (e.g., hypoglycemia), such as an insulin pump, wherein the stop alert triggers a stop of insulin delivery via the pump.

In some embodiments, the sensor electronics module is configured to directly, systematically, simultaneously (e.g., via broadcasting), regularly, periodically, randomly, on-demand, in response to a query (from the display device), based on alerts or alarms, and/or the like transmit alarm information. In some embodiments, the system further includes a repeater such that the wireless communication distance of the sensor electronics module can be increased, for example, to 10, 20, 30, 50 75, 100, 150, or 200 meters or more, wherein the repeater is configured to repeat a wireless communication from the sensor electronics module to the display device located remotely from the sensor electronics module. A repeater can be useful to families having children with diabetes. For example, to allow a parent to carry, or place in a stationary position, a display device, such as in a large house wherein the parents sleep at a distance from the child.

C. Display Devices

In some embodiments, the sensor electronics module is configured to search for and/or attempt wireless communication with a display device from a list of display devices. In some embodiments, the sensor electronics module is configured to search for and/or attempt wireless communication with a list of display devices in a predetermined and/or programmable order (e.g., grading and/or escalating), for example, wherein a failed attempt at communication with and/or alarming with a first display device triggers an attempt at communication with and/or alarming with a second display device, and so on. In one example embodiment, the sensor electronics module is configured to search for and attempt to alarm a host or care provider sequentially using a list of display devices, such as: (1) a default display device or a custom analyte monitoring device; ((2) a mobile phone via auditory and/or visual methods, such as, text message to the host and/or care provider, voice message to the host and/or care provider, and/or 911); (3) a tablet; (4) a smart watch.

Depending on the embodiment, one or more display devices that receive data packages from the sensor electronics module are "dummy displays", wherein they display the displayable sensor information received from the sensor electronics module without additional processing (e.g., prospective algorithmic processing necessary for real-time display of sensor information). In some embodiments, the displayable sensor information comprises transformed sensor data that does not require processing by the display device prior to display of the displayable sensor information. Some display devices may include software including display instructions (software programming comprising instructions configured to display the displayable sensor information and optionally query the sensor electronics module to obtain the displayable sensor information) configured to enable display of the displayable sensor information thereon. In some embodiments, the display device is programmed with the display instructions at the manufacturer and can include security and/or authentication to avoid plagiarism of the display device. In some embodiments, a display device is configured to display the displayable sensor information via a downloadable program (for example, a downloadable Java Script via the internet), such that any display device that supports downloading of a program (for example, any display device that supports Java applets) therefore can be configured to display displayable sensor information (e.g., mobile phones, tablets, PDAs, PCs and the like).

In some embodiments, certain display devices may be in direct wireless communication with the sensor electronics module, but intermediate network hardware, firmware, and/or software can be included within the direct wireless communication. In some embodiments, a repeater (e.g., a Bluetooth repeater) can be used to re-transmit the transmitted displayable sensor information to a location farther away than the immediate range of the telemetry module of the sensor electronics module, wherein the repeater enables direct wireless communication when substantive processing of the displayable sensor information does not occur. In some embodiments, a receiver (e.g., Bluetooth receiver) can be used to re-transmit the transmitted displayable sensor information, possibly in a different format, such as in a text message onto a TV screen, wherein the receiver enables direct wireless communication when substantive processing of the sensor information does not occur. In certain embodiments, the sensor electronics module directly wirelessly transmits displayable sensor information to one or a plurality of display devices, such that the displayable sensor information transmitted from the sensor electronics module is received by the display device without intermediate processing of the displayable sensor information.

In certain embodiments, one or more display devices include built-in authentication mechanisms, wherein authentication is required for communication between the sensor electronics module and the display device. In some embodiments, to authenticate the data communication between the sensor electronics module and display devices, a challenge-response protocol, such as key authentication is provided, where the challenge is a request for the key or a hash or other value based on or derived from the key, and the valid response is the correct key or a hash or other value based on or derived from the key, such that pairing of the sensor electronics module with the display devices can be accomplished by the user and/or manufacturer via the key. This may be referred to in some cases as two-way authentication. The key may be a software or hardware level key. Additionally, the key may be a password (e.g., randomly generated or set by a user or other entity), and/or may be derived from uniquely identifying features (e.g., finger print or retinal information) or information, etc.

In some embodiments, one or more display devices are configured to query the sensor electronics module for displayable sensor information, wherein the display device acts as a master device requesting sensor information from the sensor electronics module (e.g., a slave device) on-demand, for example, in response to a query. Although in some cases the display device acts as a master and the sensor electronics module acts as a slave, in other cases, these roles may be reversed. For example, the roles can reverse depending on the nature of the communication and so on. In some embodiments, the sensor electronics module is configured for periodic, systematic, regular, and/or periodic transmission of sensor information to one or more display devices (for example, every 1, 2, 5, or 10 minutes or more). In some embodiments, the sensor electronics module is configured to transmit data packages associated with a triggered alert (e.g., triggered by one or more alert conditions). However, any combination of the above described statuses of data transmission can be implemented with any combination of paired sensor electronics module and display device(s). For example, one or more display devices can be configured for querying the sensor electronics module database and for receiving alarm information triggered by one or more alarm conditions being met. Additionally, the sensor electronics module can be configured for periodic transmission of sensor information to one or more display devices (the same or different display devices as described in the previous example), whereby a system can include display devices that function differently with regard to how sensor information is obtained.

In some embodiments, a display device is configured to query the data storage memory in the sensor electronics module for certain types of data content, including direct queries into a database in the sensor electronics module's memory and/or requests for configured or configurable packages of data content therefrom; namely, the data stored in the sensor electronics module is configurable, queryable, predetermined, and/or pre-packaged, based on the display device with which the sensor electronics module is communicating. In some additional or alternative embodiments, the sensor electronics module generates the displayable sensor information based on its knowledge of which display device is to receive a particular transmission. Additionally, some display devices are capable of obtaining calibration information and wirelessly transmitting the calibration information to the sensor electronics module, such as through manual entry of the calibration information, automatic delivery of the calibration information, and/or an integral reference analyte monitor incorporated into the display device. U.S. Patent Publication Nos. 2006/0222566, 2007/0203966, 2007/0208245, and 2005/0154271, all of which are incorporated herein by reference in their entirety, describe systems and methods for providing an integral reference analyte monitor incorporated into a display device and/or other calibration methods that can be implemented with embodiments disclosed herein.

In general, a plurality of display devices (e.g., a custom analyte monitoring device (which may also be referred to as an analyte display device), a mobile phone, a tablet, a smart watch, a reference analyte monitor, a drug delivery device, a medical device and a personal computer) may be configured to wirelessly communicate with the sensor electronics module. The plurality of display devices may be configured to display at least some of the displayable sensor information wirelessly communicated from the sensor electronics module. The displayable sensor information may include sensor data, such as raw data and/or transformed sensor data, such as analyte concentration values, rate of change information, trend information, alert information, sensor diagnostic information and/or calibration information, for example.

D. Continuous Sensor

With reference to FIG. 1A, in some embodiments, analyte sensor 10 includes a continuous glucose sensor, for example, a subcutaneous, transdermal (e.g., transcutaneous), or intravascular device. In some embodiments, such a sensor or device can analyze a plurality of intermittent blood samples. The glucose sensor can use any method of glucose-measurement, including enzymatic, chemical, physical, electrochemical, spectrophotometric, polarimetric, calorimetric, iontophoretic, radiometric, immunochemical, and the like.

A glucose sensor can use any known method, including invasive, minimally invasive, and non-invasive sensing techniques (e.g., fluorescent monitoring), to provide a data stream indicative of the concentration of glucose in a host. The data stream is typically a raw data signal, which is converted into a calibrated and/or filtered data stream that is used to provide a useful value of glucose to a user, such as a patient or a caretaker (e.g., a parent, a relative, a guardian, a teacher, a doctor, a nurse, or any other individual that has an interest in the wellbeing of the host).

A glucose sensor can be any device capable of measuring the concentration of glucose. According to one example embodiment described below, an implantable glucose sensor may be used. However, it should be understood that the devices and methods described herein can be applied to any device capable of detecting a concentration of glucose and providing an output signal that represents the concentration of glucose (e.g., as a form of analyte data).

In certain embodiments, analyte sensor 10 is an implantable glucose sensor, such as described with reference to U.S. Pat. No. 6,001,067 and U.S. Patent Publication No. US-2005-0027463-A1. In embodiments, analyte sensor 10 is a transcutaneous glucose sensor, such as described with reference to U.S. Patent Publication No. US-2006-0020187-A1. In embodiments, analyte sensor 10 is configured to be implanted in a host vessel or extracorporeally, such as is described in U.S. Patent Publication No. US-2007-0027385-A1, co-pending U.S. Patent Publication No. US-2008-0119703-A1 filed Oct. 4, 2006, U.S. Patent Publication No. US-2008-0108942-A1 filed on Mar. 26, 2007, and U.S. Patent Application No. US-2007-0197890-A1 filed on Feb. 14, 2007. In embodiments, the continuous glucose sensor includes a transcutaneous sensor such as described in U.S. Pat. No. 6,565,509 to Say et al., for example. In embodiments, analyte sensor 10 is a continuous glucose sensor that includes a subcutaneous sensor such as described with reference to U.S. Pat. No. 6,579,690 to Bonnecaze et al. or U.S. Pat. No. 6,484,046 to Say et al., for example. In embodiments, the continuous glucose sensor includes a refillable subcutaneous sensor such as described with reference to U.S. Pat. No. 6,512,939 to Colvin et al., for example. The continuous glucose sensor may include an intravascular sensor such as described with reference to U.S. Pat. No. 6,477,395 to Schulman et al., for example. The continuous glucose sensor may include an intravascular sensor such as described with reference to U.S. Pat. No. 6,424,847 to Mastrototaro et al., for example.

Figure 2A:
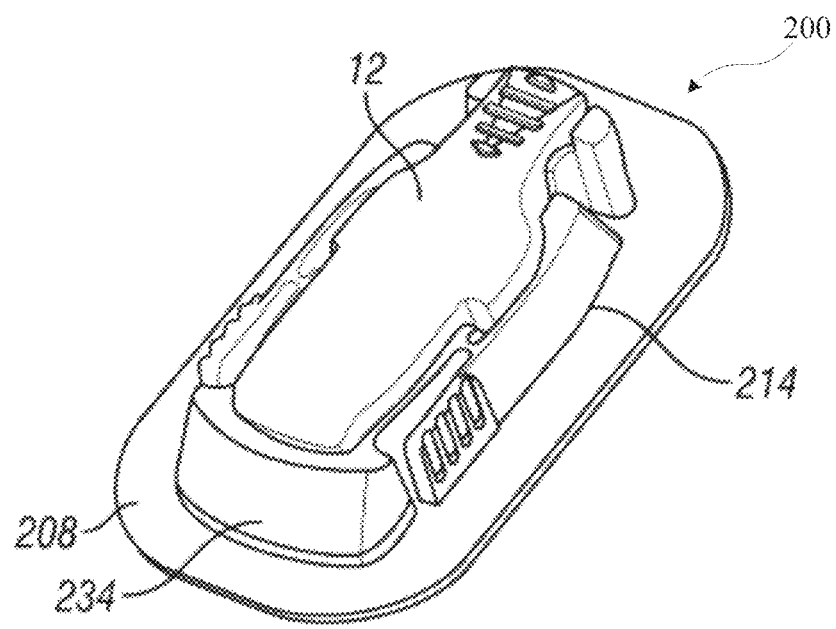
FIG. 2A is a perspective view of an example enclosure that may be used in connection with implementing embodiments of an analyte sensor system.
Figure 2B:
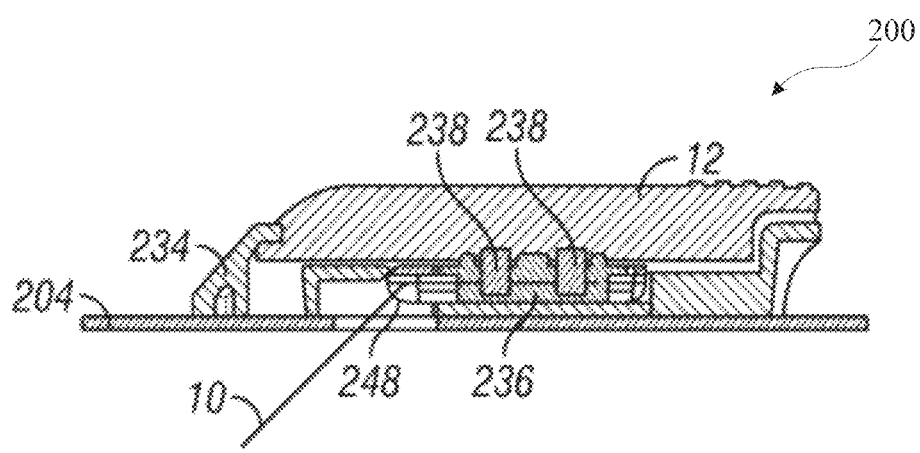
FIG. 2B is a side view of an example enclosure that may be used in connection with implementing embodiments of an analyte sensor system.

FIGS. 2A and 2B are perspective and side views of enclosure 200 that may be used in connection with implementing embodiments of analyte sensor system 8, according to certain aspects of the present disclosure. Enclosure 200 includes mounting unit 214 and sensor electronics module 12 attached thereto in certain embodiments. Enclosure 200 is shown in a functional position, including mounting unit 214 and sensor electronics module 12 matingly engaged therein. In some embodiments, mounting unit 214, also referred to as a housing or sensor pod, includes base 234 adapted for fastening to a host's or user's skin. Base 234 can be formed from a variety of hard or soft materials, and can include a low profile for minimizing protrusion of the device from the host during use. In some embodiments, base 234 is formed at least partially from a flexible material, which may provide numerous advantages over other transcutaneous sensors, which, unfortunately, can suffer from motion-related artifacts associated with the host's movement when the host is using the device. Mounting unit 214 and/or sensor electronics module 12 can be located over the sensor insertion site to protect the site and/or provide a minimal footprint (utilization of surface area of the host's skin).

In some embodiments, a detachable connection between mounting unit 214 and sensor electronics module 12 is provided, which enables improved manufacturability, namely, the potentially relatively inexpensive mounting unit 214 can be disposed of when refurbishing or maintaining analyte sensor system 8, while the relatively more expensive sensor electronics module 12 can be reusable with multiple sensor systems. In some embodiments, sensor electronics module 12 is configured with signal processing (programming), for example, configured to filter, calibrate, and/or execute other algorithms useful for calibration and/or display of sensor information. However, an integral (non-detachable) sensor electronics module can be configured.

In some embodiments, contacts 238 are mounted on or in a subassembly hereinafter referred to as contact subassembly 236 configured to fit within base 234 of mounting unit 214 and hinge 248 that allows contact subassembly 236 to pivot between a first position (for insertion) and a second position (for use) relative to mounting unit 214. The term "hinge" as used herein is a broad term and is used in its ordinary sense, including, without limitation, to refer to any of a variety of pivoting, articulating, and/or hinging mechanisms, such as an adhesive hinge, a sliding joint, and the like; the term hinge does not necessarily imply a fulcrum or fixed point about which the articulation occurs. In some embodiments, contacts 238 are formed from a conductive elastomeric material, such as a carbon black elastomer, through which sensor 10 extends.

With further reference to FIGS. 2A and 2B, in certain embodiments, mounting unit 214 is provided with adhesive pad 208, disposed on the mounting unit's back surface and includes a releasable backing layer. Thus, removing the backing layer and pressing at last a portion of base 234 of mounting unit 214 onto the host's skin adheres mounting unit 214 to the host's skin. Additionally or alternatively, an adhesive pad can be placed over some or all of analyte sensor system 8 and/or sensor 10 after sensor insertion is complete to ensure adhesion, and optionally to ensure an airtight seal or watertight seal around the wound exit-site (or sensor insertion site) (not shown). Appropriate adhesive pads can be chosen and designed to stretch, elongate, conform to, and/or aerate the region (e.g., host's skin). The embodiments described with reference to FIGS. 2A and 2B are described in more detail with reference to U.S. Pat. No. 7,310,544, which is incorporated herein by reference in its entirety. Configurations and arrangements can provide water resistant, waterproof, and/or hermetically sealed properties associated with the mounting unit/sensor electronics module embodiments described herein.

Various methods and devices that are suitable for use in conjunction with aspects of some embodiments are disclosed in U.S. Patent Publication No. US-2009-0240120-A1, which is incorporated herein by reference in its entirety for all purposes.

E. Example Configurations

Referring again to FIG. 1A, system 100 that may be used in connection with implementing aspects of an analyte sensor system is depicted. In some cases, system 100 may be used to implement various systems described herein. System 100 in embodiments includes analyte sensor system 8 and display devices 110, 120, 130, and 140, according to certain aspects of the present disclosure. Analyte sensor system 8 in the illustrated embodiment includes sensor electronics module 12 and continuous analyte sensor 10 associated with the sensor electronics module 12. Sensor electronics module 12 may be in wireless communication (e.g., directly or indirectly) with one or more of display devices 110, 120, 130, and 140. In embodiments, system 100 also includes medical device 136 and server system 134. Sensor electronics module 12 may also be in wireless communication (e.g., directly or indirectly) with medical device 136 and/or server system 134. Likewise, in some examples, display devices 110-140 may also be in wireless communication (e.g., directly or indirectly) with medical devices 136 and/or server system 134. Various couplings shown in FIG. 1A can be facilitated with wireless access point 138, as also mentioned below.

In certain embodiments, sensor electronics module 12 includes electronic circuitry associated with measuring and processing the continuous analyte sensor data, including prospective algorithms associated with processing and calibration of the sensor data. Sensor electronics module 12 can be physically connected to continuous analyte sensor 10 and can be integral with (non-releasably attached to) or releasably attachable to continuous analyte sensor 10. Sensor electronics module 12 may include hardware, firmware, and/or software that enables measurement of levels of the analyte via a glucose sensor. For example, sensor electronics module 12 can include a potentiostat, a power source for providing power to the sensor, other components useful for signal processing and data storage, and a telemetry module for transmitting data from the sensor electronics module to one or more display devices. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor.

Sensor electronics module 12 may include sensor electronics that are configured to process sensor information, such as sensor data, and generate transformed sensor data and displayable sensor information. Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entirety for all purposes.

Referring again to FIG. 1A, display devices 110, 120, 130, and/or 140 are configured for displaying (and/or alarming) the displayable sensor information that may be transmitted by sensor electronics module 12 (e.g., in a customized data package that is transmitted to the display devices based on their respective preferences). Each of display devices 110, 120, 130, or 140 can include a display such as a touchscreen display 112, 122, 132,/or 142 for displaying sensor information and/or analyte data to a user and/or receiving inputs from the user. For example, a graphical user interface may be presented to the user for such purposes. In some embodiments, the display devices may include other types of user interfaces such as voice user interface instead of or in addition to a touchscreen display for communicating sensor information to the user of the display device and/or receiving user inputs. In some embodiments, one, some, or all of the display devices is configured to display or otherwise communicate the sensor information as it is communicated from the sensor electronics module (e.g., in a data package that is transmitted to respective display devices), without any additional prospective processing required for calibration and real-time display of the sensor data.

Figure 1B:
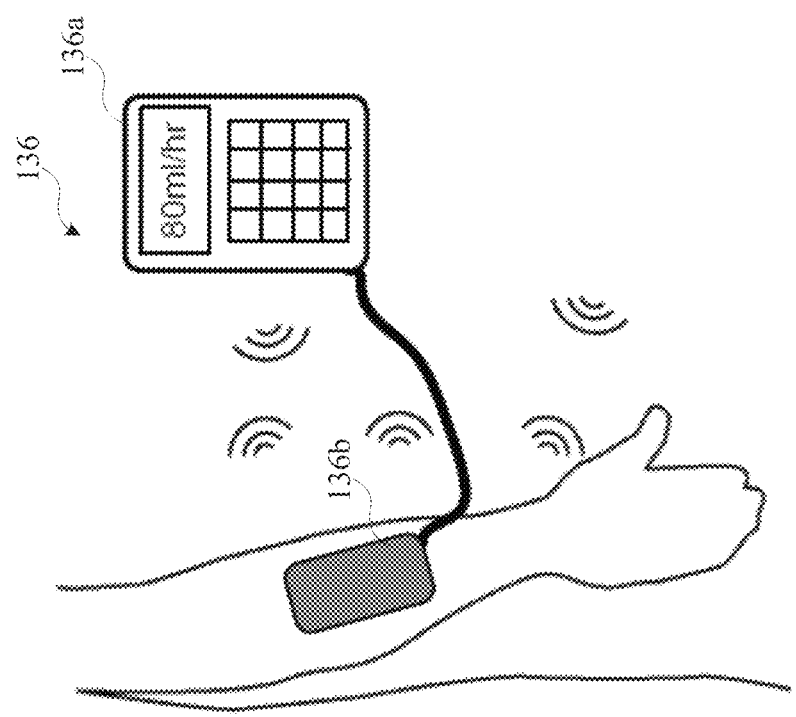
FIG. 1B illustrates aspects of an example system that may be used in connection with implementing embodiments of the disclosure.

Medical device 136 may be a passive device in example embodiments of the disclosure. For example medical device 136 may be an insulin pump for administering insulin to a user, as shown in FIG. 1B. For a variety of reasons, it may be desirable for such an insulin pump to receive and track glucose values transmitted from analyte sensor system 8. One reason is to provide the insulin pump a capability to suspend/activate insulin administration based on a glucose value being below/above a threshold value. One solution that allows a passive device (e.g., medical device 136) to receive analyte data (e.g., glucose values) without being bonded to analyte sensor system 8 is to include the analyte data in the advertisement messages transmitted from analyte sensor system 8. The data included in the advertisement messages can be encoded so that only a device that has the identification information associated with analyte sensor system 8 can decode the analyte data. Medical device 136 may include input/output portion 136a, in which, for example, glucose and other values may be displayed and input may be received via buttons, wireless connection, or other mechanisms. Medical device 136 may also include attachment portion 136b that interfaces with the user to, for example, administrate insulin responsive to the input received at input/output portion 136a. In some cases, attachment portion 136b may provide sensory alerts or other notifications to the user based on, for example, the input received and/or values calculated at input/output portion 136a.

With further reference to FIG. 1A, the plurality of display devices may include a custom display device specially designed for displaying certain types of displayable sensor information associated with analyte data received from sensor electronics module 12 (e.g., a numerical value and an arrow, in some embodiments). Analyte display device 110 is an example of such a custom device. In some embodiments, one of the plurality of display devices is smartphone, such as mobile phone 120 based on an Android, iOS or other operating system, and configured to display a graphical representation of the continuous sensor data (e.g., including current and historic data). Other display devices can include other hand-held devices, such as tablet 130, smart watch 140, medical device 136 (e.g., an insulin delivery device or a blood glucose meter), and/or a desktop or laptop computer.

Because different display devices provide different user interfaces, content of the data packages (e.g., amount, format, and/or type of data to be displayed, alarms, and the like) can be customized (e.g., programmed differently by the manufacture and/or by an end user) for each particular display device. Accordingly, in the embodiment of FIG. 1A, a plurality of different display devices can be in direct wireless communication with a sensor electronics module (e.g., such as an on-skin sensor electronics module 12 that is physically connected to the continuous analyte sensor 10) during a sensor session to enable a plurality of different types and/or levels of display and/or functionality associated with the displayable sensor information, which is described in more detail elsewhere herein.

As further illustrated in FIG. 1A, system 100 may also include wireless access point (WAP) 138 that may be used to couple one or more of analyte sensor system 8, the plurality display devices, server system 134, and medical device 136 to one another. For example, WAP 138 may provide WiFi and/or cellular connectivity within system 100. Near Field Communication (NFC) may also be used among devices of system 100. Server system 134 may be used to collect analyte data from analyte sensor system 8 and/or the plurality of display devices, for example, to perform analytics thereon, generate universal or individualized models for glucose levels and profiles, and so on.

Figure 3A:
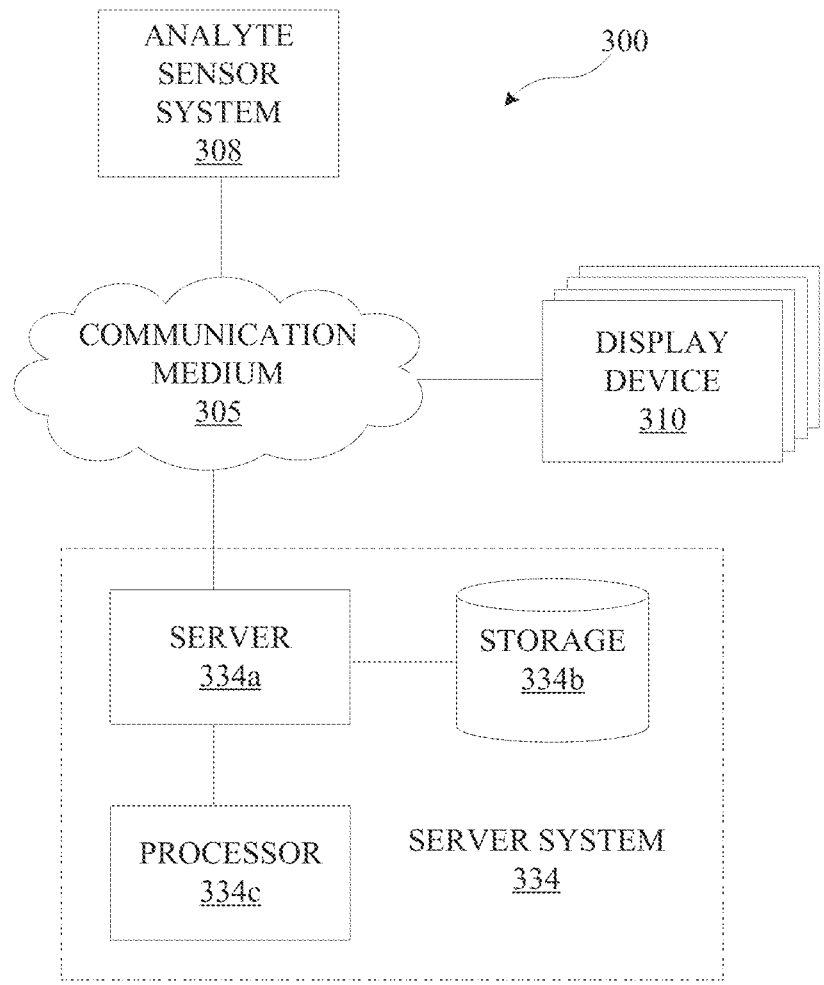
FIG. 3A illustrates aspects of an example system that may be used in connection with implementing embodiments of the disclosure.

Referring now to FIG. 3A, system 300 is depicted. System 300 may be used in connection with implementing embodiments of the disclosed systems, methods, and devices. By way of example, the various below-described components of FIG. 3A may be used to provide wireless communication of glucose data, for example between an analyte sensor system and a plurality of display devices, medical devices, servers and so on.

As shown in FIG. 3A, system 100 may include analyte sensor system 308 and one or more display devices 310. Additionally, in the illustrated embodiment, system 300 includes server system 334, which in turn includes server 334a coupled to processor 334c and storage 334b. Analyte sensor system 308 may be coupled to display devices 310 and/or server system 334 via communication medium 305. Many details of the processing, gathering, and exchanging data by analyte sensor system 308 and/or display device 310 etc. are provided, for example, with reference to FIG. 6, below.

As will be described in detail herein, analyte sensor system 308 and display devices 310 may exchange messaging via communication medium 305, and communication medium 305 may also be used to deliver analyte data to display devices 310 and/or server system 334. As alluded to above, display devices 310 may include a variety of electronic computing devices, such as, for example, a smartphone, tablet, laptop, wearable device, etc. Display devices 310 may also include analyte display device 110 and medical device 136. Here, it will be noted that a GUI of display device 310 may perform such functions as accepting user input and displaying menus as well as information derived from analyte data. The GUI may be provided by various operating systems known in the art, such as, for example, iOS, Android, Windows Mobile, Windows, Mac OS, Chrome OS, Linux, Unix, a gaming platform OS (e.g., Xbox, PlayStation, Wii), etc. In various embodiments, communication medium 305 may be based on one or more wireless communication protocols such as Bluetooth, Bluetooth Low Energy (BLE), ZigBee, WiFi, 802.11 protocols, Infrared (IR), Radio Frequency (RF), 2G, 3G, 4G, etc., and/or wired protocols and media.

In various embodiments, the elements of system 300 may be used to perform various processes described herein and/or may be used to execute various operations described herein with regard to one or more disclosed systems and methods. Upon studying the present disclosure, one of skill in the art will appreciate that system 300 may include multiple analyte sensor systems, communication media 305, and/or server systems 334.

As mentioned, communication medium 305 may be used to connect or communicatively couple analyte sensor system 308, display devices 310, and/or server system 334 to one another or to a network, and communication medium 305 may be implemented in a variety of forms. For example, communication medium 305 may include an Internet connection, such as a local area network (LAN), a wide area network (WAN), a fiber optic network, internet over power lines, a hard-wired connection (e.g., a bus), and the like, or any other kind of network connection. Communication medium 305 may be implemented using any combination of routers, cables, modems, switches, fiber optics, wires, radio (e.g., microwave/RF links), and the like. Further, communication medium 305 may be implemented using various wireless standards, such as Bluetooth®, BLE, Wi-Fi, 3GPP standards (e.g., 2G GSM/GPRS/EDGE, 3G UMTS/

CDMA2000, or 4G LTE/LTE-U), etc. Upon reading the present disclosure, one of skill in the art will recognize other ways to implement communication medium 305 for communications purposes.

Server 334a may receive, collect, or monitor information, including analyte data and related information, from analyte sensor system 308 and/or display device 310, such as input responsive to the analyte data or input received in connection with an analyte monitoring application running on analyte sensor system or display device 310. In such cases, server 334a may be configured to receive such information via communication medium 305. This information may be stored in storage 334b and may be processed by processor 334c. For example, processor 334c may include an analytics engine capable of performing analytics on information that server 334a has collected, received, etc. via communication medium 305. In embodiments, server 334a, storage 334b, and/or processor 334c may be implemented as a distributed computing network, such as a Hadoop® network, or as a relational database or the like.

Server 334a may include, for example, an Internet server, a router, a desktop or laptop computer, a smartphone, a tablet, a processor, a module, or the like, and may be implemented in various forms, including, for example, an integrated circuit or collection thereof, a printed circuit board or collection thereof, or in a discrete housing/package/rack or multiple of the same. In embodiments, server 334a at least partially directs communications made over communication medium 305. Such communications include the delivery and/or messaging (e.g., advertisement, command, or other messaging) and analyte data. For example, server 334a may process and exchange messages between analyte sensor system 308 and display devices 310 related to frequency bands, timing of transmissions, security, alarms, and so on. Server 334a may update information stored on analyte sensor system 308 and/or display devices 310, for example, by delivering applications thereto. Server 334a may send/receive information to/from analyte sensor system 308 and/or display devices 310 in real time or sporadically. Further, server 334a may implement cloud computing capabilities for analyte sensor system 308 and/or display devices 310.

Figure 3B:
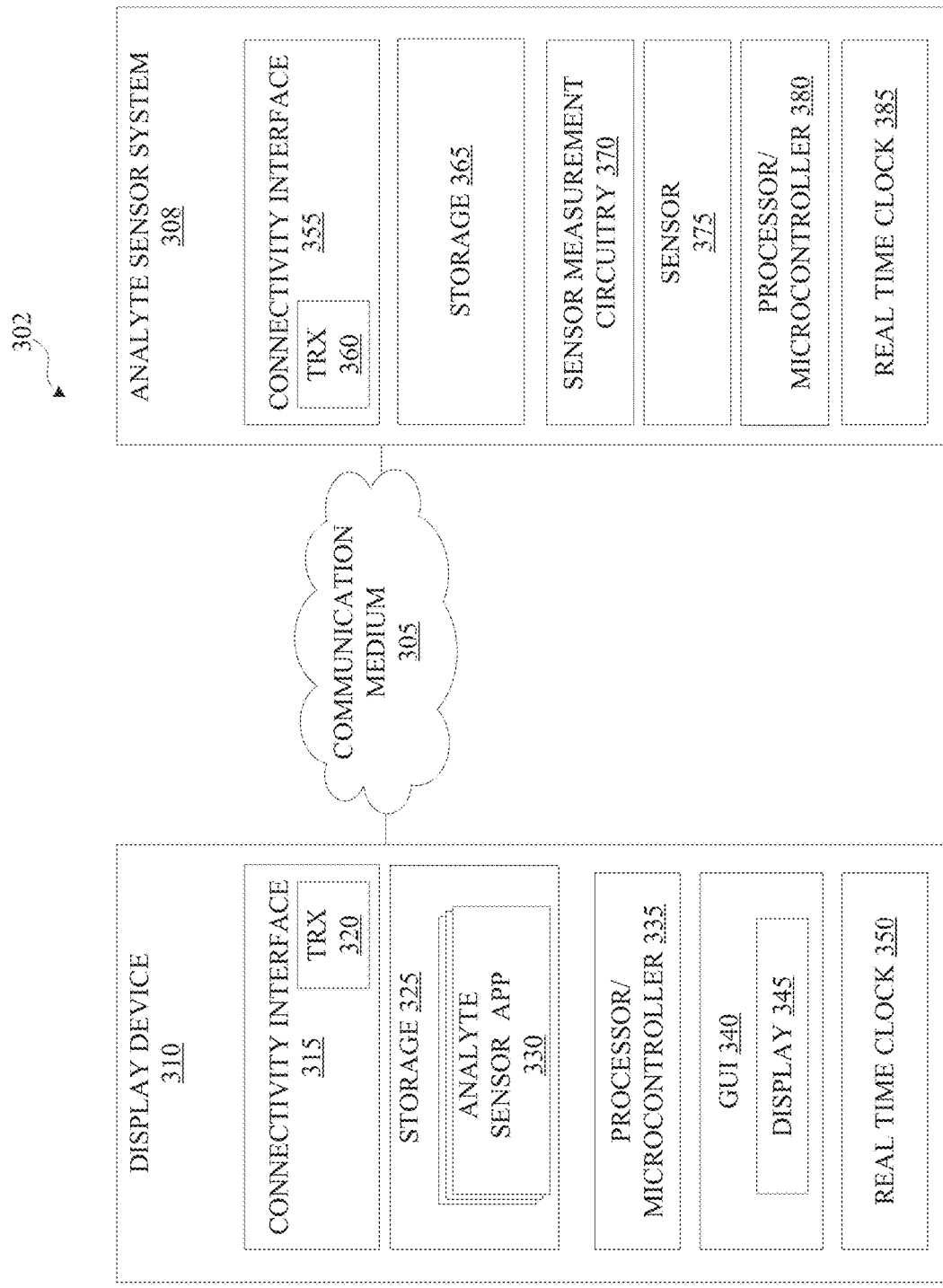
FIG. 3B illustrates aspects of an example system that may be used in connection with implementing embodiments of the disclosure.

FIG. 3B depicts system 302, which includes examples of additional aspects of the present disclosure that may be used in connection implementing an analyte sensor system. Many details of the processing, gathering, and exchanging data by analyte sensor system 308 and/or display device 310 etc. are provided, for example, with reference to FIG. 6, below. As illustrated in FIG. 3B, system 302 may include analyte sensor system 308. As shown, analyte sensor system 308 may include analyte sensor 375 (e.g., which may also be designated with the numeral 10 in FIG. 1A) coupled to sensor measurement circuitry 370 for processing and managing sensor data. Sensor measurement circuitry 370 may be coupled to processor/microprocessor 380 (e.g., which may be part of item 12 in FIG. 1A). In some embodiments, processor 380 may perform part or all of the functions of the sensor measurement circuitry 370 for obtaining and processing sensor measurement values from sensor 375. Processor 380 may be further coupled to a radio unit or transceiver 320 (e.g., which may be part of item 12 in FIG. 1A) for sending sensor data and receiving requests and commands from an external device, such as display device 310, which may be used to display or otherwise provide the sensor data (or analyte data) to a user. As used herein, the terms "radio unit" and "transceiver" are used interchangeably and generally refer to a device that can wirelessly transmit and receive data. Analyte sensor system 308 may further include storage 365 (e.g., which may be part of item 12 in FIG. 1A) and real time clock (RTC) 380 (e.g., which may be part of item 12 in FIG. 1A) for storing and tracking sensor data.

As alluded to above, wireless communication protocols may be used to transmit and receive data between analyte sensor system 308 and the display device 310 via communication medium 305. Such wireless protocols may be designed for use in a wireless network that is optimized for periodic and small data transmissions (that may be transmitted at low rates if necessary) to and from multiple devices in a close range (e.g., a personal area network (PAN)). For example, one such protocol may be optimized for periodic data transfers where transceivers may be configured to transmit data for short intervals and then enter low power modes for long intervals. The protocol may have low overhead requirements both for normal data transmissions and for initially setting up communication channels (e.g., by reducing overhead) to reduce power consumption. In some embodiments, burst broadcasting schemes (e.g., one way communication) may be used. This may eliminate overhead required for acknowledgement signals and allow for periodic transmissions that consume little power. In other embodiments, passive or active proximity-based protocols may be employed to reduce overhead (e.g., overhead associated with typical pairing operations) and/or increase security, with NFC being one specific example.

The protocols may further be configured to establish communication channels with multiple devices while implementing interference avoidance schemes. In some embodiments, the protocol may make use of adaptive isochronous network topologies that define various time slots and frequency bands for communication with several devices. The protocol may thus modify transmission windows and frequencies in response to interference and to support communication with multiple devices. Accordingly, the wireless protocol may use time and frequency division multiplexing (TDMA) based schemes. The wireless protocol may also employ direct sequence spread spectrum (DSSS) and frequency-hopping spread spectrum schemes. Various network topologies may be used to support short-distance and/or low-power wireless communication such as peer-to-peer, start, tree, or mesh network topologies such as WiFi, Bluetooth and Bluetooth Low Energy (BLE). The wireless protocol may operate in various frequency bands such as an open ISM band such as 2.4 GHz. Furthermore, to reduce power usage, the wireless protocol may adaptively configure data rates according to power consumption.

With further reference to FIG. 3B, system 302 may include display device 310 communicatively coupled to analyte sensor system 308 via communication medium 305. In the illustrated embodiment, display device 310 includes connectivity interface 315 (which in turn includes transceiver 320), storage 325 (which in turn stores analyte sensor application 330 and/or additional applications), processor/microprocessor 335, graphical user interface (GUI) 340 that may be presented using display 345 of display device 310, and real time clock (RTC) 350. A bus (not shown here) may be used to interconnect the various elements of display device 310 and transfer data between these elements.

Display device 310 may be used for alerting and providing sensor information or analyte data to a user, and may include a processor/microprocessor 335 for processing and managing sensor data. Display device 310 may include display 345, storage 325, analyte sensor application 330, and real time clock 350 for displaying, storing, and tracking sensor data. Display device 310 may further include a radio unit or transceiver 320 coupled to other elements of display device 310 via connectivity interface 315 and/or a bus. Transceiver 320 may be used for receiving sensor data and for sending requests, instructions, and/or data to analyte sensor system 308. Transceiver 320 may further employ a communication protocol. Storage 325 may also be used for storing an operating system for display device 310 and/or a custom (e.g., proprietary) application designed for wireless data communication between a transceiver and display device 310. Storage 325 may be a single memory device or multiple memory devices and may be a volatile or non-volatile memory for storing data and/or instructions for software programs and applications. The instructions may be executed by processor 335 to control and manage transceiver 320.

In some embodiments, when a standardized communication protocol is used, commercially available transceiver circuits may be utilized that incorporate processing circuitry to handle low level data communication functions such as the management of data encoding, transmission frequencies, handshake protocols, and the like. In these embodiments, processor 335, 380 does not need to manage these activities, but rather provides desired data values for transmission, and manages high level functions such as power up or down, set a rate at which messages are transmitted, and the like. Instructions and data values for performing these high level functions can be provided to the transceiver circuits via a data bus and transfer protocol established by the manufacturer of the transceiver 320, 360.

Components of analyte sensor system 308 may require replacement periodically. For example, analyte sensor system 308 may include an implantable sensor 375 that may be attached to a sensor electronics module that includes sensor measurement circuitry 370, processor 380, storage 365, and transceiver 360, and a battery (not shown). Sensor 375 may require periodic replacement (e.g., every 7 to 30 days). The sensor electronics module may be configured to be powered and active for much longer than sensor 375 (e.g., for three to six months or more) until the battery needs replacement. Replacing these components may be difficult and require the assistance of trained personnel. Reducing the need to replace such components, particularly the battery, significantly improves the convenience and cost of using analyte sensor system 308, including to the user. In some embodiments, when a sensor electronic module is used for the first time (or reactivated once a battery has been replaced in some cases), it may be connected to sensor 375 and a sensor session may be established. As will be further described below, there may be a process for initially establishing communication between display device 310 and the sensor electronics module when the module is first used or re-activated (e.g., the battery is replaced). Once display device 310 and sensor electronics module have established communication, display device 310 and the sensor electronics module may periodically and/or continuously be in communication over the life of several sensors 375 until, for example, the battery needs to be replaced. Each time sensor 375 is replaced, a new sensor session may be established. The new sensor session may be initiated through a process completed using display device 310 and the process may be triggered by notifications of a new sensor via the communication between the sensor electronics module and display device 310 that may be persistent across sensor sessions.

Analyte sensor system 308 typically gathers analyte data from sensor 375 and transmits the same to display device 310. Data points regarding analyte values may be gathered and transmitted over the life of sensor 375 (e.g., in the range of 1 to 30 days or more). New measurements may be transmitted often enough to adequately monitor glucose levels. Rather than having the transmission and receiving circuitry of each of analyte sensor system 308 and display device 310 continuously communicating, analyte sensor system 308 and display device 310 may regularly and/or periodically establish a communication channel between them. Thus, analyte sensor system 308 can in some cases communicate via wireless transmission with display device 310 (e.g., a hand-held computing device, medical device, or proprietary device) at predetermined time intervals. The duration of the predetermined time interval can be selected to be long enough so that analyte sensor system 308 does not consume too much power by transmitting data more frequently than needed, yet frequent enough to provide substantially real-time sensor information (e.g., measured glucose values or analyte data) to display device 310 for output (e.g., via display 345) to a user. While the predetermined time interval is every five minutes in some embodiments, it is appreciated that this time interval can be varied to be any desired length of time.

With continued reference to FIG. 3B, as shown, connectivity interface 315 interfaces display device 310 to communication medium 305, such that display device 310 may be communicatively coupled to analyte sensor system 308 via communication medium 305. Transceiver 320 of connectivity interface 315 may include multiple transceiver modules operable on different wireless standards. Transceiver 320 may be used to receive analyte data and associated commands and messages from analyte sensor system 308. Additionally, connectivity interface 315 may in some cases include additional components for controlling radio and/or wired connections, such as baseband and/or Ethernet modems, audio/video codecs, and so on.

Storage 325 may include volatile memory (e.g. RAM) and/or non-volatile memory (e.g. flash storage), may include any of EPROM, EEPROM, cache, or may include some combination/variation thereof. In various embodiments, storage 325 may store user input data and/or other data collected by display device 310 (e.g., input from other users gathered via analyte sensor application 330). Storage 325 may also be used to store volumes of analyte data received from analyte sensor system 308 for later retrieval and use, e.g., for determining trends and triggering alerts. Additionally, storage 325 may store analyte sensor application 330 that, when executed using processor 335, for example, receives input (e.g., by a conventional hard/soft key or a touch screen, voice detection, or other input mechanism), and allows a user to interact with the analyte data and related content via GUI 340, as will be described in further detail herein.

In various embodiments, a user may interact with analyte sensor application 330 via GUI 340, which may be provided by display 345 of display device 310. By way of example, display 345 may be a touchscreen display that accepts various hand gestures as inputs. Application 330 may process and/or present analyte-related data received by display device 310, according to various operations described herein, and present such data via display 345. Additionally, application 330 may be used to obtain, access, display, control, and/or interface with analyte data and related messaging and processes associated with analyte sensor system 308, as is described in further detail herein.

Application 330 may be downloaded, installed, and initially configured/setup on display device 310. For example, display device 310 may obtain application 330 from server system 334, or from another source accessed via a communication medium (e.g., communication medium 305), such as an application store or the like. Following installation and setup, application 330 may be used to access and/or interface with analyte data (e.g., whether stored on server system 334, locally from storage 325, or from analyte sensor system 308). By way of illustration, application 330 may present a menu that includes various controls or commands that may be executed in connection with the operating of analyte sensor system 308 and one or more display devices 310. Application 330 may also be used to interface with or control other display devices 310, for example, to deliver or make available thereto analyte data, including for example by receiving/sending analyte data directly to the other display device 310 and/or by sending an instruction for analyte sensor system 308 and the other display device 310 to be connected, etc., as will be described herein. Additionally, application 330 in some implementations may interact with one or more additional applications supported by display device 310, for example to retrieve or supply relevant data. Such applications may include, by way of example, fitness/lifestyle monitoring applications, social media applications, and so on.

Analyte sensor application 330 may include various code/functional modules, such as, for example, a display module, a menu module, a list module, and so on as will become clear in light of the description of various functionalities herein (e.g., in connection with disclosed methods). These modules may be implemented separately or in combination. Each module may include computer-readable media and have computer-executable code stored thereon, such that the code may be operatively coupled to and/or executed by processor 335 (which, e.g., may include a circuitry for such execution) to perform specific functions (e.g., as described herein with regard to various operations and flow charts etc.) with respect to interfacing with analyte data and performing tasks related thereto. As will be further described below, a display module may present (e.g., via display 345) various screens to a user, with the screens containing graphical representations of information provided by application 330. In further embodiments, application 330 may be used to display to the user an environment for viewing and interacting with various display devices that may be connectable to analyte sensor system 308, as well as with analyte sensor system 308 itself. Sensor application 330 may include a native application modified with a software design kit (e.g., depending on the operating system) in order to carry out the functionalities/features described herein.

Referring again to FIG. 3B, display device 310 also includes processor/microcontroller 335. Processor 335 may include processor sub-modules, including, by way of example, an applications processor that interfaces with and/or controls other elements of display device 310 (e.g., connectivity interface 315, application 330, GUI 340, display 345, RTC 350, etc.). Processor 335 may include a controller and/or microcontroller that provides various controls (e.g., interfaces with buttons and switches) related to device management, such as, for example, lists of available or previously paired devices, information related to measurement values, information related to network conditions (e.g., link quality and the like), information related to the timing, type, and/or structure of messaging exchanged between analyte sensor system 308 and display device 310, and so on. Additionally, the controller may include various controls related to the gathering of user input, such as, for example, a user's finger print (e.g., to authorize the user's access to data or to be used for authorization/encryption of data, including analyte data), as well as analyte data.

Processor 335 may include circuitry such as logic circuits, memory, a battery and power circuitry, and other circuitry drivers for periphery components and audio components. Processor 335 and any sub-processors thereof may include logic circuits for receiving, processing, and/or storing data received and/or input to display device 310, and data to be transmitted or delivered by display device 310. Processor 335 may be coupled by a bus to display 345 as well as connectivity interface 315 and storage 325 (including application 330). Hence, processor 335 may receive and process electrical signals generated by these respective elements and thus perform various functions. By way of example, processor 335 may access stored content from storage 325 at the direction of application 330, and process the stored content for display and/or output by display 345. Additionally, processor 335 may process the stored content for transmission via connectivity interface 315 and communication medium 305 to other display devices 310, analyte sensor system 308, or server system 334. Display device 310 may include other peripheral components not shown in detail in FIG. 3B.

In further embodiments, processor 335 may further obtain, detect, calculate, and/or store data input by a user via display 345 or GUI 340, or data received from analyte sensor system 308 (e.g., analyte sensor data or related messaging), over a period of time. Processor 335 may use this input to gauge the user's physical and/or mental response to the data and/or other factors (e.g., time of day, location, etc.). In various embodiments, the user's response or other factors may indicate preferences with respect to the use of certain display devices 310 under certain conditions, and/or the use of certain connection/transmission schemes under various conditions, as will be described in further detail herein.

It should be noted at this juncture that like-named elements as between display device 310 and analyte sensor system 308 may include similar features, structures, and/or capabilities. Therefore, with respect to such elements, the description of display device 310 above may in some cases be applied to analyte sensor system 308.

Figure 3C:
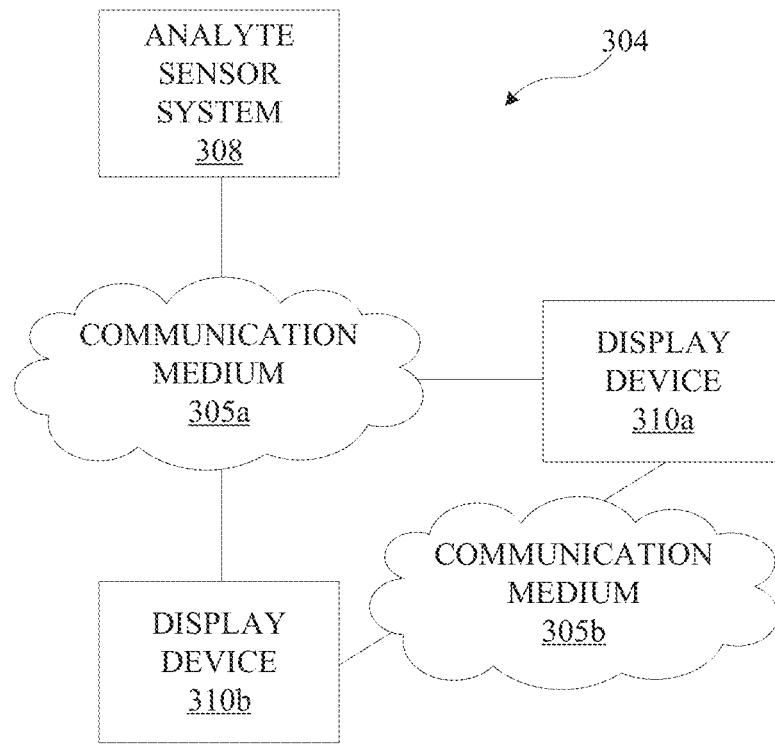
FIG. 3C illustrates aspects of an example system that may be used in connection with implementing embodiments of the disclosure.

Turning now to FIG. 3C, system 304 is depicted in accordance with embodiments of the present disclosure. As shown, system 304 includes analyte sensor system 308 communicatively coupled display devices 310a, 310b via communication medium 305a. Display device 310a is also communicatively coupled to display device 310b via communication medium 305b. By way of example, FIG. 3C illustrates that in example implementations of the disclosure, display device 310a may connect to analyte sensor system 308 using a first connection scheme and a first wireless protocol (e.g., BLE). In turn, display device 310a may also connect to display device 310b using a second connection scheme and a second wireless protocol (e.g., Wi-Fi, NFC, etc.). In embodiments, the connection between display device 310a and analyte sensor system 308 may subsequently be closed, and display device 310b may establish a connection with analyte sensor system 308 while maintaining the connection with display device 310a. Further, for example, display devices 310a and 310b may exchange analyte data with one another via communication medium 305b, where each display device 310a, 310b received the analyte data via communication medium 305a, that is, from analyte sensor system 308. Additional aspects and features represented by FIG. 3C will become apparent upon studying the entirety of the present disclosure.

Figure 17:
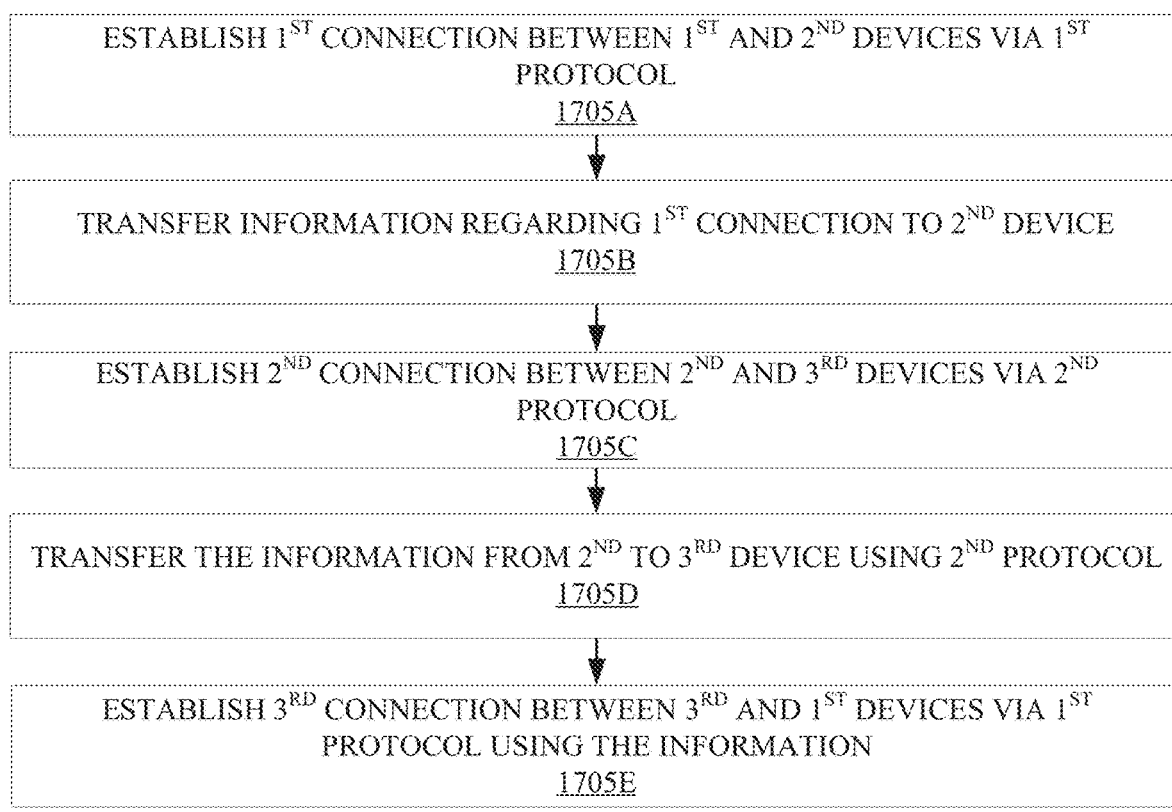
FIG. 17 is an operational flow diagram illustrating various operations that may be performed in accordance with embodiments of the disclosure.

Referring now to FIG. 17, example implementations of features of various methods such as, for example, methods

704, 706, 712, 714, 716, 718, 722, 724, and 726 are illustrated. One such example implementation includes aspects of method 1700 for wireless communication of analyte data. At operation 1705A, method 1700 includes establishing a first connection between analyte sensor system 308 (with reference to FIG. 3C) and a first display device via a first wireless protocol. By way of example, the first display device may be any of the display devices referred to herein, including, for example, display devices 310a and 310b, analyte sensor system 110, medical device 136, etc., with reference to FIGS. 1A and 3C. At operation 1705B, method 1700 includes transferring information related to the first connection from analyte sensor system 308 to the first display device. Examples of such information are described herein. In some cases, the information is not transferred from analyte sensor system 308 to the first display device but is generated and/or resident at the first display, for example by virtue of establishing the first connection and/or another mechanism (e.g., pre-programming, manual input, etc.).

At operation 1705C, method 1700 includes a second display device establishing a second connection to the first display device via a second wireless protocol. By way of example, the second display device may be any of the display devices referred to herein, including, for example, display devices 310a and 310b, analyte sensor system 110, medical device 136, etc. with reference to FIGS. 1A and 3C. At operation 1705D, method 1700 includes transferring the information related to the first connection from the first display device to the second display device using the second wireless protocol. At this juncture it is worth mentioning that any of the wireless protocols described herein may be substituted with or augmented by a wired communication protocol without departing from the spirit or scope of the present disclosure.

Embodiments of method 1700 include, at operation 1705E, establishing a third connection between the second display device and analyte sensor system 308 using the first wireless protocol and the information transferred from the first display device, in order for analyte data to be communicated between analyte sensor system 308 and the second display device. For example, the transferred information may be used to decrease the setup time that otherwise may have been associated with establishing the third connection. In example implementations, the first wireless protocol is BLE and the second wireless protocol is NFC or WiFi.

Figure 3D:
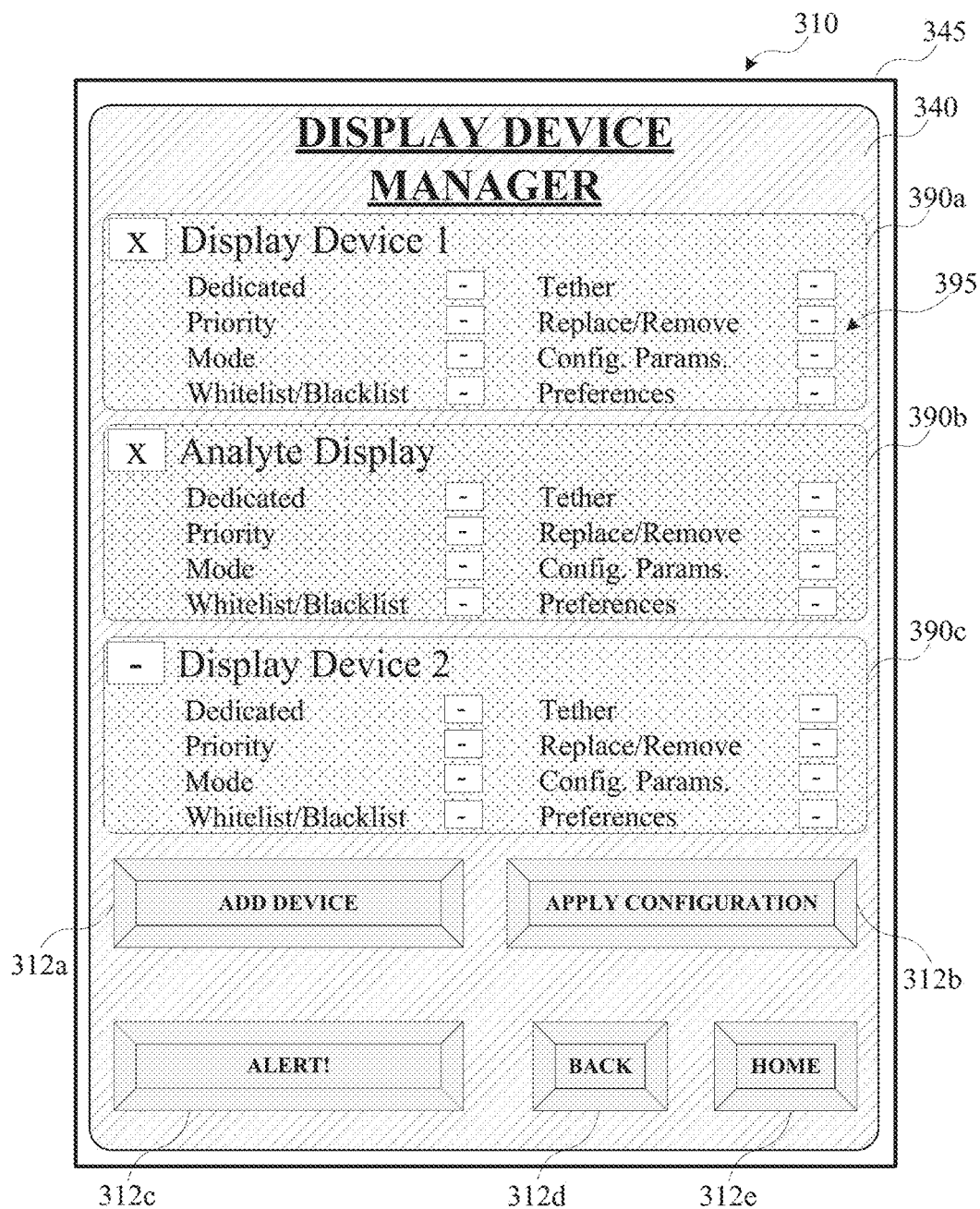
FIG. 3D illustrates aspects of an example user interface according to embodiments of the disclosure.

FIG. 3D illustrates an example implementation of GUI 340 that may be employed in accordance with embodiments of the present disclosure. As shown in FIG. 3D, GUI 340 may be presented via display 345 of display device 310, for example in connection with sensor application 330. Generally speaking, the functionality and features of GUI 340 will be described in further detail with reference to systems and methods described herein. By way of illustration, GUI 340 may present a display device manager. As shown, the display device manager may include an interface module for each of one or more display devices 310 that may be coupled to analyte sensor system 308 (see, e.g., FIGS. 3A and 3B). Interface module 390a may be used to interface with a first display device of display devices 310 ("Display Device 1" or "DD1"); interface module 390b may be used to interface with an analyte display device of display devices 310 ("Analyte Display"); and interface module 390c may be used to interface with a second display device of display devices 310 ("Display Device 2" or "DD2"). Each interface module 390a, 390b, 390c may in turn include configuration menu 395, which may include a number of buttons (e.g., touch-sensitive soft keys) to configure various settings for the device being managed. The available buttons of configuration menu 395 and their functionality can be modified, for example, based on characteristics of the display device being managed as well as other parameters.

As will be described in connection with FIG. 3E, configuration menus 395 may be used to access sub-menus that may be used to select specific management options for the display device of interest. Additional buttons that can be included in GUI 340 are buttons 312a-e. For example, button 312a may be used to add a device to the device manager; button 312b may be used to apply a pre-set configuration to the device manager; button 312c may be used to notify the user of an alert or to manage alter settings; button 312d may be used to navigate back to a previous screen shown in GUI 340 (e.g., in connection with application 330); and button 312e may be used as a soft key to return to the home screen of display device 310.

Figure 3E:
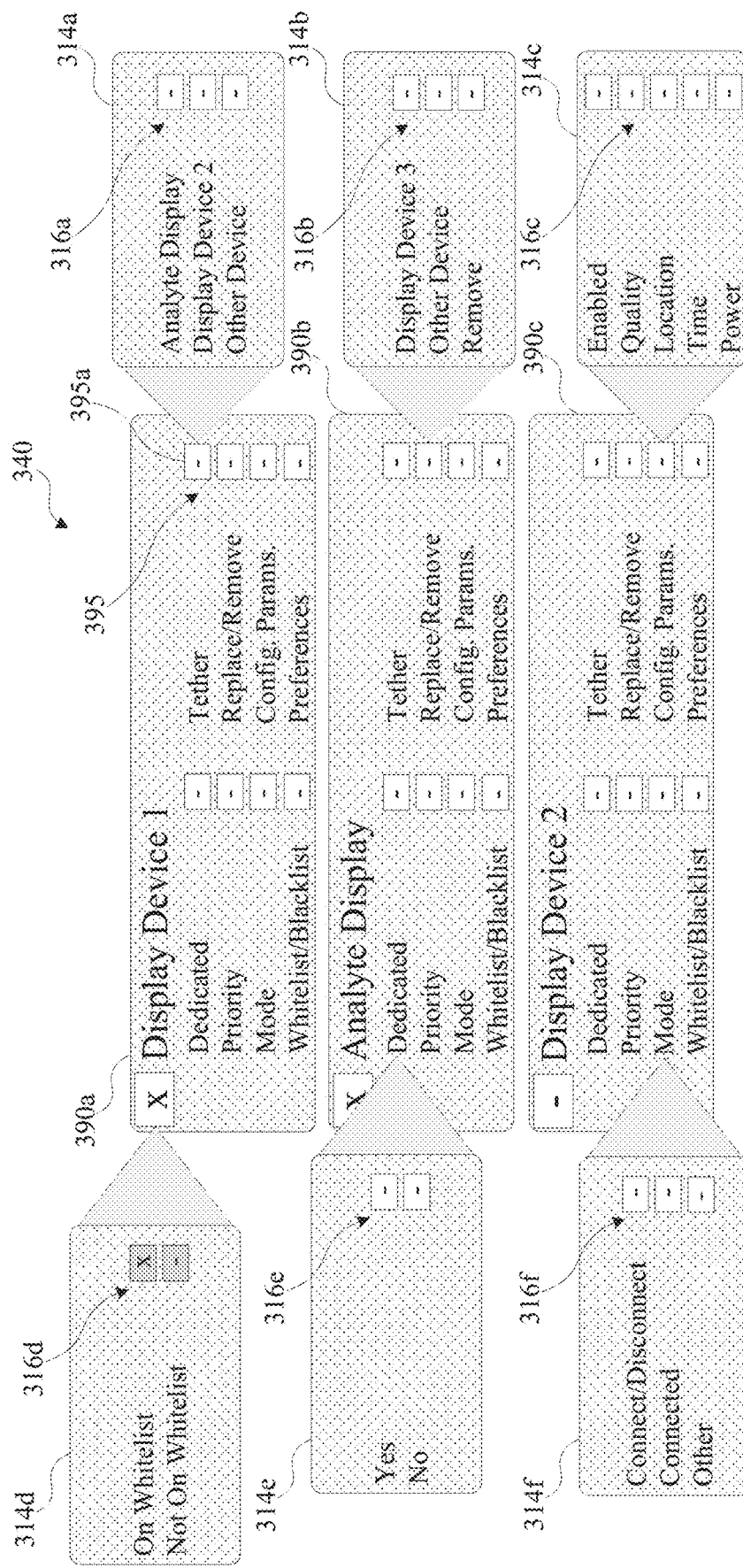
FIG. 3E illustrates aspects of an example user interface according to embodiments of the disclosure.

Turning now to FIG. 3E, additional aspects that may be implemented in connection with GUI 340 are provided. As shown in FIG. 3E, embodiments of GUI 340 involve sub-menus 314a-f of interface modules 390a, 390b, and 390c. Sub-menu 314a may be accessed via configuration menu 395 of interface module 390a. In this instance, sub-menu 314a corresponds to a "Tether" option. In this regard, when selected (e.g., via touch gesture on display 345) sub-menu 314a presents options 316a for tethering Display Device 1 to Analyte Display, Display Device 2, or Other Device. Options 316a may be used to select a device to tether to. With reference to FIG. 3C by way of specific example, tethering in this case may involve, for example, two display devices 310a and 310b connecting via communication medium 305b. Here, Analyte Display and Display Device 2 may correspond to known devices, whereas selecting the Other Device option may initiate a scan for other display devices 310 available for connection. It will be appreciated that sub-menu 314a may be implemented in connection with any other interface module (e.g., 390b etc.)

Sub-menu 314b corresponds to a "Replace/Remove" option. In this regard, when selected (e.g., via touch gesture on display 345) sub-menu 314b presents options 316b, which include options for replacing Analyte Display with another display device 310, namely Display Device 3 ("DD3") or Other Device. Within options 316b, sub-menu 314b also presents an options for to Remove Analyte Display from a list of devices (e.g., a whitelist), as will be further described herein (see, e.g., FIG. 10B). Here again, Display Device 3 may correspond to a known device, whereas selecting the Other Device option may initiate a scan for other display devices 310 available for connection to Analyte Display. It will be appreciated that sub-menu 314b may be implemented in connection with any other interface module (e.g., 390a etc.). For example, sub-menu may be used to replace a user's old smartphone with the user's new smartphone in terms of use with analyte sensor system 308.

Sub-menu 314c corresponds to a "Config. Params." or Configuration Parameters option. In this regard, when selected (e.g., via touch gesture on display 345) sub-menu 314c presents options 316c, which include options for modifying or setting various configuration parameters regarding connection with analyte sensor system 8 and the transmission of data from the same. Within options 316c, sub-menu 314c presents options concerning whether Configuration Parameters are Enabled and then lists additional options related to Configuration Parameters that may be specifically controlled by the user. In some examples, these parameters may additionally or alternatively be monitored and adjusted without user intervention (e.g., by display device 310 and/or analyte sensor system 308), for example by comparing monitored parameter values to predetermined and/or configurable/adaptable thresholds. In this regard, the user may be able to select which parameters should be monitored/adjusted by display device 310. In other cases, the selection can be made on the fly based on monitored parameter values and/or other inputs.

The Quality option may be adjusted by the user to control or interface with Configuration Parameters related to quality of service (QoS), as will be described further herein. Further, as mentioned elsewhere herein in further detail, QoS-related parameters may also be monitored/adjusted by analyte sensor system 308 and/or display device 310, for example based thresholds related to link quality and so on. The Location option may be adjusted by the user to control or interface with Configuration Parameters related to location, as will be described further herein. The Time option may be adjusted by the user to control or interface with Configuration Parameters related to time of day, as will be described further herein. The Power option may be adjusted by the user to control or interface with Configuration Parameters related to battery power, as will be described further herein. It will be appreciated that sub-menu 314c may be implemented in connection with any other interface module (e.g., 390a etc.).

Sub-menu 314d corresponds to a pop-up window option related to the device to which interface module 390a pertains (i.e., in this example, Display Device 1 (DD1)). More specifically, sub-menu 314d indicates via greyed out options 316d whether the device of interest is on the whitelist, as will be described further herein. Options 316d in this example are greyed out to indicate that they are not selectable but rather are used to present information regarding whitelist status. A different sub-menu ("Whitelist/Blacklist"), not described specifically with reference to FIG. 3E, may be used to add/remove specific devices from the whitelist (or to/from a blacklist). It will be appreciated that sub-menu 314d may be implemented in connection with any other interface module (e.g., 390a etc.).

Sub-menu 314e corresponds to a "Dedicated" option. In this regard, when selected (e.g., via touch gesture on display 345) sub-menu 314c presents options 316e, which include options for making a display device of interest (here, Analyte Display) a dedicated display device with respect to connecting to analyte sensor system 8 and the transmission of data from the same. Within options 316e, sub-menu 314e presents options for indicating Yes or No regarding whether Analyte Display is a dedicated display device, as will be described further herein. It will be appreciated that sub-menu 314e may be implemented in connection with any other interface module (e.g., 390a etc.).

Sub-menu 314f corresponds to a "Mode" option. In this regard, when selected (e.g., via touch gesture on display 345) sub-menu 314f presents options 316f, which include options for setting on connection mode as between the display device of interest (here, Display Device 2) and analyte sensor system 8. Within options 316f, sub-menu 314f presents options for Connect/Disconnect, Connected, and Other, regarding a connection mode to operate in, as will be described further herein. It will be appreciated that sub-menu 314f may be implemented in connection with any other interface module (e.g., 390a etc.).

Certain sub-menus have not been described in detail here with reference to FIG. 3E. Nevertheless, one of ordinary skill in the art upon studying the present disclosure will appreciate that GUI 340 may present various addition options with respect to these sub-menus, and will also appreciate that additional sub-menus are within the scope and spirit of the present disclosure. For example, some such sub-menus/options, such as for example the Priority option (see, e.g., discussion of method 1000), are described elsewhere herein in connection with methods and/or systems.

Figure 4:
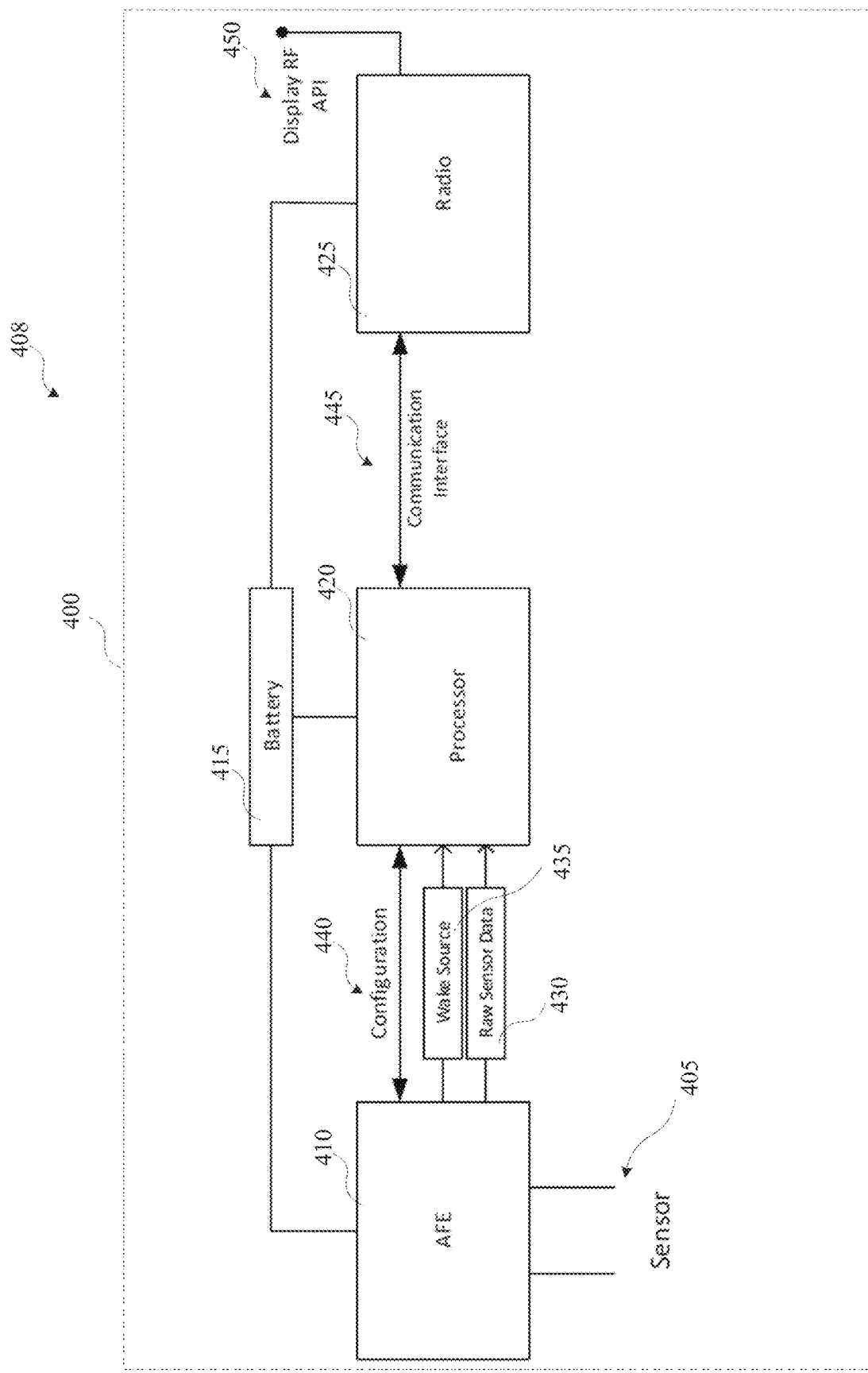
FIG. 4 is a block diagram illustrating aspects of an example analyte sensor system according to embodiments of the disclosure.

FIG. 4 is a block diagram illustrating potential aspects of analyte sensor system 408 according to embodiments of the present disclosure. The aspects of analyte sensor system 408 shown in FIG. 4 may be implemented within subsystem 400 of analyte sensor system 408 and may in general be used to manage a radio interface between analyte sensor system 408 and any display devices communicatively coupled thereto via a wireless protocol, such as BLE. For example, application programming interface (API) 450 may be provided for display devices to communicate with processor 420 (e.g., processor 380) via radio 425, which may include a BLE or other RF or microwave transceiver (e.g., transceiver 360). Processor 420 may be used to process analyte data gathered by sensor 405 (e.g., sensor 375).

As shown, within analyte sensor system 408, subsystem 400 may include sensor 405 (e.g., sensor 10), analog front end (AFE) 410 (e.g., sensor electronics module 12), battery 415, processor 420, and radio 425. The design of analyte sensor system 408, including with respect to subsystem 400 as well as related software, enables multi-chip operation and management, and particularly where such operation and/or management is carried out in accordance with power savings principles described herein and may involve implementing system configurations that support/maximize power savings. For example, the design enables system startup, inter-chip communication, application task scheduling, maximization of battery life in storage as well as active modes, and utilization of control points and indications by API 450 associated with radio 425.

A storage mode may be used for the operation of analyte sensor system 408 before analyte sensor system 408 has been inserted into a host. For example, upon detecting that sensor 405 has been inserted into the host, analyte sensor system 408 can automatically exit storage mode and enter an active mode. In storage mode, radio 425 can be at least partially disabled in order to save power. Likewise, processor 420 can be at least partially disabled, for example by disabling a clock used by processor 420 (e.g., RTC 350). Furthermore, it is contemplated that, in the storage mode, radio 425 may be configured to be in a deep sleep mode. This may advantageously extend/maximize the battery life of analyte sensor system 408. It is further contemplated that in implementations, upon interacting with display device 310, for example via NFC, analyte sensor system 408 may exit the storage mode.

In active mode, a low power mode (LPM) may still be used (e.g., to extend/maximize battery life), but RTC 350 may be activated/enabled. This may allow processor 420 to track time accurately and perform other clock-based functions while still allowing for power savings. For example, RTC 350 may be used to perform error recovery using time-based counters and interrupts. The following error recovery scenarios are provided by way of illustration. In one example, if no response messages are received from radio 425 for a given amount of time, processor 420 may reset radio 425. In another example, a periodic interrupt may be used where if logic of RTC 350 fails, analyte sensor system 408 can be reset by hardware logic. In additional implementations, if message or signal associated with wake source 435 (or AFE 410) is not received or fails, an interrupt (e.g., RTC interrupt) can be used to bring processor 420 out of LPM and perform communication functions.

Processor 420 may act as a system controller for subsystem 400 within analyte sensor system 408. For example, after initializing, radio 425 may enter a sleep state and wait for instruction from processor 420. AFE 410 may initialize to a default state and likewise wait for configuration instructions/commands from processor 420. Processor 420 may control resetting AFE 410 and/or radio 425 in case errors are detected. Processor 420 may also self-reset if internal error conditions are detected (e.g., using a hardware watchdog).

Subsystem 400 of analyte sensor system 8 may utilize a multi-chip (or multi-module) design, in which case a hardware communication bus may be used for the exchange of data among the various chips (or modules). Examples of viable options for the hardware communication bus include Inter-Integrated Circuit (I2C or I2C) and Serial Peripheral Interface (SPI). SPI may be used to achieve a reduction in powers as well as an increase in speed relative to I2C.

Wake source 435 and raw sensor data 430 may be used to maximize the battery life of analyte sensor system 408. AFE 410 may typically be used as a wake source for components of subsystem 400. Nevertheless, other wake sources may be utilized. During normal operation, AFE 410 may allow processor 420 to enter an energy efficient lower power mode (LPM). Wake source 435 can be used to signal processor 420 to exit LPM such that, e.g., processor 420 can execute operations not typically available during LPM. Wake source 435 may signal processor 420 in this manner periodically and trigger processor 420 to start processing or executing operations. Analyte sensor system 408 may include multiple processors, and as mentioned below with reference to FIG. 5, staged task processing may be implemented, in some cases in connection with wake source 435, such that not all processors are active simultaneously. This technique may reduce power consumption and hence extend battery life. By way of example, wake source 435 may first signal processor 420 to exit LPM and begin configuring the pertinent hardware and software of analyte sensor system 408 to initiate the transfer of raw sensor (analyte) data from AFE 410.

Raw sensor data 430 may include hardware that transfers sensor data gathered by sensor 405 from AFE 410 to processor 420. Such data may be referred to herein as raw sensor data or raw analyte data. Configuration 440 may be a two-way interface between processor 420 and AFE 410. In some cases, configuration 440 may be implemented using I2C, but SPI or another interface configuration may also be used. Processor 420 and radio 425 may likewise use a SPI and/or I2C bus for communication and data transfer. In some cases, additional hardware and software may be used to create an asynchronous interface between processor 420 and radio 425 when using synchronous protocols (e.g., SPI and the like).

Figure 5:
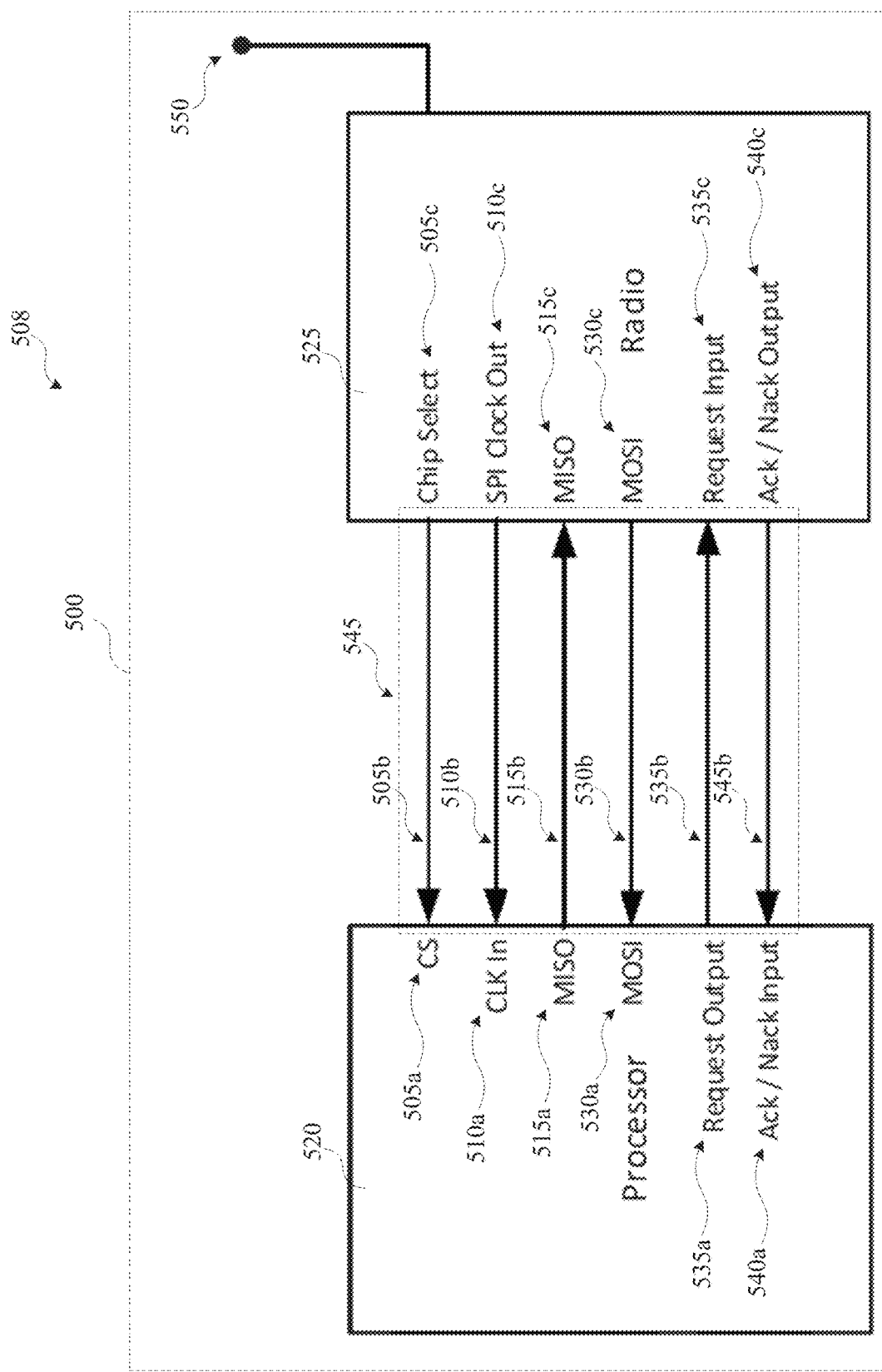
FIG. 5 is a block diagram illustrating aspects of an example analyte sensor system according to embodiments of the disclosure.

Turning now to FIG. 5, a block diagram illustrating potential aspects of analyte sensor system 508 is provided in accordance with embodiments of the present disclosure. The aspects of analyte sensor system 508 shown in FIG. 5 may be implemented within subsystem 500 of analyte sensor system 508. In particular, subsystem 500 includes processor 520 and radio 525 that may be modified to include a SPI bus and additional general purpose input/out (GPIO) relative to communication interface 445 and thus create asynchronous interface 545 that couples processor 520 to radio 525. Asynchronous interface 545 may in some cases be referred to as a message transport layer.

As shown in the example of FIG. 5, asynchronous interface 545 includes connection 505*b* that provides chip select (CS) output 505*c* of radio 525 to CS input 505*a* of processor 520. Further, asynchronous interface 545 includes connection 510*b* that provides SPI clock out 515*c* of radio 525 to CLK in 510*a* of processor 520. Asynchronous interface 545 includes connection 515*b* that provides MISO (multiple input single output) 530*a* of processor 520 to MISO input 530*c* of radio 525. Asynchronous interface 545 further includes connection 530*b* that provides MOSI (multiple output single input) output 530*c* of radio 525 to MOSI input 530*a* of processor 520. In addition, asynchronous interface 545 includes connection 535*b* that provides request output 535*a* of processor 520 to request input 535*c* of radio 525. Asynchronous interface 545 also includes connection 545*b* that provides ACK/NACK (acknowledgement/negative-acknowledgement) output 540*c* of radio 525 to ACK/NACK input 540*a* of processor 520.

Asynchronous interface 545 may provide an asynchronous communication link between processor 520 (which may be used to process analyte data) and a radio processor within radio 525 (e.g., a baseband processor). Further, asynchronous interface 545 may allow for the removal of a master/slave topology from the application layer logic. Asynchronous interface 545 may also allow for messages to be sent/received in an interrupt context, such that processor 520 and/or the radio processor remain in a low power mode until a complete message is ready to be communicated over the interface. Typically, messages sent by processor 520 use an ACK/NACK as well as a response packet to confirm/deny receipt of the message. With respect to subsystem 500, staged task processing may also be employed to limit the run-time of each of processor 520 and a processor within radio 525, so that there is as little run-time overlap as possible. This may reduce stress on battery 415 and minimize asynchronous messaging issues.

Returning again to FIG. 4, AFE 410 may sample raw analyte data from sensor 405 for a period of time (e.g., 5 minutes). During the sampling, processor 420 and a processor (e.g., baseband processor) within radio 425 may be held in low power mode (LPM). Once AFE 410 completes the sample, AFE 410 may send a signal to processor 420 indicating that processor 420 should exit LPM (i.e., should wake up). AFE 410 may then transfer the raw analyte data to processor 420 via configuration 440. AFE 410 may then re-enter LPM. Processor 420 may then process the raw analyte data (e.g., to generate an estimated glucose value) and store the processed analyte data. Processor 420 may then signal the processor of radio 425 via communication interface 445 to communicate the processed analyte data to radio 425. Processor 420 may subsequently enter LPM while waiting for radio 425 to connect to a display device (e.g., display device 310). Once such a connection is made, processor 420 may exit LPM, and the display device and processor 420 may exchange data, commands, and/or messaging via radio 425.

API 450 may be used to interface with devices remote from analyte sensor system 408 over various wireless protocols. One example of such a protocol is BLE. In this regard, API 450 may allow analyte sensor system 408 to be configured by a user of a display device (e.g., display device 310) running an application such as, for example, analyte sensor application 330. Analyte sensor application 330 may have been developed by the manufacturer of analyte sensor system 408 and/or display device 310, or may be developed by any individual or entity. In the case that the BLE standard is used to couple a display device to analyte sensor system 408, BLE Characteristics can be configurable according to system design parameters.

Figure 6:
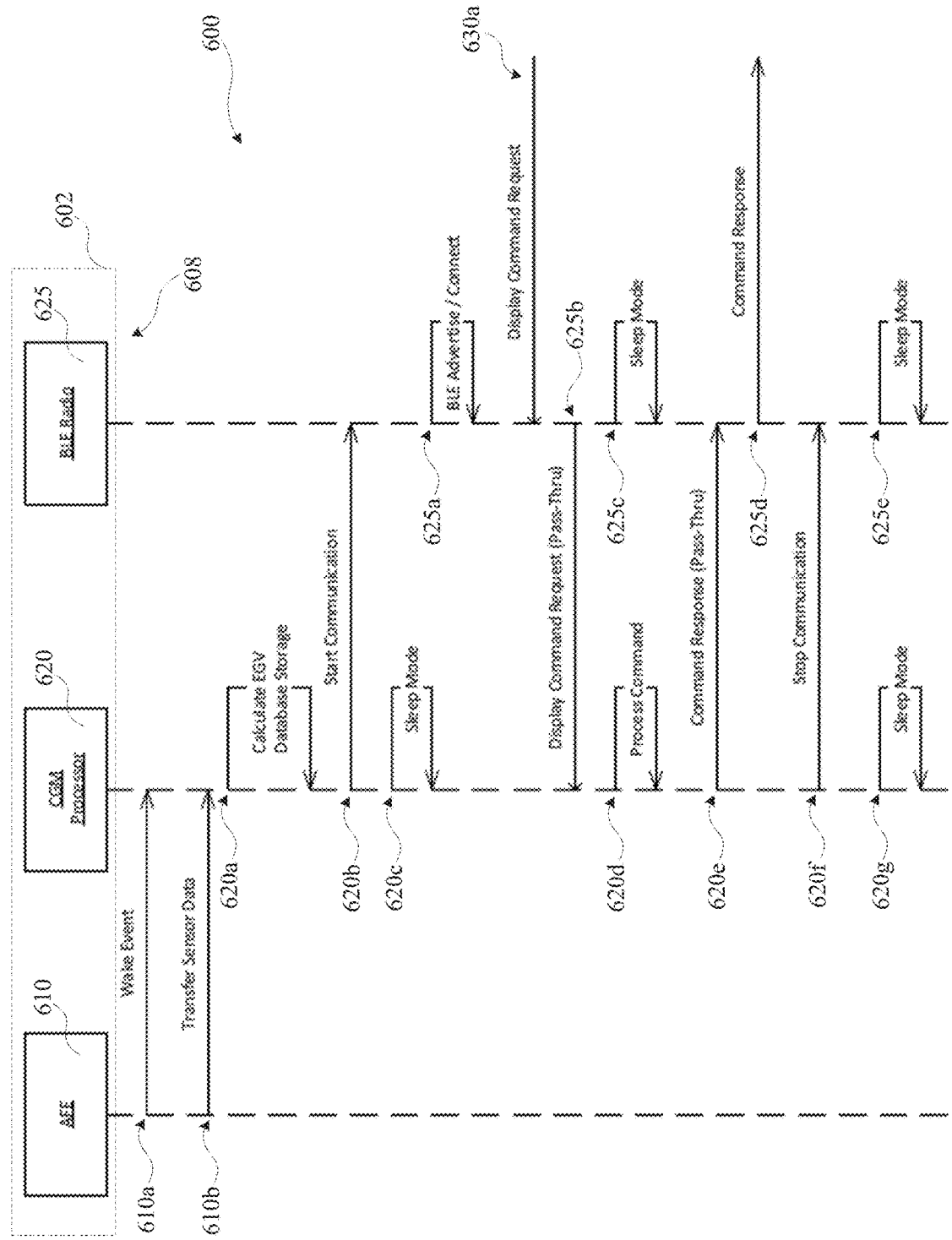
FIG. 6 is an operational flow diagram illustrating various operations that may be performed in accordance with embodiments of the disclosure.

FIG. 6 is an operational flow diagram illustrating various operations that may be implemented by, for example, analyte sensor system 408, in connection with embodiments of method 600 according to the present disclosure. For context purposes, FIG. 6 includes analyte sensor system 608 and subsystem 602. As shown, within subsystem 602, analyte sensor system 608 may include AFE 610, processor 620 (which may be used to process CGM data), and radio 625. Analyte sensor system 608 may be used to execute various operations shown in FIG. 6 in order to connect (e.g., wirelessly) to a remote device such as a display device (e.g., display device 310 or medical device 136). In this manner, analyte data may be transmitted to and processed by the display device. Further, analyte sensor system 608 and the display device may exchange messaging related to configuring the communication protocol used for connection between analyte sensor system and the display device. The operations shown in FIG. 6 may in some instances herein be described with reference to the BLE protocol, but it will in any case be appreciated by one of skill in the art upon studying the present disclosure that aspects shown in and described with reference to FIG. 6 can be applied to other communications protocols.

Before operation 610a, analyte sensor system 608 may be in LPM or a related mode in which power consumption is reduced, e.g., a "sleep mode". At operation 610a, AFE 610 signals processor 620 to initiate processing. For example, AFE 610 can signal processor 620 with a wake event that instructs processor 620 to exit a low power mode. As alluded to above, AFE 610 may act as a wake source, and operation 610a may correspond to wake source 435 referenced in FIG. 4. At operation 610b, AFE 610 passes sensor data (e.g., raw analyte or sensor data) to processor 620. In example implementations in which the analyte data relates to glucose data, processor 620 may be referred to as a continuous glucose monitor (CGM) processor.

Having been signaled to initiate processing (e.g., at operation 610a), processor 620 may, at operation 620a, processor the sensor data passed thereto at operation 610b. For example, as referenced in FIG. 6, processor 620 can calculate an estimated glucose value (EGV) from the sensor data. Processor 620 can also store the sensor data and/or another value derived therefrom (e.g., EGV) in storage and/or a database (e.g., storage 365 shown in FIG. 3B, which in some cases is flash memory). At operation 620b, processor 620 may signal radio 625 (which may in some cases be a BLE radio) to start communication. At operation 620c, processor 620 may then enter LPM or a related mode in which power consumption is reduced, e.g., a "sleep mode". In response to the signal to start communication send at operation 620b, radio 625 may at operation 625a advertise and/or connect to a display device. Examples of advertisement messaging and associated connect/disconnect protocols will be described in further detail herein.

After advertisement/connection per operation 625a, radio 625 may at operation 630a receive request signaling (e.g., a command request). The request signaling may be received from a display device and may be a request for the transmission of analyte data, and/or may relate to various configuration parameters of analyte sensor system 608 associated with advertisement and/or data transmission. In response to receiving the signaling, at operation 625b radio 625 may pass the signaling to processor 620. This may be done using interface 445 or 545 (e.g., a message transport layer). In other words, radio 625 may be configured to pass such signaling through to processor 620 using a message transport layer such that, for example, analyte sensor system 608 does not appear to be a multi-chip system to a display device sending the signaling. After passing (at operation 625b the signaling to processor 620, at operation 625c radio 625 may enter LPM or a related mode in which power consumption is reduced, e.g., a "sleep mode".

At operation 625d, after receiving the request signaling from radio 625 (operation 625b), processor 620 may process the signaling to generate response signaling (e.g., a command response). The response signaling may be passed to radio 625 at operation 620e. This may be done using interface 445 or 545 (e.g., a message transport layer). In other words, processor 620 may be configured to pass such signaling through to radio 625 using a message transport layer. Upon receiving the response signaling (sent at operation 620e), radio 625 may exit LPM or the related mode (entered at operation 625c) and send the response signaling to the display device. In short, by way of example, after receiving (at operation 630a a request from a display device for analyte data, analyte sensor system 608 can transmit response signaling (at operation 625d.

At operation 620f, processor 620 signals radio 625 to stop communication. In this manner, after sending the response signaling (at operation 625d, radio 625 may close the connection with the display device and, at operation 625e, enter LPM or the like. Likewise, processor 620 may, at operation 620g, enter LPM or the like after signaling radio 625 to stop communication. Analyte sensor system 608 may remain in LPM or the like until AFE 610 subsequently signals processor 620 to re-imitation the implementation of various of the above-described operations.

With the above description of aspects of the presently disclosed systems and methods for wireless communication of analyte data, a number of specific improvements will now be provided. It will be appreciated by one of skill in the art upon studying the present disclosure that these improvements may be implemented using features and combinations of features of the example configurations described above, whether or not explicit reference is made to the same.

F. Authentication

In scenarios involving the connection of two devices over a network (wireless or otherwise), authentication may be used in attempt to prevent unauthorized devices from making a connection. For example, where sensitive data is being exchanged, authentication can be used in attempt to prevent unauthorized devices or entities from gaining access to the data. In this regard, authentication protocols can be employed to establish or validate the identity of connecting devices.

Figure 7A:
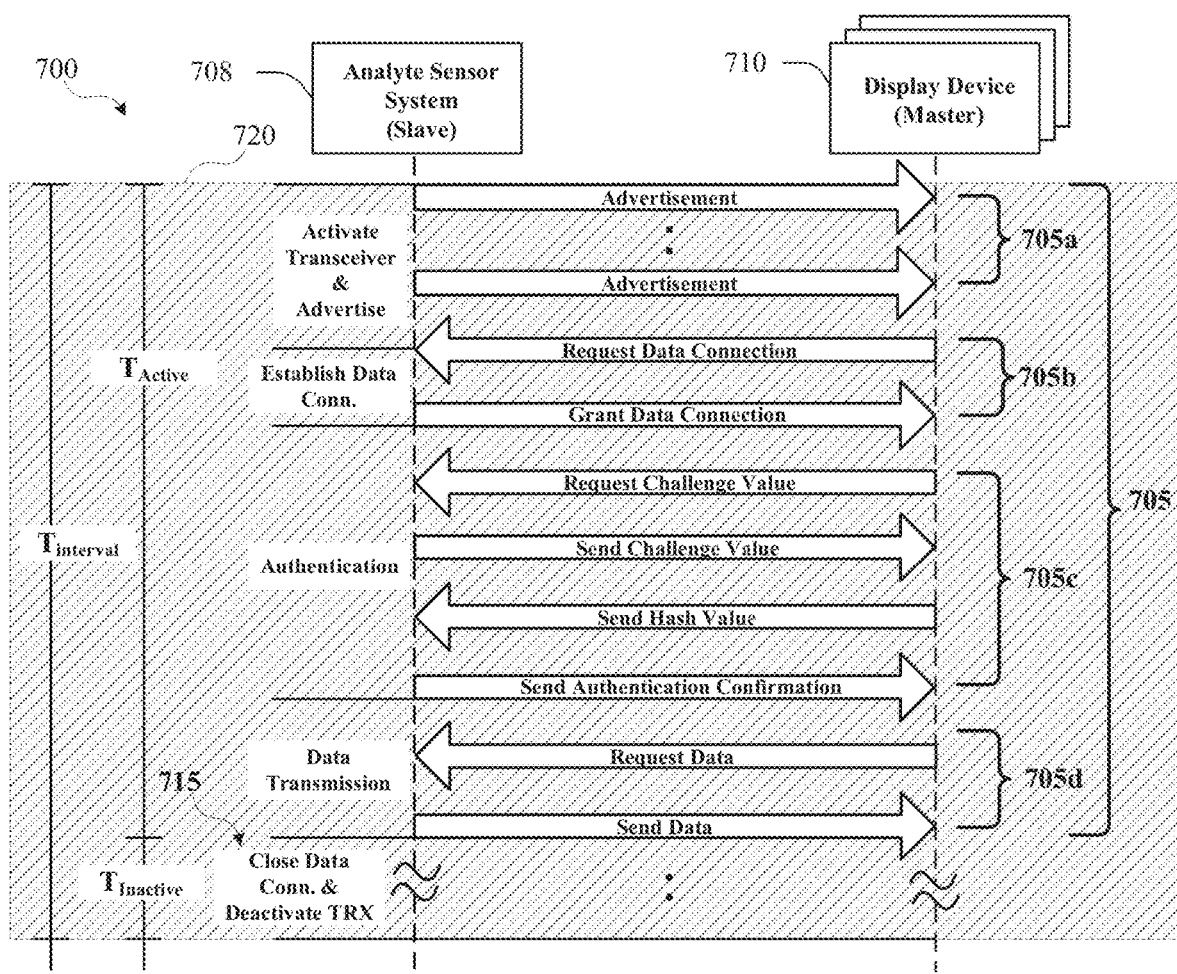
FIG. 7A is an operational flow diagram illustrating various operations that may be performed in accordance with embodiments of the disclosure.

FIG. 7A is an operational flow diagram illustrating various operations that may be performed in connection with embodiments of method 700 for wireless communication of analyte data between analyte sensor system 708 and display device 710, as well as in connection with embodiments of related systems, apparatuses, and devices. In some instances, method 700 may be used in connection with authenticating display device 710 and/or analyte sensor system 708 (e.g., in a two-way authentication), such that analyte data may be exchanged under authorized conditions.

The various tasks performed in connection with the procedure illustrated in FIG. 7A may be performed, for example, by a processor executing instructions embodied in non-transitory computer-readable medium. The tasks or operations performed in connection with the procedure may be performed by hardware, software, firmware, or any combination thereof incorporated into one or more of computing devices, such as one or more of analyte sensor system 708 and display devices 710. It will be appreciated upon studying the present disclosure that the procedure may include any number of additional or alternative tasks or operations. The operations shown by way of example in FIG. 7A need not be performed in the illustrated order, and the procedure may be incorporated into a more comprehensive procedure or process having additional functionality not described in detail herein with specific reference to FIG. 7A.

In some examples described below, the analyte values are glucose values based on one or more measurements made by analyte sensor 10 (with reference to FIGS. 1A, 2A, and 2B) and/or sensor 405 (with reference to FIG. 4) for illustration purposes. Nevertheless, it should be understood upon studying the present disclosure that the analyte values can be any other analyte value described herein. The wireless data communication between analyte sensor system 708 and one or more of display devices 710 may happen periodically, at times separated by an update interval denoted "$T_{interval}$" that may correspond to a time duration between two consecutive wireless communication sessions between the transceiver 360 of analyte sensor system 708 and transceiver 320 of display device 710 (with reference to FIG. 3B). Alternatively or additionally, the update interval may be thought of as a period of obtaining and sending a recently measured glucose value. Transmitting advertisement signals or messages, establishing a data connection (e.g., a communication channel) and requesting and sending data may occur during wireless communication sessions each lasting an active time or period denoted "$T_{Active}$" within an update interval $T_{interval}$. One caveat here is that $T_{interval}$ and/or $T_{Active}$ can vary as between sessions. In between two consecutive wireless communication sessions, components of analyte sensor system 708 (e.g., transceiver 360) may enter LPM or a like mode, such as an inactive or sleep mode for an inactive period denoted as "$T_{Inactive}$". This may enable the conservation of battery life and/or reduce peak voltage requirements, for example.

Accordingly, in some authentication and connection schemes used for the communication of analyte data, analyte sensor system 708 may periodically connect to display device 710. For example, communication session 720 may implement one such authentication and connection scheme. More specifically, as shown in FIG. 7A, communication session 720 may be implemented during a time interval $T_{interval}$. As alluded to above, $T_{interval}$ may include an active portion corresponding to $T_{Active}$ and an inactive portion corresponding to $T_{inactive}$. Generally speaking, during $T_{Active}$, analyte sensor system 708 and display device 710 are connected and actively exchanging messaging (e.g., pursuant to operation 705 and/or sub-operations thereof), though there may be periods during $T_{Active}$ during which analyte sensor system 708 enters LPM or the like, as described above.

In terms of connecting, typically, the analyte sensor system may transmit one or more advertisement messages at operation 705 during communication session 720. An advertisement message may be considered as an invitation for display device 710 to establish a data connection with analyte sensor system 708 (e.g., via transceiver 360). The transmitted advertisement messages may then be received at display devices 710 (e.g., via transceiver 320). For purposes of authentication, the analyte sensor system may share an identification number with the display device, where the identification number is associated with the analyte sensor system.

In some embodiments illustrated by way of example in FIG. 7A, it is assumed that analyte sensor system 708 should engage in an initial system setup because, for example, analyte sensor system 8 has been recently turned on for the first time and/or is currently not paired with any display devices 710. Typically, a user of display device 710 can identify a new or never-been used analyte sensor system 708 to be paired with display device 710 by entering identification information (e.g., a serial number) associated with analyte sensor system 708 via a custom application (e.g., application 330) running on display device 710 using a GUI 340 that may be presented on display 345 (e.g., a touchscreen display).

As alluded to above, during communication session 720, an authentication procedure may need to be performed in connection with a data connection process corresponding to operation 705*b* and/or a data transmission process corresponding to operation 705*d*. To establish a data connection with analyte sensor system 708, display device 710 may listen or scan continuously until an advertisement message transmitted by analyte sensor system 708 is received. Once analyte sensor system begins transmitting advertisement messages at operation 705*a*, it may take one, two, or more advertisement messages for display device 710 to receive an advertisement message and responds thereto. In some embodiments, analyte sensor system 708 stops sending additional advertisement messages once one of display devices 710 receives an advertisement message and responds thereto, for example, via an acknowledgement and/or by sending a connection request (e.g., as part of operation 705*b*). In other embodiments, analyte sensor system may continue to send additional advertisement messages even after receiving a response from one display devices 710, so that another of display devices 710 may receive and respond to one of the additional advertisement messages.

Accordingly, operation 705*b* may involve analyte sensor system receiving a connection request from display device 710 and responding thereto by granting or denying the request. If analyte sensor system 708 grant the connection request, an acknowledgement or other message may be transmitted to display device 710 as part of operation 705*b*. Then, a data connection between analyte sensor system 708 and display device 710 may be established. Nevertheless, according to operation 705*c*, an authentication procedure may be employed before data is actually exchanged at operation 705*d*. Authentication may involve the exchange of various messages, including challenge and hash values and signaling related thereto, between the analyte sensor system and the display device, in accordance with a one-way or two-way handshake process.

For example, as part of operation 705*c*, display device 710 may request a challenge value from analyte sensor system 708. In response to the request, analyte sensor system 708 sends a challenge value to display device 710. The display device may then generate a hash value based on both the challenge value received from analyte sensor system 708 and identification information associated with analyte sensor system 708. As yet another part of operation 705*c*, display device may then transmit the hash value to analyte sensor system 708. Display device 710 may transmit additional information as well (e.g., information related to the type of display device 710, whether display device is medical device or a personal electronic device, for example).

Analyte sensor system 708 (e.g., via transceiver 360) receives the hash value from display device 710, decodes the identification information from the hash value, and verifies that the received identification information matches identification information associated with the analyte sensor system 708, which may have been previously stored in storage 365 of analyte sensor system 708, such as during manufacturing/setup of analyte sensor system 708. Analyte sensor system 708 may also validate the hash value received from display device 710 by comparing the received hash value to a mirror hash value analyte system sensor 708 generated (e.g., based on the challenge value send previously). Upon verification, analyte sensor system 708 may send a signal confirming a successful authentication to display device 710. Once authenticated, the analyte sensor system 8 and display device 110, 120, 130, 140 may exchange information to determine how data will be exchanged (e.g., a specific frequency, time slot assignment, encryption, etc.). FIG. 12C also illustrates aspects of the above-described handshake process.

The above-described process may be thought of as a one-way authentication procedure. During a two-way authentication procedure (not shown specifically in FIG. 7A, but see, e.g., FIG. 12B), additional operations may take place as part of operation 705c. For example, in addition to the hash value transmitted from display device 710 to analyte sensor system 708, display device 710 can also send a new challenge value to analyte sensor system 708. Then, analyte sensor system 708 may generate an additional hash value using the new challenge value received from display device 710, and transmit the additional hash value back to display device 710. Upon receiving the additional hash value, display device 710 can validate the additional hash value. In example implementations, the validation of the additional hash value received from analyte sensor system 708 may be performed by display device 710 by comparing the received additional hash value to a mirror hash value that display device 710 generated (e.g., based on the new challenge value sent previously). In this manner, two-way authentication can be performed between analyte sensor system 708 and display device 710. Following authentication, data can be exchanged with the understanding that the data is being received by and from a valid (or approved) device. It will be appreciated that many various of operation 705c and sub-operations thereof are contemplated in the present disclosure. For example, analyte sensor system 708 and display device 710 may reverse roles with respect to operation 705c. That is, operation 705c may be initiated by analyte sensor system 708 requesting a challenge value from display device 710, thus triggering the above-described operations but in the reverse direction as between analyte sensor system 708 and display device 710.

Further, communication session 720 may also include exchanging an application key between analyte sensor system 708 and display device 710. For example, in the above-mentioned authentication process, the identification information associated with the analyte sensor system 708 may be used as an application key in order to encrypt data and other signaling transmitted between analyte sensor system 708 and display device 710. By the exchange of challenge and hash values described in connection with operation 705c, such an application key may effectively be shared between analyte sensor system 708 and display device 710. Thus, in embodiments, of the present disclosure, the application key may be used for both authentication and encryption purposes. The application key may be a random number in some cases. In some instances, the application key may literally be exchanged (whether encrypted or unencrypted) between analyte sensor system 708 and display device 710 (e.g., as a challenge value etc.). In other cases, the actual application key is not exchanged, but by exchanging the challenge and hash values, the application key can be derived respectively by the analyte sensor system 708 and display device 710. A such, the application key may be used for example by analyte sensor system 708 to encrypt analyte data for transmission to display device 710, and display device 710 may use the application key to decrypt the received analyte data. Of course, other exchanged information may likewise be encrypted.

In example deployments, the application key may be generated at a software/application level of analyte sensor system 708 and/or display device 710. In some such deployments, only the application key may be exchanged (i.e., no exchange of the hash and challenges) and then used for authentication and encryption. The application key may be, for example, a randomly generated number. Alternatively, the software-generated application key may be exchanged in addition to the hash/challenge values, for authentication and encryption purposes. Encryption, for example as described above, may be performed concurrently during authentication, or after authentication, or both, in various embodiments.

The application key, in example embodiments, may be obtained from server system 334. In some such embodiments, storage 334b may include identification information associated with analyte sensor system 708 (e.g., an identification number) and the application key. Display device 710 may request such information by sending a message to server system 334, where the message includes at least some of the identification information. By way of example, display device 710 may send an advertisement message to server system 334 that includes an identification number for a specific analyte sensor system 708 (this identification number may have been received through at least a partial pairing with analyte sensor system 708). In response, server system 334 may provide display device 710 with the application key for the relevant analyte sensor system 708. After receiving the application key, display device 710 may use the key to authenticate/communicate with analyte sensor system 708 and decrypt encrypted information received therefrom (and also encrypt information being sent thereto).

In some cases, analyte sensor system 708 may contain a mapping (e.g., in storage 365) that associates particular application keys with particular display devices 710 based on the identification information of analyte sensor system 708. As such, authentication can be performed based on the application key received by display device 710 from server system 334, and the application key can be used for encryption/decryption of analyte data sent by analyte sensor system 708. In this way, authorization regarding communications (including sharing of encrypted data) between analyte sensor 708 and a given display device 710 can be managed/established.

Alternatively or in addition, exchanging the application key may be done directly between analyte sensor system 708 and display device 710 using WiFi or NFC. Exchanging the application key may involve sharing the application key between analyte sensor system 708 and display device 710 in a secluded and/or safe area (such as in a user's home) so as to avoid interception by a foreign or unknown device. Additionally, the application key may in turn be encrypted with an additional key for added security. Characteristics of the key may be based on one or more of the type of data to be encrypted with; the network environment; and user settings. By way of example, the encryption method applied using the application key may be based on the Advanced Encryption Standard (AES) 128. Alternatively or in addition, a proprietary encryption method may be used. Such an encryption method may be run on display device 710, including in some cases on an application (e.g., application 330) running on display device 710.

The complexity of the encryption scheme employed may be based on the level of desired security. For example, different levels of complexity may be employed for different types of data. A more complex encryption scheme may be employed for the exchange of analyte data (e.g., estimated glucose values) as compared to, for example, calibration data or time synchronization data. Characteristics of the application key may also be varied in different scenarios. By way of example, the length of the application key may be chosen based on the amount of security desired and/or on the encryption scheme or protocol being employed. The encryption scheme in some cases may employ salts that may be used in connection with the exchange of hash values, and the salts may be encrypted and exchanged between analyte sensor system 708 and display device 710.

The application key may also be modified from time to time, e.g., on an event-triggered, random, and/or periodic basis. This may be done responsive to, for example, the passage of a predetermined amount of time; analyte sensor system 708 of a subsystem thereof or display device 710 being restarted; a trigger related to another device (e.g., a rouge device) attempting to connect to analyte sensor system 708; and/or user input. For example, the application key may be configured to expire after the passage of a predetermined amount of time and may be refreshed or renewed thereafter. Alternatively or in addition, if analyte sensor system 708 and/or display device 710 restarts or experiences an interruption, a new application/encryption key may be generated and shared between analyte sensor system 708 and display device 710. In some cases, the application key may be modified according to a key rotation scheme. Moreover, the frequency with which the application key may be modified may be varied according to the level of desired security (e.g., with more frequent modification corresponding to increased level of security).

With further reference to FIG. 7A, after completion of the authentication process according to operation 705c, analyte sensor system 708 and connected display device 710 engage in data communication at operation 705d, during which connected display device 710 may request and receive desired information (e.g., analyte data, control information, identification information, and/or instruction) from analyte sensor system 708. When data communication at operation 705d is completed, the data connection may be terminated at operation 715 (e.g., by closing the established communication channel). At this point, transceiver 360 and/or processor 380 of analyte sensor system 708 (or with reference to FIG. 4, radio 425 and processor 420) can be deactivated. This may be done, for example, by causing transceiver 360 and/or processor 380 (etc.) to enter a LPM mode or the like, e.g., a sleep or inactive mode. In some embodiments, transceiver 360 (or radio 425) is completely powered down during a sleep mode. In other embodiments, transceiver 360 is in a low power mode using only a small fraction (e.g., 1-10%) of the normal current/power. In FIG. 7A, this period generally corresponding to operation 715 is denoted as $T_{Inactive}$.

Figure 7B:
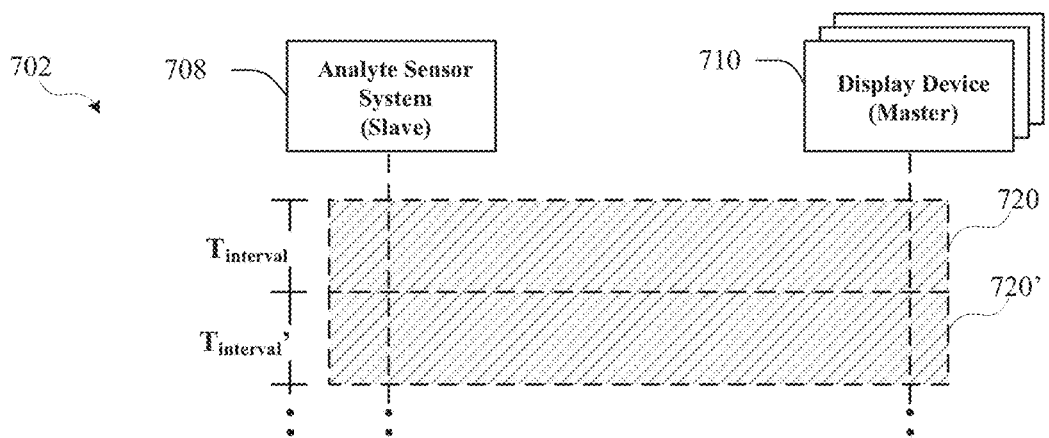
FIG. 7B is an operational flow diagram illustrating various operations that may be performed in accordance with embodiments of the disclosure.

FIG. 7B provides, by way of illustration, an example of typical intermittent communications schemes between analyte sensor system 708 and display devices 710, according to method 702 for wireless communication of analyte data between analyte sensor system 708 and display device 710. As shown in FIG. 7B, method 702 involves multiple occurrences of communication session 720. Communication session 720 occurs, having a length in time of $T_{interval}$. Subsequently, communication session 720' occurs, having a length in time of $T_{interval}'$, which may be the same as or different from $T_{interval}$, in various embodiments described herein.

It will thus be appreciated that in typical intermittent communications schemes between analyte sensor system 708 and display devices 710, the above-mentioned connection and authentication process may be repeated periodically (e.g., according to a time denoted by $T_{interval}$) for each subsequent data communication. For example, the process may involve the exchange of up to 20 or more messages before any data (e.g., analyte values) are communicated. Furthermore, the process may restart if exchanged messages fail or packets are dropped. This may result in drain of the battery of analyte sensor system 708.

Accordingly, aspects of the present disclosure include an improved authentication scheme. The improved authentication scheme of the present disclosure reduces the amount of messaging exchanged between analyte sensor system 708 and display device 710 connecting thereto, while maintaining a sufficient level of security for analyte and other data communicated between analyte sensor system 708 and display device 710. In this manner, the complexity and network load involved with communications between analyte sensor system 708 and display device 710 may be reduced, thus increasing the overall reliability of and power consumption involved with such communications. Generally, the improved authentication scheme involves stepping through the above-mentioned authentication process of communication session 720 (e.g., at operation 705c) that uses at least an application key for an authentication and connection between analyte sensor system 708 and display device 710, as well as for data encryption in embodiments, and then bypassing the authentication process in subsequent connections and/or communication sessions.

Figure 7C:
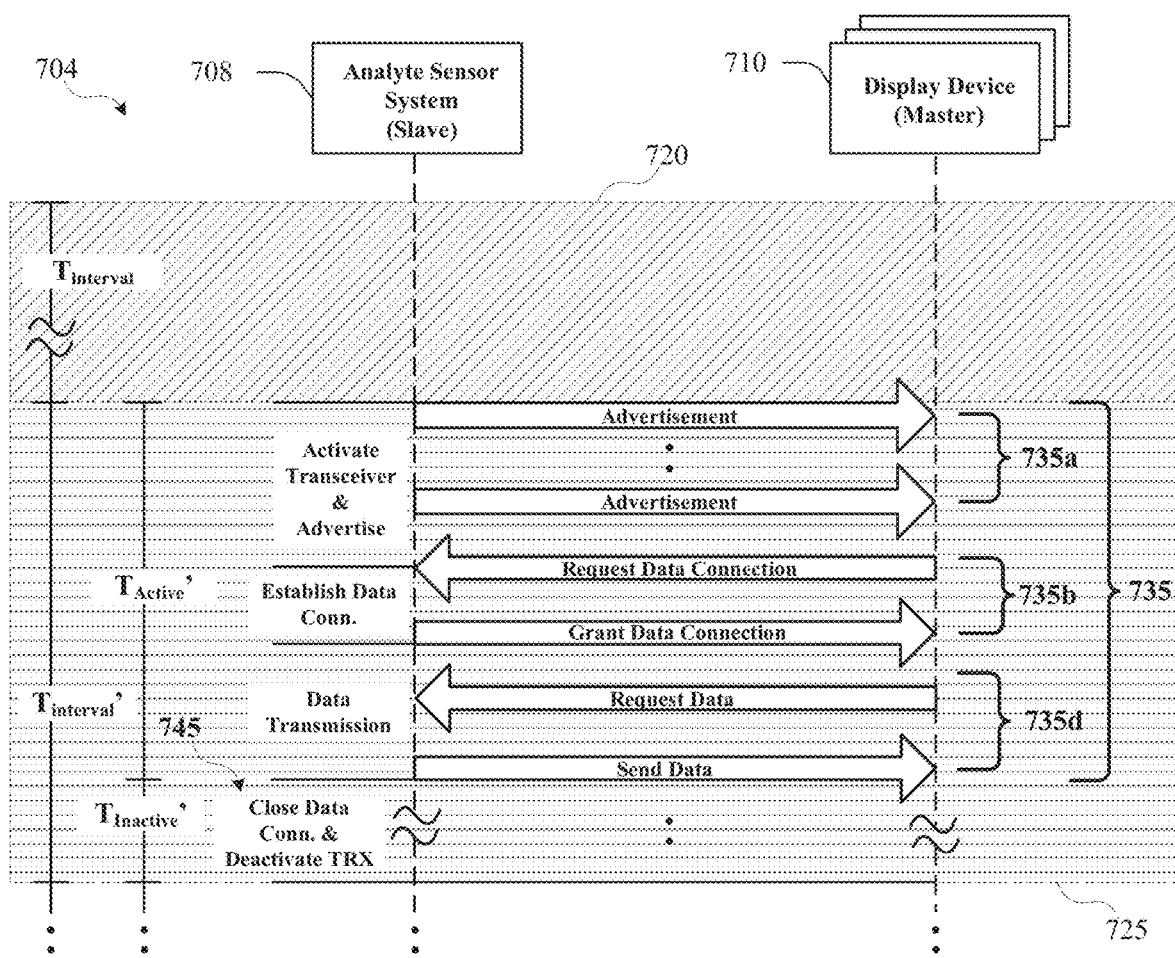
FIG. 7C is an operational flow diagram illustrating various operations that may be performed in accordance with embodiments of the disclosure.

Referring now to FIG. 7C, method 704 for wireless communication of analyte data between analyte sensor system 708 and display device 710 is illustrated in connection with implementations of the improved authentication scheme alluded to above. Method 704 includes establishing a first connection between analyte sensor system 708 and display device 710. This may occur in connection with communication session 720. As such, establishing the first connection can include performing a two-way authentication between analyte sensor system 708 and display device 710 (e.g., based on the exchange of information related to the application key, at operation 705c for example).

Method 704 also includes establishing a second connection between analyte sensor system and display device 710. As shown in FIG. 7C, in embodiments, this may occur in connection with communication session 725. More specifically, as shown in FIG. 7C, communication session 725 may be implemented during a time interval $T_{interval}'$, which may be the same as or different from $T_{interval}$. $T_{interval}'$ may include an active portion corresponding to $T_{Active}'$ and an inactive portion corresponding to $T_{Inactive}'$. During $T_{Active}'$, communication session 725 may involve operation 735 and sub-operations thereof.

Here it should be noted that in communication session 725, establishing the second connection need not include the authentication process that may be included in communication session 720 (e.g., at operation 705c). Rather, at operations 735a and 735b, advertisement and connection may occur, and upon establishing the second connection in this manner, method 704 includes data transmission at operation 735d. More specifically, at operation 735d, analyte sensor system 708 may transmit, for example, encrypted analyte values and other data to display device 710, in response to a request for data sent by display device 710. The encrypted analyte value may have been encrypted using the application key used for authentication in the authentication process in communication session 720, and/or may involve the use of encryption key. Encrypting the transmissions using an application key can maintain privacy/security even in the absence of typically authentication procedures being performed during communication session 725. In other words, in communication session 725, the above-described authentication process, including the two-way authentication, can be bypassed. In this manner, the number of messages exchanged in establishing the second connection (and hence the power consumption) may be reduced. Moreover, the application key may also be used to decrypt encrypted data exchanged between analyte sensor 708 and display device 710. For example, during operation 735d, display device 710 may decrypt encrypted data (e.g., encrypted analyte data, which may include encrypted glucose data) received from analyte sensor 708, and vice versa.

When data communication at operation 735d is completed, the data connection may be terminated at operation 745. At this point, transceiver 360 and/or processor 380 of analyte sensor system 708 (or with reference to FIG. 4, radio 425 and processor 420) can be deactivated. In FIG. 7C, this period generally corresponding to operation 745 is denoted as $T_{Inactive}'$.

Figure 12A:
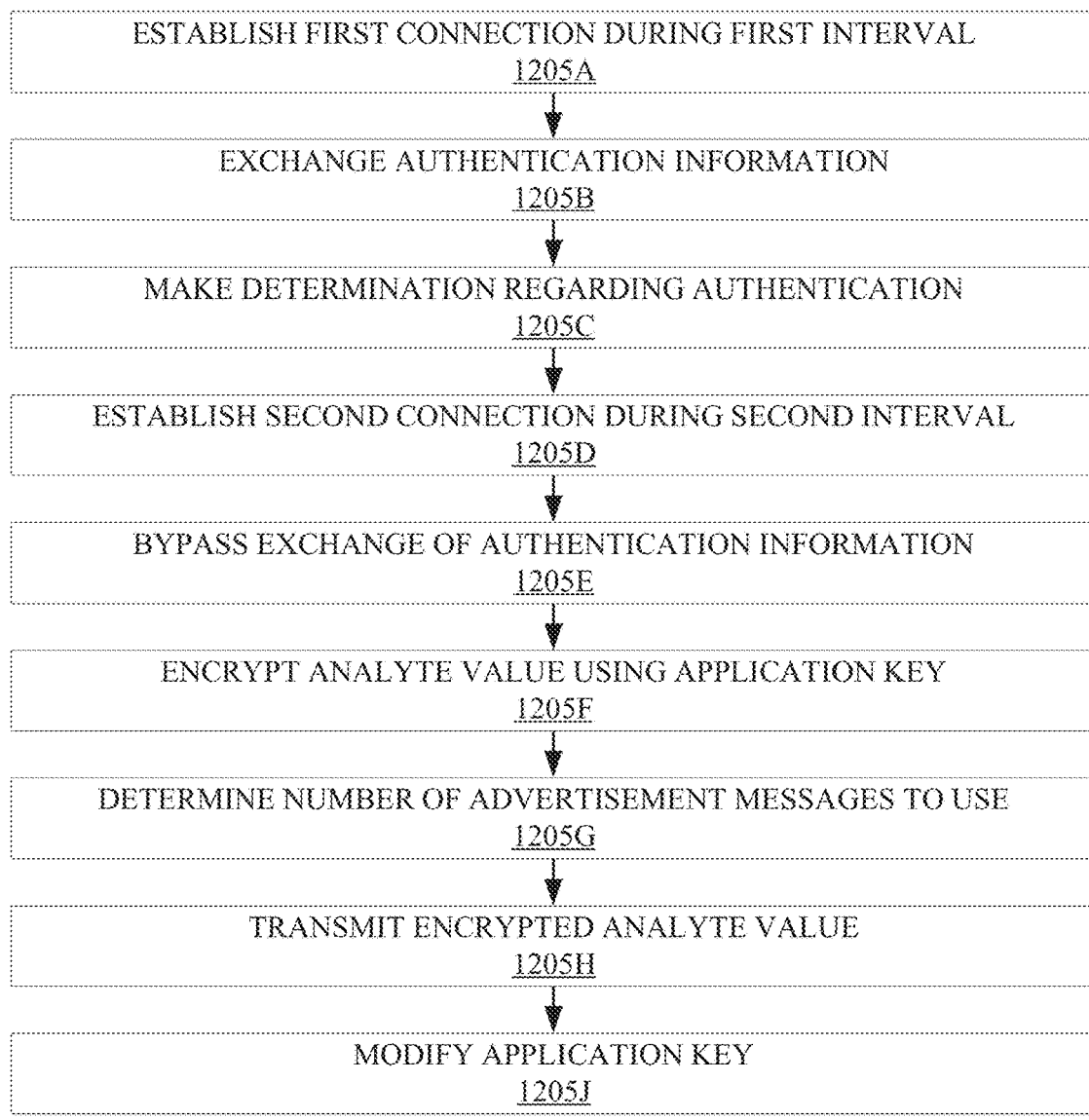
FIG. 12A is an operational flow diagram illustrating various operations that may be performed in accordance with embodiments of the disclosure.

Referring now to FIG. 12A, example implementations of features of various methods such as, for example, methods 704, 706, 712, 714, 716, 718, 722, 724, and 726 are illustrated. One such example implementation includes aspects of method 1200 for wireless communication of analyte data. As shown in FIG. 12A, at operation 1205A, method 1200 includes establishing a first connection during a first interval. For example, the first connection can be established between analyte sensor system 708 and display device 710. Operation 1205A may in instances correspond to operations 705a and/or 705b or the like, with reference to FIG. 7A. During the first connection, at operation 1205B, method 1200 involves exchanging between analyte sensor system 708 and display device 710 information related to authentication. Operation 1205B may in examples correspond to operation 705c or the like. At operation 1205C, method 1200 involves making a determination regarding whether authentication was performed during the first interval.

Figure 12B:
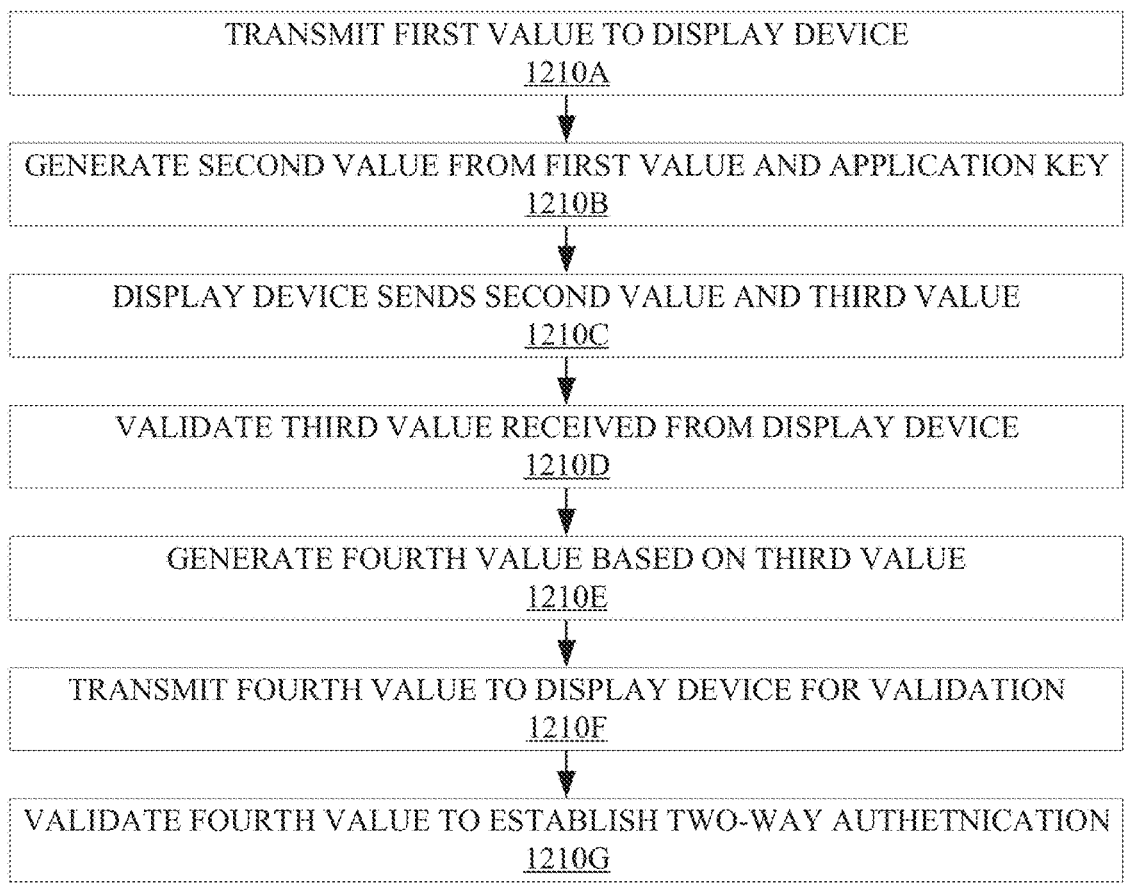
FIG. 12B is an operational flow diagram illustrating various operations that may be performed in accordance with embodiments of the disclosure.
Figure 12C:
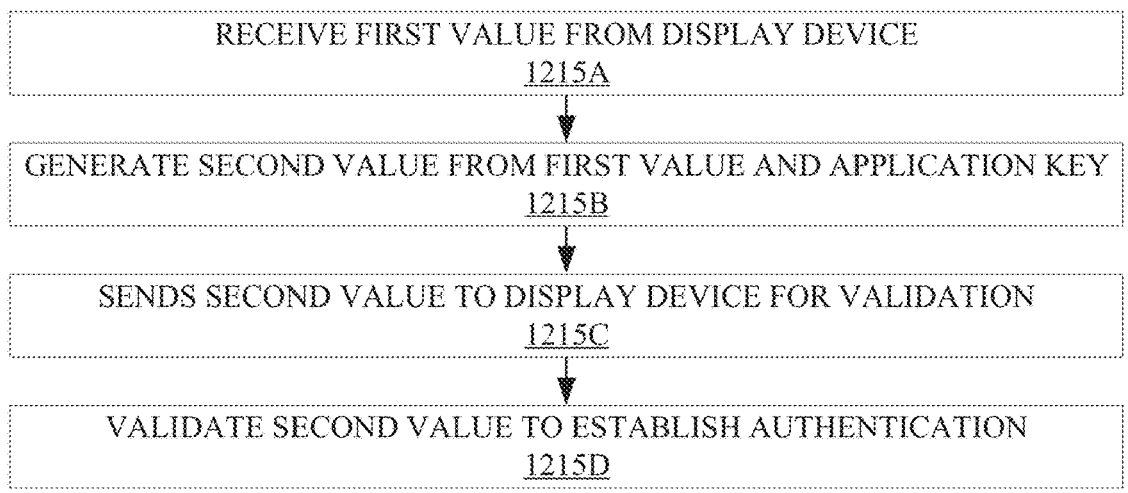
FIG. 12C is an operational flow diagram illustrating various operations that may be performed in accordance with embodiments of the disclosure.

Referring now to FIG. 12B, method 1202a illustrates example aspects of a two-way authentication procedure. Further, method 1202a illustrates example implementations of operation 1205B, in which information related to authentication is exchanged as part of a two-way authentication. At operation 1210A, method 1202a includes analyte sensor system 708 transmitting a first value to display device 710. The first value may, for example, be a random or predetermined value, and may in some cases be referred to as a challenge value. Operation 1210B involves display device 710 generating a second value from the first value and an application key. For example, the second value may be a hash of the first value and the application key. At operation 1210C, display device 710 sends the second value and a third value to analyte sensory system 708. The third value may, for example, be a random or predetermined value, and may in some cases be referred to as a challenge value. At operation 1210D, method 1202a involves analyte sensor system 708 validating the second value. Operation 1210E entails analyte sensor system 708 generating a fourth using third value. For example, the third value may be hashed with the application key to generate the fourth value. Operation 1210F involves transmitting the fourth value to display device 710 for validation. At operation 1210G, display device 710 validates the fourth value in order to establish or complete the two-way authentication. It will be noted here that although the operations of method 1202a are described in terms of analyte sensor system 708 and display device 710 performing various tasks, the roles of analyte sensor system 708 and display device 710 can be reversed without departing from the scope of the present disclosure.

Referring now to FIG. 12C, method 1202b illustrates example aspects of a one-way authentication procedure. In that regard, method 1202b illustrates example implementations of operation 1205B, in which information related to authentication is exchanged as part of a one-way authentication. At operation 1215A, method 1202b includes analyte sensor system 708 receiving a first value from display device 710. The first value may, for example, be a random or predetermined value, and may in some cases be referred to as a challenge value. Operation 1215B involves analyte sensor system 708 generating a second value from the first value and an application key. For example, the second value may be a hash of the first value and the application key. At operation 1215C, analyte sensor system 708 sends the second value to display device 710. At operation 1215D, method 1202a involves analyte sensor system 708 validating the second value in order to establish or complete the one-way authentication. It will be noted here that although the operations of method 1202b are described in terms of analyte sensor system 708 and display device 710 performing various tasks, the roles of analyte sensor system 708 and display device 710 can be reversed without departing from the scope of the present disclosure.

Referring again to FIG. 12A, at operation 1205D, method 1200 may involve, during a second interval, establishing a second connection, between analyte sensor system 708 and display device 710. Operation 1205D may in examples correspond to operation 735b or the like, with reference to FIG. 7C. At operation 1205E, method 1200 may involve, bypassing the exchanging of information related to authentication performed during the first connection. At operation 1205F, embodiments of method 1200 involve using an application key to encrypt an analyte value and generate an encrypted analyte value. At operation 1205H, method 1200 involves analyte sensor system 708 transmitting the encrypted analyte value to display device 710, if the determination of operation 1205C indicates that authentication was performed during the first interval. Operation 1205H may correspond to operation 735d, with reference to FIG. 7C. At operation 1205J, embodiments of method 1200 involve modifying the application key. By way of example, operation 1205J may be done responsive to one or more of the passage of a predetermined amount of time, analyte sensor system 708 or display device 710 being restarted, a trigger related to another device attempting to connect to analyte sensor system 708, and user input (e.g., received via GUI 340).

Figure 7D:
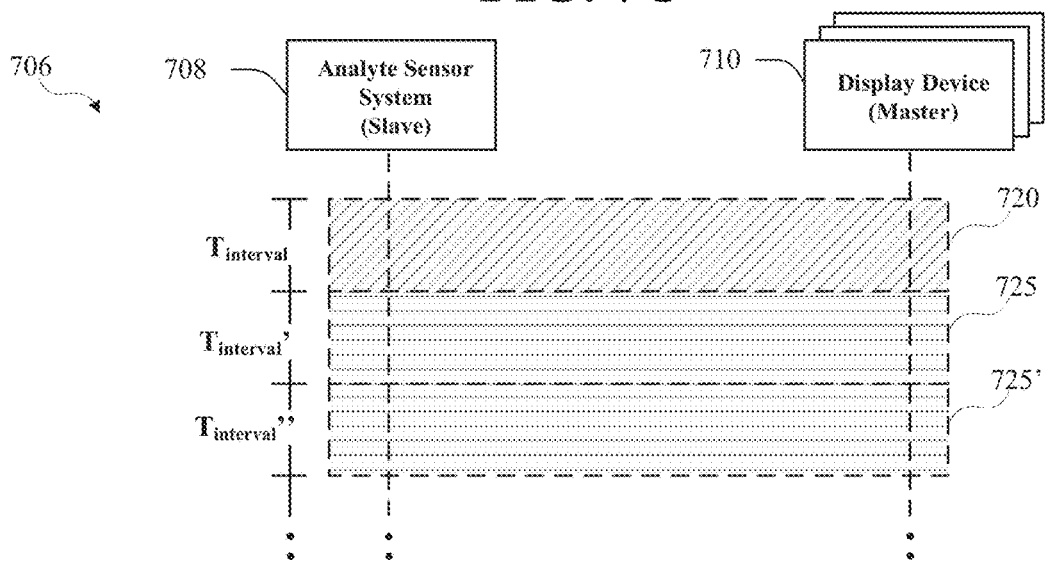
FIG. 7D is an operational flow diagram illustrating various operations that may be performed in accordance with embodiments of the disclosure.

FIG. 7D illustrates an example implementation of method 706 for wireless communication of analyte data between analyte sensor system 708 and display device 710 in connection with implementations of the improved authentication scheme discussed to above. As shown in FIG. 7D, method 706 involves communication session 720. Communication session 720 occurs, having a length in time of $T_{interval}$. Subsequently, an instance of communication session 725 occurs, having a length in time of $T_{interval}'$, which may be the same as or different from $T_{interval}$, in various embodiments described herein. Then, an instance of communication session 725' occurs, having a length in time of $T_{interval}''$, which may be the same as or different from $T_{interval}'$, in various embodiments described herein. Communication session 725' may be substantially similar to communication 725, aside from potentially having a different interval length.

By following communication session 720 with one or more instances of communications 725, 725', etc., the overall number of messages exchanged during communication of analyte data (and hence the power consumption) may be reduced. It will be noted here, however, that in some cases, method 706 may involve reverting back to communication session 720 after implementing communication session 725, 725', etc. For one or more connections. This may be done adaptively or based on user inputs, and may be done for security purposes based on network conditions or triggered events (e.g., a rogue device attempting to connect). In other words, reverting back to communication session 720 from time to time, for example to exchange information regarding a new/modified application key, as discussed above, may enable increased security.

Figure 7E:
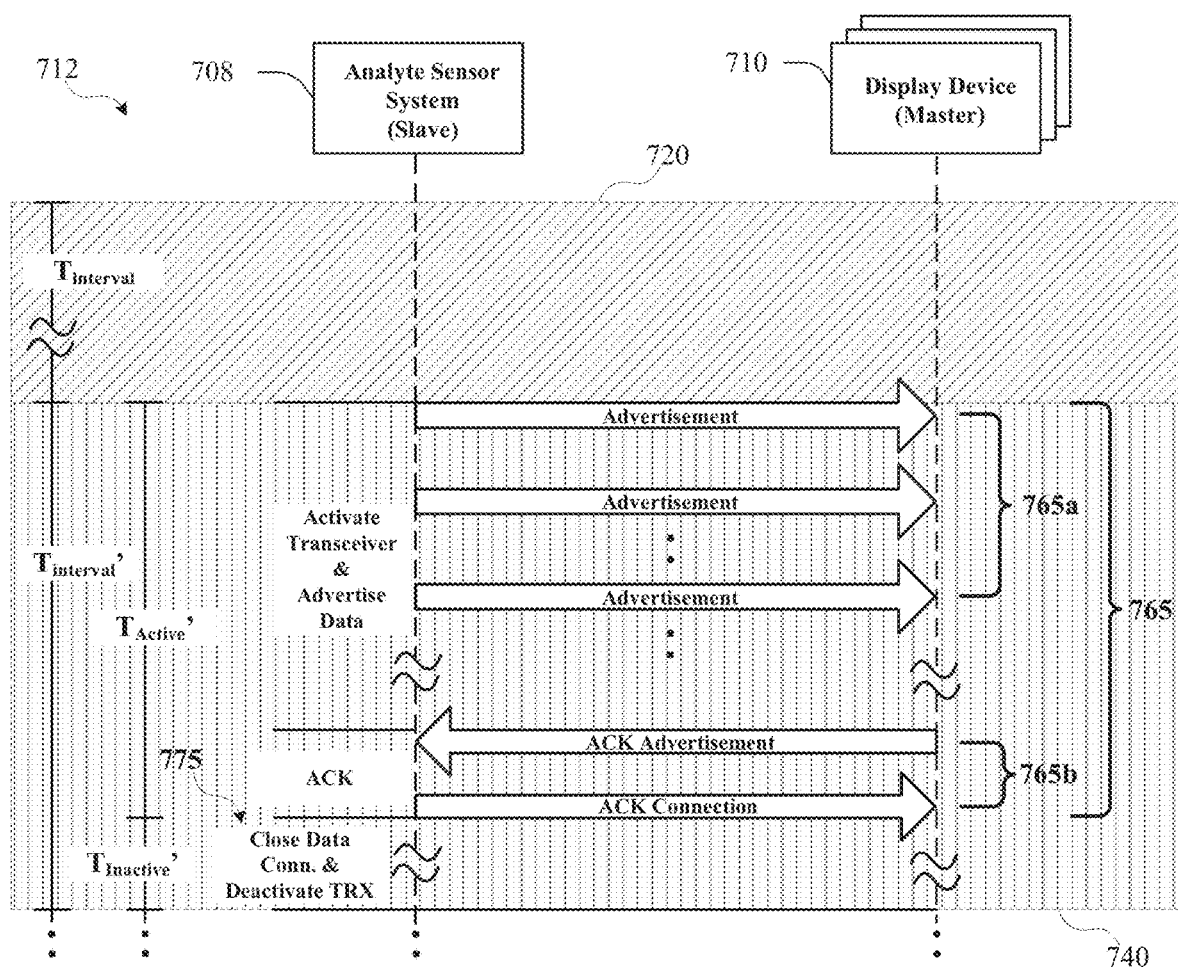
FIG. 7E is an operational flow diagram illustrating various operations that may be performed in accordance with embodiments of the disclosure.

Referring now to FIG. 7E, method 712 for wireless communication of analyte data between analyte sensor system 708 and display device 710 is illustrated in connection with implementations of the improved authentication scheme alluded to above. Method 712 includes establishing a first connection between analyte sensor system 708 and display device 710. This may occur in connection with communication session 720 corresponding to $T_{interval}$. As such, establishing the first connection can include performing a two-way authentication between analyte sensor system 708 and display device 710.

Method 704 also includes establishing communication session 740 that may be implemented during a time interval $T_{interval}'$, which may be the same as or different from $T_{interval}$. $T_{interval}'$ may include an active portion corresponding to $T_{Active}'$ and an inactive portion corresponding to $T_{Inactive}'$. During $T_{Active}'$, communication session 740 may involve operation 765 and sub-operations thereof.

Here it should be noted that communication session 740 may not include establishment of a second connection between analyte sensor system 708 and display device 710. For example, communication session 740 as illustrated does not include the data connection aspects of operation 735*b* shown in FIG. 7C in connection with communication session 725. Nor does communication session 740 as illustrated include the authentication process that may be included in communication session 720 (e.g., at operation 705*c*). Rather, at operation 765*a*, method 712 involves sending one or more advertisement messages to display device 710.

As such, as part of communication session 740, analyte sensor system 708 may transmit a first advertisement message (e.g., during operation 765*a*). The first advertisement message may include at least a first portion of the analyte value. The analyte value may but need not have been encrypted (e.g., using an application key) prior to transmission. In other words, with regard to communication session 740, analyte sensor system 708 may use one or more advertisement messages to transmit encrypted or non-encrypted analyte values or analyte data and/or other signaling (such as, e.g., timing and control information) in addition to other information typically included in advertisement messages.

In some cases, as will be described in further detail with reference to FIG. 8 for example, an advertisement message may take the form of a packet. By way of example, the analyte value (whether encrypted or not) may be included in a reserved field in the advertisement message packet. Specifically, in some cases, a manufacturing data or other slot in the packet may include a reserved field of 1 byte or more. This reserved field is one example of how an analyte data or other form of payload may be included in the advertisement message. As alluded to above, in addition or instead of the analyte value, the advertisement message may also include a time stamp associated with the analyte value.

In some example implementations, however, there may be insufficient space in the advertisement message/packet for both the analyte value and the associated time stamp. In some such cases, method 712 may involve breaking the payload, which may include the (encrypted) analyte value and associated data, into multiple parts. The first advertisement message may then indicate that a second advertisement message includes a second portion of the analyte value and/or associated data. The first advertisement may so indicate by tagging the first portion of the payload, where the tag represents to display device 710 receiving the advertisement message that a subsequent advertisement message may include a second portion of the payload.

The above-mentioned tagging of the first portion of the payload may take various forms. For example, a relatively simple tag may indicate only that a subsequent advertisement message includes a second portion of the payload. A relatively more complex tag may additionally indicate the type of content that will be included in the second portion of the payload, or how the payload has been split or distributed amongst advertisement messages. The first portion may, for example, include an encrypted analyte value, and the tag applied may indicate that the subsequent advertisement message will include the associated time stamp.

In other words, according to communication session 740, advertisement messages may be transmitted during operation 765*a* for the purposes of communicating analyte data to display devices 710. With the payload encrypted using an application key, privacy/security can be maintained even in the absence of typically authentication procedures being performed during communication session 740. In other words, in communication session 740, the above-described authentication process, including the two-way authentication, can be bypassed. Likewise, because the payload is included in the advertisement messages, the data connection request and data transmission processes (e.g., operations 735*b* and 735*d*, respectively) can also be bypassed or avoided. In this manner, the number of messages exchanged in pursuant to communication session 740 (and hence the power consumption) may be reduced relatively to other communication sessions.

Returning to FIG. 7E, communication session 740 may also include, at operation 765*b*, display device 710 acknowledging receipt of the advertisement message(s) sent during operation 765*a*, by sending an acknowledgement (ACK) message. In some cases this acknowledgement may trigger a data connection process between analyte sensor system 708 and the acknowledging display device 710. For example, analyte sensor system 708 may in turn send an ACK to display device 710 and thus form a connection. The data connection process established in connection with operation 765*b*, in example deployments, may be used for renewing the application and/or encryption key(s) and/or for exchanging other data, such as, for example, calibration data, timing information, and the like. When communications at operation 765 are completed, data transmission may be terminated at operation 775. At this point, transceiver 360 and/or processor 380 of analyte sensor system 708 (or with reference to FIG. 4, radio 425 and processor 420) can be deactivated. In FIG. 7E, this period generally corresponding to operation 775 is denoted as $T_{inactive}'$.

With further reference to FIG. 12A, embodiments of method 1200 include, at operation 1205G, determining a number of advertisement messages to use for transmission of the encrypted analyte value. For example, operation 1205G may be used in connection with method 712, with reference to FIG. 7E. As mentioned above, operation 1205H of method 1200 involves analyte sensor system 708 transmitting the encrypted analyte value to display device 710 (e.g., as part of an advertisement message), if the determination of operation 1205C indicates that authentication was performed during the first interval. Operation 1205H may correspond to operation 765a, with reference to FIG. 7E. In some cases, however, the transmission is not conditioned on the indication that authentication was performed previously.

Figure 7F:
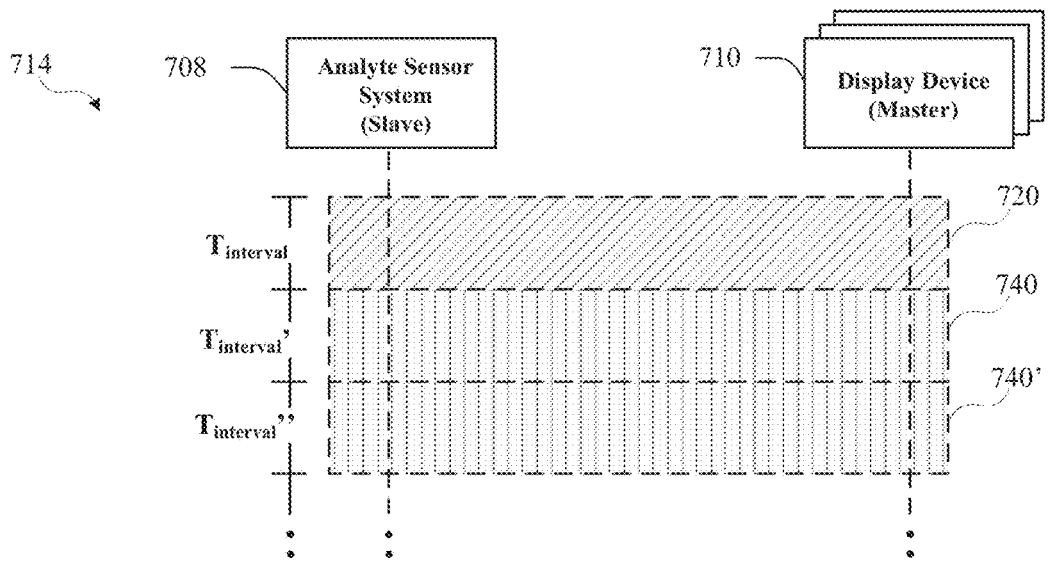
FIG. 7F is an operational flow diagram illustrating various operations that may be performed in accordance with embodiments of the disclosure.

FIG. 7F illustrates an example implementation of method 714 for wireless communication of analyte data between analyte sensor system 708 and display device 710 in connection with implementations of the improved authentication scheme discussed above. As shown in FIG. 7F, method 714 involves communication session 720. Communication session 720 occurs, having a length in time of $T_{interval}$. Subsequently, an instance of communication session 740 occurs, having a length in time of $T_{interval}'$, which may be the same as or different from $T_{interval}$, in various embodiments described herein. Then, an instance of communication session 740' occurs, having a length in time of $T_{interval}''$, which may be the same as or different from $T_{interval}'$, in various embodiments described herein. Communication session 725' may be substantially similar to communication 725, aside from potentially having a different interval length.

By following communication session 720 with one or more instances of communication sessions 740, 740', etc., the overall number of messages exchanged during communication of analyte data (and hence the power consumption) may be reduced. It will be noted here, however, that in some cases, method 714 may involve reverting back to communication session 720 after implementing communication session 740, 740', etc. For one or more connections. This may be done adaptively or based on user inputs, and may be done for security purposes based on network conditions or triggered events (e.g., a rogue device attempting to connect). In other words, reverting back to communication session 720 from time to time may enable increased security.

Figure 7G:
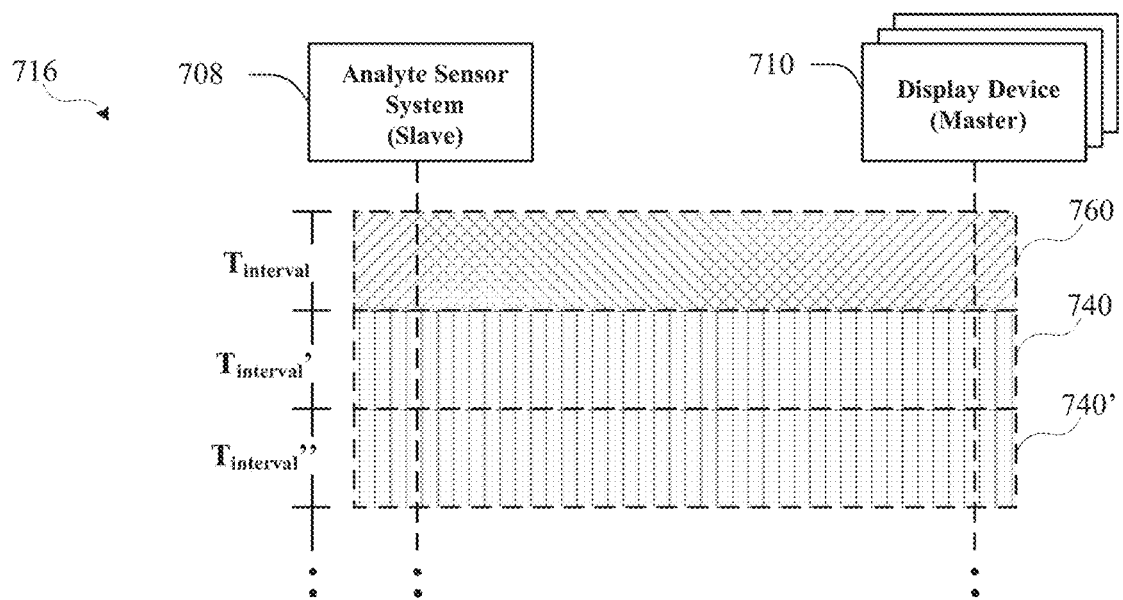
FIG. 7G is an operational flow diagram illustrating various operations that may be performed in accordance with embodiments of the disclosure.

FIG. 7G illustrates an example implementation of method 716 for wireless communication of analyte data between analyte sensor system 708 and display device 710 in connection with implementations of the improved authentication scheme discussed above. As shown in FIG. 7G, method 716 involves communication session 760. In example deployments of method 716, communication session 760 involve the exchange of information related to pairing, application keys, and timing parameters related to potential communications between analyte sensor system 708 and display device 710 using a first wireless protocol. But such an exchange may be streamlined by using certain types of wireless protocols. By way of example, the first wireless protocol may be WiFi or Near Field Communication (NFC). In other examples, the first wireless protocol may utilize RFID, another proximity based wireless connection, or the like.

In this manner, authentication, such as may occur using BLE (e.g., according to operation 705c with reference to FIG. 7A) may be circumvented, along with the typically associated exchange of numerous messages. By way of illustration, NFC may be used between analyte sensor system 708 and display device 710 in order to exchange information such as pairing, encryption information (e.g., application key information and/or scheme), advertising parameters (including, e.g., frequency/period, duration, timing, and/or nature of advertisements), connection interval information, and information related to display device 710 (e.g., type of display device, preferences, etc.). The exchanged information may then be used by display device 710 to receive and decrypt (where applicable) analyte values transmitted by analyte sensor system 708. Using NFC to exchange authentication related information in this fashion may extend the battery life of analyte sensor system 708 and increase the reliability of communications between analyte sensor system 708 and display device 710.

As shown in FIG. 7G, after communication session 760 is used to exchange information, communication session 740 occurs, having a length in time of $T_{interval}$. In some deployments, communication session 740, including, for example, establishing connection and transmitting the analyte values, may be carried out using a second wireless protocol different than the first wireless protocol used in connection with communication session 760. The second wireless protocol may be Bluetooth Low Energy (BLE), for example. Communication session 740 occurs, having a length in time of $T_{interval}'$, which may be the same as or different from $T_{interval}$, in various embodiments described herein. Then, an instance of communication session 740' may occur, having a length in time of $T_{interval}''$, which may be the same as or different from $T_{interval}'$, in various embodiments described herein.

Figure 12D:
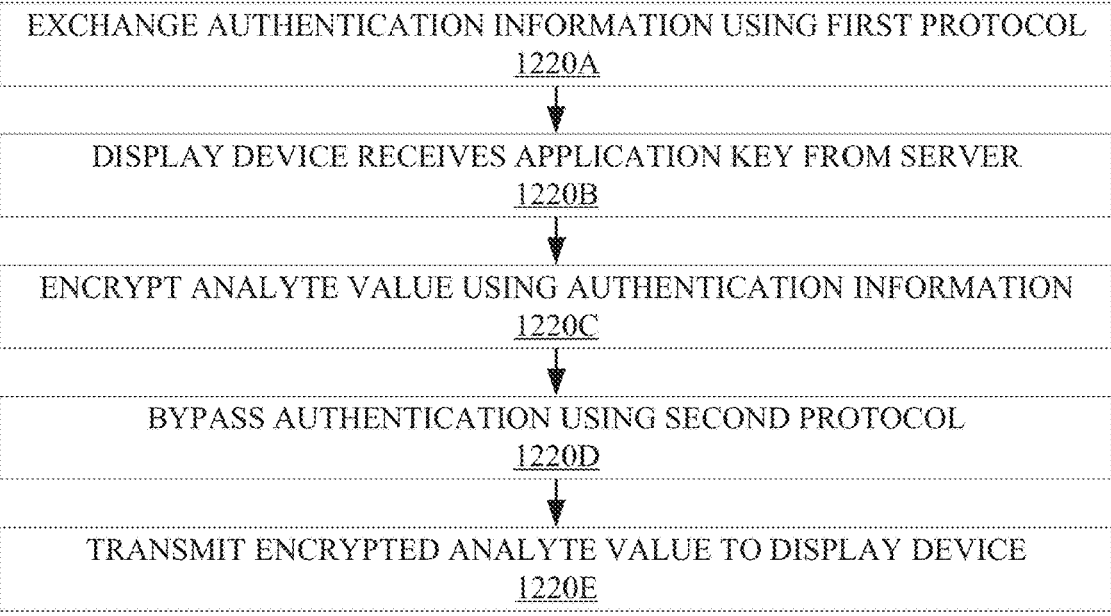
FIG. 12D is an operational flow diagram illustrating various operations that may be performed in accordance with embodiments of the disclosure.

Referring now to FIG. 12D, example implementations of features of various methods such as, for example, methods 704, 706, 712, 714, 716, 718, 722, 724, and 726 are illustrated. One such example implementation includes aspects of method 1204 for wireless communication of analyte data. As shown in FIG. 12D, at operation 1220A, method 1204 includes using a first wireless protocol to perform an exchange of information related to authentication information. The exchange of the information may be performed between analyte sensor system 708 and display device 710 during a first interval. Operation 1220A may not include a one- or two-way authentication such as described above in connection with FIGS. 7A, 12A, 12B, and 12C. Rather, as mentioned above, for example, authentication, such as may occur using BLE (e.g., according to operation 705c with reference to FIG. 7A) may be circumvented. By way of illustration, embodiments of method 1204 involve display device 710 receiving an application key and/or other information related to authentication from a server (e.g., server system 334). At operation 1220C, method 1204 involves encrypting an analyte value to generate an encrypted analyte value using the information related to authentication exchanged at operation 1220A. At operation 1220D, method 1204 involves bypassing the exchange of information related to authentication (e.g., as described above in connection with operation 705c). At operation 1220E, method 1204 involves using a second wireless protocol to transmit the encrypted analyte value to display device 710.

With further reference to FIG. 7G, by following using communication session 760 before one or more instances of communication sessions 740, 740', etc., the overall number of messages exchanged for communication of analyte data (and hence the power consumption) may be reduced, particularly with regard to the above-described authentication process and exchange of pairing information and the like. It will be noted here, however, that in some cases, method 716 may involve reverting back to communication session 760 after implementing communication session 740, 740', etc. For one or more connections. This may be done adaptively or based on user inputs, and may be done for security purposes based on network conditions or triggered events (e.g., a rogue device attempting to connect). In other words, reverting back to communication session 760 from time to time may enable increased security.

Figure 7H:
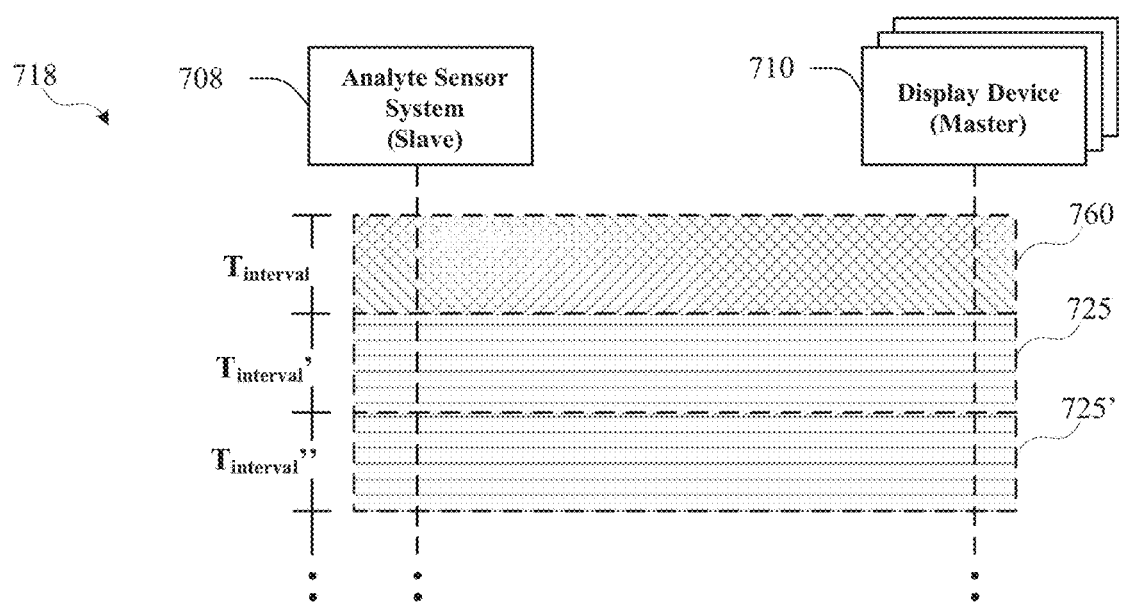
FIG. 7H is an operational flow diagram illustrating various operations that may be performed in accordance with embodiments of the disclosure.

FIG. 7H illustrates an example implementation of method 718 for wireless communication of analyte data between analyte sensor system 708 and display device 710 in connection with implementations of the improved authentication scheme discussed above. In some respects, method 718 is substantially similar method 716. One difference is that after implementing communication session 760, method 718 involves implementing communication session 725 rather than communication session 740. Subsequently, an instance of communication session 725' may occur, having a length in time of $T_{interval}''$, which may be the same as or different from $T_{interval}'$, in various embodiments described herein. It will be appreciated, however, that various of the above-described communications sessions (e.g., 720, 725, 740, 760) may be mixed and matched in accordance with the above-described methods.

G. Connection Models

Aspects of the present disclosure also include various connected models for communications between analyte sensor system 708 and display devices 710. One connection model for communications may be referred to as a connect/disconnect or intermittent/periodic connection model. In accordance with a connect/disconnect scheme, communications between analyte sensor system 708 and display device 710 may be periodic or intermittent in nature, following a defined or event-based/asynchronous schedule. For example, display device 710 may establish connection with analyte sensor system 708 periodically (e.g., once every five minutes) in order to receive analyte and other data from analyte sensor system 708 and/or in order to transmit data thereto.

It may be the case, however, that even if display device 710 successfully connects to analyte sensor system 708, analyte sensor system 708 may not have data ready to be transferred. In such a case, the length of time between successive receipts of data by display device 710 may be increased. The present disclosure additionally includes connection models that may reduce latency between the collection of analyte data at analyte sensor system 708 and the transmission of such data to display devices 710 connecting thereto, while maintaining a sufficiently low power consumption for analyte sensor system. One example of such a connection model may be referred to as a connected or an always connected model. At a high level, the connected model can involve an initial pairing between analyte sensor system 708 and display device 710, after which analyte sensor system 708 and display device 710 remain connected, essentially not closing the connection or disconnecting. That is, connection and the exchange of data is not done periodically or intermittently as with the connected/disconnect scheme (e.g., as discussed with reference to FIGS. 7A-7B), but instead, the connected devices periodically exchange messaging to maintain the connection. Once data is available at analyte sensor system 708 (e.g., gathered by sensor 405 and/or processed by processor 420), the data can be transmitted to display device 710 in near real time. In this manner, the overall accuracy and responsiveness of communications related to analyte data is increased. An additional advantage associated with the connected model is that analyte sensor system 708 may be enabled to better mitigate against interferences caused by undesired devices (e.g., in some cases, undesired display devices 710) seeking to connect with analyte sensor system 708.

Figure 7J:
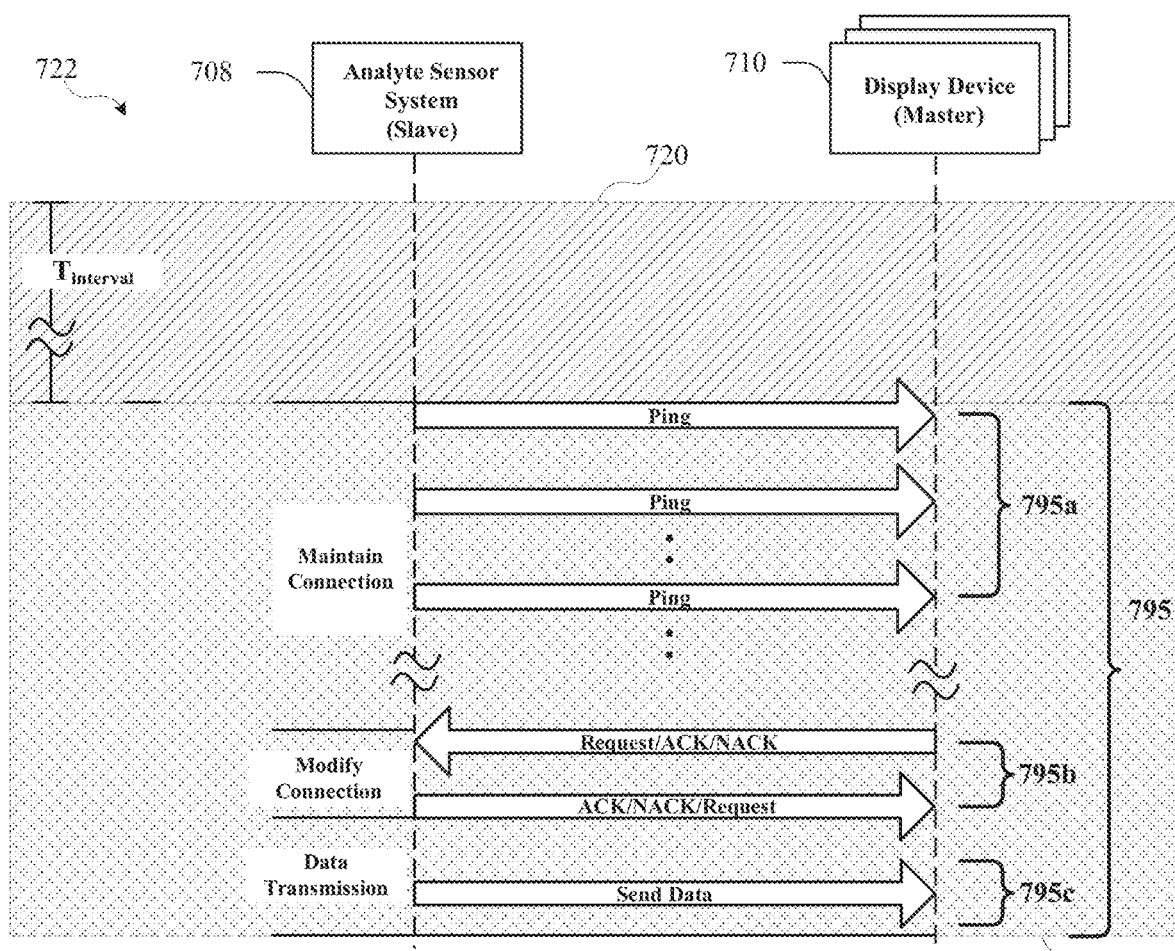
FIG. 7J is an operational flow diagram illustrating various operations that may be performed in accordance with embodiments of the disclosure.

In this connection, FIG. 7J illustrates example implementations of method 722 for wireless communication of analyte data between analyte sensor system 708 and display device 710 is illustrated in connection with implementations of the connected model alluded to above. Method 722 involves establishing a first connection between analyte sensor system 708 and display device 710. This may be done during $T_{interval}$ using, for example, communication session 720 or 760. Thus, analyte sensor system 708 may be connected to display device 710, such that, for example, authentication and the exchange of application key information, timing information, pairing information, etc., can occur.

Subsequently, communication session 780 can be initiated in connection with method 722. More specifically, as shown in FIG. 7J, communication session 780 may involve operation 795 and sub-operations thereof. At operations 795a, analyte sensor system 708 periodically exchanges messaging with display device 710 in order to maintain a connection therewith. For example, such messages may be transmitted to/from analyte sensor system 708 simply to indicate that the transmitting device is still connected to the receiving device (e.g., a "ping"). This may be done periodically according to a predetermined period (e.g., once every 2 seconds or any amount of time). The period may in some case be varied according to criteria such as network parameters or conditions, the type or other characteristic of display device 710 connected to analyte sensor system 708, the frequency with which data is being transmitted or generated/gathered by analyte sensor system 708, and so on.

Through the periodic exchange of messaging, connection between analyte sensor system 708 and display device 710 may be maintained, thus allowing for gathered analyte data to be exchanged in near real time. In this regard, method 722 includes, at operation 795c, analyte sensor system 708 transmitting the analyte data to display device 710, upon the analyte data becoming available for transmission. In embodiments, the combination of periodically exchanging messaging (operation 795a) and transmitting the analyte data to display device 710 (operation 795c), upon the analyte data becoming available for transmission, is done responsive to an indication of a use preference related to display device 710. This use preference may be communicated to/from analyte sensor system 708 at operation 795b. For example, in one situation, the user of display device 710 may indicate that the connected model is preferred relative to the connect/disconnect model, or vice versa. In example implementations, operation 795c involves the transmission of advertisement messages that include analyte data, for example as described above in connection with operation 765a of FIG. 7E. In these and other respects, method 722 may include at operation 795b modifying the connection between analyte sensor system 708 and display device 710.

For example, if the user prefers a first display device 710 (e.g., a smartphone), such that, e.g., that is the only display device 710 the user will be using to capture analyte data, then analyte sensor system 708 may operate in the connected mode according to communication session 780 after connecting to the preferred display device 710. The user's preference may be indicated manually by the user, or may be derived from data relating to usage of first display device 710 as well as other devices, for example, as is described in detail herein. Deriving the user's preference may be done based on data relating to the time of day, location, radio link conditions, packet loss rates, and network parameters, for example. In some embodiments, a prioritization scheme may be configured with respect to multiple display devices 710. In order to implement the priority scheme for a particular display device 710, communication session 780 may be used for that particular display device 710. In some cases, for example, if packet loss increases above a threshold, the connected model may be employed in order to decrease packet loss. In some cases, the connected model or the connect/disconnect model may serve as a default mode, and the corresponding communication session (e.g., 720, 725, 740, 780) can be employed. The default mode may be selectable, e.g., according to user input or adaptively based on various of the parameters described above.

To illustrate, analyte sensor system 708 and a first display device 710 may be communicating analyte data using the connect/disconnect model as described above. In this scenario, the first display device 710 may, for example, be a user's smartphone. Analyte sensor system 708 may also, according to the connect/disconnect model, be communicating analyte data with a second display device 710, which may, for example, be a medical device (e.g., an insulin pump, medical device 136, or the like) or a proprietary display device (e.g., a device designed specifically for the communication of analyte data, such as display device 110, with reference to FIG. 1A). The user may then provide, for example via GUI 740, an indication that the user will only be using the smartphone and not the medical device. As mentioned, this may be done via GUI 340 provided on the smartphone in connection with an application, such as application 330, that may be related to the communication of analyte data. For example, with reference to FIG. 3E, the users may select one of options 316e to indicate that a display device 710 is or is not preferred and should or should not be dedicated for transmission of analyte data.

The smartphone (or other type of display device 710) in this example may then transmit the user's indication to analyte sensor system 708, which upon receiving the indication may initiate operation under the connected model according to communication session 780. With reference to FIG. 7J, the user's indication may be transmitted from display device 710 to analyte sensor system 708 at operation 795b, in the form of a request message. Although other display devices 710 (including, e.g., a medical device such as medical device 136) can listen to the analyte sensor system 708 (that is, receive messages therefrom), only the preferred display device 710—in this example, the smartphone—is operating under the connected model, and hence exchanging analyte data in near real time.

Operation 795b may also be used to send an ACK message to analyte sensor system 708 indicating that one or more messages exchanged during operation 795a have been received. Likewise, if such messages were expected but not received, display device 710 may send a negative ACK (or NACK) in connection with operation 795b. With further regard to operation 795b, the request or user indication etc. may be ACKed or NACKed by analyte sensor system 708. Alternatively or in addition, analyte sensor system can respond to the request from display device 710 with a request (e.g., a counter-offer) pursuant to operation 795b.

By way of example, in connection with other use preference situations, operation 795a may involve display device 710 sending requests to modify the period of or other aspects regarding the exchange of messaging that may occur during operation 795a. In some scenarios, display device 710 may request an increased/decreased time period for the exchange of messaging, and/or a range of time periods for the same. Analyte sensor system 708 may then reject or accept this request via an ACK/NACK response. Alternatively or in addition, analyte sensor system 708 may, respond with a counter-proposal, for example, including a different time period and/or a subset within the requested range of time periods to be used for the exchange of messaging in operation 795a.

In embodiments, the combination of periodically exchanging messaging and transmitting the analyte data to the display device, upon the analyte data becoming available for transmission, according to communication session 780 is done adaptively. For example, depending on the time of day, there may be an advantage to operating under the connected model according to communication session 780 (as opposed to, for example, another form of communication session described herein) for some users and/or display devices 710. Particular users may experience more severe glucose variations during certain times of day. The glucose variations, for example, may be more rapid and/or large in magnitude at certain times. In some instances, such variations may not be ideally addressed by analyte sensor system 708 operating under the connect/disconnect model according to communication sessions 720, 725, and/or 740, for example, since analyte values are not necessarily exchanged in a near real time fashion. Thus, during times when glucose variations are typically severe, analyte sensor system 708 and/or display device 710 may initiate operation under the connected model pursuant to communication session 780. With reference to FIGS. 7C and 7J, by way of example, this may be done by implementing operation 795b in connection with operation 735. In this manner, the connection model used can be toggled/switched adaptively.

In another example, network parameters, network conditions, the quality of the radio link, the number of display devices 710 seeking connection to or in communication with analyte sensor system 708, and/or a prioritization scheme (e.g., as determined by a user or otherwise), may serve as the basis for operating under the connected model (communication session 780) on an adaptive basis. With respect to network parameters or conditions, and/or with respect to radio link quality, a degradation may result in packet loss. Such packet loss, as alluded to above, may be more critical to the exchange of analyte data under the connect/disconnect model, since data is typically not exchanged as frequently relative to the connected model. Accordingly, in order to mitigate degradation of network parameters or conditions, and/or radio link quality, when such degradation is detected, analyte sensor system 708 and display device 710 may initiate operation under the connected model pursuant to communication session 780 (e.g., via operation 795b). As mentioned above, display device 710 may monitor network parameters, network conditions, and/or radio link quality. These measurements may then be compared to a threshold such that switching the mode of operation (e.g., between various communication sessions) may be done adaptively responsive to the threshold being crossed.

With respect to the number of devices seeking a connection to analyte sensor system 708, or being in communication therewith, adaptation of the operating mode/connection model can be described as follows. A large number of display devices 710 may be in range from analyte sensor system 708, and attempting to connect thereto may result in interference, and hence packet loss and/or increased power consumption. To avoid such packet loss and increased power consumption, even in the face of numerous display devices 710 seeking a connection, analyte sensor system 708 may initiate operation under the connected model with a preferred display device 710.

This may be done by analyte sensor system 708 maintaining a count of the number of display device 710 devices seeking a connection thereto, and signaling a preferred display device 710 to enter operation under the connected model if the count surpasses a threshold. Such signaling may be implemented, for example, similarly to operation 795b but may be used, as alluded to above, as part of operation 735 (with reference to FIG. 7C), or may be included in an advertisement message as part of operation 765a or an ACK message as part of operation 765b (with reference to FIG. 7E), for example. Alternatively or additionally, packet loss may be monitored (e.g., at display device 710 and/or analyte sensor system 708). Further, the source of such packet loss may be determined, or approximated, e.g., at display device 710 and/or analyte sensor system. If the source of the packet loss is determined to be interference (due, for example, to numerous display devices 710 attempting to connect to analyte sensor system 708), operation under the connected model may be initiated.

Here, the preferred display device 710 may also be determined instantaneously or nearly so, may be determined on the fly, and may be determined without user intervention. For example, the preferred display device 710 may be determined based on frequency of use, a previously determined prioritization scheme, the quality of connection or radio link (e.g., based on signal power, channel loss, bit error rate, RTT, RSSI, etc.), the time of day, etc. Alternatively or in addition, the user may be queried via GUI 740, e.g., as part of application 330 running on display device 710, as to the preferred display device 710.

With respect to terminating the connection established and maintained pursuant to communication session 780, several techniques may be employed. As mentioned above, operation 795a may involve the exchange of messaging according to a period. Such messages may be thought of as "ping" messages.

The sequential exchange of such messaging may involve a first message and a second message that is successively transmitted with respect to the first message, and so on with respect to third, fourth, and fifth messages, etc. The first such message may be configured to include a messaging interval that indicates when the next message in the sequence will be transmitted to display device 710, or in other words may include a scheduled amount of time between the sequential exchange of the first and second messages.

This messaging interval may be varied between the messages exchanged at operation 795a. If display device 710 does not receive the second message within the expected messaging interval, the connection between display device 710 and analyte sensor system 708 may be terminated. In another instance, the connection may be terminated if a proposed messaging time interval is NACKed or otherwise rejected, e.g., at operation 795b. That is, if analyte sensor system 708 and display device 710 do not agree upon a messaging interval, the connection may be closed. An ACK/NACK may also be sent following each ping message (e.g., multiplexed ACK/NACK) or following a predetermined or adaptively varied number of such messages (e.g., bundled ACK/NACK), e.g., at operation 795. Thus, aspects of operation 795b may be interlaced with the exchange of messaging at operation 795a.

In embodiments, the messages exchanged at operation 795a may include a timeout value. Supervision timeout and related techniques may also be employed with respect to the period exchange of messaging. For example, upon expiry of the timeout value, if a second message has not been received, method 722 may involve terminating the connection. When the connection is terminated, communication session 780 may end. At this point, transceiver 360 and/or processor 380 of analyte sensor system 708 (or with reference to FIG. 4, radio 425 and processor 420) can be deactivated. In FIG. 7C, this period generally corresponding to operation 745 is denoted as $T_{Inactive}$'.

With further regard to communication session 780, at this juncture, it should be noted that the various transmissions shown in communication session 780 are not necessarily limited to the directions or sequences shown. For example, operation 795a may alternatively or additionally involve messaging sent from display device 710 to analyte sensor system, including, for example, ping or other messages that may be used to maintain a connection, as well as ACK/NACK/request messages.

With further regard to connection models, in embodiments the present disclosure different connection models can be used for different connected devices. With reference to FIG. 3C, for example, communication session 780 can be employed as between display devices 310a and 310b, while at the same time a different communication session (e.g., 720, 725, 740, etc.) can be employed as between display devices 310a and/or 310b, on the one hand, and analyte sensor system 708 on the other hand. In embodiments, one of display devices 310a and 310b may not be connected to analyte sensor system 708 but may nevertheless receive analyte data therefrom via another display device 310b or 310a that is connected to analyte sensor system 708. In some cases, this may be referred to as tethering. Such configurations can be implemented, for example, using sub-menu 314a presented by GUI 340, with reference to FIGS. 3D and 3E.

Figure 13A:
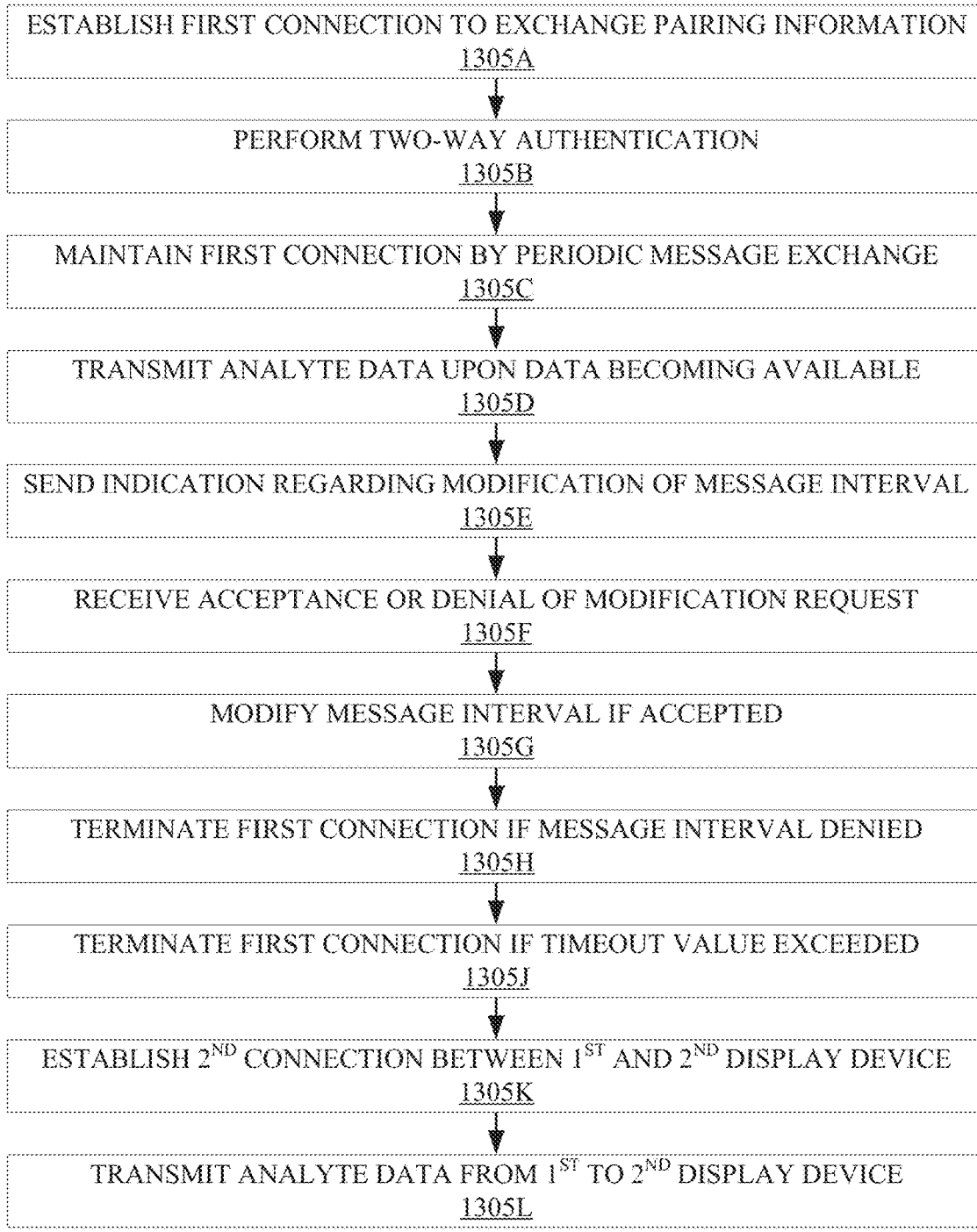
FIG. 13A is an operational flow diagram illustrating various operations that may be performed in accordance with embodiments of the disclosure.

Referring now to FIG. 13A, example implementations of features of various methods such as, for example, methods 704, 706, 712, 714, 716, 718, 722, 724, and 726 are illustrated. One such example implementation includes aspects of method 1300 for wireless communication of analyte data. As shown in FIG. 13A, at operation 1305A, method 1300 includes establishing a first connection during a first interval. For example, the first connection can be established between analyte sensor system 708 and display device 710. The first connection can be established in order to exchange pairing information between analyte sensor system 708 and display device 710. In some cases, method 1300 involves, at operation 1305B, performing a two-way authentication, for example, in the manner described above in connection with FIG. 12B. Operation 1305C involves maintaining the first connection by periodically exchanging messages between analyte sensor system 708 and display device 710. Operation 1305C may in examples correspond to operation 795a or the like, with reference to FIG. 7J. At operation 1305D, while analyte sensory system 708 and display device 710 remain connected, method 1300 involves analyte sensor system 708 transmitting analyte data to display device 710, upon the analyte data becoming available for transmission. Operation 1305D may in examples correspond to operation 795c or the like.

In embodiments, method 1300 includes, at operation 1305E, sending a request regarding modification of a message interval. The request may be sent from analyte sensor system 708 to display device 710, or vice versa. Operation 1305F involves receiving an acceptance or denial of the request regarding modification of the message interval. The request may be received by analyte sensor system 708 or display device 710, depending on the sending entity. At operation 1305G, if the request is accepted, method 1300 may include modifying the message interval if the request is accepted. At operation 1305H, method 1300 may include terminating the first connection and/or terminating analyte sensor system 708 periodically exchanging messages with display device 710, such that analyte sensor system 708 and display device 710 do not remain connected, responsive to the request being denied. At operation 1305J, method 1300 may include terminating the first connection and/or terminating analyte sensor system 708 periodically exchanging messages with display device 710, if a timeout is exceeded.

With further reference to FIG. 13A, method 1300 may involve, at operation 1305K, establishing a second connection, with the second connection being between display device 710 and another display device 710, such that the display devices 710 remain connected. For example, display devices 310*a* and 310*b* may be connected as shown in FIG. 3C. While the two display devices 710 are connected to each other, display information may be relayed (or transmitted) at operation 1305L from analyte sensor system 708 through a first display device 710 (which may have established the first connection with analyte sensor system 708 at operation 1305A and thus received the analyte data) and a second display device 710. In this manner, second display device 710 may effectively be tethered to analyte sensor system 708.

Figure 7K:
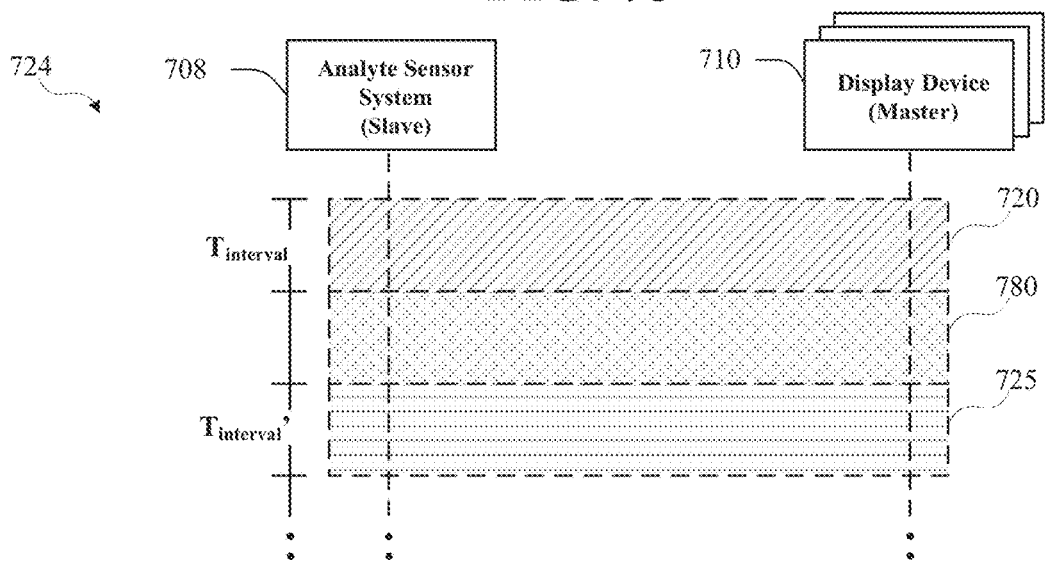
FIG. 7K is an operational flow diagram illustrating various operations that may be performed in accordance with embodiments of the disclosure.

FIG. 7K illustrates an example implementation of method 724 for wireless communication of analyte data between analyte sensor system 708 and display device 710 in connection with implementations of various connection models discussed above. As shown in FIG. 7K, method 724 involves communication session 720. Communication session 720 occurs, having a length in time of $T_{interval}$. Subsequently, an instance of communication session 780 occurs, in which analyte sensor system 708 and display device 710 may remain connected until the connection is closed for various of the potential reasons described above. Then, an instance of communication session 725 occurs, having a length in time of $T_{interval}'$, which may be the same as or different from $T_{interval}$, in various embodiments described herein. A request to modify the connection model (e.g., send according to operation 795*b*) may result in the terminating the connection established as part of communication session 780, and the triggering of a different connection model, for example by initiating communication session 725. In some cases, the connection model may be controlled manually via GUI 340. With reference to FIG. 3E, a user may be presented with sub-menu 314*f* which allows selection of a connection model using options 316*f*.

Figure 13B:
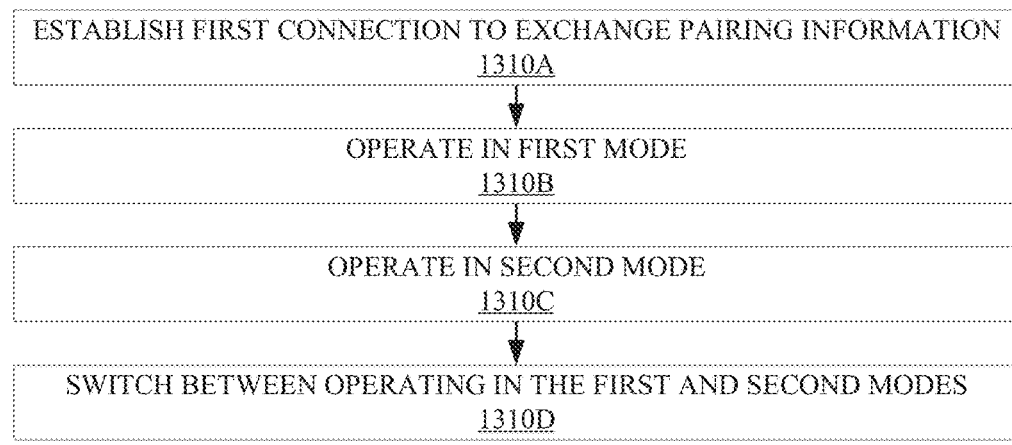
FIG. 13B is an operational flow diagram illustrating various operations that may be performed in accordance with embodiments of the disclosure.

Referring now to FIG. 13B, example implementations of features of various methods such as, for example, methods 704, 706, 712, 714, 716, 718, 722, 724, and 726 are illustrated. One such example implementation includes aspects of method 1302 for wireless communication of analyte data. As shown in FIG. 13B, at operation 1310A, method 1302 includes establishing a first connection between analyte sensor system 708 and display device 710. The first connection can be established in order to exchange pairing information between analyte sensor system 708 and display device 710. At operation 1310B, method 1302 involves operating in a first mode. At operation 1310C, method 1302 involves operating in a second mode. At operation 1310D, method 1302 optionally involves switching between operation in the first mode and operating in the second mode.

Figure 13C:
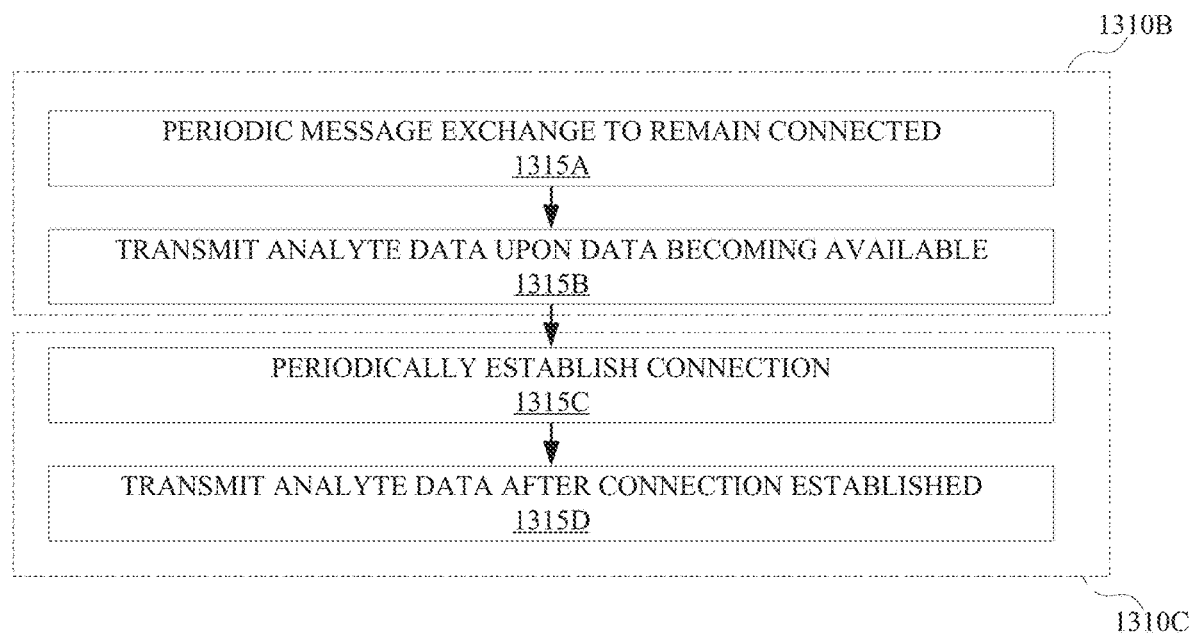
FIG. 13C is an operational flow diagram illustrating various operations that may be performed in accordance with embodiments of the disclosure.

FIG. 13C illustrates method 1304, which includes further detail regarding operations 1310B and 1310C, mentioned above with reference to FIG. 13B. As shown in FIG. 13C, operation 1310B includes at operation 1315A, periodically exchanging messages between analyte sensor system and display device 710, such that analyte sensor system 708 and display device 710 remain connected. Operation 1315A may in examples correspond to operation 795*a* or the like, with reference to FIG. 7J. At operation 1315B, operation 1310B includes analyte sensor system 708 transmitting analyte data to display device 710, upon the data becoming available for transmission. Operation 1315C may in examples correspond to operation 795*c* or the like, with reference to FIG. 7J. Operation 1310C includes at operation 1315C, periodically establishing a second connection between analyte sensor system 708 and display device 710. At operation 1315D, after the second connection has been established, operation 1310C includes transmitting the analyte data to display device 710. Operation 1315C may in examples correspond to operation 735*d* or the like, with reference to FIG. 7C.

Referring again to FIG. 7K, in some cases, aspects of operating in the first mode according to operation 1310B may correspond to communication 780, while aspects of operating in the second mode may correspond to communication session 720 and/or 725 etc. By following communication session 720 with one or more instances of communications sessions 780, 725, and/or other communication sessions described here, or the like, the overall number of messages exchanged during communication of analyte data (and hence the power consumption) may be reduced. Method 724 thus provides a highly flexible and adaptable technique for the communication of analyte data.

H. Advertisement Timing and Structure

An additional aspect involves the order and manner in which various devices (e.g., display devices 710) connect to the analyte sensor system (e.g., analyte sensor system 708), which can depend upon the order, timing, structure, and manner of advertisement messages transmitted to such display devices 710 devices. Here it will be noted that the numerals 708 and 710 are referred to, but the description can apply to any of the analyte sensor systems and/or display devices described herein, as will be appreciated by one of ordinary skill in the art upon studying the present disclosure. One potential scheme for the ordering of connection for various devices may be described as follows.

Analyte sensor system 708 advertises and connects to display devices 710 that are available for connection, that is, to in-range display devices 710. This may be done, for example, by transmitting advertisement messages. By way of example, reference is made to operation 705*a* shown in FIG. 7A. On the display device side, display devices 710 seeking to connect to analyte sensor system 708 may typically scan for analyte sensor system 708 or another like sensor system to connect to. This generally entails receiving and processing advertisement messages that are being broadcast by analyte sensor system 708 etc., in order to determine whether any such messages are being transmitted by a compatible/desirable analyte sensor system 708.

Display device 710 may then respond to the advertisement message by sending a connection request back to analyte sensor system 708. By way of example, reference is made to operation 705*b* shown in FIG. 7A. Upon receiving the connection request, analyte sensor system 708 may accept, deny, or simply ignore the request. Typically, analyte sensor system 708 serves only one display device 710 connection at a time. Therefore, one ground for denying or ignoring a connection request is that analyte sensor system 708 is already connected to a display device 710. If there are no grounds for denying or ignoring a connection request, analyte sensor system 708 may accept the request and connect to the display device 710 that sent the request. For example, operation 705*b* shows analyte sensor system 708 accepting the request by sending signaling to display device 710 to indicate that the connection is granted.

Once connected, display device 710 and analyte sensor system 708 may exchange messaging, including analyte sensor system 708 transmitting analyte data to display device 710. By way of example, reference is made to operation 705*d* shown in FIG. 7A. In embodiments, in order to prevent display device 710 from staying connected to analyte sensor system 708 longer than is expected or desired, analyte sensor system 708 may enforce timeouts, and/or may cause timeouts to be enforced. That is, for example, there may be a predetermined limit set with respect to the duration of the connection, and upon the expiry of the same, the connection to analyte sensor system 708 may be terminated. By way of example, reference is made to operation 715 shown in FIG. 7A. This may allow for other display devices 710 to connect or attempt to connect to analyte sensor system 708. Analyte sensor system 708 may maintain a list of display devices 710 that have recently connected to analyte sensor system 708. In some cases, this may be known as a whitelist. Analyte sensor system 708 may use this list to permit only listed display devices (i.e., that have recently connected) to connect to analyte sensor system 708.

Figure 9A:
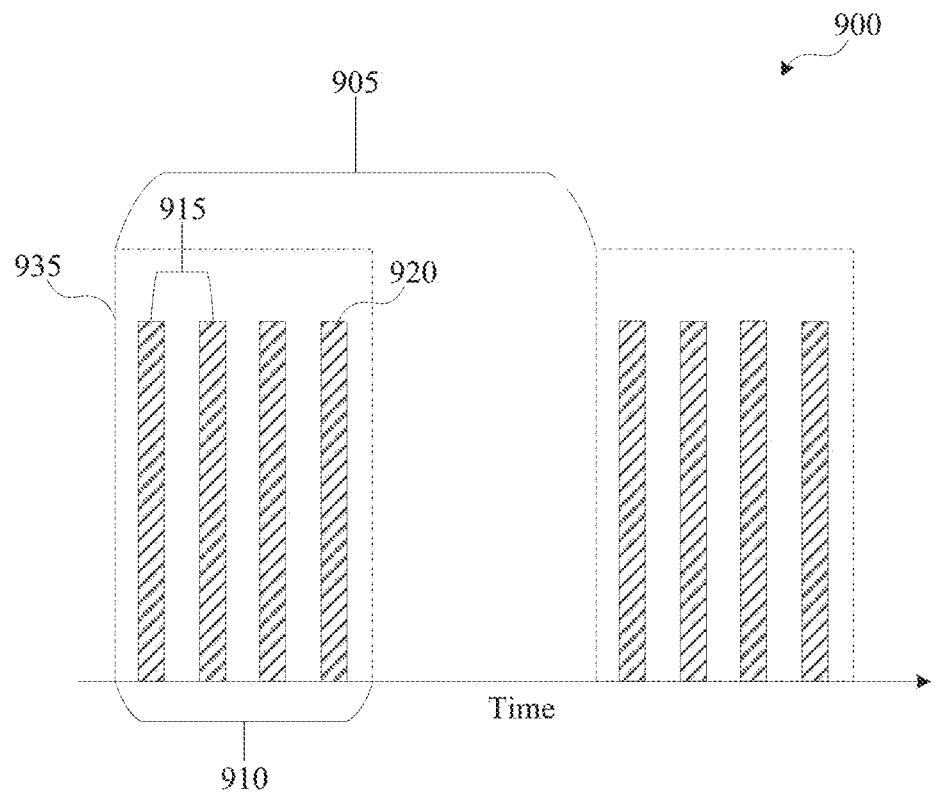
FIG. 9A is a timing diagram illustrating the transmission of advertisement messages in accordance with embodiments of the present disclosure.

FIG. 9A is a timing diagram illustrating an example of the transmission of advertisement messages in accordance with the present disclosure. More specifically, FIG. 9A provides an example embodiment of advertisement duration structure 935 that may be used in connection with pairing or connecting analyte sensor system 708 to display device 710 and/or analyte display device 110. In connection with the above and in accordance with embodiments of advertisement duration structure 935, advertisement messages 920 may be sent according to a time interval that occurs periodically based on a schedule. This may be known in some cases as an advertisement window interval 905. This period of repetition of the occurrence of this interval may be any length of time, but in one specific example is 5 minutes. Nevertheless advertisement window interval may be configured or set to vary depending upon the nature of the operation of analyte sensor system 708 with respect to gathering and processing analyte data. Thus, every 5 minutes (in this example), there will be a time window for advertisement messages to be transmitted. The time window for advertisement messages is a duration of time during which advertisement messages may actually be transmitted. This may also be known in some cases as advertisement duration 910. By way of example, this window may range from 7 to 22 seconds. It will be appreciated by one of ordinary skill in the art upon studying the present disclosure, however, that the window for the advertisement duration may range from 0 to any reasonable amount of time. Typically, the duration of the window is shorter than advertisement window interval 905.

During advertisement duration window 910, advertisement messages 920 may be transmitted, in some cases periodically, though not necessarily so, according to advertisement message interval 915. Advertisement message interval 915 may be thought of as a time interval between sequential or successive advertisement messages 920. One specific example range for the advertisement interval 915 is between 20 and 90 msec, though it will be appreciated upon studying the present disclosure that the advertisement message interval 915 may be shorter or longer, and/or may be adaptively variable or configurable in length, depending on the relevant circumstances. After advertisement window interval has elapsed, advertisement messages 920 may resume transmission, and advertisement duration structure 935 may be repeated (e.g., as 935'). It should also be noted that one or more of the advertisement message interval, advertisement duration length, and advertisement window interval can be reconfigured as between advertisement duration structures 935 and 935'.

For convenience for the purposes of the following discussion, display devices will be referred to as display devices 710, whereas analyte display devices will be referred to as analyte display device 110. It will be appreciated, however, that in other places herein, the term display devices 710 is broad enough to cover any display device or collection of display devices, including analyte display device 110 and medical devices 136.

The above-mentioned advertisement window interval 905, advertisement duration 910, and advertisement message interval 915 can each vary based on a variety of factors. For example, the values of these parameters may vary based on the type and/or number of display devices 710 present, and/or on how recently such display devices 710 have connected to analyte sensor system 708. These values of these parameters can also vary in order to optimize battery life, to speed up connection time, etc. Any one of a decreased advertisement window interval 905, an increased advertisement duration 910, and a decreased advertisement message interval 915 may increase the likelihood that a particular display device 710 successfully connects to the targeted analyte sensor system 708. Typically, however, there may be a concomitant increase in power consumption.

In terms of connecting to display devices 710 in a particular order, during a time window corresponding to advertisement duration 910, analyte sensor system 708 may in some cases first attempt to connect with display device 710 (e.g., a smartphone) and then with analyte display device 110 (e.g., a proprietary device, which can be a device be designed for the purpose of receiving and present analyte data). One potential issue with this connection protocol, in terms of the order used, is that more time of advertisement duration 910 may need to be dedicated for the connection with display device 710 as compared to the connection with analyte display device 110, for example since being a proprietary display device, analyte display device 110 may be optimized for use with analyte sensor system 708.

Furthermore, there may occasionally be difficulties connecting with display device 710. If display device 710 is unable to connect during a time segment (not shown FIG. 9A) of advertisement duration 910 specifically allocated to display device 710, analyte display device 110 may still be able to connect subsequently by sending advertisement messages 920 during other portions or time segments within advertisement duration 910. But in some cases, the time segment allocated to display device 710 within advertisement duration 910 is bounded by another time segment dedicated to the analyte display device 110, such that it may not be feasible to allocate display device 710 additional time segments in which to connect. Alternatively, if additional time from advertisement duration 910 is allocated to display device 710, the analyte display device 110 may not be left with sufficient time available to make a connection.

Accordingly, aspects of the present disclosure also include configuring the ordering of connection for various display devices 710, including with respect to analyte display device 110, as well as configuring advertisement window interval 905, advertisement duration 910, and advertisement message interval 915, and other features associated with advertisement messaging and/or related thereto. Configuring the ordering of connection for various display devices 710 and analyte display device 110 according to the present disclosure may increase the likelihood of establishing a connection between such display devices, including display devices 710 and analyte display device 110, on the one hand, and analyte sensor system 708 on the other hand, while also reducing power consumption due to increased efficiency of the connection protocol. In this manner, the overall reliability of communications related to analyte data is increased, while the power consumption is decreased. In this connection, methods for connecting analyte sensor system 708 to analyte display device 110 and display device 710 are provided.

Figure 9B:
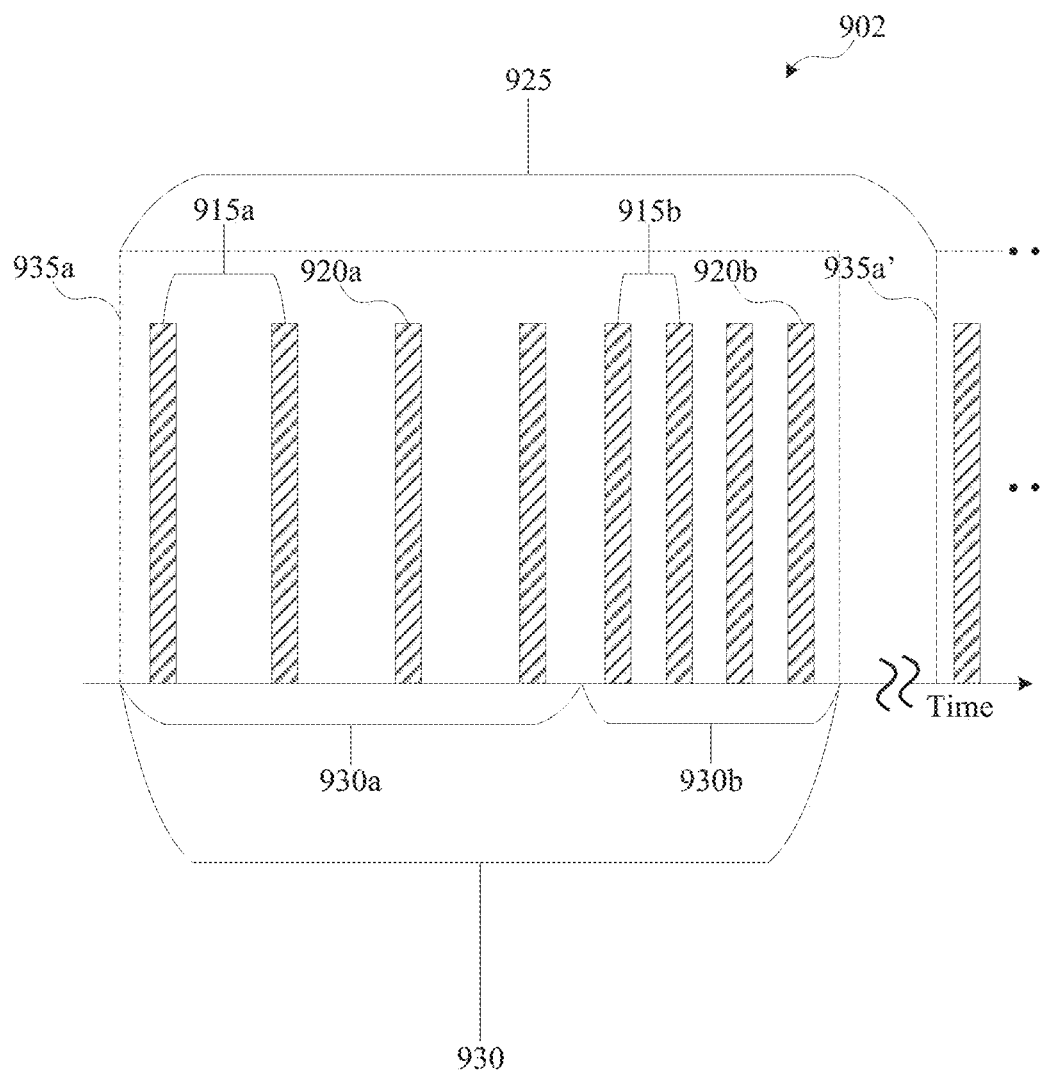
FIG. 9B is a timing diagram illustrating example aspects of the transmission of advertisement messages in accordance with embodiments of the present disclosure.

FIG. 9B is a timing diagram illustrating an example of the transmission of advertisement messages in accordance with the present disclosure. More specifically, FIG. 9B provides an example embodiment of advertisement duration structure 935a that may be used in connection with pairing or connecting analyte sensor system 708 to display devices 710 and/or analyte display device 110. In accordance with embodiments of advertisement duration structure 935a, during first time segment 930a of advertisement duration 930, advertisement messages 920a may be sent (e.g., with the targeted device being display device 710) according to first advertisement message interval 915a. During second time segment 930b of advertisement duration 930, advertisement messages 920b may be sent (e.g., with the targeted device being analyte display device 110) according to second advertisement message interval 915b. In specific embodiments, first time segment 930a may be about 20 seconds long, and second time segment 930b may be about 2 seconds long. It will also be appreciated that with respect to this specific embodiment as well as other embodiments, that first and second time segments 930a and 930b may be switched in terms of temporal order, as will be shown in connection with FIG. 9D, for example.

After advertisement window interval 925 has elapsed, advertisement messages 920 may resume transmission, and advertisement duration structure 935a may be repeated (as advertisement duration structure 935a'). First and second time segments 930a and 930b may be allocated to different devices (as alluded to above with respect to the possibility that certain devices may be targeted), and thusly used to connect to different devices at different points during advertisement duration 930. For example, time segment 930a may be allocated to display device 710, and second time segment 930b may be allocated to analyte display device 110. As shown, within advertisement duration 930, first time segment 930a precedes second time segment 930b. In some cases, however, first and second time segments 930a and 930b may be switched in terms of temporal order (in which case, the allocation to analyte display device 110 and display device 710 may also switch). It should also be noted that one or more of the advertisement message interval, time segment length, advertisement duration length, and advertisement window interval can be reconfigured as between advertisement duration structures 935a and 935a'.

FIG. 9C is a timing diagram illustrating an example of the transmission of advertisement messages in accordance with the present disclosure. More specifically, FIG. 9C provides an example embodiment of advertisement duration structure 945a that may be used in connection with pairing or connecting analyte sensor system 708 to analyte display device 110 and/or display devices 710. Aspects of FIG. 9C are substantially similar to those shown in FIG. 9B, though unlike FIG. 9B, FIG. 9C does not show specific advertisement messages (e.g., 920a, 920b, with reference to FIG. 9B) but does show multiple full advertisement duration structures 945a, 945a'. For example, in accordance with embodiments of advertisement duration structure 945a, during first time segment 950a of advertisement duration 950, advertisement messages 955a may be sent (e.g., with the targeted device being display device 710) according to a first advertisement message interval (e.g., advertisement interval 915a, with reference to FIG. 9C). During second time segment 950b of advertisement duration 950, advertisement messages 955b may be sent (e.g., with the targeted device being analyte display device 110) according to a second advertisement message interval (e.g., advertisement interval 915b, with reference to FIG. 9B).

After advertisement window interval 940 has elapsed, advertisement messages 955a' and 955b' may resume transmission, and advertisement duration structure 935a may be repeated (as advertisement duration structure 945a'). First and second time segments 950a and 950b may be allocated to different devices, as alluded to above with respect to devices being targeted, and thusly used to connect to different devices at different points during advertisement duration 950. For example, time segment 950a may be allocated to display device 710, and second time segment 950b may be allocated to analyte display device 110. As shown, within advertisement duration 950, first time segment 950a precedes second time segment 950b. In some cases, however, first and second time segments 950a and 950b may be switched in terms of temporal order (in which case, the allocation to analyte display device 110 and display device 710 may also switch). It should also be noted that one or more of the advertisement message interval, time segment length, advertisement duration length, and advertisement window interval can be reconfigured as between advertisement duration structures 945a and 945a'.

Figure 9D:
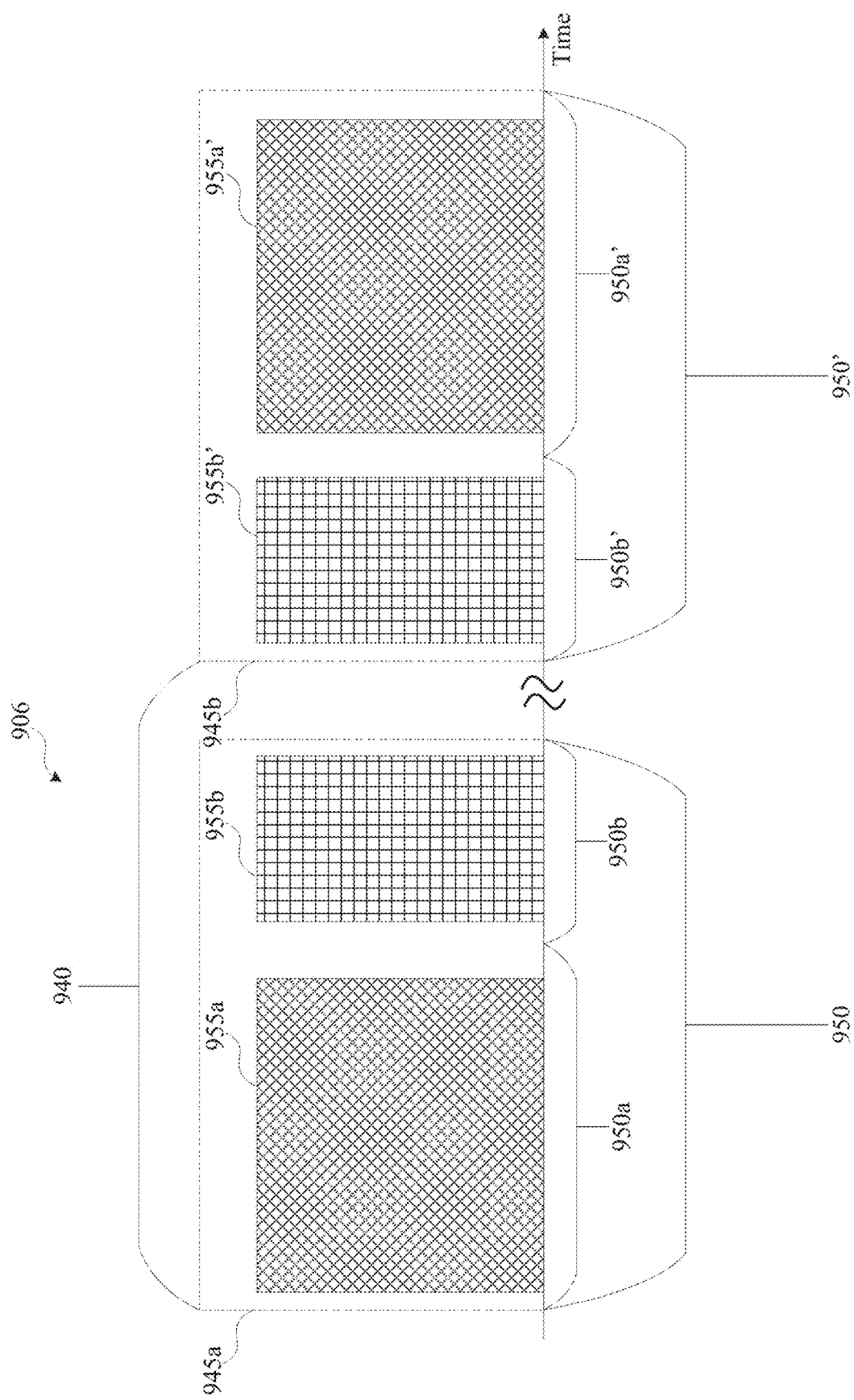
FIG. 9D is a timing diagram illustrating example aspects of the transmission of advertisement messages in accordance with embodiments of the present disclosure.

FIG. 9D is a timing diagram illustrating an example of the transmission of advertisement messages in accordance with embodiments of the present disclosure. More specifically, FIG. 9D provides an example embodiment of advertisement duration structures 945a and 945b that may be used in connection with pairing or connecting analyte sensor system 708 to display devices 710 and/or analyte display device 110. In accordance with embodiments, advertisement duration structure 945a may be substantially similar to the like-numbered element shown in FIG. 9C.

After advertisement window interval 950 has elapsed, in advertisement duration 950', advertisement duration structure 945a may have be reconfigured into advertisement duration structure 945b. For example, this reconfiguration may entail swapping the order of time segments 950a and 950b (and likewise swapping the order in which devices are targeted for connection, as will be explained). In this regard, advertisement duration structure 945b may include advertisement messages 955b' being transmitted in time segment 950b' preceding advertisement messages 955a' being transmitted in time segment 950a'. In other words, where in advertisement duration structure 945a time segment 950a may have been allocated to display device 710, and time segment 950b may have been allocated to analyte display device 110, in advertisement duration structure 945b, analyte display device 110 and display device 710 have been swapped in terms of the temporal order of time segment allocation relative to advertisement duration structure 945a.

By swapping the order and allocating a first portion of advertisement duration 950' for connection to analyte display device 110 rather than display device 710, the remainder of advertisement duration 950' can then be dedicated to advertising to display device 710 (e.g., in some cases, time segment 950a' can be expanded to allow additional time for display device 710 to connect to analyte sensor system 708). It will also be noted here that the length of the time segment allocated to analyte display device 110 may typically though not always be shorter than the length of the time segment allocated to display device 710.

It may also be the case that one or more of the advertisement message interval, time segment length, advertisement duration length, and advertisement window interval are reconfigured as between advertisement duration structures 945a and 945b. For example, time segment 950a' may be extended to be encompass a span of time less than or equal to the remainder of advertisement duration 950', which may likewise be extended to a span of time less than or equal to the remainder of an advertisement window interval (not shown) associated with advertisement duration structure 945b.

Figure 14A:
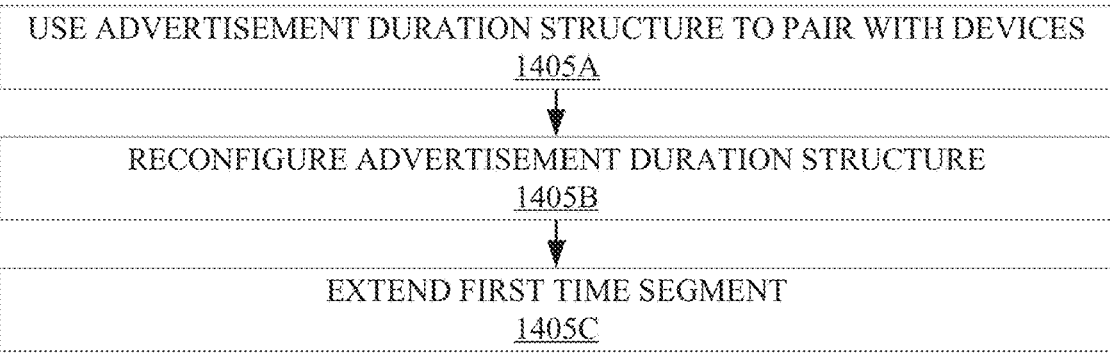
FIG. 14A is an operational flow diagram illustrating various operations that may be performed in accordance with embodiments of the disclosure.

Referring now to FIG. 14A, example implementations of features of various methods such as, for example, methods 704, 706, 712, 714, 716, 718, 722, 724, and 726 are illustrated. One such example implementation includes aspects of method 1400 for connecting analyte sensor system 708 to a first display device (e.g., analyte display device 110, which may be referred to here as DD1 or display device 710a) and a second display device (which, e.g., may be a smartphone or the like, and may be referred to here as DD2 or display device 710b). As shown in FIG. 14A, at operation 1405A, method 1400 includes using an advertisement duration structure (e.g., advertisement duration structure 945a or the like) in attempt to pair analyte sensor system 708 with DD1 and DD2. According to the advertisement duration structure, an advertisement duration (e.g., advertisement duration structure 945a or the like, with reference to FIG. 9D) includes a first time segment (e.g., time segment 950a or the like) and a second time segment (e.g., time segment 950b or the like). The first time segment is allocated to DD2. The second time segment is allocated to DD1. In connection with operation 1405A, the first time segment precedes the second time segment.

Figure 9E:
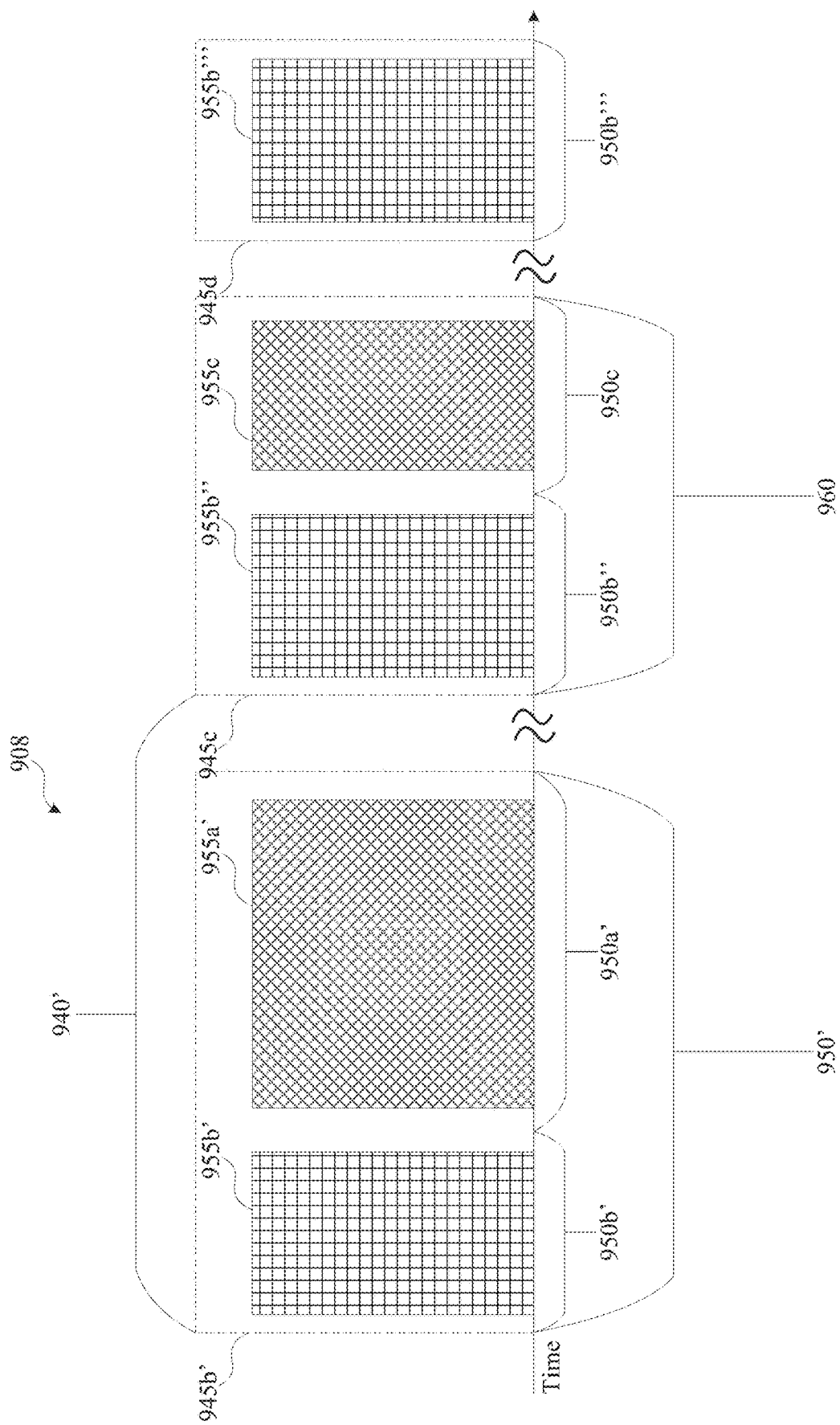
FIG. 9E is a timing diagram illustrating example aspects of the transmission of advertisement messages in accordance with embodiments of the present disclosure.

At operation 1405B, method 1400 includes reconfiguring the advertisement duration structure such that the second time segment precedes the first time segment. With reference to FIG. 9D, an example of a reconfigured advertisement duration structure may be advertisement duration structure 945b. In embodiments, at operation 1405C, reconfiguring the advertisement duration structure may entail extending the first time segment to a span of time being less than or equal to a remainder of an advertisement duration (e.g., advertisement duration 950). With reference to FIG. 9E, described in further detail below, operation 1405C may also involve shortening, eliminating, or otherwise modifying time segments of advertisement duration structures. With the reconfigured advertisement duration structure, as shown, DD1 is now targeted for connection using advertisement messages before DD2 is targeted for connection.

FIG. 9E is a timing diagram illustrating an example of the transmission of advertisement messages in accordance with the present disclosure. More specifically, FIG. 9E provides an example embodiment of advertisement duration structures 945b', 945c, and 945d that may be used in connection with pairing or connecting analyte sensor system 708 to display devices 710 and/or analyte display device 110. In some cases, advertisement duration structure 945b' may be replaced by advertisement duration structure 945a. In accordance with embodiments, advertisement duration structure 945b' may be substantially similar to the like-numbered element shown in FIG. 9D, although advertisement window interval 940' may in some cases be a modified version of advertisement window interval 940 shown in FIG. 9C.

In accordance with embodiments of advertisement duration structure 945c, during time segment 950b'' of advertisement duration 960, advertisement messages 955b'' may be sent according to an advertisement message interval. During time segment 950c of advertisement duration 960, advertisement messages 955c may be sent according to an advertisement message interval. In accordance with embodiments of advertisement duration structure 945d, during time segment 950b''' (which is essentially the advertisement duration of advertisement duration structure 945d of advertisement duration 960, advertisement messages 955b''' may be sent according to an advertisement message interval.

In some cases, time segments 950b', 950b'', and 950b''' may be substantially similar and may be allocated to the same display device. In embodiments time segments 950b', 950b'', and 950b''' are dedicated to analyte display device 110. In some such embodiments, time segments 950a and 950c may be allocated to the same display device, for example, display device 710, which may be a smartphone. As illustrated in FIG. 9E, as between advertisement duration structures 945b' and 945c, the length of time segments 950a' is reduced to the length of time segment 950c. This may be advantageous if, for example, display device 710 to which time segments 950a' and 950c may have been allocated is not being used (e.g., is not on the whitelist or has not ever or recently been paired with analyte sensor system 708). By reducing the length of time segment 950a' (e.g., from 20 seconds, in specific examples) to the length of time segment 950c (e.g., to 7 seconds or less, in specific examples), less advertisement messages 955c will be transmitted to display device 710, thus saving power at basically no expense to reliability since display device 710 is likely not being used. Likewise, with regard to advertisement duration structure 945d, relative to advertisement duration structures 945b and 945c, the length of time segments 950a' and 950c are reduced to zero, thus further reducing power consumption. In example deployments NFC may be used to convey an instruction to modify the length of one or more time segments. For example, after the length of time segment 950a' has been reduced (e.g., to time segment 950c or to zero), NFC may be used to restore the length to pre-reduction its pre-reduction state.

As mentioned, in example implementations, to determine whether or not display device 710 is being used, the whitelist or another indicator regarding the likelihood that display device 710 will be used may be consulted. In this regard, the whitelist or other indicator may provide an assessable value that indicates whether or not analyte sensor system 708 has paired with a particular display device 710 and/or analyte display device 110. If, for example, display device 710 or analyte display device 110 is going to be used (e.g., is on the whitelist), a greater length may be used for the corresponding time segment, and this may increase the likelihood of successfully connecting display device 710 or analyte display device 110. Pairing display device 710 or analyte display device 110 with analyte sensor system 708 via NFC may be used to place the display device 710 or analyte display device 110 on the whitelist and trigger setting the allocated time segment to an increased value.

Example implementations also involve setting the a particular time segment to zero seconds, for example if device allocated that time segment has not been paired with analyte sensor system 708. Alternatively or in addition, other mechanisms may be used to set the particular time segment to a decreased value, including zero seconds in some cases. For example, even if the device has been paired with analyte sensor system 708 and is on the whitelist, the device may be removed from the whitelist, triggering a decrease in the second time segment. This may be done in some cases based on user input received via GUI 340. With reference to FIG. 3E, for example, sub-menu 314*b* shows how a user may select to remove a device or replace a device with another device.

Figure 14B:
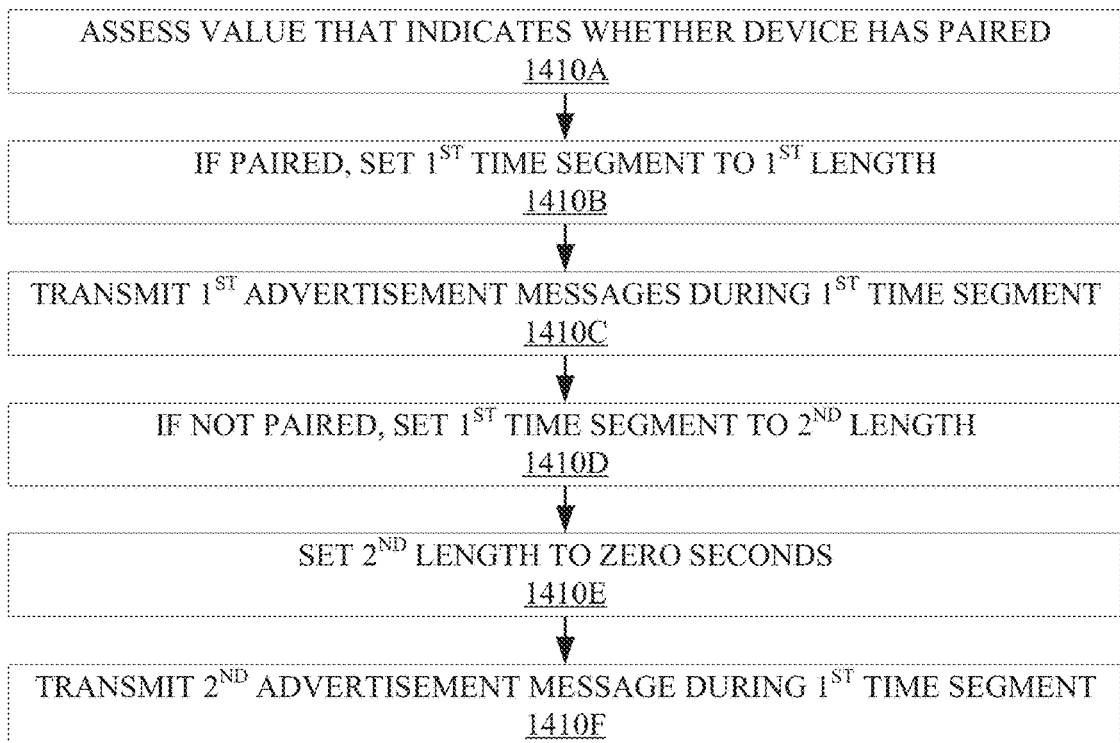
FIG. 14B is an operational flow diagram illustrating various operations that may be performed in accordance with embodiments of the disclosure.

Referring now to FIG. 14B, example implementations of features of various methods such as, for example, methods 704, 706, 712, 714, 716, 718, 722, 724, and 726 are illustrated. One such example implementation includes aspects of method 1402 for connecting analyte sensor system 708 to a first display device (e.g., analyte display device 110, which may be referred to here as DD1 or display device 710*a*) and a second display device (which, e.g., may be a smartphone or the like, and may be referred to here as DD2 or display device 710*b*). As shown in FIG. 14B, at operation 1410A, method 1402 includes assessing a value that indicates whether or not analyte sensor system 708 has previously paired with DD2. The value may be derived from a whitelist or the like.

At operation 1410B, if the value indicates that analyte sensor system 708 has paired with DD2, method 1402 includes setting a first time segment (e.g., time segment 950*a*', with reference to FIG. 9E) of a first advertisement duration (e.g., advertisement duration 950') to a first length. At operation 1410C, if the value indicates that analyte sensor system 708 has paired with DD2, method 1402 involves transmitting a first set of advertisement messages (e.g., advertisement messages 955*a*') to DD2 during the first time segment. Although reference is made to FIG. 9E here, it will be noted that advertisement duration structure 945*a* (with reference to FIG. 9D) can also be used in connection with method 1402. At operation 1410D, if the value indicates that analyte sensor system 708 has not paired with DD2, method 1402 includes setting the first time segment (e.g., time segment 950*a*') to a second length (e.g., time segment 950*c* within advertisement duration 960) that in some cases is less than the first length. Although reference is made to FIG. 9E here, it will be noted that advertisement duration structure 945*a* (with reference to FIG. 9D) can also be used in connection with operation method 1402.

In embodiments, method 1402 further involves, at operation 1410E, setting the second length of the first time segment to zero seconds if the value indicates that analyte sensor system 708 has not paired with DD2. For example, this may be illustrated by advertisement duration structure 945*d* of FIG. 9E. As shown in advertisement duration structure 945*d*, the first time segment (e.g., time segment 950*a*' and/or 950*c*) allocated to DD2 has been eliminated, and only the second time segment (e.g., time segment 950*b*', 950*b*'', and/or 950*b*''') remains. In embodiments, operation 1410B and/or 1410E may be done responsive to signaling received via a proximity-based wireless protocol such, for example, as NFC. At operation 1410F, if the value indicates that analyte sensor system 708 has not paired with DD2, method 1402 involves transmitting a second set of advertisement messages (e.g., advertisement messages 955*c*) to DD2 during the first time segment of the second length (e.g., time segment 905*c*), if the length of the first time segment is not zero seconds.

Figure 14C:
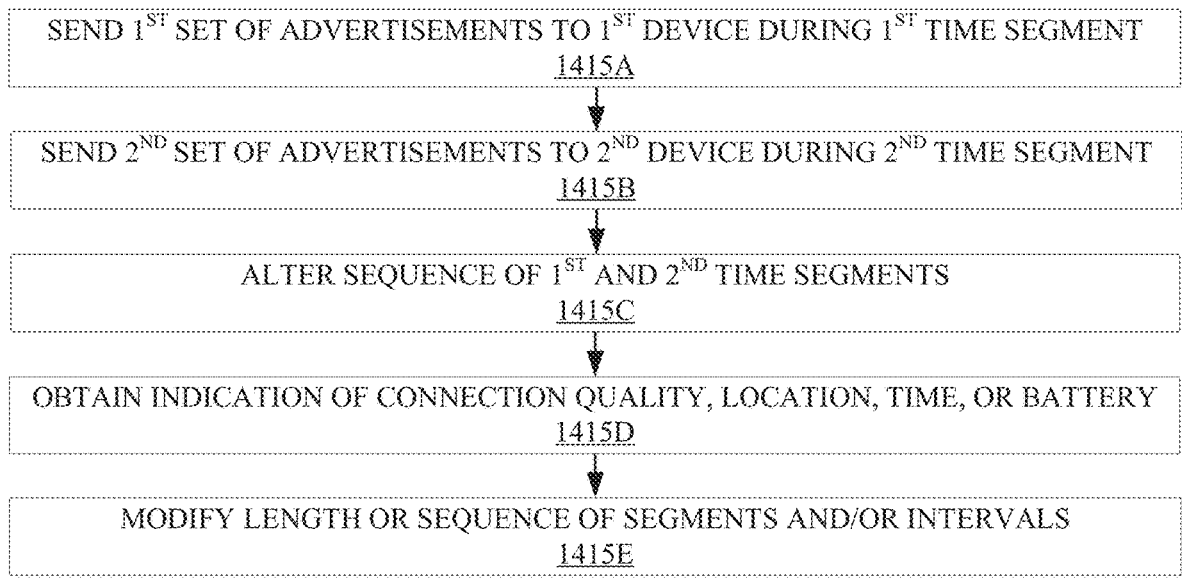
FIG. 14C is an operational flow diagram illustrating various operations that may be performed in accordance with embodiments of the disclosure.

Referring now to FIG. 14C, example implementations of features of various methods such as, for example, methods 704, 706, 712, 714, 716, 718, 722, 724, and 726 are illustrated. One such example implementation includes aspects of method 1404 for connecting analyte sensor system 708 to a first display device (e.g., analyte display device 110, which may be referred to here as DD1 or display device 710*a*) and a second display device (which, e.g., may be a smartphone or the like, and may be referred to here as DD2 or display device 710*b*). As shown in FIG. 14C, at operation 1415A, method 1404 includes, during a first time segment (e.g., time segment 950*a*, with reference to FIG. 9D) within an advertisement duration (e.g., advertisement duration 950), transmitting or sending a first set of advertisement messages (e.g., advertisement messages 955*a*) to DD2 according to a first advertisement interval. Advertisement intervals may be thought of as the spacing in time between transmissions of successive advertisement messages. At operation 1415B, method 1404 includes, during a second time segment (e.g., time segment 950*b* within the advertisement duration, transmitting or sending a second set of advertisement messages (e.g., advertisement messages 955*b* to DD1 according to a second advertisement interval.

Method 1404 optionally includes, at operation 1415C, altering a sequence of the first and second time segments such that the second time segment precedes the first time segment. One example of the altered sequence is shown in FIG. 9D in advertisement duration structure 945*b*. The sequence in some cases may be altered based on a value that indicates whether or not analyte sensory system 708 has paired with DD2. Alternatively or in addition, the alteration of the sequence may be based on a value that indicates one or more of a connection quality, time of day, location, and battery life.

Method 1404 may include, at operation 1415D, obtaining an indication of a quality of a connection between analyte sensor system 708 and DD1 (e.g., or analyte display device 110) and/or between analyte sensor system 708 and DD2 (e.g., or other display devices 710). Method 1404 may also include, at operation 1415E, modifying one or more of the length of the first time segment (e.g., time segment 950*a* or the like), the first advertisement interval, the second time segment (e.g., time segment 950*b* or the like), and/or the second advertisement interval. The modification can be based on the quality obtained at operation 1415D. Additionally or alternatively, the modification may be initiated based on signaling sent to analyte sensory system 708 from DD1, DD2, and/or another source (e.g., user or sensor input). The modification may in embodiments be based on a value that indicates one or more of a connection quality, time of day, location, and battery life.

Figure 14D:
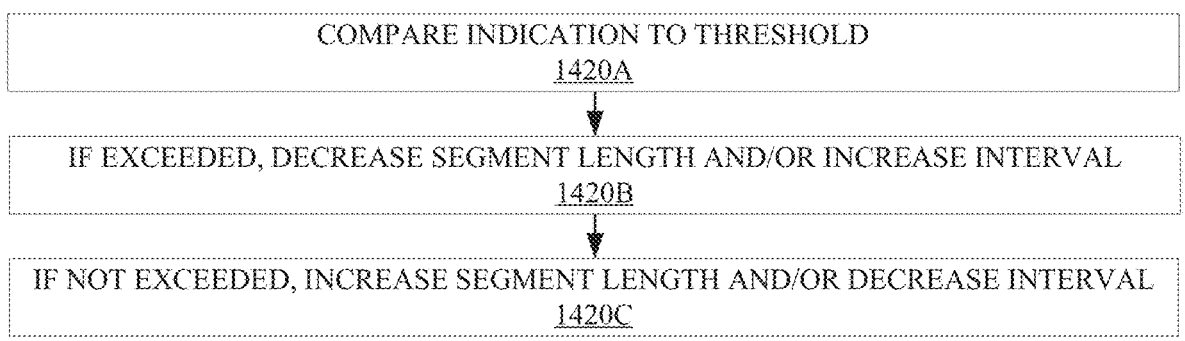
FIG. 14D is an operational flow diagram illustrating various operations that may be performed in accordance with embodiments of the disclosure.

Referring now to FIG. 14D, example embodiments of operation 1415E are illustrated. Operation 1420A, for example, involves comparing the indication of the quality (obtained at operation 1415D with reference to FIG. 14C) to a threshold. At operation 1420B, if the indication is related to DD2 and exceeds the threshold, the modification occurring at operation 1415E may include decreasing the length of the first time segment (compare, e.g., time segment 950*a*' to time segment 950*c*) and/or increasing the second advertisement interval. If, however, the indication is related to DD1 and exceeds the threshold, the modification occurring at operation 1415E may include decreasing the length of the second time segment (e.g., 950b') and/or increasing the first advertisement interval.

At operation 1420C, if the indication is related to DD2 and falls below the threshold, the modification occurring at operation 1415E may include increasing the length of the first time segment (compare, e.g., time segment 950c to time segment 950a') and/or decreasing the second advertisement interval. If, however, the indication is related to DD1 and falls below the threshold, the modification occurring at operation 1415E may include increasing the length of the second time segment (e.g., 950b') and/or decreasing the first advertisement interval. Hysteresis may be employed in connection with the above comparison and subsequent action, for example, to determine the appropriate modification (or not) if the indication equals the threshold. Alternatively or in addition, the appropriate modification (or not) if the indication equals the threshold may be based on pre-programmed instructions, user preferences, etc.

Figure 14E:
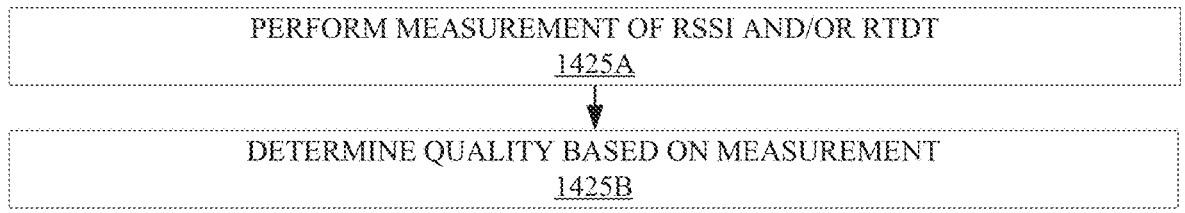
FIG. 14E is an operational flow diagram illustrating various operations that may be performed in accordance with embodiments of the disclosure.

Referring now to FIG. 14E, example embodiments of operation 1415D are illustrated. Operation 1425A, for example, involves performing a measurement of one or more of an RSSI and an RTDT. This may be done at analyte sensor system 708, DD1, DD2, and/or other display devices 710. At operation 1425B, operation 1415D includes determining the quality based on the measurement.

Figure 9F:
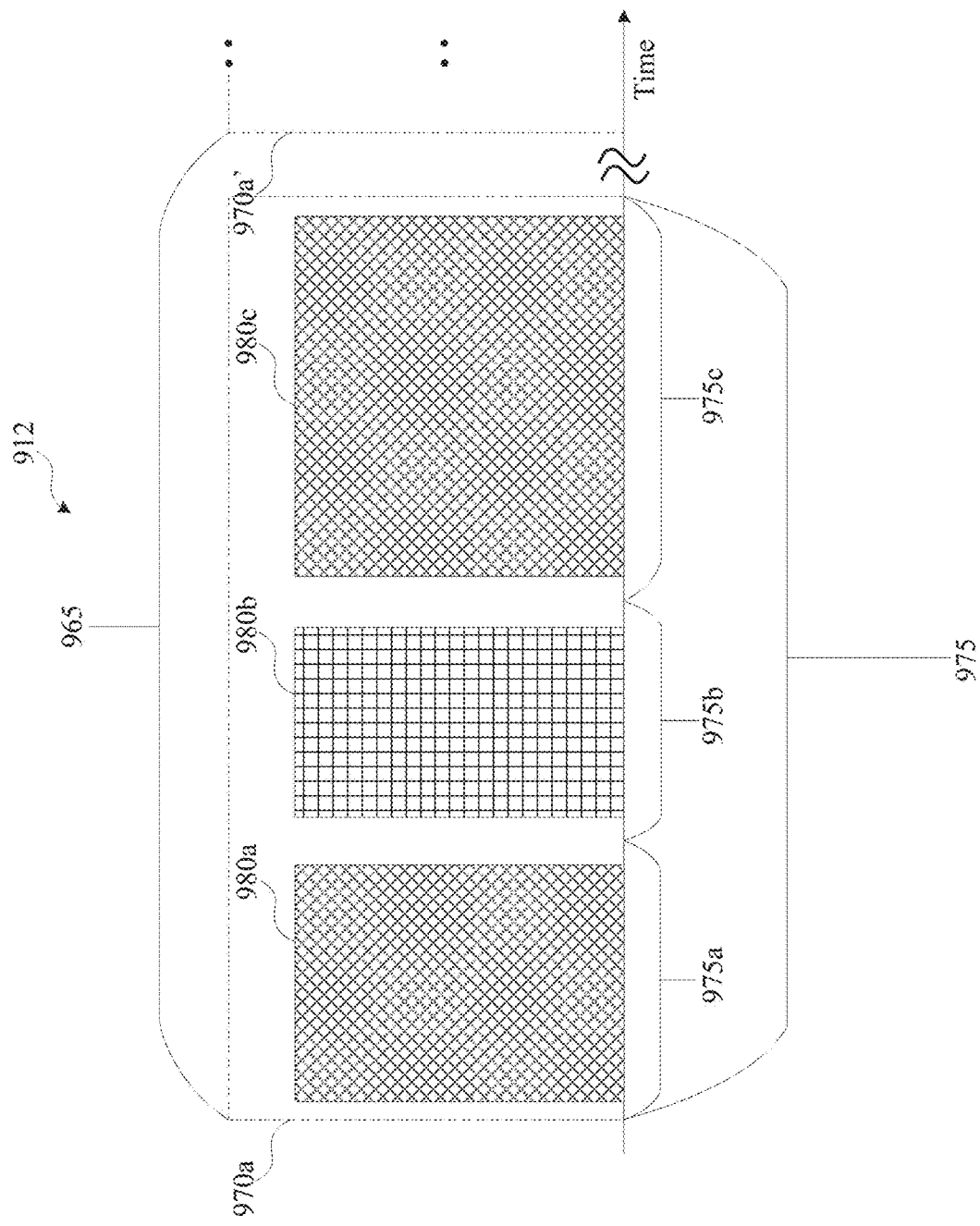
FIG. 9F is a timing diagram illustrating example aspects of the transmission of advertisement messages in accordance with embodiments of the present disclosure.

FIG. 9F is a timing diagram illustrating an example of the transmission of advertisement messages in accordance with the present disclosure. More specifically, FIG. 9F provides an example embodiment of advertisement duration structures 970a that may be used in connection with pairing or connecting analyte sensor system 708 to display devices 710 and/or analyte display device 110. In accordance with embodiments of advertisement duration structure 970a, during first time segment 975a of advertisement duration 975, advertisement messages 980a may be sent according to an advertisement message interval. During time segment 975b of advertisement duration 975, advertisement messages 980b may be sent according to an advertisement message interval. In accordance with embodiments of advertisement duration structure 970a, during time segment 980c of advertisement duration 975, advertisement messages 980c may be sent according to an advertisement message interval.

As mentioned above in connection with various advertisement duration structures, for some embodiments of advertisement duration structure 970a, time segment 975a may be allocated to display device 710, whereas time segment 975b may be allocated to analyte display device 110. Optionally, time segment 975c may be allocated to display device 710 or analyte display device 110. For example, if display device 710 fails to connect to analyte sensor system 708 during time segment 975a, time segment 975c may be allocated to provide display device 710 an additional opportunity to connect with analyte sensor system 708. It should be noted at this juncture that time segments 975a-c can be arranged in different sequences within advertisement duration 975 and can be allocated to one or more display devices 710 and/or analyte display device 110.

As described in connection with various timing diagrams mentioned above and shown in FIGS. 9A-9E, aspects of the advertisement duration structures described may be made configurable or variable. Such aspects may be configured by analyte sensor system 708 or a remote device connected thereto (e.g., display device 710 or analyte display device 110). In example embodiments, the sequence or length of time segments within an advertisement duration structure, and/or other characteristics of the advertisement duration structure, can be configured based on various conditions or input parameters. One such condition or input parameter is a value that indicates whether or not analyte sensor system 708 has previously been paired with display device 710 or analyte display device 110. In some cases, a whitelist can be maintained and/or assessed for this purpose. Another such condition or parameter is the quality of a connection to analyte sensor system 708 (e.g., with display device 710, analyte display device 110, and/or another remote device). Such conditions and parameters may be generated by display device 710 and/or analyte display device 110 and signaled to analyte sensor system 708, or may be generated by analyte sensor system itself. Alternatively or in addition, multiple devices can work in collaboration to generate such conditions or parameters.

With respect to varying advertisement duration structures based on conditions or parameters, embodiments of a method for connecting analyte sensor system 708 to analyte display device 110 and/or display device 710 may include receiving an indication of a quality of a connection between analyte sensor system 708 and analyte display device 110 and/or display device 710. The method may also include modifying aspects of one or more advertisement duration structures based on the indication. In other words, quality of service (QoS) may be used to adaptively or intelligently configure the nature and/or timing of the transmission of advertisement messaging, for example, in order to control power consumption, error rate, and/or likelihood of connection. The indication of the quality may have been determined using one or more of a received signal strength indication (RSSI) and a return trip delay time (RTT).

By way of example, display device 710 (e.g., a smartphone) or analyte display device 110 may be capable of measuring and/or quantifying RSSI and/or RTT. The RSSI or RTT or both may then be compared to an expected value or a threshold. The comparison can in turn indicate the quality of the radio link—e.g., quantitatively and/or in degrees of poor to good according to various gradations. In some cases, the indication of the quality may include that no data is being received at all, or that there is a particular error rate in the received data. In other cases, it may be that the indication is used by analyte sensor system 708 to select a particular display device 710 and/or 110. For example, certain display devices 710 and/or 110 may be more robust than others with respect to variations in link quality and/or network conditions and the like.

Varying advertisement duration structures based on conditions or parameters may also be based on one or more of a location of analyte display device 110 and a location of display device 710 (e.g., based on various location determination signals and modules, such as GPS, A-GPS, and WiFi, etc.). By way of illustration, a connection between analyte sensor system 708 and analyte display device 110 or display device 710 may vary depending on as a function of the device's location. Location thus may be used as a proxy for connection quality, assuming the relationship between the two is understood. If not initially understood, this relationship can be monitored over time as a device tracks information about the quality and location and correlates to the two. Regardless, as with the quality, the device can use the location information to adaptively or intelligently configure the nature and/or timing of advertisement messaging, for example, in order to control power consumption, error rate, and/or likelihood or timing of successful connection.

Furthermore, there may be a device preference related to location. For example, a user may manually indicate that a particular display device 710 (e.g., a smartphone) is a preferred device when the user is at work in an office building, but that another display device (e.g., a smartwatch or analyte display device 110) is preferred when the user is at home or within a specific room of the home. The user may be prompted to make such manual indications, for example by a pop-up triggered by application 330 running on the display device. With reference by way of example to FIG. 3E, GUI 340 may provide sub-menu 314*c* related to configuration parameters, which in turn include options 316*c*, one of which related to location. Options 316*c* can thus be used to receive a manual indication related to a user's preference with respect to location or any other configuration parameter.

Alternatively or additionally, a device may track user preference over time, e.g., based on frequency of use that shows a particular display device 710 is favored, and correlate this to monitored locations to determine if there exist any location-based device preferences. If such preferences exits, the device may trigger modifications to the nature and/or timing of advertisement messaging, based on the device's current location. This information may also be handled by analyte sensor system 708 in embodiments. Moreover, a device such as, for example, server system 334 may perform processing of such information, and relay preference information to display device 710 and/or analyte sensor system 708 (e.g., directly or via display device 710), which may then in turn prioritize connection to the preferred device (e.g., by employing the above-described advertising techniques to the same).

Varying advertisement duration structures based on conditions or parameters may also be based on the time of day. For example, a connection between analyte sensor system 708 and analyte display device 110 or display device 710 may vary depending on the time of day. Time of day may thus be used as a proxy for connection quality, assuming the relationship between the two is understood. As with location, if not initially understood, this relationship can be monitored over time as a device tracks information about quality and time of day and correlates to the two. In any event, as with the quality and location, the device can use the time of day to adaptively or intelligently configure the nature and/or timing of advertisement messaging, for example, in order to control power consumption, error rate, and/or likelihood of connection.

Furthermore, there may be a device preference or other reason for adaptation based on the time of day. For example, a user may manually indicate that a particular display device 710 (e.g., a smartphone) is a preferred device for particular times of day, but that another display device 710 (e.g., a smartwatch or analyte display device 110) is preferred at other times of day. As mentioned above in connection with location, the user may be prompted to make such manual indications, for example by a pop-up triggered by application 330 running on the device. With reference by way of example to FIG. 3E, GUI 340 may provide sub-menu 314*c* related to configuration parameters, which in turn include options 316*c*, one of which related to time (or time of day). Options 316*c* can thus be used to receive a manual indication related to a user's preference with respect to time of day.

Alternatively or additionally, a device may track user preference over time, e.g., based on frequency of use that shows a particular device is favored, and correlate this to the time of day to determine if there exist any time-based device preferences. If such preferences exits, the device may trigger modifications to the nature and/or timing of advertisement messaging depending on the time of day. This information may also be handled by analyte sensor system 708 in embodiments. Moreover, the device or for example server system 334 may do more heavy lifting in terms of handling such information, and relay preference information to analyte sensor system 708, which may then in turn prioritize connection to the preferred device (e.g., by employing the above-described advertising techniques to the same).

In some cases, particular events may be known or determined to occur at certain times of day. For example, some operating systems running on display device 710 such as smartphones and the like may be updated periodically during certain hours of the day. Such updates may or may not be within a user's control, and may involve restarting the device. The associated rebooting process may take several minutes or more. In these types of instances, it may be preferable for analyte sensor system 708 to connect to a different display device, such as a device that is not rebooting at that particular time (e.g., analyte display device 110). In this fashion, analyte data can continue to be received and analyzed by a display device, even if other display devices are unavailable. Here again, the timing of such events may be indicated manually be a user, or may be determined by a device through the tracking and correlation of information.

Varying advertisement duration structures based on conditions or parameters may also be based on battery life for analyte sensor system 708. Analyte sensor system may monitor its own remaining battery life, including a projected battery life, continuously or intermittently, and generate an indication of the same. In some cases, this monitoring may be done throughout the communications processes such that a real-time projection of battery life may be maintained. In example implementations, analyte sensor system 708 also monitors events that can affect battery life. Such events may include how often particular display devices 710 are out of range of analyte sensor system 708 and thus unavailable for connection. If, for example, display devices 710 are often out of range, analyte sensor system 708 may make fewer transmissions to such display devices 710, and thus may be projected to have a longer battery life. Conversely, if display devices 710 are more often in range, and/or are more often requesting to connect to analyte sensor system 708, it may be more likely for analyte sensor system 708 to make more transmissions to display devices 710. As such, the battery life may be projected to be shorter. Another indicator of projected battery life may include the advertisement window interval, advertisement duration, and/or advertisement message interval, as well as time segment lengths, and configurations related to the same. Depending on the value of each, the number of transmissions may be increased or decreased, hence affecting battery life. Alternatively, or additionally, varying advertisement duration structures based on conditions or parameters may also be based on glucose level of a user and/or when the analyte sensor system gets compressed (e.g., when the user is lying on belly on a bed). For example, if a user has an alert condition such as an "Urgent Low glucose level" or "Urgent Low glucose level soon", and the user is out of range of her display devices 710, a small communication window may not be sufficient for the analyte sensor system 708 to connect to the display devices 710 in time for the alert to display.

In such an example, the analyte sensor system 708 may modify its advertising pattern to advertise longer, and/or advertise more frequently, and/or with higher resolution intervals, and/or with higher transmission power. This may advantageously increase the chances of the analyte sensor system of being detected by the display devices 710. Once the display device connects and/or once the alert condition is not active, the analyte sensor system may go back to normal advertising patterns.

In this connection, modifying one or more aspects of the advertisement duration structure may beneficially be based on the indication of the battery life. As mentioned above, the number of transmissions, such as transmission of advertisement messages, can affect battery life. Thus, each of the time segments, advertisement durations, advertisement window intervals, and advertisement message periods, can likewise affect battery life; and modifying these features may provide a means for controlling battery life. Other factors may also be adapted based on the indication of the battery life. For example, transmission power may affect battery life and may thus be varied in order to more precisely and efficiently use battery power and hence extend battery life. Transmission power may be decreased in situations such as when devices are very close to analyte sensor system 708 or are operating in a friendly (non-hostile) network environment, thus extending battery life.

Referring again to FIG. 9F, in example implementations, time segment 975a precedes time segment 975b, and time segment 975b precedes time segment 975c. It should be noted, however, that the order of time segments 975a-c can be modified as desired. Thus, embodiments of the disclosure include configuring time segment 975b to precede time segment 975a and time segment 975a to precede time segment 975c. Modifying or configuring the order of the various time segments disclosed herein may be done based on an input parameter or condition. Additionally, the number of time segments used may likewise be based on the input parameter or condition and made adaptable/configurable.

For example, at a high level, the input parameter (or set of parameters or conditions in some cases), may indicate that is likely easier or more difficult for particular display devices 710 (e.g., smartphones) to connect to analyte sensor system 708. If connection is likely to be easier—e.g., more likely to be successful, or more likely to be successful quickly—time segment 975c may be shortened or jettisoned. If, however, connection is likely to be more difficult, the time segment 975c may provide an increased likelihood that display device 710 successfully connects to analyte sensor system 708. It will also be appreciated that the nature and timing aspects of the time segment 975c, including the length thereof and the advertisement message interval used therein, may be modified and/or configured according to the parameters and conditions described above.

As described above in connection with embodiments of the present disclosure, the input parameter/condition may be based on one or more of a location of analyte display device 110, a location of display device 710, and a location of analyte sensor system 708. Further, the input parameter or condition may be based on an indication of a quality of a connection with analyte sensor system 708. For example, the indication may be determined based on one or more of a received signal strength and a return trip delay time. Additionally or alternatively, the input parameter may be based on a time of day. Further, the input parameter may be based on an indication of a battery life for analyte sensor system 708. In short, the arrangement as well as the nature/timing of within advertisement duration structure 970a may be configured according to various input parameters, including where such configuration is adaptive and/or done on-the-fly. The configuration may also be based on the type of operating system being run on a given display device 710, on the type of display device 710, and/or on a combination of types of display devices 710 connecting or attempting to connect to analyte sensor system 708.

Figure 14F:
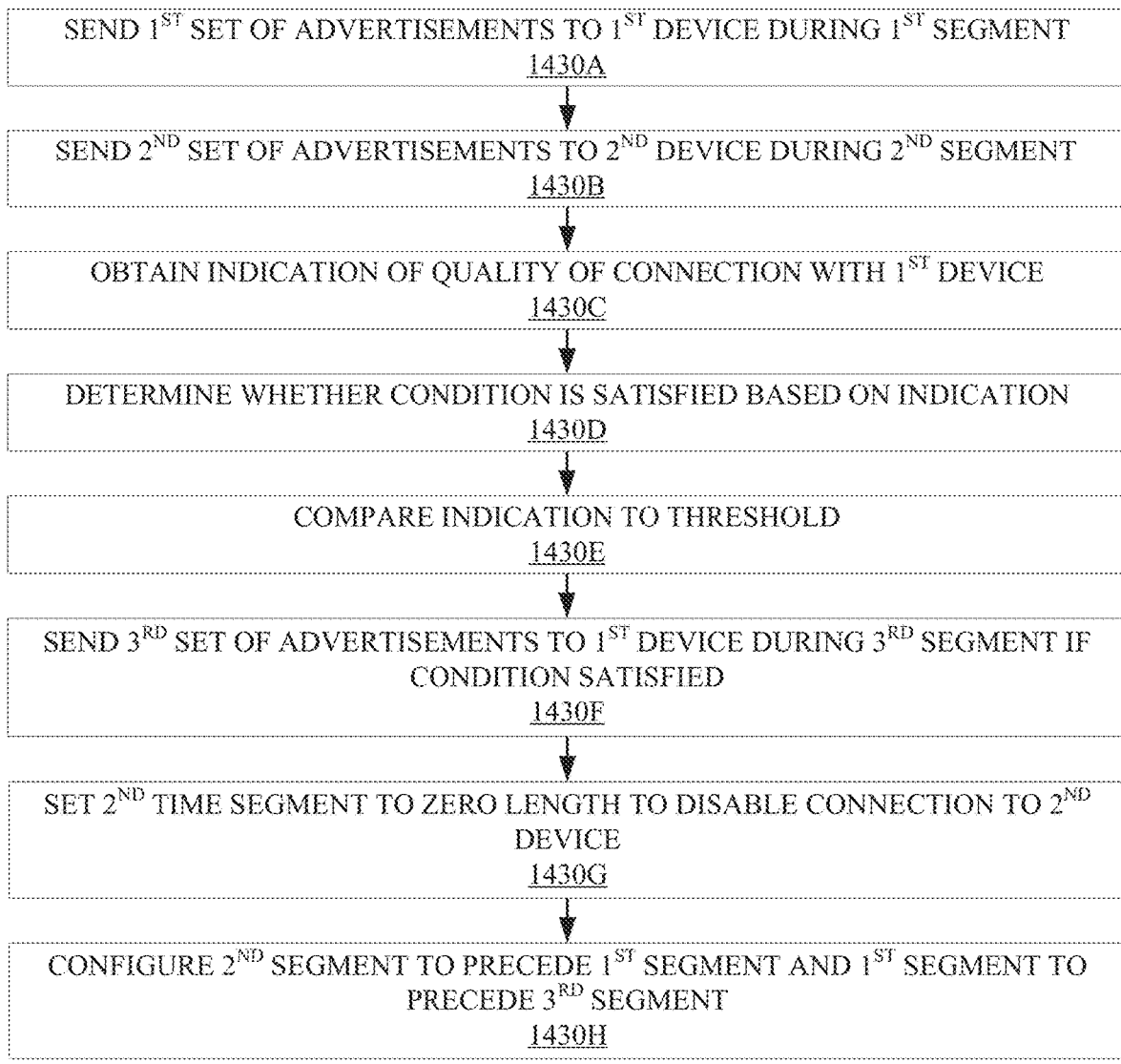
FIG. 14F is an operational flow diagram illustrating various operations that may be performed in accordance with embodiments of the disclosure.

Referring now to FIG. 14F, example implementations of features of various methods such as, for example, methods 704, 706, 712, 714, 716, 718, 722, 724, and 726 are illustrated. One such example implementation includes aspects of method 1406 for connecting analyte sensor system 708 to a first display device (e.g., analyte display device 110, which may be referred to here as DD1 or display device 710a) and a second display device (which, e.g., may be a smartphone or the like, and may be referred to here as DD2 or display device 710b). As shown in FIG. 14F, at operation 1430A, method 1406 includes, during a first time segment (e.g., time segment 975a, with reference to FIG. 9F) within an advertisement duration (e.g., advertisement duration 975), transmitting a first set of advertisement messages (e.g., advertisement messages 980a) to DD2. At operation 1430B, method 1406 includes, during a second time segment (e.g., time segment 975b within the advertisement duration, transmitting a second set of advertisement messages (e.g., advertisement messages 980b to DD1, if a length of the second time segment has not been set to zero seconds. In embodiments, method 1406 may involve, at operation 1430G, setting the length of the second time segment to zero to disable connection to DD1. At operation 1430F, method 1406 includes, during a third time segment (e.g., time segment 975c) within the advertisement duration, transmitting a third set of advertisement messages (e.g., advertisement messages 980c) to DD2, if a condition is satisfied. At operation 1430H, method 1406 may involve configuring the second time segment to precede the first time segment and the first time segment to precede the third time segment. The first and third time segments may be allocated to DD2, whereas the second time segment may be allocated to DD1.

With respect to operation 1430F, the condition may be satisfied if DD2 did not connect to analyte sensor system 708 during the first time segment. The first, second, and third sets of advertisement messages may each have respective advertisement intervals. At operation 1430C, method 1406 includes obtaining an indication of a quality of a connection to analyte sensor system 708. For example, the connection may be between analyte sensor system 708 and DD1, DD2, and/or other display devices 710 or the like. For example, the connection may be between analyte sensor system 708 and DD1, DD2, and/or other display devices 710 or the like. At operation 1430C, method 1406 includes determining whether the condition is satisfied, based on the indication. Determining whether the condition is satisfied, in embodiments, involves, at operation 1430E, comparing the indication of the quality to a threshold. Some examples of how operations 1430C-E may be carried out are discussed in connection with FIGS. 14C-E. In some cases, alternatively or in addition to being related to quality, the indication can be based at least in part on time of day, location, battery life, user input, etc.

I. Advertisement Messages

FIG. 8 illustrates an example structure for advertisement message 800 that in some cases may be transmitted for purposes of establishing a connection between two devices, according to various aspects of the present disclosure (e.g., with reference to FIG. 7A, at operation 705, and the like). In some cases, advertisement message 800 may be considered to be a packet or an advertisement packet. In the illustrated example, advertisement message 800 includes rows (fields)

800*a*-800*i* and columns 805', 810', and 815'. Though advertisement message 800 is represented in matrix form for visual/organization convenience, one of skill in the art will appreciate upon studying the present disclosure that in terms of a digital signal, advertisement message 800 may be represented by an one-dimensional array of bits or bytes typically arranged in a pre-determined fashion, for example, according to fields and sub-fields. In other words, if rows 800*a-i* of the matrix format of advertisement message 800 were to be unstacked and concatenated end to end, message 800 would appear as a one-dimensional array. Each field 800*a*, 800*b*, . . . 800*i* may be considered to correspond to a row of advertisement message 800, while a sub-field may be considered to correspond to a cell of a particular column within a particular row. Accordingly, in example implementations, within field 800*a*, range 805*a* is a sub-field or cell corresponding to column 805'.

Column 805' in example embodiments corresponds to address 805. Address 805 includes ranges 805*a-i*, where each range 805*a-i* may represent a range of bytes reserved for the corresponding field. Within each field 800*a-i*, a number of bytes may be reserved for each cell. That is, by way of illustration, one byte (address 805*a* may refer to byte zero "0" as the address of field 800*a* within message 800) may be used for preamble 810*a*. The number of bytes need not but in some cases may be the same for each cell of a column across various fields 800*a-i*. That is, by way of illustration, two bytes may be used for each cell 805*a-i* of address 805 and two bytes may be used for each cell 810*a-i* of description 810. Moreover, a variable number of bytes may be used in cells 815*a-i* of value 815. In other examples, different numbers of bytes may be used and numerous variations are contemplated within the scope and spirit of the present disclosure. It will also be appreciated that any number of rows and columns may be used, subject of course to the laws of physics and in some cases standardized communication protocols.

With further reference to FIG. 8, Column 805' in this example corresponds to address 805. Cells 805*a-i* may each contain a value (e.g., binary or hexadecimal or the like) that represents the length of the corresponding field 800*a-i*. Each length may in some cases be represented by a starting and ending position for the respective field. Column 810' in this example corresponds to description 810. Cells 810*a-i* may each contain a value that represents a description of the corresponding field 800*a-i*. For example, field 800*a* in this example is described by the value in cell 810*a* as a preamble for advertisement message 800. Column 815' in the illustrated example corresponds to value 815. Cells 815*a-i* may each contain a value that represents the value (e.g., as opposed to address or description) of the corresponding field 800*a-i*. By way of example, cell 815*e* may contain bytes amounting to a value that represents the devices name (e.g., for analyte sensor system 708). MAC address 810*d* may include an address for analyte sensor system 708.

Embodiments of the present disclosure may involve exploiting aspects of message 800 to improve the reliability, speed, and/or efficiencies of aspects related to the wireless communication of analyte data. In some cases, the value 815*d* of the MAC address field 810*d* may be dynamically configurable to be made specific to a particular display device 710 or set of display devices 710, or other remote devices connectable to and being targeted by analyte sensor system 708. This will be described in further detail elsewhere herein (see, e.g., operations 735*a*, 735*a'*, 765, and 765' with reference to FIG. 7L). In some cases, analyte data and/or related control signaling and the like, or portions thereof, may be included in reserved slots within advertisement packets (e.g., operation 765*a* with reference to FIG. 7E). For example, analyte data and such can be included in manufacturing data field 800*h*. Other slots may be used for similar purposes in accordance with various implementations. Other such embodiments utilizing aspects of advertisement message 800 advantageously will become apparent upon studying the present disclosure.

J. Addressing

Some transmission schemes use a single address when advertising to multiple devices, including multiple types of devices. Such devices may include display devices 710 of various types, such as, for example, consumer/commercial/enterprise devices (e.g., smart watch 140 and tablet 130, display elements of server system 134, or a television, fixed or mobile screen in an automobile, plane, or other vehicle, etc.); application-specific display devices (e.g., analyte display device 110); medical devices 136; and so on. With respect to addressing, by way of example, the same MAC address may be transmitted in an general advertisement message being broadcast or multicast to such devices (e.g., at operation 705*a* with reference to FIG. 7A).

In some cases, such an addressing transmission scheme may be employed regardless of which devices have recently been connected—that is, irrespective of whether and what devices (e.g., display devices 710) may be on a whitelist for the transmitting device, which may be, for example, a sensor system such as analyte sensor system 708. One potential issue with this type of (single-address) transmission scheme results from the use of a common address being advertised to multiple devices. In particular, using a common address may result in multiple devices responding requesting a connection at the same time (e.g., at operation 705*b* with reference to FIGS. 7A and 7L), which may cause interference at the transmitting device and may ultimately lead to dropped data packets and/or increased power consumption.

Accordingly, additional aspects of the present disclosure involve utilizing device-specific advertising. Such advertising reduces the likelihood of interference that may be created by multiple devices concurrently or nearly concurrently attempting to connect to analyte sensor system 708. As mentioned above, such interference may lead to dropped data packets, and hence a less reliable, less efficient system. Additionally, rather than device-side scanning being relegated to assigned time windows (e.g., time segment 930*a* of advertisement duration 930, with reference to FIG. 9B) during which connection attempts can be made, device-specific addressing allows for devices to scan for analyte sensor system 708 indefinitely, and to attempt to establish a connection in response to receiving a particular address (e.g., dynamically configurable MAC Address having value 815*d*, with reference to FIG. 8) in an advertisement message (e.g., message 800). In this manner, the overall flexibility, reliability, and power consumption of the analyte data communication system may be improved.

Figure 7L:
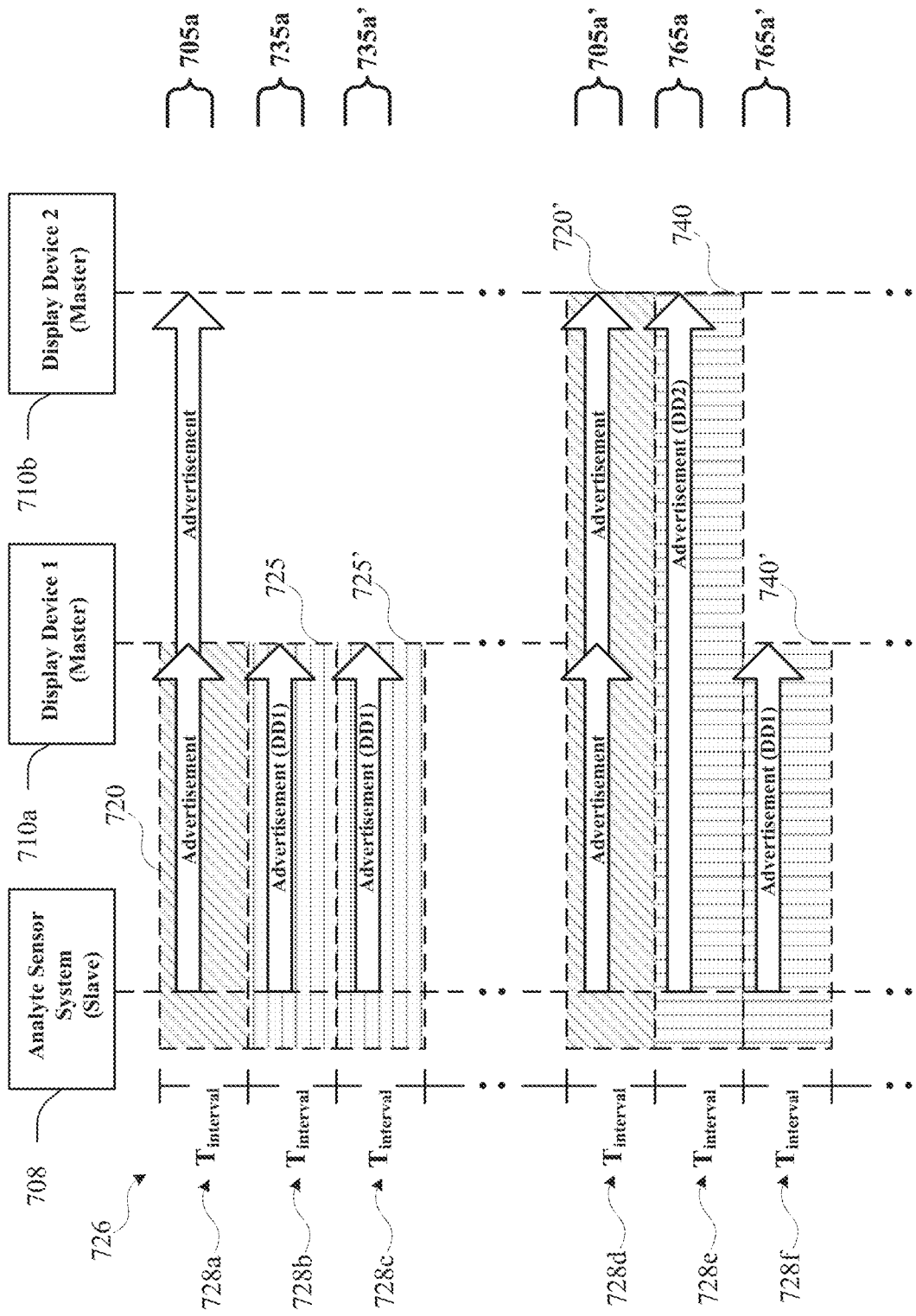
FIG. 7L is an operational flow diagram illustrating various operations that may be performed in accordance with embodiments of the disclosure.

In this connection, FIG. 7L is an operation flow diagram illustrating various operations that may be performed in accordance with embodiments of method 726 for wireless communication of analyte data between analyte sensor system 708 to, for example, display devices device 710*a* and 710*b*, including, in some cases, using device-specific advertising. It will be appreciated that in some instances, display device 710*a* and/or display device 710*b* can be application-specific devices such as analyte display device 110 and medical device 136, or may also be a consumer device such as a smartphone and the like.

As alluded to above, the MAC address or BLE address or the like (e.g., MAC address 810*d*, with reference to FIG. 8) of analyte sensor system 708, as represented in the advertisement messages (e.g., advertisement message 800) that may be transmitted thereby at, e.g., operation 705*a*, may be made configurable in terms of the address that is seen by other devices that are scanning for advertisement messages (e.g., display devices 710*a*, 710*b*, etc.). One way this may be done is to dynamically write the address into the slot for value 815*d* of advertisement message 800. For example, analyte sensor system 708 may utilize a first MAC address value 815*d* for medical device 136, a second address MAC value 815*d* for analyte display device 110, and a third MAC address value 815*d* for display device 710*a* that may be a smartphone, for example. A general MAC address common to multiple devices may also be used.

With the transmission of device-specific addresses in the slot of field 800*d* for value 815*d*, multiple devices can continually scan for advertisement messages 800 and make connection requests to analyte sensor system 708 upon receiving such an advertisement message 800 containing the expected address (i.e., the address specific to the particular display device 710*a*, 710*b*, etc.). By contrast, with only a single address being transmitted, scanning devices typically respond with connection requests according to specific time windows allocated to single devices. Typically though not always, general advertising using a common address may be done to establish connection with one or more display devices 710*a*, 710*b*, before device-specific advertising is done. Other scenarios are possible, as will be described herein.

In additional embodiments, analyte sensor 708 may utilize a single device-specific address. In this manner, connections to analyte sensor system 708 may be controlled and/or limited, because, for example, when the device-specific address is transmitted, only the targeted device would respond with connection requests to analyte sensor system 708. Subsequent to establishing connection to the targeted device, analyte sensor system 708 in such example embodiments may erase and/or remove/replace the previously used device-specific address and may utilize a new device-specific address in order to connect to a new targeted device. Using device-specific advertising in this manner may allow for reliable, dedicated, and/or targeted connection with a single device (e.g., display device 710) at a time.

Referring again to FIG. 7L, method 726 may in time interval 728*a* include implementing one or more aspects of a communication session such as communication session 720, including operation 705*a*. With respect to operation 705*a*, during an advertisement duration of communication session 720, one or more advertisement messages (e.g., advertisement message 800) sent pursuant thereto may be general advertisement messages. In other words, operation 705*a* may take place before analyte sensor system 708 has paired with or connected to display devices 710*a* and/or 710*b* (and/or placed such devices on the whitelist). As such, the address 815*d* included in the advertisement messages sent at operation 705*a* in this case may be common to display devices 710*a* and 710*b*, as well as any other receiving device. It should be noted here that other of the communication sessions described herein (e.g., communication sessions 725 and/or 730) can likewise be used to perform this initial advertisement in which generic advertisement messages are transmitted. This communication session may be the same or different from the communication session implemented during subsequent time intervals. It should also be noted that in embodiments, any device making a connection during time interval 728*a* (or any other time interval) may be placed on a whitelist.

With respect to time interval 728*a*, multiple outcomes are possible. In a first outcome, general advertisement message(s) sent at operation 705*a* (for example) may result in both display devices 710*a* and 710*b* connecting to analyte sensor system 708 (e.g., both devices may be placed on a whitelist). For example, during communication session 720, display device 710*a* and 710*b* may have received advertisement message 800 containing a common address in MAC address value 815*d*. Responsive thereto, display device 710*a* and 710*b* may have requested and been granted a data connection at operation 705*b*, may have gone through authentication at operation 705*c*, and may have requested and received data at operation 705*d*.

As part of or in connection with this process (i.e., operation 705), analyte sensor system 708 may signal display devices 710*a* and 710*b* with respective device-specific addresses, and write these addresses into respective slots for value 815*d* of advertisement messages 800 during subsequent advertisement durations. Device-specific advertisement may then be used, for example, as illustrated in connection with time intervals 728*b* and 728*c*, in which at operation 735*a*, one or more advertisement messages may be sent that contain a MAC address specific to DD1 710*a*. With respect to time intervals 728*b* and/or 728*c*, the advertisement message(s) sent at operation 735*a* are labelled in FIG. 7L as being specific to DD1 710*b*. Further, it will be appreciated that Display Device 2 (710*b* does not respond to such advertisement messages, as they are addressed to DD1 710*a*. As such, for graphical representation, the advertisement message(s) sent at operation 735*a* are shown as being received only by DD1 710*a*, and not by DD2 710*b*. In reality, however, such messages would typically be broadcast or multicast, and not unicast, but DD2 710*b* would not respond given that the address is specific to DD1 710*a*.

Likewise, device-specific advertisement may also be used, for example, as illustrated in connection with time interval 728*e*, in which at operation 765*a*, an advertisement message may be sent that contains a MAC address specific to Display Device 2 (710*b* (DD2). With respect to time interval 728*e*, the advertisement message(s) sent at operation 765*a* are labelled as being specific to DD2 710*b*. Further, it will be appreciated that DD1 710*a* does not respond to such advertisement messages, as they are addressed to DD2 710*b*. As such, for graphical representation, the advertisement message(s) sent at operation 765*a* are shown as being received only by DD2 710*b* and not DD1 710*a* (i.e., this is mean to be indicated by the dashed vertical line extending from DD1 710*a* being absent from time interval 728*e*). In reality, however, such messages would typically be broadcast or multicast, and not unicast and thus would be received by DD1 710*a*, but DD1 710*a* would not respond given that the address is specific to DD2 710*b*.

In a second outcome, during time interval 728*a*, analyte sensor system 708 connects to DD1 710*a* but not DD2 710*b* (e.g., DD1 710*a* may be placed on a whitelist). Device-specific advertisement may then be used, for example, as illustrated in connection with time interval 728*b*, in which at operation 735*a*, one or more advertisement messages may be sent that contain a MAC address specific to DD1 710*a*. In embodiments employed in connection with this scenario, the general address sent at operation 705*a* may be assigned to DD1 710*a* and used for device-specific advertisements thereto, while another address may subsequently be used for general advertising or other purposes.

Additionally, following time interval 728*a* in this example, a further general advertisement can be initiated in attempt to connect to DD2 710*b*. For example, at time interval 728*d*, at operation 705*a*', an advertisement message may be sent that contains a common address, which may but need not be the same as the address used in time interval 728*a*. With respect to time interval 728*d*, the advertisement message(s) sent at operation 705*a*' are labelled as generic. Further, it will be appreciated that DD1 710*a* may in some cases not respond to such advertisement messages, as DD1 710*a* has already connected to analyte sensor system 708 (and may have been whitelisted). As such, for graphical representation, the advertisement message(s) sent at operation 705*a*' are shown as being received only by DD2 710*b* and not DD1 710*a* (i.e., this is mean to be indicated by the dashed vertical line extending from DD1 710*a* being absent from time interval 728*d*). In reality, however, such messages would typically be broadcast or multicast, and not unicast and thus would be received by DD1 710*a*, but DD1 710*a* may not respond, as described above. In embodiments employed in connection with this scenario, the general address sent at operation 705*a*' may be assigned to DD2 710*b* and used for device-specific advertisements sent thereto, while another address may subsequently be used for general advertising or other purposes.

In a third outcome, during time interval 728*a*, analyte sensor system 708 connects to DD2 710*b* but not DD1 710*a* (e.g., DD2 710*b* may be placed on a whitelist). Device-specific advertisement may then be used, for example, as illustrated in connection with time interval 728*e*, in which at operation 765*a*, one or more advertisement messages may be sent that contain a MAC address specific to DD2 710*b*. In embodiments employed in connection with this scenario, the general address sent at operation 705*a* may be assigned to DD2 710*b* and used for device-specific advertisements thereto, while another address may subsequently be used for general advertising or other purposes.

Additionally, following time interval 728*a* in this example, a further general advertisement can be initiated in attempt to connect to DD1 710*a*. This is not explicitly shown in FIG. 7L, but one example deployment in this regard may involve simply repeating the communication session shown in time interval 728*a*. Namely, by way of example, sending general advertisement at operation 705*a* pursuant to communication session 720 or the like. For example, at repeated time interval 728*a* in this scenario, at operation 705*a*', an advertisement message may be sent that contains a common address that may but need not be the same as the address used in initial time interval 728*a*. With respect to repeated time interval 728*a*, the advertisement message(s) sent at operation 705*a* in the second instance are labelled as generic. It will be appreciated, however, that DD2 710*b* may in some cases not respond to such advertisement messages, as DD2 710*b* has already connected to analyte sensor system 708 (and may have been whitelisted). This is not necessarily represented graphically in FIG. 7L. It should be noted as well that such messages would typically be broadcast or multicast, and not unicast and thus would be received by DD2 710*b*, but DD2 710*b* may not respond, as described above.

In a fourth outcome, during time interval 728*a*, analyte sensor system 708 connects to neither DD1 710*a* nor DD2 710*b*. Here, a further general advertisement can be initiated in attempt to connect one or more of DD1 710*a* and DD2 710*b*. This may, for example, entail repeating the communication session used at time interval 728*a* (e.g., communication session 720). In other instances, however, a different communication session (e.g., communication session 725, 740, 760) may be used. In other cases, aspects of the communication used in time interval 728*a* may be modified or reconfigured in order to increase the likelihood of making a connection (e.g., as described in connection with FIGS. 9A-F).

In embodiments, analyte sensor system 708 may receive through a communication session such as communication session 760, information related to pairing. In communication session 760, NFC, for example, may be used to exchange information that may enable analyte sensor system 708 to send device-specific advertisement messages to display devices 710*a*, 710*b* without connecting thereto beforehand via general advertising (e.g., via communication session 720). For example, Display Device 1 (710*a*), or DD1, may exchange such information with analyte sensor system 708 pursuant to communication session 760.

As such, following communication session 760, device-specific advertisement may be used, for example as illustrated in connection with time interval 728*b*, in which at operation 735*a*, an advertisement message may be sent that contains a MAC address specific to DD1 710*a*. With respect to time interval 728*b*, the advertisement message(s) sent at operation 735*a* are labelled as being specific to DD1 728*b*. Further, it will be appreciated that Display Device 2 (710*b* does not respond to such advertisement messages, as they are addressed to DD1 710*a*. As such, for graphical representation, the advertisement message(s) sent at operation 735*a* are shown as being received only by DD1 728*b*. In reality, however, such messages would typically be broadcast or multicast, and not unicast. In example implementations, device-specific addresses may be preprogrammed with respect to analyte sensor system and one or more display devices 710*a*, 710*b*, thus allowing communication sessions to be bypassed before utilizing device-specific advertising.

With respect to the above scenarios, device-specific addresses may be specific to one or more display devices 710*a*, 710*b*, etc. The one or more display devices 710*a*, 710*b*, etc. may span a number of different categories of devices, including personal electronic devices, medical devices, application-specific deices, and so on, as described herein. By way of example, a personal electronic devices may include one or more of a smartphone, a smartwatch, a tablet, a computer, and a television. A set of one or more of display devices 710*a*, 710*b*, etc. may be defined according to a classification scheme. In this regard, in some cases, a group of devices can be identified by an address specific to that group. These devices may be grouped arbitrarily or based on a variety of criteria. For example, the group of devices may be formed based on device characteristics, such as whether the devices are wearable, portable, or stationary; device ownership, such as, personal, work, or family member devices; devices use location, such as, car, office, home, work-out-related devices, etc.

With reference to FIG. 7L and the above description thereof, groups of devices can be used in place of display device 710*a*, 710*b*, etc. For example, if a device from a first group of display devices 710*a* connects to analyte sensor system 708 during time interval 728*a*, but no devices from a second group of display devices 710*b* connects, this may correspond to the second outcome described above. For example, a first group of display devices 710*a* may be defined to include consumer devices (e.g., smartphone, tablet, etc.) while a second group of display devices 710*b* may be defined to include an application-specific device (e.g., analyte display device 110) and a medical devices (e.g., medical device 136). Within a group of devices, device-specific advertising can also be employed—that is, there may be a group-specific address as well as an address specific to a device within the group.

As alluded to above, establishing connection with one or more display devices 710a, 710b, etc. may result in the devices being placed on a list such as a whitelist that reflects that the devices previously and/or recently connected to analyte sensor system 708. Such a list can be maintained, for example, in storage 365 of analyte sensor system 308, with reference to FIG. 3B, and/or within storage 325 of display device 310 (e.g., one or more of display devices 710a, 710b, etc.). Alternatively or in addition, such a list can be maintained in storage 334b of server system 334, with reference to FIG. 3A. The list can take the form of a database, for example.

The list may then be assessed to determine which if any display devices 710a, 710b, etc. are included on the list. If the list includes a particular display device 710 (e.g., analyte display device 110), a time segment (e.g., time segment 930a, with reference to FIG. 9B) of an advertisement duration (e.g., advertisement duration 930) may be allocated to the particular display device 710. If another display device 710 (e.g., a smartphone) is included on the list, a time segment (e.g., time segment 930b may be allocated to that display device 710. This allocation may be effected by the use of display specific advertisement during the time segments. As such, during subsequent time intervals, for time segments allocated to specific devices, device-specific advertising may be used, such that each display device 710 can respond to advertisement messages by sending connection requests only in time segments allocated specifically to the display device 710. This approach can aid in reducing interference with respect to connection requests, reducing packet loss, and also increasing the likelihood of display devices 710 successfully connecting to analyte sensor system 708. In some cases, a separate list may be maintained and queried for each group of display devices 710. This enables the allocation of time segments to occur on the fly, depending on which device-specific address is used for advertisement messages.

Another potential advantage of display-specific advertising as described herein is that it may facilitate rescheduling for reconnection, since as mentioned above, display devices 710 and other devices (e.g., medical devices 136) connecting to analyte sensor system 708 need not be relegated to assigned time slots in terms of scanning for connection. Rather, if rescheduling for reconnection is desired, analyte sensor system 708 may simply transmit an advertisement message containing the address specific to the targeted device, and await a response request from that device. In other words, analyte sensor system 708 need not wait until a particular time segment dedicated to the target display device in order to advertise thereto.

In this regard, with further reference to FIG. 7L, analyte sensor system 708 can in embodiments, in response to an unexpected loss of a connection to display device 710a, transmit one or more advertisement messages that include an address specific to display device 710a. Likewise, analyte sensor system 708 can in embodiments, in response to an unexpected loss of a connection to display device 710b, transmit one or more advertisement messages that include an address specific to display device 710b. This approach may allow for relatively rapid rescheduling for re-reestablishing the unexpectedly lost connection.

In some instances, where one or more device-specific addresses are available for use in advertisement messages (e.g., at the group or individual device level), the device-specific addresses may be selected based upon information related to one or more parameters such as quality of service, time of day, location, battery life and the like, including with respect to how the same impact device preferences and/or performance (e.g., connection time/success, reliability, etc.).

Referring now to FIG. 15A, example implementations of features of various methods such as, for example, methods 704, 706, 712, 714, 716, 718, 722, 724, and 726 are illustrated. One such example implementation includes aspects of method 1500 for wireless communication of analyte data. At operation 1505A, method 1500 includes, during a first advertisement period (e.g., within time interval 728a, with reference to FIG. 7L), analyte sensor system 708 transmitting a first advertisement message that includes a first address. At operation 1505B, method 1500 may involve determining whether a first connection has been established between analyte sensor system 708 and an analyte display device (e.g., analyte display device 110, with reference to FIG. 1, which may be referred to here as DD1 or display device 710a, with reference to FIG. 7L), and/or analyte sensor system 708 and one or more secondary display devices (e.g., display device 710b, which may be a smartphone for example and may be referred to as DD2). For example, this may entail accessing a whitelist or the like. During a second advertisement period (e.g., within time interval 728e), if a first connection has been established between analyte sensor system 708 and DD1, method 1500 includes at operation 1505C transmitting a second advertisement message that includes a second address specific to DD2. Moreover, during the second advertisement period, if a second connection has been established between analyte sensor system 708 and DD2, method 1500 includes at operation 1505D transmitting a third advertisement message that includes a third address specific to DD1.

Embodiments of method 1500 include, at operation 1505E, assessing whether a list includes DD1 and/or DD2. If the list includes DD1 and DD2, method 1500 may include, at operation 1505F, allocating a first time segment (e.g., time segment 950a, with reference to FIG. 9D) of a third advertisement period (e.g., within time interval 728e) for transmission of the second advertisement message to DD2 and/or other secondary display devices. Further to operation 1505F, if the list includes DD1 and DD2, method 1500 may include allocating a second time segment (e.g., time segment 950b, with reference to FIG. 9D) of a third advertisement period for transmission of the third advertisement message to DD1. Here it will be noted that although time interval 728e of FIG. 7L does not explicitly show multiple respective device-specific advertisement messages being sent to corresponding devices, the same is contemplated in connection with aspects of method 1500 as well as method 726 and the like. That is, for example, each time interval 728a-f shown in FIG. 7L may include multiple time segments (see, e.g., FIG. 9D). At operation 1505G, method 1500 may include analyte sensor system 708 transmitting the third advertisement message (e.g., at operation 1505D), responsive to an unexpected loss of a connection to DD1. Further, operation 1505G may in some cases entail analyte sensor system 708 transmitting the second advertisement message (e.g., at operation 1505C), responsive to an unexpected loss of a connection to DD2 or the like. In some cases, this may enable reconnection to the disconnected device without unnecessary delay.

At operation 1505H, method 1500 may include defining a set of one or more secondary display devices such as, for example, DD2 and the like, according to a classification scheme. In this manner, device specific advertisement messages can be generated and transmitted according to the classification scheme. In embodiments, the second address is specific to a first set of the secondary display devices. In embodiments, a fourth address is specific to a second set of the secondary display devices. In embodiments, method 1500 includes, at operation 1505J, selecting between the second and fourth addresses for transmission, based on one or more of an indication of relative qualities of connection to analyte sensor system 708, as between the first and second sets of secondary display devices; an indication related to one or more of a location of the first set of secondary display devices and a location of the second set of secondary display devices; an indication related to a time of day; an indication related to a battery life of analyte sensor system 708; and so on, as would be apparent to one of skill in the art upon studying the present disclosure.

Figure 15B:
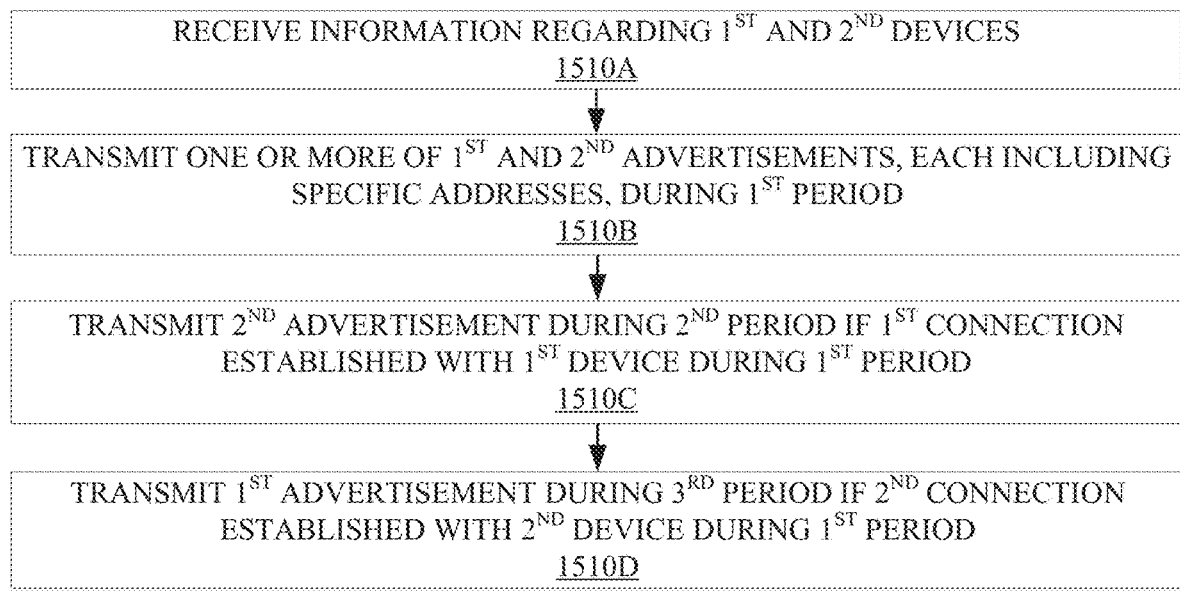
FIG. 15B is an operational flow diagram illustrating various operations that may be performed in accordance with embodiments of the disclosure.

Referring now to FIG. 15B, example implementations of features of various methods such as, for example, methods 704, 706, 712, 714, 716, 718, 722, 724, and 726 are illustrated. One such example implementation includes aspects of method 1502 for wireless communication of analyte data.

At operation 1510B, method 1502 includes, during a first advertisement period (e.g., within time interval 728b and/or 728e, with reference to FIG. 7L), analyte sensor system 708 transmitting one of a first and second advertisement message. The first advertisement message includes a first address specific to one or more display devices such as DD2. The second advertisement message includes a second address specific to DD1 (e.g., analyte display device 110). If, according to operation 1510B, a first connection has been established between analyte sensor 708 and a first display device of the one or more display devices (e.g., DD2 etc.), then, at operation 1510C, method 1502 includes transmitting the second advertisement message during a second advertisement period subsequent to the first advertisement period (e.g., time interval 728c and/or 728f). If, according to operation 1510B, a second connection has been established between analyte sensor 708 and DD1, then, at operation 1510D, method 1502 includes transmitting the first advertisement message during a third advertisement period subsequent to the first advertisement period (e.g., time interval 728c and/or 728f). In embodiments, at operation 1510A, method 1502 includes receiving information regarding DD1 and the one or more display devices (e.g., DD2) before the first advertisement period.

At operation 1505B, method 1500 may involve determining whether a first connection has been established between analyte sensor system 708 and an analyte display device (e.g., analyte display device 110, with reference to FIG. 1, which may be referred to here as DD1 or display device 710a, with reference to FIG. 7L), and/or analyte sensor system 708 and one or more secondary display devices (e.g., display device 710b, which may be a smartphone for example and may be referred to as DD2). For example, this may entail accessing a whitelist or the like. During a second advertisement period (e.g., within time interval 728e, if a first connection has been established between analyte sensor system 708 and DD1, method 1500 includes at operation 1505C transmitting a second advertisement message that includes a second address specific to DD2. Moreover, during the second advertisement period, if a second connection has been established between analyte sensor system 708 and DD2, method 1500 includes at operation 1505D transmitting a third advertisement message that includes a third address specific to DD1.

K. Indication-Initiated Connection

As mentioned above, in some cases, it may be desirable for analyte sensor system 708 to connect to a particular display device (e.g., display device 710a) without experiencing interference from another device (e.g., display device, 710b or the like). For illustration purposes, numerals from FIG. 7L may be referenced here, but it will be appreciated that this description can apply to like components throughout, whether or not such components bear the same numerals referenced here. For example, display device 710a (e.g., a smartphone) may be preferred over display device 710b (e.g., medical device 136 or analyte display device 110), based on the quality, reliability, or throughput of data captured by display device 710a.

As such, it may be desirable at times for analyte sensor system 708 to effectively connect exclusively to display device 710a. Notwithstanding, there may be some latency involved in analyte sensor system 708 switching over to effectively being dedicated to display device 710a. In some cases, for example, there may be a delay before display device 710b is removed from a list that may be associated with preferred devices, such as a whitelist (e.g., a given device may age off the whitelist, or be removed therefrom if there is no subsequent connection made, after 15 minutes). This delay may degrade the quality of data captured, or in any case may prevent the best possible data capture from occurring due to the optimal or preferred display device 710a not being used.

In this connection, aspects of the present disclosure involve input-initiated direct advertisement or display switching (e.g., addition/removal/etc.). By allowing input, which in some cases is user input, to indirectly or directly initiate direct advertisement, and/or allowing input (e.g., manually received user input) to switch between display devices 710a and 710b, a more robust dataset can be captured, and greater ease of use may be achieved. In this regard, methods for wireless communication of analyte data are provided.

Figure 10A:
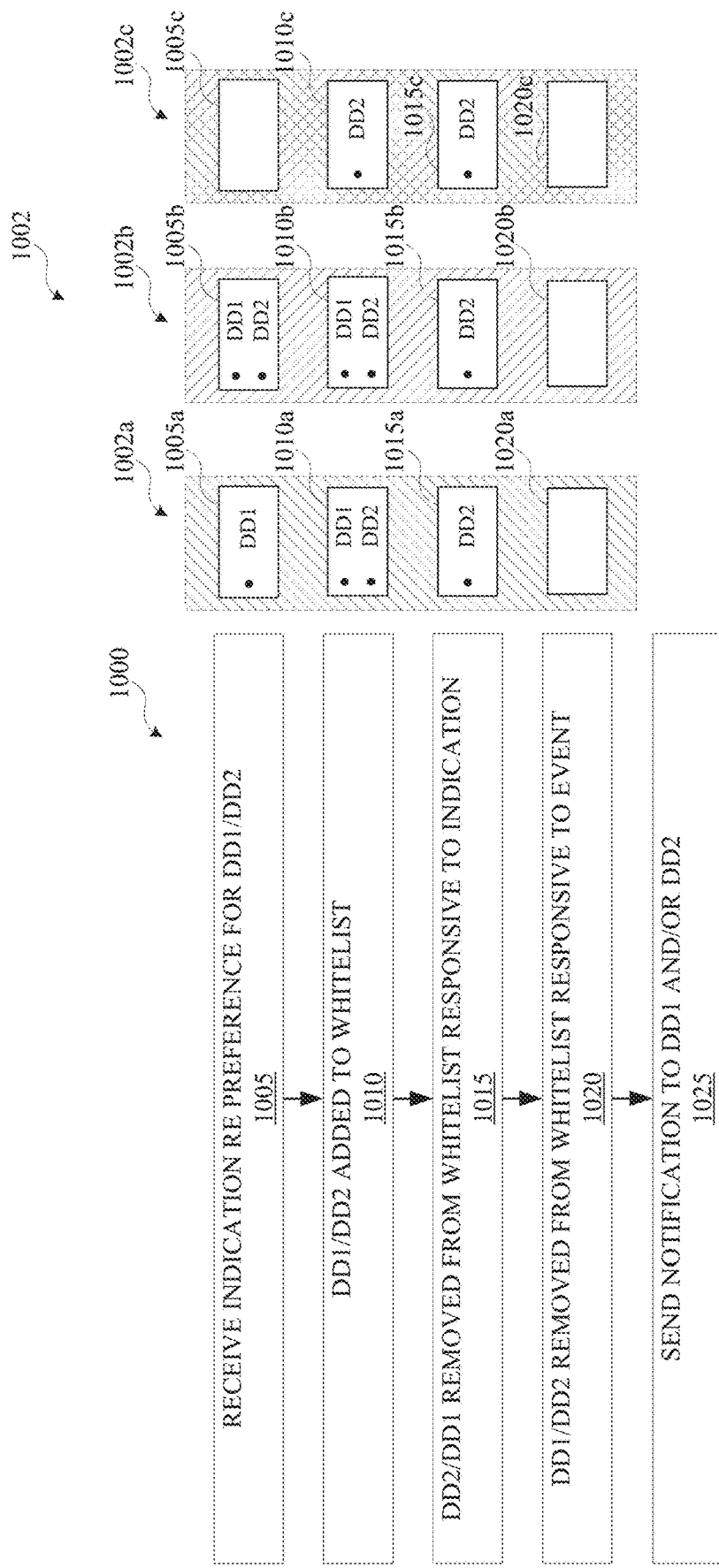
FIG. 10A is an operational flow diagram illustrating various operations that may be performed in accordance with embodiments of the disclosure.

FIG. 10A is an operation flow diagram illustrating method 1000 wireless communication of analyte data, in accordance with embodiments of the disclosure. FIG. 10A also illustrates in sequence diagram 1002 how in scenarios 1002a, 1002b, and 1002c, a list of display devices 710a (DD1), 710b (DD2), etc. that may be maintained in example operations that may be implemented according to method 1000. The list may reflect an overall level of preference for the display devices 710a (DD1), 710b (DD2), etc. By way of illustration, the overall preference may include a prioritization for one or more display devices 710a (DD1), 710b (DD2), etc. In example deployments, this list may in aspects be or include a whitelist or may be or include a list akin to a whitelist. For example, the list may include a representation of one or more display devices 710a (DD1), 710b (DD2), etc. that have previously and/or recently connected to analyte sensor system 708.

At operation 1005, method 1000 includes receiving an indication regarding a level of preference for one or more display devices 710a (DD1), 710b (DD2), etc. The indication may be received from a user via a mobile application (e.g., analyte sensor application 330) running one a display device 710a (DD1), 710b (DD2), etc. For example, with reference to FIG. 3E, using options 316e of GUI 345, a user may indicate that analyte display device 110 (which may be included as DD1 710*a*, for example) should or should not be dedicated. One or more devices may be dedicated simultaneously. Alternatively or in addition, a user may select a priority level for display device 710*b* by selecting the Priority drop-down in component shown in FIGS. 3D and 3E. Selectable priority options may be provided (not shown in FIG. 3E), for example on a numerical scale with the lower numbers representing a higher priority classification. Alternatively or additionally, the indication may be received through Replace/Remove sub-menu 314*b* and options 316*b*, which can allow the user to replace a particular display device 710*a* with another device, or to remove display device 710*a* altogether. In embodiments, the indication may be received through the Whitelist/Blacklist field shown in GUI 345 (with reference to FIGS. 3D and 3E), which can be used to manually place/remove devices on/from the list, to place/remove devices on/from the a blacklist (which typically is the opposite of the whitelist).

In other cases, the indication may be generated in an automated fashion based on information related to parameters generated and/or maintained by one or more display devices 710*a* (DD1), 710*b* (DD2), etc. For example, such information may relate to parameters such as quality of service, time of day, location, battery life and the like, including with respect to how the same impact device preferences and/or performance (e.g., connection time/success, reliability, etc.). In this regard, the level of preference (and the indication regarding the same) may account for network and other environmental conditions described herein, and/or may account for user preference in an intelligent fashion that does not necessarily require direct user input. For example, user preference may be gleaned by frequency of use for a particular device or group of devices during certain times of day, at certain locations, under certain network conditions, under certain battery life conditions, etc. In embodiments, the indication may be generated based on, for example, trends or patterns in device usage and/or preference. Such trends may be monitored or detected by application 330 running on display device 710*a*, 710*b*, etc., or may be monitored or detected by analyte sensor system 708. The information related to parameters may be detected/generated over time, for example, as data indicative of the preference, or indicative of optimal performance, is gathered, monitored, and/or analyzed.

In each of scenarios 1002*a*-1002*c*, at operation 1005, the received indication tends to show a level of preference regarding DD2 710*b* and/or DD1 710*a*—e.g., in the illustrated example, that DD2 should be added to the list. In scenario 1002*a*, at instance 1005*a* corresponding to operation 1005, DD1 is included on the list that may be maintained and that may reflect the overall level of preference for the display devices 710*a* (DD1), 710*b* (DD2), etc. (e.g., the whitelist). In scenario 1002*b*, at instance 1005*b* corresponding to operation 1005, both DD1 and DD2 are included on the list. In scenario 1002*c*, at instance 1005*c*, no display devices 710*a*, 710*b*, etc., are included on the list.

Responsive to the indication regarding the level of preference, method 1000 may involve implementing a procedure to support the preference. Method 1000 may include analyte sensor system 708 transmitting a message that includes an indication that the procedure is being implemented. Such a message may trigger a notification, e.g., a pop-up or in-application notification or the like, being presented to the user to communicate that actions are being taken in accordance with the list being maintained, including in some cases in response to the user's input (and/or acknowledging the same). Such notifications may be presented via GUI 345. Various types of procedures may be implemented, depending on the particular circumstances. Implementing the procedure, in some cases, includes modifying maintenance of the list of preferred display devices 710*a*, 710*b*, etc. (e.g., a whitelist). The modification may take several forms.

Modifying the maintenance list according to some implementations includes adding one or more display devices 710*a*, 710*b*, etc. to the list. In this regard, at operation 1010, for example, method 1000 may include adding DD2 710*b* to the list, responsive to the indication (received at operation 1005) that tends to shown the level of preference regarding DD2 710*b*. Of course, DD1 710*a* or another device(s) may be added, depending on the indication/preference. Accordingly, in scenario 1002*a*, at instance 1010*a* corresponding to operation 1010, DD2 is added to the list such that both DD1 and DD2 are included on the list. In scenario 1002*b*, no change occurs with respect to instance 1010*b* because both DD1 and DD2 were already included on the list. In scenario 1002*c*, at instance 1010*c*, DD2 710*b* has been added to the list.

Modifying the maintenance list according to some implementations includes removing one or more display devices 710*a*, 710*b*, etc. from the list. In this regard, at operation 1015, for example, method 1000 may include removing DD1 710*a* from the list at operation 1005, responsive to the indication (received at operation 1005) that tends to show the level of preference regarding DD2 710*b* and/or DD1 710*a*. Of course, DD2 710*b* or another device(s) may be removed, depending on the indication/preference. Here, the indication may be that DD2 710*b* is preferred as a dedicated device for exclusive use, or that it is preferred that DD1 710*b* not be used. Accordingly, in scenario 1002*a*, at instance 1015*a* corresponding to operation 1015, DD1 710*a* is removed from the list such that only DD2 is included on the list. Likewise, in scenario 1002*b*, DD1 710*a* is removed from the list such that only DD2 is included on the list. In scenario 1002*c*, there is no change because DD1 710*a* was not previously on the list. In embodiments, the indication may cause DD1 710*a* to be removed from the list for a predetermined and/or configurable amount of time, or until a particular event occurs (e.g., signaling received via NFC, user input, etc.).

As alluded to above, modifying the maintenance list according to some implementations includes removing DD2 710*b* (or other devices), from the list, even where the indication tends to show a preference for such a device. In this regard, at operation 1020, for example, method 1000 may include removing DD1 710*a*, even though the indication (received at operation 1005) tends to shown the level of preference regarding DD2 710*b*. Here, despite the indication that DD2 710*b* may be preferred as a dedicated device for exclusive use, conditions may occur that can cause DD2 710*b* to be removed from the list. Such conditions may in some examples include the occurrence of an event. For example, this may entail removing DD2 710*b* from the list if the device goes out of range, gets switched off, falls below a certain amount of battery life, exceeds a certain temperature, or is being used for other purposes; responsive to user input; responsive to the passage of a predetermine amount of time; responsive to various of the parameters described herein; etc.

Accordingly, in scenario 1002*a*, at instance 1020*a* corresponding to operation 1020, DD2 710*b* is removed from the list such that the list is empty. Likewise, in scenarios 1002*b* and 1002*c*, DD2 710*b* is removed such that the lists are empty. In embodiments, DD2 710*b* may be removed from the list for a predetermined and/or configurable amount of time, or until a particular event occurs (e.g., signaling received via NFC, user input, etc.). In embodiments, modifying the maintenance of the list may include allowing any of the one or more display devices 710a and/or 710b etc. that become unavailable for connection to be removed from the list. This may be true whether or not such devices are associated with an indication the devices are preferred over other devices, and may occur responsive to one or more of the above-mentioned conditions or events.

Method 1000 optionally includes, at operation 1025 transmitting a message comprising an indication related to whether a display device 710a, 710b, etc. has been added or removed from the list and/or that an aspect of the list has been modified. In example deployments the indication is an addition/removal/modification notification sent to the added/removed device(s) or device(s) affected by the modification. Such indication or notice may be a message, and/or may trigger a notification, e.g., a pop-up or in-application notification or the like, audible indication, sensory indication, etc., being provided to the user to communicate that the user's indication was received, or simply that actions are being taken in accordance with the list being maintained (e.g., in some cases via GUI 345).

Figure 10B:
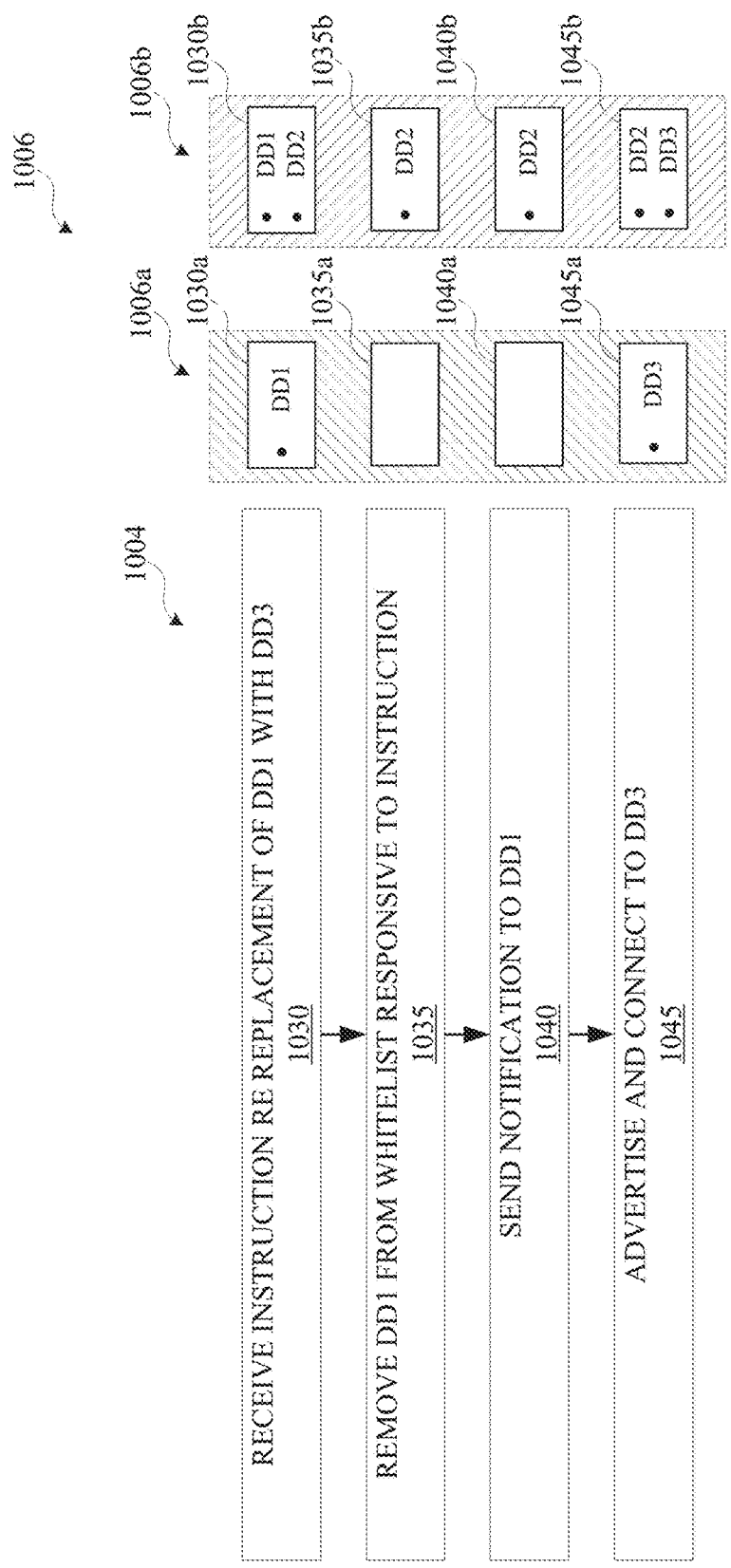
FIG. 10B is an operational flow diagram illustrating various operations that may be performed in accordance with embodiments of the disclosure.

FIG. 10B is an operation flow diagram illustrating method 1004 for wireless communication of analyte data, in accordance with embodiments of the disclosure. With reference to FIG. 10B, specific examples of implementing a procedure to support a preference will be described for illustration purposes. Among other features, FIG. 10B illustrates that display devices 710a, 710b, etc. may be removed from the list for reasons additional to those mentioned above. With respect to such other reasons, by way of example, a user may have received a new phone and wish to replace the old phone with the new one.

As such, the user may, through entering inputs manually (e.g., via GUI 345 with reference to FIGS. 3B, 3D, and 3E), remove the old phone from the list and add the new phone to the list. Accordingly, in some cases, modifying the maintenance of the list as mentioned above may also (or may alternatively) include adding one or more display devices 710a, 710b, etc. to the list, according to a received indication. In such cases, method 1004 optionally includes transmitting a message or notification that indicates the list has been modified and/or indicates the nature of the modification. Here, notifications may be triggered similar to as described above in connection with method 1000. It should be noted that devices can be added in many different scenarios in addition to the user obtaining a new device.

With reference to FIG. 10B, specific examples of implementing a procedure to support the preference will be described for illustration purposes, including more specifically, procedures for removing and adding display devices. It will nevertheless be appreciated that many various are encompassed by the description of this particular example. FIG. 10B also illustrates in sequence diagram 1006 how in scenarios 1006a, 1006b, and 1006c, a list of display devices 710a (DD1), 710b (DD2), etc. that may be maintained in example operations that may be implemented according to method 1004.

At operation 1030, method 1004 may involve receiving an instruction regarding switching from, e.g., display device 710a to a new device (which in this example is a different device than display device 710b). This may be done in a variety of ways. For example, the user may desire to replace an old phone (display device 710a) with a new phone (new device). Accordingly, method 1004 may involve removing the old phone from the list. The user may provide input related to removing the old phone (display device 710a) from operation or replacing the old phone with the new phone. In some cases, this is done using GUI 345 presented on the old phone (display device 710a), the new phone, or on another display device (e.g., a tablet or the like, analyte display device 110, etc.).

With reference to FIG. 3D, the user may, for example, navigate the display device manager and select, within interface module 390a, configuration menu 395 corresponding to Replace/Remove a device. With reference to FIG. 3E, the user's selection may then trigger a sub-menu 314b that displays options for replacing DD1 710a with another display device DD3, or "Other Device", or alternatively, removing DD1 710a from the list. The "Other Device" may be identified by DD1 710a scanning and identifying devices present and capable of forming a connection to analyte sensor system 708. It will also be appreciated that with respect to FIG. 3E, although option 314b corresponds to Analyte Display Device, the illustrate concept shows that option 314b could likewise correspond to DD1 390a. In some cases, rather than being based on user input, the instruction may be generated intelligently, similar to the generation of the indication described with reference to FIG. 10A. For example, the instruction may be based on information related to the above-described parameters.

Responsive to receiving the instruction, at operation 1035, method 1004 in some cases may involve sending the instruction to analyte sensor system 708 such that the list may be modified. If the instruction is received at a remote device (e.g., one of display devices 710a, 710b, etc.) this sending may be done in real time or near real time, or during a subsequent connection to analyte sensor system 708. After receiving the instruction, method 1004 may involve, at operation 1035, removing the old phone (DD1 710a) from the list, responsive to the instruction. As shown in FIG. 10B, in scenario 1006a, at instance 1030a corresponding to operation 1030, DD1 710a is present on the list. At instance 1035a, DD1 710a has been removed from the list, and hence the list appears empty. In scenario 1006b, at instance 1030b, DD1 710a and DD2 710b are present on the list. At instance 1035b, DD1 710a has been removed from the list, leaving DD2 710b remaining thereon.

At operation 1040, method 1004 optionally includes sending a removal notification to DD1 710a and/or other devices. For example, analyte sensor system 708 could then send such a notification in order to acknowledge that the instruction was received and successfully processed (at operations 1030 and 1035). Upon receiving the removal notification (or in some cases acknowledgement message), GUI 345 or other mechanism of DD1 710a or and/the other devices could indicate to the user that the old phone has been successfully removed from the list and that the new phone (DD3) may be added to the list in place of the old phone (DD1 710a). This notification may be presented to the user by visual, audio, or sensory stimuli, as referenced above with respect to operation 1025. Since operation 1040 does not modify the list, the lists shown in instances 1040a and 1040b are the same as the lists shown in instances 1035a and 1035b. Method 1004 may include, at operation 1045, one or more of advertising and connecting to DD3. This may be done in accordance with the various communication sessions 720, 725, 740, 780, and/or method 726, as described herein with reference to FIGS. 7A-7L, 8, and 9A-9F. As shown in FIG. 10B, at instances 1045a and 1045b, DD3 has been added to the list and is present thereon in both scenarios 1006*a* and 1006*b* (here DD2 710*b* is also present on the list), as a result of the advertisement/connection to DD3 occurring at operation 1045.

Referencing methods 1000 and 1004 as shown in FIGS. 10A and 10B and described in connection therewith, some example cases, implementing the procedure to support the preference may include analyte sensor system 708 transmitting an advertisement message that includes an address specific to at least one of the one or more display devices 710*a*, 710*b*, etc., according to the indication. This may entail utilizing one or more of the device-specific advertisement techniques discussed above. Implementing the procedure, in embodiments, includes analyte sensor system 708 transmitting, for each of display devices 710*a*, 710*b*, etc. (or for a group of one or more such devices), an advertisement message specific to the display device (or specific to the group), according to the indication.

In this manner, a prioritization scheme may be implemented and signaled in the advertisement messages sent by analyte sensor system 708. In some such cases, implementing the procedure includes analyte sensor system 708 transmitting, for each of the one or more display devices 710*a*, 710*b*, etc., an advertisement message specific to the display device, in an order based on a prioritization scheme for various of the devices. By way of illustration, the prioritization may have been established through received indications—for example, by a user interacting with the Priority field shown in GUI 345 (with reference to FIGS. 3D and 3E), or more automatically/intelligently through information related to parameters, as described herein. In this regard, for example, aspects of the advertisement duration structure (with reference to FIGS. 9A-9F) used to advertise to various of display device 710*a*, 710*b*, etc. may be varied based on the prioritization scheme. In embodiments, the user may alternatively or additionally manually initiate device-specific advertisements, for example by accessing the Preferences field shown in GUI 345 (with reference to FIGS. 3D and 3E). In embodiments, this may be done for example by the user accessing the Whitelist/Blacklist field shown in GUI 345 (with reference to FIGS. 3D and 3E).

Figure 16A:
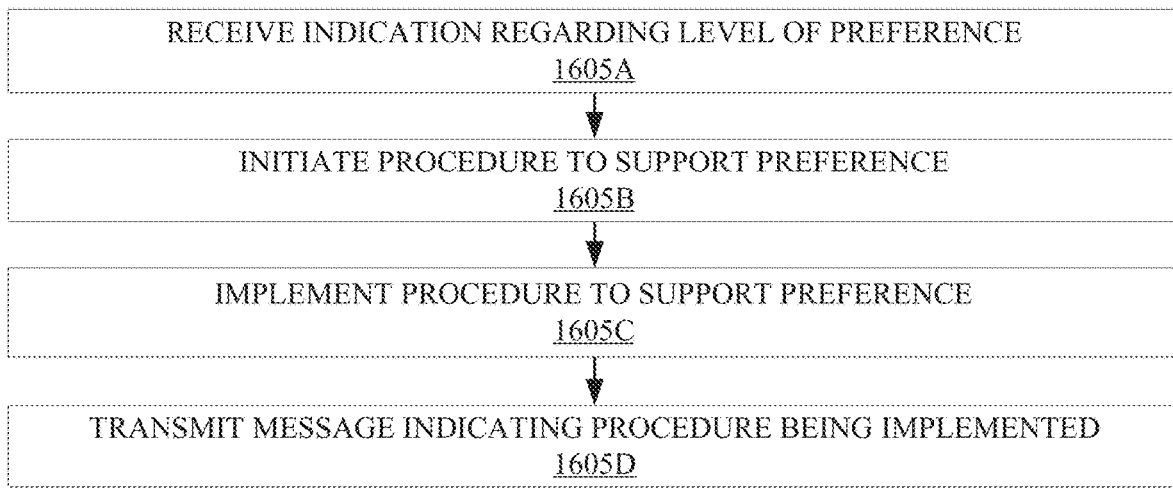
FIG. 16A is an operational flow diagram illustrating various operations that may be performed in accordance with embodiments of the disclosure.

Referring now to FIG. 16A, example implementations of features of various methods such as, for example, methods 704, 706, 712, 714, 716, 718, 722, 724, 726, 1000, and 1004 are illustrated. One such example implementation includes aspects of method 1600 for wireless communication of analyte data. At operation 1605A, method 1600 includes receiving an indication regarding a level of preference for one or more of a plurality of display devices capable of being connected to analyte sensory system 708. In embodiments, the indication is received by analyte sensor system 708. In embodiments, the indication is received by one or more of the display devices. Such display devices may include, for example, analyte display device 110 (with reference to FIG. 1), any of the other devices shown in FIG. 1 (e.g., including medical device 136, server system 134, and WAP 138), display devices 710, etc.

At operation 1605B, method 1600 may involve initiating a procedure to support the preference. By way of example, operation 1605B may be carried out by analyte sensor system 708 and/or any of the display devices. If the indication is received in the form of user input via GUI 340 presented by a mobile device, for example, then operation 1605B may entail the mobile device (e.g., a transceiver/processor thereof) triggering a routine, sending a message, performing additional operations described herein, etc. to initiate the procedure. If the indication is received at analyte sensor system 708 in the form of a message (e.g., sent by the mobile device as a results of the user input), then the operation 1605B may entail analyte sensor system 708 triggering a routine, sending a message, performing additional operations described herein, etc. to initiate the procedure.

At operation 1605C, responsive to the indication received at operation 1605A, method 1600 involves implementing the procedure to support the preference. In example implementations, operation 1605C is carried out by analyte sensor system 708 and/or one of the display devices. At operation 1605C, responsive to the indication received at operation 1605A, method 1600 involves implementing the procedure to support the preference. Operation 1605C may be carried out by analyte sensory system 708 and/or one or more of the display devices. At operation 1605D, method 1600 may involve transmitting a message that includes an indication that the procedure is being implemented. Examples of procedures that may be implemented include those describe above with reference to FIGS. 10A and 10B.

Figure 16B:
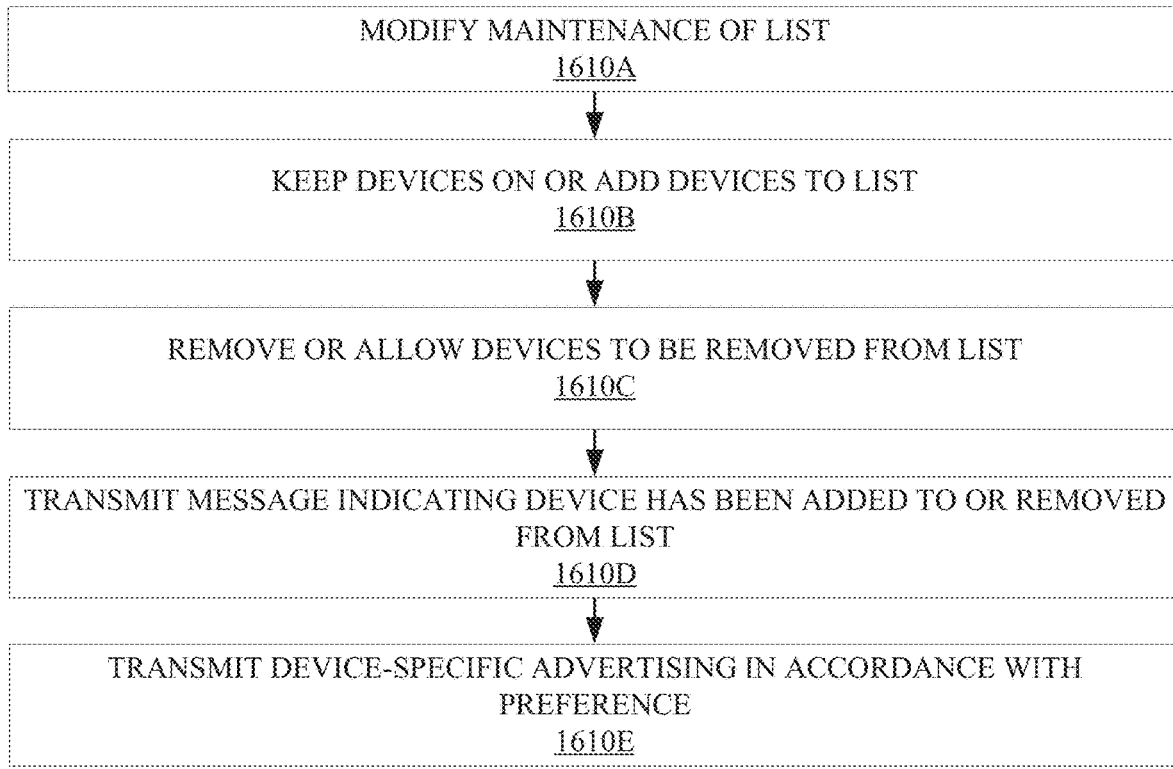
FIG. 16B is an operational flow diagram illustrating various operations that may be performed in accordance with embodiments of the disclosure.

Referring now to FIG. 16B, example embodiments of operation 1605C—that is, implementing the procedure to support the preference responsive to the indication—are illustrated. Operation 1610A, for example, involves modifying maintenance of a list of an overall level of preference for the one or more display devices. In example implementations of operation 1605C, at operation 1610B, modifying the maintenance of the list may include keeping the one or more display devices on the list, according to the indication. Alternatively or in addition, at operation 1610B, modifying the maintenance of the list may include adding one or more of the display devices to the list, according to the indication.

In embodiments of operation 1605C, at operation 1610C, modifying the maintenance of the list may include allowing any of the display devices to be removed from the list, for example if the display devices become unavailable for connection. Alternatively or in addition, at operation 1610C, modifying the maintenance of the list may include removing one or more of the display devices to the list, according to the indication. At operation 1610D, operation 1605C may include transmitting a message that includes an indication that the one or more display devices have been added to or removed from the list. The list may reflect whether display devices have previously connected to analyte sensor system 708. For example, the list may be a whitelist.

At operation 1610E, operation 1605C may include analyte sensor system 708 transmitting an advertisement message specific to one or more of the display devices added, kept on, removed from, and/or allowed to be removed from the list (e.g., at operations 1610B, 1610C). Alternatively or in addition, operation 1610E may entail transmitting the advertisement message specific to one or more of the display devices in accordance with the preference. In embodiments, the preference includes a prioritization for the display devices. In some such embodiments, operation 1610E may entail transmitting the advertisement message specific to one or more of the display devices using a configuration based on the prioritization and/or in an order based on the prioritization.

L. Reduction of Setup Time

With respect to wireless communication of analyte data, in certain situations, there may be a setup time involved with connecting analyte sensor system 308 to one or more display devices 310*a*, 310*b*, etc. Here, reference is made to some of the numerals from FIG. 3C and in some cases FIGS. 7A-7L, but it will be appreciated that this description can apply to like components throughout, whether or not such components bear the same numerals referenced here.

In some cases, display device 310a may already be configured for connecting to analyte sensor system 308. For example, display device 310a may have been set up with a set of information, such as: (1) a WiFi password and other settings; (2) identifying information for analyte sensor system 708 (including, e.g., an identification number associated therewith); (3) alert settings related to the analyte level, or trends related to the same, as measured at analyte sensor system 708; (4) an archive of previously measured analyte data values and/or historical information related to the same; (5) scheduling information for an upcoming transmission; (6) a current analyte value, e.g., a current estimated glucose value (EGV); (7) information regarding active alerts based on the analyte value being measured or trends in the same; (8) calibration data; (9) information regarding an application key, encryption scheme, modifications to be applied to the application key, or information regarding security levels for various types of data/devices; etc. This set up may have occurred during a connection established (e.g., using communication session 720) over communication medium 305a using a first wireless protocol (e.g., BLE). A set or subset of such information may be stored at analyte sensor system 708 (e.g., in storage 365, with reference to FIG. 3B), and may have been exchanged with display device 310a as part of the communication session used.

Upon forming a new connection to display device 310b, or in some cases establishing a connection thereto for the first time, analyte sensor system 308 may transmit the above-described set or subset of information to display device 310b, for example using communication session 720 (with reference to FIG. 7A). Communication medium 305a may be used for this transmission. One issue with this approach, however, is that the transmission of this set or subset for information takes time, and may lead to packet loss due to gaps in the transmission of analyte values being measured. For example, transferring the information may occur over one or more transmission slots that would have otherwise been used for the transmission of analyte values. Such transmission typically also involves the consumption of power. Thus, it may be beneficial to reduce the time and/or number of transmission used to transfer such information.

Accordingly, further aspects of the present disclosure involve using alternate wireless protocols to transfer connection-related data and thus reduce setup time for a display device connecting to the analyte sensor system. In addition to reducing setup time, as mentioned above, using alternate wireless protocols to transfer connection-related data may also reduce power consumption and increase reliability as well as robustness with respect to data capture. In this connection, techniques, methods, and systems for wireless communication of analyte data are provided.

One such method includes exchanging, between analyte sensor system 308 and display device 310a via a first wireless protocol (e.g., over communication medium 305a), information related to a connection with analyte sensory system 308. For example, the method may include establishing a connection between analyte sensor system 308 and display device 310a via the first wireless protocol. Subsequently, the method may include transferring information regarding the connection from analyte sensor system 308 to display device 310a. The first wireless protocol may, for example, be BLE or any other wireless protocol. This exchange, connection, and/or transfer may be accomplished using aspects of the two-way authentication protocol described above—for example, using communication session 720. In this manner, display device 710a can store (e.g., in storage 325, with reference to FIG. 3B) information related to the connection with analyte sensor system 308, such as the set of information described above.

The method may also include display device 310b connecting to display device 310a via a second wireless protocol (e.g., using communication medium 305b). By way of example, the second wireless protocol may be NFC or WiFi, or may be any other wireless protocol. Additionally, the method may include transferring, from display device 310a to display device 310b, at least some of the information related to the connection with analyte sensor system 308, using the second wireless protocol. The use of NFC for the second wireless protocol may provide a benefit where the first wireless profile is BLE, because NFC can be used to transfer information relatively quickly and with less steps. For example, it may not be necessary to wait for a transmission interval in order to transmit the information. Rather, the information may be exchanged in at least near real time. Furthermore, this technique can be beneficial in that it may reduce the number of transmissions that may be used by analyte sensor system 308. This can be beneficial because in some implementations, analyte sensor system 308 is subject to stringent power consumption requirements.

In this manner, information may be transferred between devices more quickly using, e.g., NFC, as compared to transferring the same information from analyte sensor system 308 to display device 310b using BLE, and power drain on analyte sensor system 308 can be reduced. In turn, display device 310b can get setup and begin receiving analyte values from analyte sensor system 308 more quickly and efficiently, thus potentially reducing gaps in data capture. As mentioned above, WiFi may also be used as the second wireless protocol, having pros and cons relative to NFC in this circumstance. For example, WiFi may be used with less range restrictions than NFC, but may in some cases be less secure. Alternatively or in addition, RFID, ZigBee, and/or unlicensed bands or other protocols may also be used for these purposes, such as but not limited to protocols described with reference to communication medium 305 or otherwise herein.

In embodiments, the method includes display device 310b connecting to analyte sensor system 308 using the first wireless protocol (e.g., BLE) and at least some of the information transferred from display device 310a (using, e.g., NFC) in order to receive analyte data from analyte sensor system 308. This may entail, for example, display device 310b decrypting and received analyte values using information regarding the application key and/or encryption scheme transferred to display device 310b from the display device 310a using the second wireless protocol. Likewise, the transmitter identification number and other information can also be used. To illustrate further, historical data in terms of previously analyte values and trends in the same (as received from display device 310a) can be used by display device 310b to backfill a session such that the a more robust history of the analyte values is provided at display device 310b.

Another such method includes establishing a connection between analyte sensor system 308 and display device 310a via a first wireless protocol (e.g., using communication medium 305a). The method may also include analyte sensor system 308 transferring to display device 310a information related to the connection with analyte sensor system 308. These operations as such may be substantially similar to those described above. Additionally, the method may include analyte sensor system 308 connecting to display device 310b via the first wireless protocol (e.g., using communication medium 305a). This pairing can be facilitated using at least some of the information related to the connection with analyte sensor system 308, where at least some of the information was received from display device 310b via a second wireless protocol (e.g., using communication medium 305b). Accordingly, the connection process may be streamlined and/or made more efficient. The first wireless protocol may be BLE; and the second wireless protocol may be NFC or WiFi.

With respect to the above methods, the second wireless protocol may also be used to exchange data over communication medium 305b such that the data may be synchronized across display devices 310a and 310b. This may entail, for example, applying an alert triggered at display device 310a to display device 310b or vice versa. Likewise, if an alert is cleared at display device 310a, synchronization may allow the alert to be cleared at display device 310b as a result. Moreover, user preferences entered on one device can also be communicated to other devices using the second wireless protocol (e.g., via communication medium 305b). Additional information that may be synchronized across devices using the second wireless protocol may include information related to the updates/modifications to the application key or encryption scheme, user-specific information, and information related to parameters such as quality of service, time of day, location, and the like, including with respect to how the same impact device preferences.

M. Additional Embodiments

One of skill in the art will appreciate upon studying the present disclosure that various additional embodiments not described explicitly herein are within the spirit and scope of the present disclosure.

Figure 11:
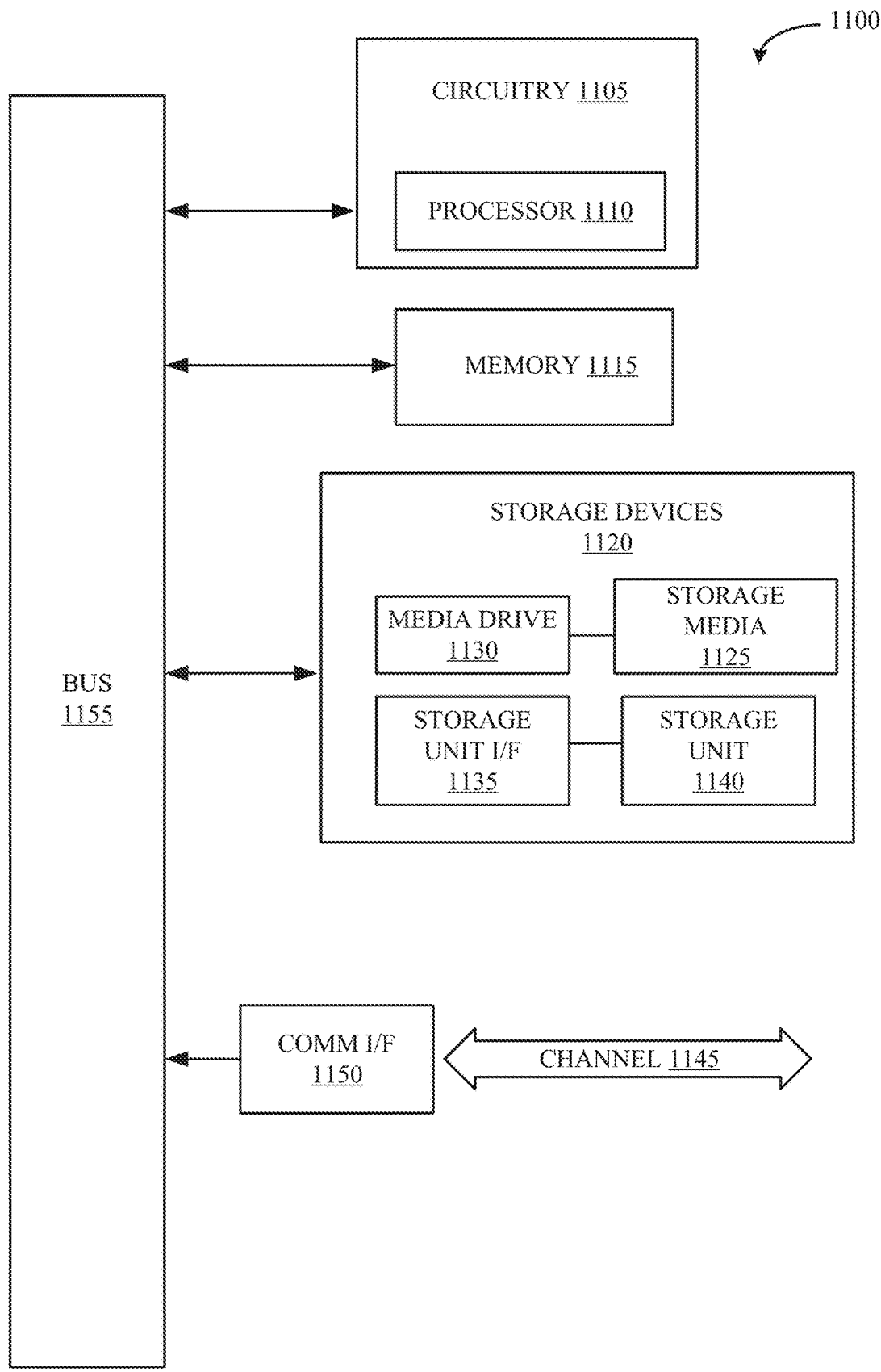
FIG. 11 illustrates an example computing module in accordance with embodiments of the present disclosure.

FIG. 11 illustrates example computing module 1100, which may in some instances include a processor/microprocessor/controller resident on a computer system (e.g., in connection with server system 334, any of the display devices described herein (e.g., display devices 120, 130, 140, 310(a, b), 710(a, b), as well as analyte display device 110 and medical device 136), and/or analyte sensor system 8, 308, 708, etc. Computing module 1100 may be used to implement various features and/or functionality of embodiments of the systems, devices, apparatuses, and methods disclosed herein. With regard to the above-described embodiments set forth herein in the context of systems, devices, apparatuses, and methods described with reference to the various FIGS. of the present disclosure, including embodiments analyte sensor system 708, analyte display device 110, display devices 710a, 710b, etc., server system 334 and components thereof, etc., one of skill in the art will appreciate additional variations and details regarding the functionality of these embodiments that may be carried out by computing module 1100. In this connection, it will also be appreciated by one of skill in the art that features and aspects of the various embodiments (e.g., systems, devices, and/or apparatuses, and the like) described herein may be implemented with respected to other embodiments (e.g., methods, processes, and/or operations, and the like) described herein without departing from the spirit of the disclosure.

As used herein, the term module may describe a given unit of functionality that may be performed in accordance with one or more embodiments of the present application. As used herein, a module may be implemented utilizing any form of hardware, software, or a combination thereof. For example, one or more processors, controllers, ASICs, PLAs, PALs, CPLDs, FPGAs, logical components, software routines or other mechanisms may be implemented to make up a module. In implementation, the various modules described herein may be implemented as discrete modules or the functions and features described may be shared in part or in total among one or more modules. In other words, as would be apparent to one of ordinary skill in the art after reading this description, the various features and functionality described herein may be implemented in any given application and may be implemented in one or more separate or shared modules in various combinations and permutations. Even though various features or elements of functionality may be individually described or claimed as separate modules, one of ordinary skill in the art will understand that these features and functionality may be shared among one or more common software and hardware elements, and such description shall not require or imply that separate hardware or software components are used to implement such features or functionality.

Where components or modules of the application are implemented in whole or in part using software, in one embodiment, these software elements may be implemented to operate with a computing or processing module capable of carrying out the functionality described with respect thereto. One such example computing module is shown in FIG. 11. Various embodiments are described in terms of example computing module 1100. After reading this description, it will become apparent to a person skilled in the relevant art how to implement the application using other computing modules or architectures.

Referring now to FIG. 11, computing module 1100 may represent, for example, computing or processing capabilities found within mainframes, supercomputers, workstations or servers; desktop, laptop, notebook, or tablet computers; hand-held computing devices (tablets, PDA's, smartphones, cell phones, palmtops, etc.); other display devices, application-specific devices, or other electronic devices, and the like, depending on the application and/or environment for which computing module 1100 is specifically purposed.

Computing module 1100 may include, for example, one or more processors, microprocessors, controllers, control modules, or other processing devices, such as a processor 1110, and such as may be included in circuitry 1105. Processor 1110 may be implemented using a special-purpose processing engine such as, for example, a microprocessor, controller, or other control logic. In the illustrated example, processor 1110 is connected to bus 1155 by way of circuitry 1105, although any communication medium may be used to facilitate interaction with other components of computing module 1100 or to communicate externally.

Computing module 1100 may also include one or more memory modules, simply referred to herein as main memory 1115. For example, random access memory (RAM) or other dynamic memory may be used for storing information and instructions to be executed by processor 1110 or circuitry 1105. Main memory 1115 may also be used for storing temporary variables or other intermediate information during execution of instructions to be executed by processor 1110 or circuitry 1105. Computing module 1100 may likewise include a read only memory (ROM) or other static storage device coupled to bus 1155 for storing static information and instructions for processor 1110 or circuitry 1105.

Computing module 1100 may also include one or more various forms of information storage devices 1120, which may include, for example, media drive 1130 and storage unit interface 1135. Media drive 1130 may include a drive or other mechanism to support fixed or removable storage media 1125. For example, a hard disk drive, a floppy disk drive, a magnetic tape drive, an optical disk drive, a CD or DVD drive (R or RW), or other removable or fixed media drive may be provided. Accordingly, removable storage media 1125 may include, for example, a hard disk, a floppy disk, magnetic tape, cartridge, optical disk, a CD or DVD, or other fixed or removable medium that is read by, written to or accessed by media drive 1130. As these examples illustrate, removable storage media 1125 may include a computer usable storage medium having stored therein computer software or data.

In alternative embodiments, information storage devices 1120 may include other similar instrumentalities for allowing computer programs or other instructions or data to be loaded into computing module 1100. Such instrumentalities may include, for example, fixed or removable storage unit 1140 and storage unit interface 1135. Examples of such removable storage units 1140 and storage unit interfaces 1135 may include a program cartridge and cartridge interface, a removable memory (for example, a flash memory or other removable memory module) and memory slot, a PCMCIA slot and card, and other fixed or removable storage units 1140 and storage unit interfaces 1135 that allow software and data to be transferred from removable storage unit 1140 to computing module 1100.

Computing module 1100 may also include a communications interface 1150. Communications interface 1150 may be used to allow software and data to be transferred between computing module 1100 and external devices. Examples of communications interface 1150 include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface configured to operation with the communication media described herein. Software and data transferred via communications interface 1150 may typically be carried on signals, which may be electronic, electromagnetic (which includes optical) or other signals capable of being exchanged by a given communications interface 1150. These signals may be provided to/from communications interface 1150 via channel 1145. Channel 1145 may carry signals and may be implemented using a wired or wireless communication medium. Some non-limiting examples of channel 1145 include a phone line, a cellular or other radio link, an RF link, an optical link, a network interface, a local or wide area network, and other wired or wireless communications channels.

In this document, the terms "computer program medium" and "computer usable medium" and "computer readable medium", as well as variations thereof, are used to generally refer to transitory or non-transitory media such as, for example, main memory 1115, storage unit interface 1135, removable storage media 1125, and/or channel 1145. These and other various forms of computer program media or computer usable/readable media may be involved in carrying one or more sequences of one or more instructions to a processing device for execution. Such instructions embodied on the medium, may generally be referred to as "computer program code" or a "computer program product" or "instructions" (which may be grouped in the form of computer programs or other groupings). When executed, such instructions may enable the computing module 1100, circuitry related thereto, and/or a processor thereof or connected thereto to perform features or functions of the present disclosure as discussed herein (for example, in connection with methods described above and/or in the claims), including for example when the same is/are incorporated into a system, apparatus, device and/or the like.

Various embodiments have been described with reference to specific example features thereof. It will, however, be evident that various modifications and changes may be made thereto without departing from the broader spirit and scope of the various embodiments as set forth in the appended claims. The specification and figures are, accordingly, to be regarded in an illustrative rather than a restrictive sense.

Although described above in terms of various example embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the present application, whether or not such embodiments are described and whether or not such features are presented as being a part of a described embodiment. Thus, the breadth and scope of the present application should not be limited by any of the above-described example embodiments.

Terms and phrases used in the present application, and variations thereof, unless otherwise expressly stated, should be construed as open ended as opposed to limiting. As examples of the foregoing: the term "including" should be read as meaning "including, without limitation" or the like; the term "example" is used to provide illustrative instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Similarly, the plural may in some cases be recognized as applicable to the singular and vice versa. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic, circuitry, or other components, may be combined in a single package or separately maintained and may further be distributed in multiple groupings or packages or across multiple locations.

Additionally, the various embodiments set forth herein are described in terms of example block diagrams, flow charts, and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration. Moreover, the operations and sub-operations of various methods described herein are not necessarily limited to the order described or shown in the figures, and one of skill in the art will appreciate, upon studying the present disclosure, variations of the order of the operations described herein that are within the spirit and scope of the disclosure.

In addition, the operations and sub-operations of methods described herein may be carried out or implemented, in some cases, by one or more of the components, elements, devices, modules, circuitry, processors, etc. of systems, apparatuses, devices, environments, and/or computing modules described herein and referenced in various of FIGS. of the present disclosure, as well as one or more sub-components, elements, devices, modules, processors, circuitry, and the like depicted therein and/or described with respect thereto. In such instances, the description of the methods or aspects thereof may refer to a corresponding component, element, etc., but regardless of whether an explicit reference is made, one of skill in the art will recognize upon studying the present disclosure when the corresponding component, element, etc. may be used. Further, it will be appreciated that such references do not necessarily limit the described methods to the particular component, element, etc. referred to. Thus, it will be appreciated by one of skill in the art that aspects and features described above in connection with (sub-) components, elements, devices, modules, and circuitry, etc., including variations thereof, may be applied to the various operations described in connection with methods described herein, and vice versa, without departing from the scope of the present disclosure.

What is claimed is:

1. A method for wireless communication of analyte data, the method comprising:
    measuring analyte data in a host using a continuous analyte sensor of an analyte sensor system;
    initiating a first data connection between the analyte sensor system and a first display device, wherein the first display device is configured to display information related to the analyte data;
    exchanging authentication information between the analyte sensor system and the first display device;
    establishing the first data connection and maintaining the established first data connection by periodically exchanging messages between the analyte sensor system and the first display device;
    while the analyte sensor system and the first display device remain connected, the analyte sensor system transmitting the measured analyte data to the first display device via the first data connection;
    establishing a second data connection between the first display device and a second display device, wherein the second display device is configured to display information related to the analyte data;
    transmitting by the first display device to the second display device information related to the analyte data after receiving the analyte data from the analyte sensor system; and
    determining whether one or more alerts indicative of a medical condition of the host is to be triggered based on the analyte data measured by the continuous analyte sensor; and
    triggering at least one alert and providing a notification on the first display device and/or the second display device when the determination indicates that the at least one alert is to be triggered indicative of the medical condition of the host based on the analyte data measured by the continuous analyte sensor.

2. The method of claim 1, initiating the first data connection comprises performing a two-way authentication between the analyte sensor system and the first display device.

3. The method of claim 2, wherein performing the two-way authentication comprises:
    the analyte sensor system transmitting a first value to the first display device;
    the analyte sensor system receiving from the first display device a second value and a third value, wherein the second value is based on the first value and an application key;
    the analyte sensor system validating the second value;
    the analyte sensor system generating a fourth value using the third value; and
    the analyte sensor system transmitting the fourth value to the first display device for validation.

4. The method of claim 1, wherein the combination of periodically exchanging messages and transmitting the analyte data to the first display device, upon the analyte data becoming available for transmission, is done responsive to an indication of a user preference for the first display device.

5. The method of claim 1, wherein the combination of periodically exchanging messages and transmitting the analyte data to the display device, upon the analyte data becoming available for transmission, is done adaptively.

6. The method of claim 1, wherein the messages exchanged periodically between the analyte sensor system and the first display device comprise a first message and a second message, the first and second messages being configured for sequential exchange; and wherein the first message comprises a messaging interval corresponding to a scheduled amount of time between the sequential exchange of the first message and second messages.

7. The method of claim 1, wherein each of the messages exchanged periodically between the analyte sensor system and the first display device comprises a message interval corresponding to an amount of time until a successive message is to be exchanged.

8. The method of claim 7, further comprising sending a request to modify the message interval.

9. The method of claim 8, further comprising terminating the analyte sensor system periodically exchanging messages with the first display device, such that the analyte sensor system and the display device do not remain connected, responsive to the request being denied.

10. The method of claim 1, wherein each of the messages exchanged periodically between the analyte sensor system and the first display device comprises a timeout value, and wherein the method further comprises terminating the analyte sensor system periodically exchanging messages with the first display device, such that the analyte sensor system and the first display device do not remain connected, if the timeout value included in a first message of the messages is exceeded before a second message of the messages successive to the first message is exchanged.

11. The analyte sensor system of claim 1, wherein the processor is further configured to cause the analyte sensor system to:
    establish the first connection and exchange the information related to authentication using a first wireless protocol; and
    transmit the encrypted analyte data using a second wireless protocol;

wherein the first wireless protocol allows bypassing, during the second interval, the exchange of information related to authentication.

12. The method of claim 1, comprising storing the analyte values in a memory based on which the at least one alert is triggered.

13. The method of claim 1, wherein the notification comprises an audible or a vibratory alarm provided on the first display device.

14. The method of claim 1, wherein the second display device is a mobile device or a wearable device.

15. The method of claim 1, wherein the transmission of the information related to the analyte data from the first display device to the second display device is over a short-range communication protocol.

16. A method for wireless communication of analyte data, the method comprising:
    measuring analyte data in a host using a continuous analyte sensor of an analyte sensor system;
    establishing a first data connection between the analyte sensor system and a first display device, upon exchanging authentication information between the analyte sensor system and the first display device, wherein the first display device is configured to display information related to the analyte data;
    operating in a first mode, comprising:
        the analyte sensor system periodically exchanging messages with the first display device such that the analyte sensor system and the first display device remain connected; and
        while the analyte sensor system and the first display device remain connected, the analyte sensor system transmitting the measured analyte data to the first display device via the first data connection; and
    operating in a second mode, comprising:
        periodically establishing a second data connection between the analyte sensor system and the first display device;
        after the second data connection has been established, transmitting the measured analyte data to the first display device; and
    while operating in the first mode or the second mode:
        establishing a second connection between the first and a second display device, wherein the second display device is configured to display information related to the analyte data;
        transmitting by the first display device to the second display device information related to the analyte data after receiving the analyte data from the analyte sensor system;
        determining whether one or more alerts indicative of a medical condition of the host is to be triggered based on the analyte data based on the analyte data measured by the continuous analyte sensor; and
        triggering at least one alert and providing a notification on the first and/or the second display device when the determination indicates that the at least one alert is to be triggered indicative of the medical condition of the host based on the analyte data measured by the continuous analyte sensor.

17. The method of claim 16, wherein operating in the first mode occurs responsive to an indication related to one or more of:
    user input regarding a use preference for the first display device;
    time of day;
    location;
    packet loss; and
    a priority scheme that includes the first display device.

18. The method of claim 16, wherein operating in the second mode occurs if the analyte sensor system is transmitting analyte data and is not operating in the first mode.

19. The method of claim 16, further comprising switching between operating in the first mode and operating in the second mode.

20. A system, comprising:
    a continuous analyte sensor configured to measure analyte data in a host;
    a first display device, wherein the first display device is configured to display information related to the analyte data;
    an analyte sensor system, comprising:
        a transceiver configured to transmit and receive wireless signals; and
        a processor operatively coupled to a transceiver and configured to cause the analyte sensor system to:
            establish a first data connection between the analyte sensor system and the first display device, upon exchanging authentication information between the analyte sensor system and the first display device;
            maintain the first data connection by periodically exchanging messages between the analyte sensor system and the first display device; and
            transmit the analyte data to the first display device via the first data connection;
    a second display device, wherein the second display device is configured to display information related to the analyte data;
    wherein the first display device is configured to:
        establish a second data connection with the second display device such that the first and second display devices remain connected;
        while the first and second display devices remain connected, transmit information related to the analyte data to the second display device, after receiving the analyte data from the analyte sensor system; and
    wherein the system is configured to:
        determine whether one or more alerts indicative of a medical condition of the host is to be triggered based on the analyte data measured by the continuous analyte sensor; and
        trigger at least one alert and provide a notification on the first and/or the second display device when the determination indicates that the at least one alert is to be triggered indicative of the medical condition of the host based on the analyte data measured by the continuous analyte sensor.

* * * * *

UNITED STATES PATENT AND TRADEMARK OFFICE
CERTIFICATE OF CORRECTION

| | |
|---|---|
| PATENT NO. | : 10,771,607 B2 |
| APPLICATION NO. | : 15/651851 |
| DATED | : September 8, 2020 |
| INVENTOR(S) | : Aditya Sagar Mandapaka et al. |

It is certified that error appears in the above-identified patent and that said Letters Patent is hereby corrected as shown below:

On the Title Page

On page 2, in Column 2, item (56), Line 16, delete "Hoffman" and insert --Hoffmann--.

On page 2, in Column 2, item (56), Line 54, delete "Korlyama" and insert --Koriyama--.

In the Drawings

In sheet 29 of 40, FIG. 12B, reference numeral 1210G, Line 1, delete "AUTHETNICATION" and insert --AUTHENTICATION--.

In the Specification

In Column 8, Line 28, after "system" insert --to--.

In Column 33, Line 58, delete "andrenostenedione;" and insert --androstenedione;--.

In Column 34, Line 7, delete "diptheria" and insert --diphtheria--.

In Column 34, Line 14, delete "perioxidase;" and insert --peroxidase;--.

In Column 34, Line 23, delete "sissomicin;" and insert --sisomicin;--.

In Column 34, Line 27, delete "duodenalisa" and insert --duodenalis--.

In Column 34, Line 35, delete "Trepenoma pallidium," and insert --Treponema pallidum,--.

In Column 34, Line 36, delete "stomatis" and insert --stomatitis--.

Signed and Sealed this
Tenth Day of November, 2020

Andrei Iancu
*Director of the United States Patent and Trademark Office*

CERTIFICATE OF CORRECTION (continued)
U.S. Pat. No. 10,771,607 B2

In Column 35, Line 5, delete "(FHIAA)." and insert --(5-HIAA)--.

In Column 37, Line 41, delete "((2)" and insert --(2)--.

In Column 58, Line 3, delete "625b" and insert --625b)--.

In Column 58, Line 18, delete "630a" and insert --630a)--.

In Column 58, Line 20, delete "625d." and insert --625d).--.

In Column 58, Line 23, delete "625d," and insert --625d),--.

In Column 59, Line 49, delete "Tinactive." and insert --$T_{Inactive}$.--.

In Column 67, Line 15, delete "For" and insert --for--.

In Column 69, Line 3, delete "Tinactive'" and insert --$T_{Inactive}$'--.

In Column 69, Line 41, delete "For" and insert --for--.

In Column 71, Line 4, delete "For" and insert --for--.

In Column 77, Line 44, delete "795b" and insert --795b)--.

In Column 84, Line 18, delete "945d" and insert --945d)--.

In Column 86, Line 24, delete "950b" and insert --950b)--.

In Column 86, Line 26, delete "955b" and insert --955b)--.

In Column 92, Line 20, delete "975b" and insert --975b)--.

In Column 92, Line 22, delete "980b" and insert --980b)--.

In Column 96, Line 32, delete "(710b" and insert --(710b)--.

In Column 96, Line 44, delete "(710b" and insert --(710b)--.

In Column 98, Line 27, delete "(710b" and insert --(710b)--.

In Column 98, Line 44, delete "deices," and insert --devices,--.

In Column 99, Line 27, delete "930b" and insert --930b)--.

In Column 101, Line 61, delete "728e," and insert --728e),--.

CERTIFICATE OF CORRECTION (continued)
U.S. Pat. No. 10,771,607 B2

In Column 110, Line 8, delete "305b." and insert --305b).--.

In the Claims

In Column 117, Line 4, Claim 12, after "the" insert --measured--.

In Column 118, Line 36, Claim 20, after "the" insert --measured--.

In Column 118, Line 48 (approx.), Claim 20, after "the" insert --measured--.